United States Patent
Sperl et al.

(10) Patent No.: US 6,348,032 B1
(45) Date of Patent: Feb. 19, 2002

(54) METHOD OF INHIBITING NEOPLASTIC CELLS WITH BENZIMIDAZOLE DERIVATIVES

(75) Inventors: Gerhard Sperl, North Wales; Rifat Pamukcu, Spring House, both of PA (US); Ulrich Ixkes, Carluke (GB); Gary A. Piazza, Doylestown, PA (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/199,094

(22) Filed: Nov. 23, 1998

(51) Int. Cl.$^7$ ......................... A61K 31/44; A61K 31/41; A61K 31/415
(52) U.S. Cl. ...................... 574/338; 574/361; 574/362; 574/363; 574/394; 574/395
(58) Field of Search ............................ 514/338, 361, 514/394, 395, 362, 363

(56) References Cited

U.S. PATENT DOCUMENTS

| | | | |
|---|---|---|---|
| 4,950,680 A | 8/1990 | Taylor et al. | 514/350 |
| 5,696,159 A | 12/1997 | Gross et al. | 514/468 |
| 5,767,138 A * | 6/1998 | Camden | 514/396 |

FOREIGN PATENT DOCUMENTS

| WO | WO 95/19978 | 7/1995 |
|---|---|---|
| WO | WO 00/15222 | 3/2000 |

OTHER PUBLICATIONS

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Constitutive Transcriptional Activation by a β–Catenin–Tcf Complex in APC$^{-/-}$ Colon Carcinoma, Science, vol. 275, pp. 1784–1786, Mar. 21, 1997.

Mahmoud, N. et al., *Apc* Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlationin Murine *Apc* Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutation in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

* cited by examiner

Primary Examiner—Jerome D. Goldberg
(74) Attorney, Agent, or Firm—Robert W. Stevenson

(57) ABSTRACT

A method for inhibiting neoplasia, particularly cancerous and precancerous lesions by exposing the affected cells to benzimidazole derivatives.

2 Claims, No Drawings

METHOD OF INHIBITING NEOPLASTIC CELLS WITH BENZIMIDAZOLE DERIVATIVES

This invention relates to compounds and methods for inducing or promoting apoptosis and for arresting uncontrolled neoplastic cell proliferation, methods that are specifically useful in the arresting and treatment of neoplasias, including precancerous and cancerous lesions.

BACKGROUND OF THE INVENTION

Pharmaceuticals that are effective against early stage neoplasias comprise an emerging and expanding area of research and potential commercial development. Such pharmaceuticals can delay or arrest development of precancerous lesions into cancers. Each year in the United States alone, untold numbers of people develop precancerous lesions, which exhibit a strong statistically significant tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), cervical displasia (cervical cancer) and other such neoplasms.

Such compounds and methods are particularly beneficial to sub-populations of patients who repeatedly develop precancerous lesions, and therefore have a statistically higher probability of getting cancer, many cancer types (e.g., breast, colon, prostate etc.) have such patient subpopulations.

The search for drugs useful for treating and preventing neoplasias in their earliest stages is intensive because chemotherapy and surgery on cancer itself is often not effective, and current cancer chemotherapy has severe side effects. Such cancer-preventative compounds are also envisaged for recovered cancer patients who retain a risk of cancer reoccurrence, and even for cancer patients who would benefit from compounds that selectively induce apoptosis in neoplastic, but substantially not in normal cells.

Because it is believed that chronic administration of cancer-preventative pharmaceuticals is necessary to inhibit or arrest the development of neoplasia, standard cancer chemotherapeutic drugs are not considered appropriate drugs for cancer chemoprevention because whatever cancer preventative (as opposed to cancer-fighting) capabilities those drugs may possess do not outweigh their severe side effects most standard chemotherapeutics are now believed to kill cancer cells by inducing apoptosis (also sometimes referred to as "programmed cell death"). Apoptosis naturally occurs in many tissues in the body. Apoptosis plays a critical role in tissue homeostasis, that is, it ensures that the number of new cells produced are correspondingly offset by an equal number of cells that die. Apoptosis is especially pronounced in self-renewing tissues such as bone marrow, immune cells, gut, and skin. For example, the cells in the intestinal lining divide so rapidly that the body must eliminate cells after only three days to protect and prevent the overgrowth of the intestinal lining.

Standard chemotherapeutics promote apoptosis not only in cancer cells, but also in normal human tissues, and therefore have a particularly severe effect on tissues where apoptosis is especially pronounced (e.g. hair, gut and skin). The results of those effects include hair loss, weight loss, vomiting and bone marrow immune suppression. Thus, standard chemotherapeutics are inappropriate for cancer prevention, particularly if chronic administration is indicated.

Several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the continued prophylactic use of currently available NSAIDs, even in high colon cancer-risk patients, is still marked by severe side reactions that include gastrointestinal irritations, perforations, ulcerations and kidney toxicity believed to be produced by inhibition of prostaglandin synthetase activity ("PGE-2"). Such inhibition is a requirement for the NSAIDs anti-inflammatory action since elevated levels of PGE-2 are associated with inflammation. PGE-2 plays a protective function in the gastrointestinal tract, which is the reason such gastric side effects arise with chronic NSAID therapy, which is rarely indicated for arthritis sufferers, acute therapy being the norm for them. However, chronic administration of sulindac is important for high cancer-risk patients to eliminate and prevent future polyps which causes gastric side effects in many such patients. Once NSAID treatment is terminated due to such complications, the neoplasms return, particularly in high risk patients.

Compounds such as those disclosed in U.S. Pat. No. 5,643,959 have exhibited advantages in the treatment of neoplastic lesions since such compounds have been shown to induce apoptosis in neoplastic cells but not in normal cells in humans. Thus, the severe side effects due to induction of apoptosis in normal cells by conventional chemotherapeutics are avoided by these novel therapeutics (see, Van Stolk, et al., *Gastroenterology* 112 (4): A673, 1997). In addition, such compounds do not exhibit the gastric side effects associated with NSAIDs since such compounds do not substantially inhibit PGE-2. more potent compounds with such neoplasia specificity but without substantial PGE-2 activity are desirable.

SUMMARY OF THE INVENTION

This invention represents potent compounds that induce apoptosis in neoplastic cells (but not substantially in normal cells), for treating patients with neoplastic lesions without substantially inhibiting PGE-2. This invention also involves methods for inducing such specific apoptosis in neoplastic cells by exposing such cells to a pharmacologically effective amount of those compounds described below to a patient in need of such treatment. Such compositions are effective in modulating apoptosis and modulating the growth of neoplasms, but are not suffering from the side effects of conventional chemotherapeutics and NSAIDs.

DETAILED DESCRIPTION OF THE INVENTION

As discussed above, the present invention utilizes compounds of Formula I below

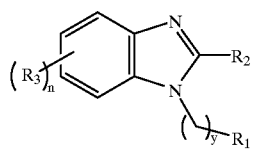

Formula I wherein $R_1$ is selected from a group consisting of hydrogen, lower alkyl, benzenesulfonyl, and substituted or unsubstituted aryl, wherein said aryl group is selected from the group consisting of phenyl, benzyl, pyridyl, dibenzofuranyl, dioxymethylene benzyl, naphthyl, quinolinyl or isoquinolinyl and wherein said substituents are one to three independently selected from the group consisting of halogen, lower alkyl, lower alkoxy, halo- or cyano-substituted or unsubstituted phenyloxy or benzyloxy, lower haloalkyl, CN, amino, nitro, phenyl, thiadiazole, aryloxy, arylsulfonyl methyl, arylsulfonyl amino, benzoyl, benzylamidyl, benzenesulfonyl methyl, phenylethyl, and phenylethenyl, wherein said aryl group is selected from the group consisting of phenyl, benzyl and pyridyl;

$R_2$ is selected from a group consisting of hydrogen, lower alkyl, haloalkyl, lower alkoxy, amino, alkylamino, lower alkoxyalkyl, or carboxyl;

$R_3$ is selected from a group consisting of halo-carbonyl, carboxyl, haloalkyl carbonyl, lower alkoxy carbonyl, carboxyalkenyl, alkoxycarbonylalkenyl, aminosulfonyl, CN, —C(O)—NR$_4$R$_5$, substituted or unsubstituted carbamoylalkyl, carbamoylalkenyl, or aryloxy carbonyl, wherein said aryl group is selected from the group consisting of benzyl, phenyl and pyridyl, and wherein said substituents are one to three selected from the group consisting of halogen, lower alkyl, lower alkoxy, CN, amino, and nitro, or said substituent is one selected from the group consisting of phenyl, benzyl, pyridyl, pyridylmethyl, benzenesulfonyl, alkyl sulfonyl, and alkyl carbonyl.

$R_4$ and $R_5$ are independently selected from a group consisting of hydrogen, lower alkyl, —SO$_2$R$_6$, substituted or unsubstituted aryl, wherein said alyl group is selected from the group consisting of phenyl, benzyl or pyridyl, pyridylmethyl, pyridinyl-oxide-2 -methyl, piperonyl, quinolinyl, thiazolyl, tetrazolyl, thiadiazolyl, and triazolyl, and wherein said substituents are one to three selected from the group consisting of halogen, lower alkyl, lower alkoxy, amino, and dimethylamino; or $R_4$ and $R_5$ together form substituted or unsubstituted morpholinyl, thiomorpholinyl, propansultamyl, homopiperidyl, or pyrrolidyl, wherein said substituents are one to three independently selected from the group consisting of halogen, lower alkyl, lower alkoxy, or carboxyl;

$R_6$ is selected from a group consisting of substituted or unsubstituted lower alkyl, benzyl, phenyl naphthyl and tolyl, wherein said substituents are one to three selected from the group consisting of halogen, lower alkyl, lower alkoxy, alkylmercapto, haloalkyl, trimethylsilyl, nitro, phenyloxy, and benzyloxy; and y is 0, 1, or 2; and n is 0, 1,or2.

The present invention is also a method of treating individuals with neoplastic lesions by administering a pharmacologically effective amount of an enterically coated pharmaceutical composition that includes compounds of this invention.

Preferably, such compounds are administered without therapeutic amounts of an NSAID.

Also, the present invention is a method of inhibiting the growth of neoplastic cells by exposing the cells to an effective amount of compounds of Formula I, wherein $R_1$, $R_2$, $R_3$, etc. are defined as above.

In still another form, the invention is a method of inducing apoptosis in human cells by exposing those cells to an effective amount of compounds of Formula I, wherein $R_1$ etc. are defined as above where such cells are sensitive to these compounds.

Additionally, in yet another form, the invention is a method of treating a patient having a disease which would benefit from regulation of apoptosis by treating the patient with an effective amount of compounds of Formula I, wherein $R_1$ through $R_7$ etc. are defined as above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "cancerous" refers to lesions that are malignant. Examples include malignant melanomas, breast cancer, prostate cancer and colon cancer.

As used herein, the term "neoplasm" refers to both precancerous and cancerous lesions and hyperplasia.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to C1 to C8 alkyl groups.

The term "lower alkoxy" refers to alkoxy groups having from 1 to 8 carbons, including straight, branched or cyclic arrangements.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example. Representative acid addition salts include the hydrochloride, hydrobromide, sulfate, bisulfate, acetate, valerate, oleate, palmatate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

Compounds of this invention may be formulated into pharmaceutical compositions together with pharmaceutically acceptable carriers for oral administration in solid or liquid form, or for rectal or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

There are several general schemes for producing compounds useful in this invention.

Scheme I

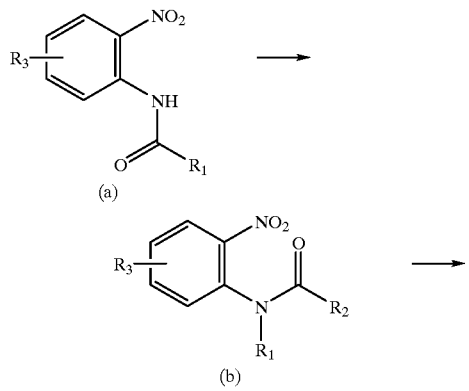

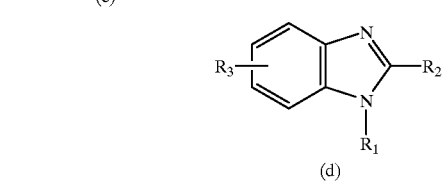

A substituted amide (a) is allowed to react with a base such as sodium hydride, lithium diusopropylamide. Reaction with a compound expressed by $R_2Z$ (Z represents a halogen atom or a sulfonyl chloride) gives the tertiary amide (b). There are several methods to obtain a compound of the formula (c). (A) Reduction with iron or zinc under an acidic condition, (B) reduction with a transition metal catalyst primarily exemplified by palladium, platinum, ruthenium, and nickel under a hydrogen environment, (C) reduction with a transition metal catalyst primarily exemplified by palladium, platinum, ruthenium, and nickel under a presence of formic acid, or (D) reduction with sodium hydrosulfite. In many cases when method (A) is used, a compound of the formula (c) is reduced within the reaction system to directly produce a compound of the formula (d). Some compounds may partially produce a compound of the formula (d) under any condition in the methods (A) through (D). A compound of the formula (d) is produced from a compound of the formula (c) with a carboxylic acid such as acetic acid, p-toluenesulfonic acid, hydrochloric acid, sulfuric acid, or phosphoric acid, sulfonic acid, or an inorganic acid.

Scheme II

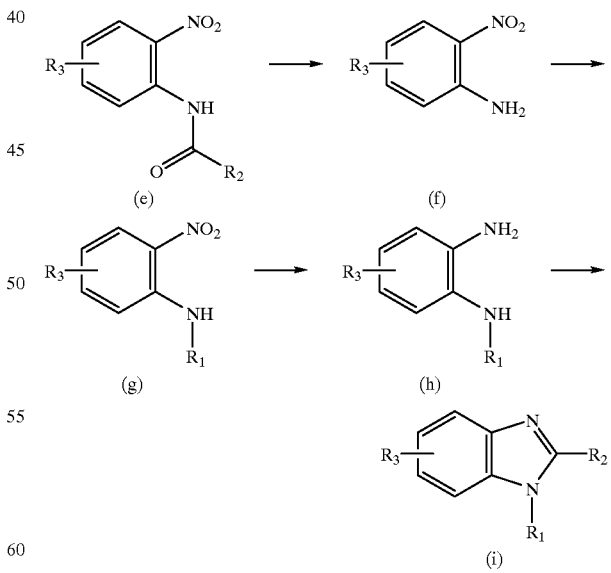

In scheme II, a compound of the formula (e) undergoes a hydrolysis or solvolysis with a base such as lithium bicarbonate, lithium carbonate, lithium hydroxide, sodium bicarbonate, sodium carbonate, sodium hydroxide, potassium bicarbonate, potassium carbonate, or potassium hydroxide, a carboxylic acid such as acetic acid, p-toluenesulfonic acid, hydrochloric acid, sulfuric acid, or phosphoric acid, sulfonic acid, or an inorganic acid and produces a compound expressed by the formula (f). A compound of the formula (f) is processed with a base such as sodium hydride, lithium diisopropylamide, and is processed with a compound expressed by $R_{1b}Z$ (Z represents a halogen or sulfonyl chloride) in order to produce a compound of the formula (g). A compound of the formula (g) can be altered to a compound of the formula (h) by a method such as (A) reducing it with iron or zinc under an acidic condition, (B) reducing it with a transition metal catalyst primarily exemplified by palladium, platinum, ruthenium and nickel under a hydrogen environment, (C) reducing it with a transition metal catalyst primarily exemplified by palladium, platinum, ruthenium, and nickel under a presence of formic acid, and (D) reducing it with sodium hydrosulfite. A compound of the formula (i) is produced from a compound of the formula (h) and a corresponding carboxylic acid, acid chloride, acid bromide, or acid anhydride.

Scheme III

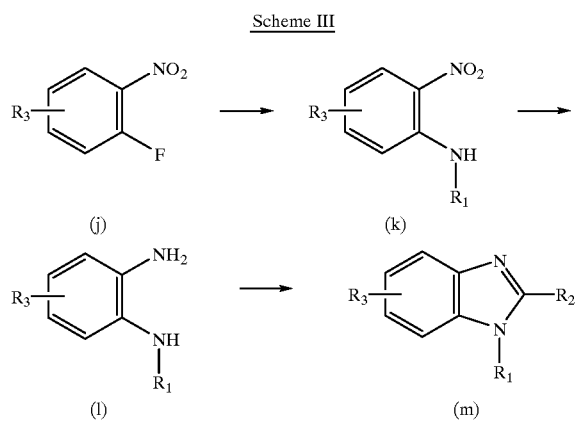

In scheme III, a compound of the formula (k) is produced from a compound of the formula 0) and a compound expressed by $R_1NH_2$. The alteration of a compound of the formula (k) to a compound of the formula (m) is the same as that of a compound of the formula (g) to a compound of the formula (i) in scheme II.

Scheme IV

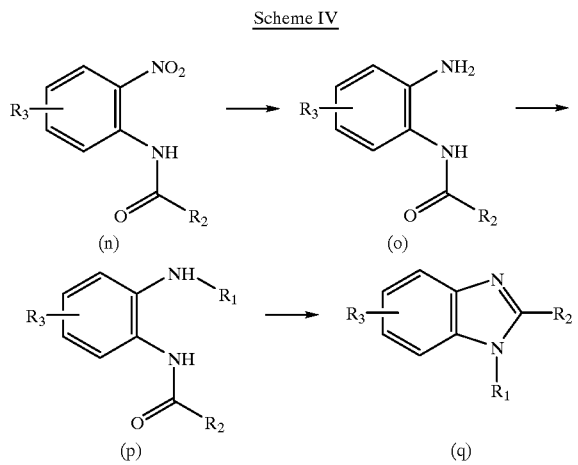

In scheme IV, a compound of the formula (n) can be altered to a compound of the formula (o) by a method such as (A) reducing it with a transition metal catalyst primarily exemplified by palladium, platinum, ruthenium, and nickel under a hydrogen environment, and (B) reducing it with sodium hydrosulfite. A compound of the formula (o) is processed with a base such as lithium bicarbonate, lithium carbonate, lithium hydroxide, sodium bicarbonate, sodium carbonate, sodium hydroxide, potassium bicarbonate, potassium carbonate, or potassium hydroxide, and with a compound expressed by $R_1Z$ (Z represents a halogen atom, or a sulfonyl chloride.) in order to produce a compound of the formula (p). A compound of the formula (q) is produced from a compound of the formula (p) with a carboxylic acid such as acetic acid, p-toluenesulfonic acid, hydrochloric acid, sulfuric acid, or phosphoric acid, sulfonic acid, or an inorganic acid.

Scheme V

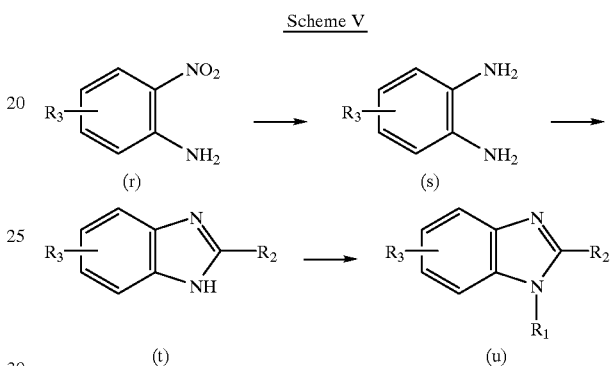

In scheme V, a compound of the formula (r) can be altered to a compound of the formula (s) by a method such as (A) reducing it with reduced iron or zinc under an acidic condition, (B) reducing it with a transition metal catalyst primarily exemplified by palladium, platinum, ruthenium, and nickel under a hydrogen environment, (C) reducing it with a transition metal catalyst primarily exemplified by palladium, platinum, ruthenium, and nickel under a presence of formic acid, and (D) reducing it with sodium hydrosulfite. A compound of the formula (t) is produced from a compound of the formula (s) and a corresponding carboxylic acid, acid anhydride, acid chloride, or acid bromide. A compound of the formula (t) is processed with a base such as sodium hydride or lithium diusopropylamide, and is processed with a compound expressed by $R_1Z$ (Z represents a halogen atom, or a sulfonyl chloride.) in order to produce a compound of the formula (u).

These methods usually produce a compound of the formula (u) having $R_3$ at mixed substitution positions of the fifth and sixth or of the fourth and seventh. The materials can be purified by a means such as recrystallization, column chromatography, thin film chromatography, or high speed liquid chromatography.

Scheme IV

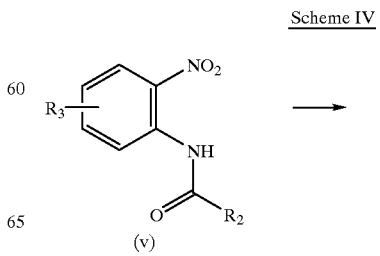

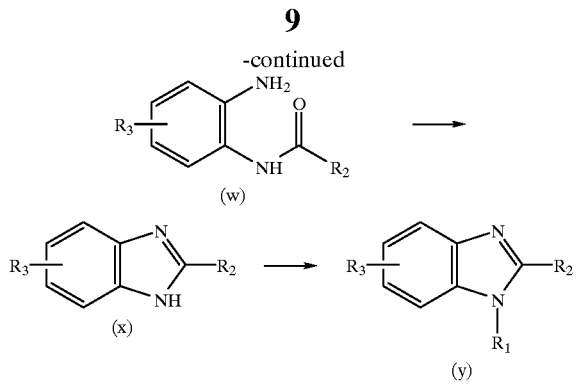

In scheme VI, a compound of the formula (v) can be altered to a compound of the formula (w) by a method such as (A) reducing it with reduced iron or zinc under an acidic condition, (B) reducing it with a transition metal catalyst primarily exemplified by palladium, platinum, ruthenium, and nickel under a hydrogen environment, (C) reducing it with a transition metal catalyst primarily exemplified by palladium, platinum, ruthenium, and nickel under a presence of formic acid, and (D) reducing it with sodium hydrosulfite. In many cases when the method (A) is used, a compound of the formula (w) forms a ring within the reaction system to directly produce a compound of the formula (x). Some compounds may partially produce a compound of the formula (x) under any condition in the methods (A) through (D). A compound of the formula (x) is produced from a compound of the formula (w) with a carboxylic acid such as acetic acid, p-toluenesulfonic acid, hydrochloric acid, sulfuric acid, or phosphoric acid, sulfonic acid, or an inorganic acid. A compound of the formula (x) can be altered to a benzimidazole compound by using the alteration method from the formula (t) to the formula (u) in scheme V. These methods usually produce a compound of the formula (y) having $R_3$ at mixed substitution positions of the fifth and sixth or of the fourth and seventh. The materials can be purified by a means such as recrystallization, column chromatography, thin film chromatography, or high speed liquid chromatography.

Scheme VIII

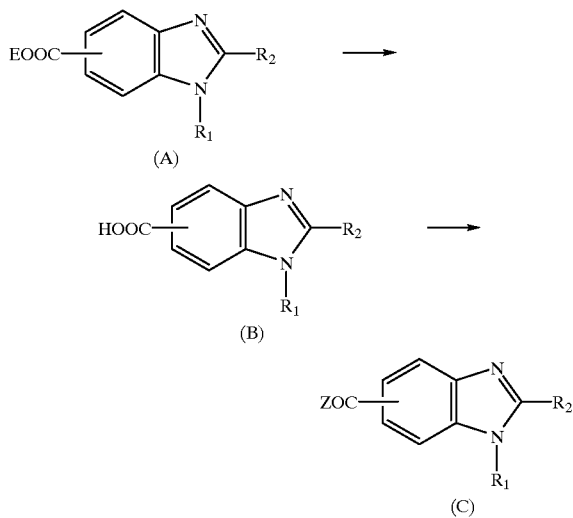

In scheme VII, a compound of the formula (A) undergoes a hydrolysis with a base such as lithium hydroxide, sodium hydroxide, and produces a compound of the formula (B). A compound of the formula (B) is processed with carbonyldulmidazole and then is processed with an amine or a sulfonamide under a presence of a base to further produce benzimidazole derivatives.

A compound of the formula (B) can be altered to an acid halide expressed by the formula (C) by thionyl chloride, thionyl bromide, phosphorus trichloride, phosphorus pentachloride, or phosphorus oxychloride. Benzimidazole derivatives can be further produced by reacting a compound of the formula (C) with an amine or a sulfonamide.

Scheme VIII

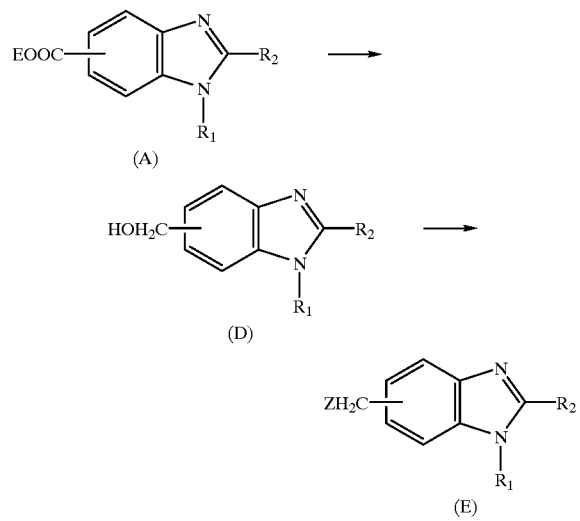

In scheme VIII, a compound of the formula (A) can be altered by reduction to a compound of the formula (D). Furthermore, a compound of the formula (D) can be altered to a compound of the formula (E) by thionyl chloride, thionyl bromide, phosphorus oxychloride, phosphorus oxybromide, phosphorus trichloride, phosphorus pentachloride, methanesulfonyl chloride, or toluenesulfonyl chloride.

The foregoing may be better understood from the following examples that are presented for the purposes of illustration and are not intended to limit the scope of the invention. As used in the following examples, the references to substituents such as R1 Y, A, etc. refer to the corresponding substituents in Formula I above.

EXAMPLES

Example 1

2-Methyl-1H-5-Methoxybenzimidazole

A.) 4-Methoxy-2-nitrophenyl-N-acetamide

4-Methoxy-2-nitroaniline (50 mmole, 7.6 g) is added to a solution of pyridine (75 mmole, 6.0 ml) in dichloromethane (120 ml). The mixture is charged slowly with acetylchloride (50 mmole, 3.6 ml) in dichloromethane (40 ml) and is stirred for 48 hours. The reaction mixture is washed with water, the organic layer is dried with $Na_2SO_4$, is filtered, evaporated and is dried in vacuo (86%).

B.) 2-Methyl-1H-5-methoxybenzimidazole

A mixture of 4-methoxy-2-nitrophenyl-N-acetamide (21.41 mmole, 4.5 g) in acetic acid (100 ml) and iron (Fe) (0.1 mole, 5.57 g) is refluxed for three hours and is stirred at room temperature over night. The solvent is evaporated, the residue is extracted with ethylacetate (120 ml) and is washed with saturated NaHCO$_3$. The organic layer is washed with water (100 ml), dried with MgSO$_4$, is filtered and is evaporated. Recrystallisation in ethylacetate gives the title compound (55%). $^1$H-NMR (CDCl$_3$, δ): 2.60 (s, 3H, CH3), 3.81 (s, 3H, OCH3), 6.86 (dd, 1H, aromatic H, J=2.1 Hz und 8.7 Hz), 7.02 (d, 1H, aromatic H, J=2.4 Hz), 7.43 (d, 1H, aromatic H, J=9 Hz). (R$_1$=H, R$_2$=methyl, R$_3$=OCH$_3$, n=1, y=0)

Example 2

2-Methyl-5-Fluoro-1-(3,4,5-Trimethoxybenzyl) Benzimidazole

A.) 4-Fluoro-2-nitrophenyl-N-acetamide

4-Fluoro-2-nitroaniline (50 mmole, 7.81 g) is added to a solution of pyridine (75 mmole, 6.0 ml) in dichloromethane (125 ml). The mixture is charged slowly with acetylchloride (50 mmole, 3.56 ml) in dichloromethane (40 ml) and is stirred for 48 hours. The reaction mixture is washed with 10% HCl and water, the organic layer is dried with Na$_2$SO$_4$, is filtered and is evaporated.

B.) 2-Methyl-5-fluorobenzimidazole

Iron (Fe) (176.75 mmole, 9.87 g) is added to a solution of 4-fluoro-2-nitrophenyl-N-acetamide (35.35 mmole, 7.5 g) in acetic acid (160 ml) and the mixture is refluxed for one hour and is stirred at room temperature over night. The solvent is evaporated. The residue is extracted with ethylacetate and is washed with saturated NaHCO$_3$. The organic layer is washed with water, dried with NaSO$_4$, is filtered and evaporated. Recrystallisation in ethylacetate gives the title compound (80.4%).

C.) 2-Methyl-5-fluoro-1-(3,4,5-trimethoxybenzyl) benzimidazole

Sodium hydride (18.31 mmole, 0.44 g, 60% in mineral oil) is added in small amounts under nitrogen to an ice cooled solution of 2-methyl-5-fluorobenzimidazole (16.64 mmole, 2.5 g) in dry DMA (9 ml). The mixture is stirred at the same temperature for 30 minutes. Trimethoxybenzyl chloride (18.31 mmole, 3.97 g) in DMA (4 ml) is added in several portions and the mixture is allowed to stir at room temperature over night. The reaction mixture is poured on to ice, the precipitate is collected and dissolved in dichloromethane. The organic solution is washed several times with water, is dried with Na$_2$SO$_4$, is filtered and is evaporated.

(R$_1$=3,4,5-trimethoxybenzyl, R$_2$=CH$_3$, R$_3$=F, n=1, y=0)

Example 3

1-(2-Bromobenzyl)-6-Ethoxycarbonyl-2-n-Propylbenzimidazole

A.) 3-[N-(2-Bromobenzyl)butyrylamino]-4-nitro-ethylbenzoate

In a nitrogen environment and at room temperature, sodium hydroxide (100 mg, 60% oil suspension) is added to an N,N-dimethylformamide (10 ml) solution of 3-butyrylamino-4-nitro-ethylbenzoate (247 mg) in a number of separate repetitions. The reaction suspension is stirred for 1 hour at the same temperature. The N,N-dimethylformamide (2 ml) solution of 2-bromobenzylbromide (244 mg) is gradually dripped over a 10 minute span. After the reaction mixture is stirred for 1 hour at room temperature, it is then poured into ice water. Precipitated oily material is extracted with methylene chloride. The organic solvent layer is washed with water, dried, and then concentrated under reduced pressure. The residue is developed through silica gel flush column chromatography, and extraction is performed using 25% ethyl acetate/n-hexane. Thus, yellow and oily 3-[N-(2-bromobenzyl)butyrylamino]-4-nitro-ethylbenzoate (540 mg) is obtained. $^1$H-NMR (CDCl$_3$): 0.87 (3H, t, J=8 Hz), 1.48 (3H, t, J=8 Hz), 1.68 (2H, sextet, J=8 Hz), 2.03 (2H, t, J=8 Hz), 4.30–4.46 (2H, m), 4.70 (1H, d, J=15 Hz), 5.40 (1H, d, J=15 Hz), 7.08–7.34 (2H, m), 7.43 (1H, dd, J=1, 8 Hz), 7.58 (1H, dd, J=1, 8 Hz), 7.66 (1H, d, J=1 Hz), 7.96 (1H, d, J=8 Hz), 8.16 (1H, dd, J=1,8 Hz).

B.) 1-(2-Bromobenzyl)-6-ethoxycarbonyl-2-n-propylbenzimidazole 9 3-[N-(2-bromobenzyl)butyrylamino]-4-nitro-ethylbenzoate (390 mg) and reduced iron (210 mg) are added to the mixture solution of acetic acid (1 ml) and ethanol (2 ml), then the suspension is refluxed for one hour while being stirred briskly. After the reaction, the reaction solution is cooled, separated through filtration using celite, and then the filtrate is concentrated through evaporation under reduced pressure. Ethyl acetate and sodium bicarbonate are added to the residue, and the mixture separated into layers. After the organic layer is dried, the solvent is removed through evaporation under reduced pressure, and a brown residue is obtained. The residue is purified through flush column chromatography, and yellow crystal of 1-(2-bromobenzyl)-6-ethoxycarbonyl-2-n-propylbenzimidazole (160 mg) is obtained. $^1$H-NMR (CDCl$_3$): 1.04 (3H, t, J=8 Hz), 1.40 (3H, t, J=8 Hz), 1.78–1.98 (2H, m), 2.34 (2H, t, J=8 Hz), 4.38 (2H, q, J=8 Hz), 5.45 (2H, s), 6.65 (1H, t, J=8 Hz), 7.00 (1H, t, J=8 Hz), 7.13 (1H, t, J=8 Hz), 7.28 (1H, t, J=8 Hz), 7.78 (1H, d, J=10 Hz), 7.99 (1H, d, J=10 Hz), 8.02 (1H, s).

mp=134–135° C. (R$_1$=2-bromobenzyl, R$_2$=2-n-propyl, R$_3$=ethoxycarbonyl, n=1, y=0)

Example 4

1-(2-Cyanobenzyl)-6-Ethoxycarbonyl-2-n-Propylbenzimidazole

A.) 3-[N-(2-Cyanobenzyl)butyrylamino]-4-nitro-ethylbenzoate

Potassium carbonate (296 mg) is added to an N,N-dimethylformamide solution of 3-butyrylamino-4-nitro-ethylbenzoate (200 mg) and 2-cyanobenzylbromide (154 mg), and the solution is stirred for 3 hours at 20° C. The reaction mixture is separated using ethyl acetate and water. After washing the organic layer with water and a saline solution, it is dried using magnesium sulfate. By removing the solvent through evaporation under reduced pressure, yellow and oily 3-[N-(2-cyanobenzyl)butyrylamino]-4-nitro-ethylbenzoate (330 mg) is obtained. $^1$H-NMR (CDCl$_3$): 0.86 (3H, t, J=8 Hz), 1.49 (3H, t, J=8 Hz), 1.67 (2H, sextet, J=8 Hz), 2.02 (2H, t, J=8 Hz), 4.28–4.52 (2H, m), 4.90 (1H, d, J=15 Hz), 5.28 (1H, d, J=15 Hz), 7.40 (1H, t, J=8 Hz), 7.61 (1H, dt, J=1, 8 Hz), 7.70 (1H, d, J=1 Hz), 7.74 (1H, dd, J=1, 8 Hz), 8.02 (1H, d, J=10 Hz), 8.22 (1H, dd, J=1, 10 Hz).

B.) 1-(2-Cyanobenzyl)-6-ethoxycarbonyl-2-n-propylbenzimidazole

Colorless crystals of 1-(2-cyanobenzyl)-6-ethoxycarbonyl-2-n-propylbenzimidazole (160 mg) are obtained from 3-[N-(2-cyanobenzyl) butyrylamnino]-4-nitro-ethylbenzoate (390 mg) by using the same method as described in Example 3.

$^1$H-NMR (CDCl$_3$): 1.04 (3H, t, J=8 Hz), 1.40 (3H, t, J=8 Hz), 1.88 (2H, sextet, J=8 Hz), 2.80 (2H, t, J=8 Hz), 4.38 (2H, q, J=8 Hz), 5.62 (2H, s), 6.57–6.63 (1H, m), 7.38–7.50 (2H, m), 7.78 (1H, dd, J=1, 8 Hz), 7.79 (1H, d, J=8 Hz), 7.94 (1H, d, J=1 Hz), 8.03 (1H, dd, J=1, 8 Hz).

mp=132–134° C. (R$_1$=2-cyanobenzyl, R$_2$=2-n-propyl, R$_3$=ethoxycarbonyl, n=1, y=0)

Example 5

6-Ethoxycarbonyl-1-(2-Fluorobenzyl)-2-n-Propylbenzimidazole

Colorless crystals of 6-ethoxycarbonyl-1-(2-fluorobenzyl)-2-n-propylbenzimidazole (160 mg) are obtained from 3-[N-(2-fluorobenzyl) butyrylamino]-4-nitro-ethylbenzoate (390 mg) by using the same method as described in example 3 (jap ex. 1). $^1$H-NMR (CDCl$_3$): 1.04 (3H, t, J=8 Hz), 1.40 (3H, t, J=8 Hz), 1.78–1.98 (2H, m), 2.34 (2H, t, J=8 Hz), 4.38 (2H, q, J=8 Hz), 5.45 (2H, s), 6.65 (1H, t, J=8 Hz), 7.00 (1H, t, J=8Hz), 7.13 (1H, t, J=8 Hz), 7.28 (1H, t, J=8 Hz), 7.78 (1H, d, J=10 Hz), 7.99 (1H, d, J=10 Hz), 8.02 (1H, s).

mp=134–135° C.
(R$_1$=2-fluorobenzyl, R$_2$=2-n-propyl, R$_3$=ethoxycarbonyl, n=1, y=0)

Example 6

6-Ethoxycarbonyl-1-(4-Fluorobenzyl)-2-n-Propylbenzimidazole

Colorless crystals of 6-ethoxycarbonyl-1-(4-fluorobenzyl)-2-n-propylbenzimidazole (160 mg) are obtained from 3-[N-(4-fluorobenzyl) butyrylamino]-4-nitro-ethylbenzoate (400 mg) by using the same method as described in example 3 (jap. Ex 1). $^1$H-NMR (CDCl$_3$): 1.04 (3H, t, J=8 Hz), 1.40 (3H, t, J=8 Hz), 1.88 (2H, sextet, J=8 Hz), 2.82 (2H, t, J=8 Hz), 4.38 (2H, q, J=8 Hz), 5.38 (2H, s), 7.00 (4H, d, J=7 Hz), 7.77 (1H, d, J=8 Hz), 7.98 (1H, d, J=1 Hz), 8.00 (1H, dd, J=1, 8 Hz).

mp=134–135° C.
(R$_1$=4-fluorobenzyl, R$_2$=2-n-propyl, R$_3$=ethoxycarbonyl, n=1, y=0)

The following examples 7 to 14 are synthesized by using the same method as described in Example 1.

Example 7

6-Ethoxycarbonyl-2-n-Propyl-1-(2-Pyridylmethyl) Benzimidazole $^1$H-NMR CDCl$_3$, δ): 1.03 (3H, t, J=7.5 Hz), 1.39 (3H, t, J=7.5 Hz), 1.89 (2H, m), 2.86 (2H, t, J=7.5 Hz), 4.38 (2H, q, J=7.5 Hz), 5.50 (2H, s), 6.72 (1H, d, J=7.5 Hz), 7.24 (1H, m), 7.58 (1H, dt, J=7.5, 1.5 Hz), 7.79 (1H, d, J=7.5 Hz), 7.96–8.02 (2H, m), 8.60 (1H, d, J=4 Hz).

mp=84–85° C.
(R$_1$=2-pyridylmethyl, R$_2$=2-n-propyl, R$_3$=ethoxycarbonyl, n=1, y=0)

Example 8

6-Ethoxycarbonyl-1-(3-Fluorobenzyl)-2-n-Propylbenzimidazolc $^1$H-NMR CDCl$_3$, δ): 1.04 (3H, t, J=7.5 Hz), 1.39 (3H, t, J=7.5 Hz), 1.90 (2H, m), 2.81 (2H, t, J=7.5 Hz), 4.39 (2H, q, J=7.5 Hz), 5.39 (2H, s), 6.70–6.84 (2H, m), 7.00 (1H, dt, J=8.5 and 1.5 Hz), 7.78 (1H, d, J=8.5 Hz), 7.96 (1H, s), 8.00 (1H, d, J=8.5 Hz).

mp=142–146° C.
(R$_1$=3-fluorobenzyl, R$_2$=2-n-propyl, R$_3$=ethoxycarbonyl, n=1, y=0)

Example 9

1-(2,6-Dichlorobenzyl)-6-Ethoxycarbonyl-2-n-Propylbenzimidazole $^1$H-NMR (CDCl$_3$, δ): 1.03 (3H, t, J=7.5 Hz), 1.38 (3H, t, J=7.5 Hz), 1.88 (2H, m), 2.93 (2H, t, J=7.5 Hz), 4.34 (2H, q, J=7.5 Hz), 5.61 (2H, s), 7.26 (1H, d, J=7.5 Hz), 7.39 (2H, d, J=7.5 Hz), 7.68 (1H, d, J=7.5 Hz), 7.84 (1H, d, J=1.5 Hz), 7.91 (2H, d, J=7.5 Hz).

mp=153–156° C.
(R$_1$=2,6-dichlorobenzyl, R$_2$=2-n-propyl, R$_3$=ethoxycarbonyl, n=1, y=0)

Example 10

1-(3-Methylbenzyl)-6-Ethoxycarbonyl-2-n-Propylbenzimidazole

Colorless solid $^1$H-NMR CDCl$_3$, δ): 1.02 (3H, t, J=7.5 Hz), 1.41 (3H, t, J=7.5 Hz), 1.89 (2H, m), 2.29 (3H, s), 2.82 (2H, t, J=7.5 Hz), 4.38 (2H, q, J=7.5 Hz), 5.35 (2H, s), 6.79–6.86 (2H, m), 7.09 (1H, d, J=7.5 Hz), 7.20 (1H, d, J=7.5 Hz), 7.76 (1H, d, J=7.5 Hz), 7.95–8.02 (2H, m).
(R$_1$=3-methylbenzyl, R$_2$=2-n-propyl, R$_3$=ethoxycarbonyl, n=1, y=0)

Example 11

2-Cyclopropyl-6-Ethoxycarbonyl-1-(2-Fluorobenzyl) Benzimidazole $^1$H-NMR (CDCl$_3$, δ): 1.10 (2H, m), 1.27 (2H, m), 1.40 (3H, t, J=7.5 Hz), 1.95 (1H, m), 4.37 (2H, q, J=7.5 Hz), 5.56 (2H, s), 6.77 (1H, t, J=7.5 Hz), 7.03 (1H, t,J=7.5 Hz), 7.13 (1H, t, J=7.5 Hz), 7.29 (1H, m), 7.69 (1H, d, J=7.5 Hz), 7.96 (1H, d, J=7.5 Hz), 8.02 (1H, d, J=2 Hz).

mp=122–126° C.
(R$_1$=2-fluorobenzyl, R$_2$=2-cyclopropyl, R$_3$=ethoxycarbonyl, n=1, y=0)

Example 12

1-(2-Chlorobenzyl)-6-Cyano-2-Cyclopropylbenzimidazole $^1$H-NMR (CDCl$_3$, δ): 1.04–1.24 (2H, m), 1.24–1.39 (2H, m), 1.83–2.01 (1H, m), 5.58 (2H, s), 6.54 (1H, d, J=9 Hz), 7.16 (1H, td, J=9, 2 Hz), 7.22–7.38 (1H, m), 7.43–7.56 (3H, mn), 7.74 (1H, dd, J=9, 2 Hz).

Mass (FAB): 308 (M+1)
IR (Nujol): 2210 cm$^{-1}$
(R$_1$=2-chlorobenzyl, R$_2$=2-cyclopropyl, R$_3$=cyano, n=1, y=0)

Example 13

1-(2-Chlorobenzyl)-2-Cyclobutyl-6-Ethoxycarbonylbenzimidazole $^1$H-NMR (CDCl$_3$, δ): 1.38 (3H, t, J=7.5 Hz), 1.90–2.21 (2H, m), 2.21–2.24 (2H, m), 2.46–2.70 (2H, m), 3.52–3.73 (1H, m), 4.37 (2H, q, J=7.5 Hz), 5.39 (2H, s), 6.34 (1H, dd, J=9, 2 Hz), 7.06 (1H, td, J=9, 2 Hz), 7.23 (1H, td, J=9, 2 Hz), 7.46 (1H, dd, J=9, 2 Hz), 7.83 (1H, d, J=9 Hz), 7.92 (1H, d, J=2Hz) 8.01 (1H, dd, J=9, 2 Hz).

mp=111–113° C.
(R$_1$=2-chlorobenzyl, R$_2$=2-cyclobutyl, R$_3$=ethoxycarbonyl, n=1, y=0)

Example 14

1-(2-Chlorobenzyl)-6-Ethoxycarbonyl-2-n-Pentylbenzimidazole $^1$H-NMR (CDCl$_3$, δ): 0.87 (3H, t, J=7.5 Hz), 1.22–1.47 (7H, m), 1.74–1.93 (2H, m), 2.80 (2H, t, J=7.5 Hz), 4.37 (2H, q, J=7.5 Hz), 5.47 (2H, s), 6.39 (1H, dd, J=9, 2 Hz), 7.08 (1H, td, J=9, 2Hz), 7.19–7.33 (1H, m), 7.48 (1H, dd, J=9, 2 Hz), 7.79 (1H, d, J=9 Hz), 7.94 (1H, d, J=2 Hz) 8.00 (1H, dd, J=9, 2 Hz).
(R$_1$=2-chlorobenzyl, R$_2$=2-n-pentyl, R$_3$=ethoxycarbonyl, n=1, y=0)

Example 15

5-Carboxyl-1-(2-Chlorobenzyl)-2-n-Propylbenzimidazole

Ethanol (20 ml) and 10% sodium hydroxide aqueous solution (10.4 g) are added to 1-(2-chlorobenzyl)-5-ethoxycarbonyl-2-n-propylbenzimidazole (2.8 g). The solution is then refluxed by heating for four hours. After cooling the reaction solution, the acidity of the solution is adjusted to pH 6 with 10% hydrochloric acid. Crystals are collected, washed with water, dried through by evaporation under reduced pressure, and colorless solids of 5-carboxyl-1-(2-chlorobenzyl)-2-n-propylbenzimidazole (2.46 g) are obtained. $^1$H-NMR (DMSO-d$_6$, δ): 0.93 (3H, t, J=7.5 Hz), 1.75 (2H, m), 2.79 (2H, t, J=7.5 Hz), 5.61 (2H, s), 6.49 (1H, d, J=7.5 Hz), 7.21 (1H, t, J=7.5 Hz), 7.33 (1H, t, J=7.5 Hz), 7.46 (1H, d, J=7.5 Hz), 7.56 (1H, d, J=7.5 Hz), 7.80 (1H, d, J=7.5 Hz) 8.20 (1H, s).
(R$_1$=2-chlorobenzyl, R$_2$=2-n-propyl, R$_3$=carboxyl, n=1, y=0)

The following examples 16 to 19 are synthesized by using the same method as described in Example 15.

Example 16

6-Carboxy-1-(3-Methylbenzyl)-2-n-Propylbenzimidazole

Colorless solid. $^1$H-NMR (DMSO-d$_6$, δ): 0.97 (3H, t, J=7.5 Hz), 1.78 (2H, m), 2.23 (3H, s), 3.86 (2H, q, J=7.5 Hz), 5.53 (2H. s), 6.80 (1H, d, J=7.5 Hz), 6.91 (1H, s), 7.07 (1H, d, J=7.5 Hz), 7.21 (1H, t, J=7.5 Hz), 7.65 (1H, d, J=7.5 Hz), 7.79 (1H, d, J=7.5 Hz), 8.04 (1H, s). (R$_1$=3-methylbenzyl, R$_2$=2-n-propyl, R$_3$=carboxyl, n=1, y=0)

Example 17

2-n-Butyl-7-Carboxy-1-(2-Chlorobenzyl) Benzimidazole $^1$H-NMR (DMSO-d$_6$, δ): 0.84 (3H, t, J=7.5 Hz), 1.34 (2H, m), 1.71 (2H, m), 2.80 (2H, t, J=7.5 Hz), 5.89 (2H. s), 6.03 (1H, d, J=7.5 Hz), 7.13 (1H, t, J=7.5 Hz), 7.27 (2H, t, J=7.5 Hz), 7.48 (1H, d, J=7.5 Hz), 7.63 (1H, d, J=7.5 Hz), 7.87 (1H, d, J=7.5 Hz).
(R$_1$=2-chlorobenzyl, R$_2$=2-n-butyl, R$_3$=carboxyl, n=1, y=0)

Example 18

6-Carboxy-2-Cyclopropyl-1-(2-Fluorobenzyl) Benzimidazole $^1$H-NMR (DMSO-d$_6$, δ): 1.04–1.19 (4H, m), 2.37 (1H, m), 5.79 (2H, s), 7.00 (1H, t, J=7.5 Hz), 7.15 (1H, t, J=7.5 Hz), 7.27 (1H, t, J=10.5 Hz), 7.37 (1H, m), 7.60 (1H, d, J=7.5 Hz), 7.82 (1H, d, J=7.5 Hz), 8.11 (1H, s).

mp: 224–229° C. (R$_1$=2-fluorobenzyl, R$_2$=-cyclopropyl, R$_3$=carboxyl, n=1, y=0)

Example 19

2-n-Butyl-6-Carboxy-1-(2-Fluorobenzyl) Benzimidazole $^1$H-NMR (DMSO-d$_6$, δ): 0.87 (3H, t, J=7.5 Hz), 1.26–1.48 (2H, m), 1.60–1.80 (2H, m), 2.90 (2H, t, J=7.5 Hz), 5.63 (2H. s), 6.89 (1H, td, J=9, 2 Hz), 7.13 (1H, td, J=9, 2 Hz), 7.20–7.44 (2H, m), 7.64 (1H, d, J=9 Hz), 7.80 (1H, dd, J=9, 2 Hz), d, J=2 Hz).

mp: 216–219° C. (R$_1$=2-fluorobenzyl, R$_2$=2-n-butyl, R$_3$=carboxyl, n=1, y=0)

Example 20

1-(2-Chlorobenzyl)-6-Chlorocarbonyl-2-Cyclopropylbenzimidazole Hydrochloride A suspension is prepared by adding 6-carboxy-1-(2-chlorobenzyl)-2-cyclopropylbenzimidazole (390 mg) to methylene chloride (10 ml) which includes N,N-dimethylformamide (one drop). Oxalyl chloride (0.208 ml) is dripped into the suspension over a period of a few minutes at room temperature. After stirring for two hours at the same temperature, the mixed material is concentrated under reduced pressure. Isopropyl ether is added to the residue, which is then turned into powder. Thus, white powder of 1-(2-chlorobenzyl)-6-chlorocarbonyl-2-cyclopropylbenzimidazole hydrochloride (450 mg) is obtained. Because this material is unstable, it is used as a source material for the next process without purification.
(R$_1$=2-chlorobenzyl, R$_2$=2-cyclopropyl, R$_3$=chlorocarbonyl, n=1, y=0)

Example 21

1-(2-Chlorobenzyl)-6-(4-Dimethylaminophenylmethylcarbamoyl)-2-n-Propylbenzimidazole 6-Carboxy-1-(2-chlorobenzyl)-2-n-propylbenzimidazole (400 mg) is dissolved in methylene chloride (3 ml) to which one drop of N,N-dimethylformamide has been added. Oxalyl chloride (0.208 ml) is added to this solution at 5 C. After the obtained solution is stirred for one hour at room temperature, the solution is concentrated under reduced pressure. The residue is dissolved in methylene chloride (3 ml), which is then added at room temperature to a mixture solution prepared by adding 4-dimethylaminobeintzylamine hydrochloride (271 mg) and triethylamine (1 ml) to methylene chloride (10 ml) . The obtained reaction mixture is stirred for one hour at the same temperature, washed with water, dried, and then concentrated under reduced pressure. The residue is developed and purified using thin film chromatography, and 1-(2-chlorobenzyl)-6-(4-dimethylamino-phenylmethylcarbamoyl)-2-n-propylbenzimidazole (215 mg) is obtained. (Colorless crystal). $^1$H-NMR CDCl$_3$): 1.01 (3H, t, J=7 Hz), 1.88 (2H, sextet, J=7 Hz), 2.76 (2H, t, J=7 Hz), 2.95 (6H, s), 4.50 (2H, d, J=5 Hz), 5.45 (2H, s), 6.32 (1H, d, J=5 Hz), 6.36 (1H, d, J=7 Hz), 6.72 (2H, d, J=10 Hz), 7.07 (1H, dt, J=1, 8 Hz), 7.20–7.25 (3H, m), 7.46 (1H, dd, J=1, 8 Hz), 7.58 (1H, dd, J=1, 8 Hz), 7.76 (1H, d, J=8 Hz), 7.82 (1H, d, J=1 Hz).

mp: 155–156° C. (R$_1$=2-chlorobenzyl, R$_2$=2-n-propyl, R$_3$=carbamoyl, R$_4$=4-dimethylamino-phenylmethyl, R$_5$=H, n=1, y=0).

Example 22

1-(2-Chlorobenzyl)-6-Morpholinocarbamoyl-2-n-Propylbenzimidazole

By using the same method of example 21, 1-(2-chlorobenzyl)-6-morpholinocarbamoyl-2-n-propylbenzimidazole (205 mg) is obtained from 6-carboxy-1-(2-chlorobenzyl)-2-n-propylbenzimidazole (200 mg) and 4-aminomoipholine (124 mg). (Colorless crystal). $^1$H-NMR (CDCl$_3$): 1.03 (3H, t, J=8 Hz), 1.88 (2H, sextet, J=8 Hz), 2.62 (4H, bs), 2.72 (2H, t, J=8 Hz), 3.85 (4H, bs), 5.42 (2H, s), 6.42 (1H, dd, J=1, 8 Hz), 7.08 (1H, dt, J=1, 8 Hz), 7.20–7.28 (3H, m), 7.47 (1H, dd, J=1, 8 Hz), 7.78 (1H, dd, J=1, 8 Hz).

mp: 195–197° C. ($R_1$=2-chlorobenzyl, $R_2$=2-n-propyl, $R_3$=—C(O)—NR$_4$R$_5$, $R_4$ and $R_5$=morpholino, n=1, y=0)

Example 23

1-(2-Chlorobenzyl)-2-n-Propyl-6-Thiomorpholinocarbonylbenzimidazole

By using the same method of example 21, 1-(2-chlorobenzyl)-2-n-propyl-6-thiomorpholinocarbonylbenzimidazole (160 mg) is obtained from 6-carboxy-1-(2-chlorobenzyl)-2-n-propylbenzimidazole (200 mg) and thiomorpholine (125 mg). (Colorless crystal). $^1$H-NMR (CDCl$_3$): 1.03 (3H, t, J=8 Hz), 1.88 (2H, sextet, J=8 Hz), 2.78 (2H, t, J=8 Hz), 2.96 (4H, bt, J=5 Hz), 3.88 (4H, bt, J=5 Hz), 5.46 (2H, s), 6.34 (1H, dd, J=1, 8 Hz), 7.08 (1H, dt, J=1, 8 Hz), 7.26 (2H, dt, J=1, 8 Hz), 7.47 (1H, dd, J=1, 8 Hz), 7.58 (1H, bd, J=1, 8 Hz), 7.76 (1H, s), 7.78 (1H, d, J=8 Hz).

mp: 160–162° C. ($R_1$=2-chlorobenzyl, $R_2$=2-n-propyl, $R_3$=carbamoyl, $R_4$ and $R_5$=thiomorpholino, n=1, y=0)

Example 24

2-n-Butyl-1-(2-Chlorobenzyl)-6-[(2-Pyridylmethyl) carbamoyll Benzimidazole

By using the same method of example 21, 2-n-butyl-1-(2-chlorobenzyl)-6-[(2-pyridylmethyl)carbamoyl]benzimidazole (230 mg) is obtained from 6-carboxy-2-n-butyl-1-(2-chlorobenzyl)benzimidazole (200 mg) and 2-aminomethyl-pyridine (126 mg). (Colorless crystal). $^1$H-NMR CDCl3,): 0.92 (3H, t, J=8 Hz), 1.42 (2H, sextet, J=8 Hz), 1.82 (2H, quintet, J=8 Hz), 2.82 (2H, t, J=8 Hz), 4.76 (1H, d, J=5 Hz), 5.46 (2H, s), 6.38 (1H, dd, J=1, 8 Hz), 7.08 (1H, dt, J=1, 8 Hz), 7.18–7.26 (2H, s), 7.32 (1H, d, J=8 Hz), 7.46 (1H, dd, J=1, 8 Hz), 7.62 (1H, dt, J=1, 8 Hz), 7.72 (1H, dt, J=1, 8 Hz), 7.82 (1H, d, J=8 Hz), 7.88 (1H, d, J=1 Hz), 8.56 (1H, dd, J=1, 8 Hz).

mp: 175–176° C. ($R_1$=2-chlorobenzyl, $R_2$=2-n-butyl, $R_3$=—C(O)NR$_4$R$_5$, $R_4$ =2-pyridylmethyl, $R_5$=H, n=1, y=0)

Example 25

2-n-Butyl-5-Carbamoyl-1-(2-Chlorobenzyl) Benzimidazole

By using the same method of example 21, 2-n-butyl-5-carbamoyl-1-(2-chlorobenzyl)benzimidazole (170 mg) is obtained from 2-n-butyl-1-(2-chlorobenzyl)-5-carboxybenzimidazole (100 mg). (Colorless crystal). $^1$H-NMR (DMSO-d6,): 0.84 (3H, t, J=8 Hz), 1.35 (2H, sextet, J=8 Hz), 1.68 (2H, quintet, J=8 Hz), 2.78 (2H, t, J=8 Hz), 5.58 (2H, s), 6.50 (1H, dd, J=1, 8 Hz), 7.25 (1H, dt, J=1, 8 Hz), 7.28 (1H, bs), 7.35 (1H, dt, J=1, 8 Hz), 7.42 (1H, d, J=10 Hz), 7.56 (1H, dd, J=1, 8 Hz), 7.74 (1H, dd, J=1, 10 Hz), 7.96 (1H, bs), 8.20 (1H, d, J=1 Hz).

mp: 195–198C.

($R_1$=2-chlorobenzyl, $R_2$=2-n-butyl, $R_3$=carbamoyl, n=1, y=0)

Example 26

1-(2-Chlorobenzyl)-2-Cyclopropyl-6-Morpholinocarbonylbenzimidazole 1-(2-Chlorobenzyl)-6-chlorocarbonyl-2-cyclopropylbenzimidazole hydrochloride (140 mg) is added at room temperature to a solution which has been prepared by adding morpholine (298 mg, a 30% methanol solution) to methylene chloride (10 ml) . After the reaction mixture is stirred for one hour at the same temperature, it is washed with water, dried and concentrated under reduced pressure. The residue is recrystallized using ether and thus, 1-(2-chlorobenzyl)-2-cyclopropyl-6-morpholino-carbonylbenzimidazole (20 mg) is obtained. (Colorless crystal). $^1$H-NMR (CDCl3,): 1.04–1.12 (2H, m), 1.25–1.32 (2H, m), 1.82–1.96 (1H, m), 3.68 (8H, bs), 5.56 (2H, s), 6.55 (1H, dd, J=1, 8 Hz), 7.13 (1H, dt, J=1, 8 Hz), 7.22–7.29 (2H, m), 7.30 (1H, d, J=1 Hz), 7.46 (1H, dd, J=1, 8 Hz), 7.77 (1H, d, J=8 Hz).

mp: 193–195° C. ($R_1$=2-chlorobenzyl, $R_2$=2-cyclopropyl, $R_3$=—C(O)NR$_4$R$_5$, $R_4$ and $R_5$ =morpholino, n=1, y=0)

Example 27

1-(2-Chlorobenzyl)-2-Cyclopropyl-6-[(2-Pyridylmethyl) Carbamoyl]Benzimidazole By using the same method of example 21, 1-(2-chlorobenzyl)-2-cyclopropyl-6-[(2-pyridylmethyl) carbamoyl]benzimidazole (95 mg) is obtained from 1-(2-chlorobenzyl)-6-chlorobarbonyl-2-cyclopropylbenzimidazole hydrochloride (150 mg) and 2-aminomethylpyridine (85 mg). (Colorless crystal). $^1$H-NMR (CDCl$_3$): 1.02–1.13 (2H, m), 1.24–1.32 (2H, m), 1.82–1.95 (1H, m), 4.76 (2H, d, J=5 Hz), 5.59 (2H, s), 7.11 (1H, dt, J=1, 8 Hz), 7.20–7.26 (2H, m), 7.34 (1H, d, J=8 Hz), 7.46 (1H, dd, J =1, 8 Hz), 7.60 (1H, t, J=5 Hz), 7.66 (1H, dd, J=1, 8 Hz), 7.73 (1H, s), 7.88 (1H, s).

mp: 134–135C.

($R_1$ =2-chlorobenzyl, $R_2$=2-cyclopropyl, $R_3$=—C(O)NR$_4$R$_5$, $R_4$=2-pyridylmethyl, $R_5$=H, n=1, y=0)

The following examples 28 to 45 are synthesized by using the same method as described in example 26.

Example 28

1-(2-Chlorobenzyl)-2-Cyclopropyl-6-(2-Pyridylcarbamoyl) Benzimidazole $^1$H-NMR (CDCl$_3$): 1.16 (2H, m), 1.32 (2H, m), 1.92 (1H, m), 5.61 (2H, s), 6.57 (1H, d, J=7.5 and 1.5 Hz), 7.15 (1H, dt, J=7.5 and 1.5 Hz), 7.22–7.31 (2H, m), 7.48 (1H, dd, J=7.5 and 1.5 Hz), 7.77 (11H, d, J=9 Hz), 8.05 (2H, m).

mp: 206–209° C. ($R_1$=2-chlorobenzyl, $R_2$=2-cyclopropyl, $R_3$=—C(O)NR$_4$R$_5$, $R_4$=2,-pyridyl, $R_5$=H, n=1, y=0)

Example 29

6-(2-Carboxy-1-Pyrrolidinocarbonyl)-1-(2-Chlorobenzyl)-2-n-Proplybenzimidazole $^1$H-NMR (DMSO-d$_6$): 0.92 (3H, t, J=7.5 Hz), 1.65–1.99 (5H, m), 2.25 (1H, m), 2.77 (2H, t, J=7.5 Hz), 3.50 (2H, m), 4.40 (1H, m), 5.52 (2H, s), 6.53 (1H, d, J=7.5 Hz), 7.21–7.71 (6H, m).

mp: 96° C. ($R_1$=2-chlorobenzyl, $R_2$=2-n-propyl, $R_3$=$R_3$=—C(O)$NR_4R_5$, $R_4$ and $R_5$=pyrrolidino, n=1, y=0)

Example 30

1-(2-Chlorobenzyl)-2-Cyclobutyl-6-[(2-Pyridylmethyl)carbamoyl]Benzimidazole $^1$H-NMR (CDCl$_3$): 1.90–2.21 (2H, m), 2.25–2.37 (2H, m), 2.40–2.65 (2H, m), 3.64 (1H, m), 4.76 (2H, d, J=5 Hz), 5.39 (2H, s), 6.33 (1H, d, J=7.5 Hz), 7.05 (1H, t, J=7.5 Hz), 7.16–7.26 (2H, m), 7.33 (1H, d, J=7.5 Hz), 7.46 (1H, d, J=7.5 Hz), 7.69–7.76 (3H, m), 7.73 (1H, d, J=7.5 Hz), 7.86 (1H, s), 8.55 (1H, d, J=5 Hz).

mp: 183–185 C.
($R_1$=2-chlorobenzyl, $R_2$=2-cyclobutyl, $R_3$=—C(O)$NR_4R_5$, $R_4$=2-pyridylmethyl, $R_5$=H, n=1, y=0)

Example 31

(1-(2-Chlorobenzyl)-2-n-Propyl-5-[(2-Pyridylmethyl)carbamoyl]Benzimidazole $^1$H-NMR CDCl$_3$): 1.03 (3H, t, J=7.5 Hz), 1.90 (2H, m), 2.80 (2H, t, J=7.5 Hz), 4.80 (2H, d, J=5 Hz), 5.44 (2H, s), 6.40 (1H, d, J=7.5 Hz), 7.09 (1H, t, J=7.5 Hz), 7.21– 7.27 (3H, m), 7.34 (1H, d, J=7.5 Hz), 7.47 (1H, d, J=7.5 Hz), 7.64–7.72 (2H, m), 7.83 (1H, dd, J=7.5 and 2 Hz), 8.30 (1H, d, J=2 Hz), 8.56 (1H, d, J=5 Hz).

mp: 115–116° C. ($R_1$=2-chlorobenzyl, $R_2$=2-n-propyl, $R_3$=—C(O)$NR_4R_5$, $R_4$=2-pyridylmethyl, $R_5$=H, n=1, y=0)

Example 32

1-(2-Chlorobenzyl)-6-[N-methyl-N-(2-Pyridylmethyl)carbamoyl]-2-n-Propylbenzimidazole $^1$H-NMR (DMSO-d$_6$): 1.03 (3H, t, J=7.5 Hz), 1.87 (2H, m), 2.79 (2H, t, J=7.5 Hz), 3.05 (3H, brs), 4.60 (1H, brs), 4.87 (1H, brs), 5.40 (2H, d, J=unknown), 6.38 (1H, d, J=unknown), 7.05 (1H, brs), 7.20 (3H, m), 7.35–7.49 (3H, m), 7.60–7.81 (2H, m), 8.54 (1H, brs).

mp: 99° C. ($R_1$=2-chlorobenzyl, $R_2$=2-n-propyl, $R_3$=—C(O)$NR_4R_5$, $R_4$=2-pyridylmethyl, $R_5$=methyl, n=1, y=0)

Example 33

1-(2-Chlorobenzyl)-6-Piperonylcarbamoyl-2-n-Propylbenzimidazole $^1$H-NMR (CDCl$_3$): 1.01 (3H, t, J=7.5 Hz), 1.88 (2H, m), 2.78 (2H, t, J=7.5 Hz), 4.54 (2H, d, J=5 Hz), 5.45 (2H, s), 5.95 (2H, s), 6.36 (1H, d, J=7.5 Hz), 6.44 (2H, d, J=5 Hz), 6.75–6.85 (3H, m), 7.08 (1H, t, J=7.5 Hz), 7.23 (1H, t, J=7.5 Hz), 7.45 (1H, d, J=7.5 Hz), 7.67 (1H, dd, J=7.5, 2 Hz), 7.78 (2H, d, J=7.5 Hz), 7.83 (1H, s).

mp: 131–134 C.
($R_1$=2-chlorobenzyl, $R_2$=2-n-propyl, $R_3$=—C(O)$NR_4R_5$, $R_4$=piperonyl, $R_5$=H, n=1, y=0)

Example 34

1-(2-Chlorobenzyl)-6-Phenylcarbamoyl-2-n-Propylbenzimidazole $^1$H-NMR (CDCl$_3$, δ): 1.03 (3H, t, J=7.5 Hz), 1.90 (2H, m), 2.81 (2H, t, J=7.5 Hz), 5.47 (2H, s), 6.40 (1H, d, J=7.5 Hz), 7.06–7.18 (2H, m), 7.26 (1H, t, J=7.5 Hz), 7.35 (2H, t, J=7.5 Hz), 7.48 (1H, d, J=7.5 Hz), 7.64 (2H, d, J=7.5 Hz), 7.72 (1H, dd, J=7.5 and 2 Hz), 7.85–7.95 (3H, m).

mp: 168° C.
($R_1$=2-chlorobenzyl, $R_2$=2-n-propyl, $R_3$=—C(O)$NR_4R_5$, $R_4$=phenyl, $R_5$=H, 0)

Example 35

1-(2-Chlorobenzyl)-2-n-Propyl-6-[(4-Pyridylmethyl)carbamoyl]Benzimidazole $^1$H-NMR (DMSO-d$_6$, δ): 0.93 (3H, t, J=7.5 Hz), 1.76 (2H, m), 2.78 (2H, t, J=7.5 Hz), 4.49 (2H, d, J=5 Hz), 6.42 (1H, d, J=7.5 Hz), 7.22 (1H, t, J=7.5 Hz), 7.27 (2H, d, J=7.5 Hz), 7.34 (1H, t, J=7.5 Hz), 7.57 (1H, d, J=7.5 Hz), 7.69 (1H, d, J=7.5 Hz), 7.80 (1H, d, J=7.5 Hz), 7.97 (1H, s), 8.48 (2H, t, J=7.5 Hz), 9.03 (1H, t, J=5 Hz).

mp: 170–173° C.
($R_1$=2-chlorobenzyl, $R_2$=2-n-propyl, $R_3$=—C(O)$NR_4R_5$, $R_4$=4-pynidylmethyl, $R_5$=H, n=1, y=0)

Example 36

1-(2-Chlorobenzyl)-2-n-Proply-6-[(3-Pyridylmethyl)carbamoyl]Benzimidazole $^1$H-NMR (DMSO-d$_6$): 0.95 (3H, t, J=7.5 Hz), 1.76 (2H, m), 2.80 (2H, t, J=7.5 Hz), 4.50 (2H, d, J=5 Hz), 5.60 (2H, s), 6.42 (1H, d, J=7.5 Hz), 7.23 (1H, t, J=7.5 Hz), 7.30–7.58 (2H, m), 7.57 (1H, d, J=7.5 Hz), 7.67–7.74 (2H, mn), 7.75 (1H, d, J=7.5 Hz), 7.97 (1H, s), 8.46 (1H, d, J=5 Hz), 8.56 (1H, s), 9.0 (1H, t, J=5 Hz).

mp: 193–195 C.
($R_1$=2-chlorobenzyl, $R_2$=2-n-propyl, $R_3$=—C(O)$NR_4R_5$, $R_4$=3-pyridylmethyl, $R_5$=H, n=1, y=0)

Example 37

1-(2-Chlorobenzyl)-6-[N-Methyl-N-(2-Pyridyl)carbamoyl]-2-n-Propylbenzimidazole $^1$H-NMR (DMSO-d$_6$, δ): 0.90 (3H, t, J=7.5 Hz), 1.70 (2H, m), 2.73 (2H, t, J=7.5 Hz), 3.40 (3H, s), 5.42 (2H, s), 6.23 (1H, d, J=7.5 Hz), 6.91 (1H, d, J=7.5 Hz), 6.98 (1H, m), 7.15–7.25 (3H, m), 7.36 (1H, t, J=7.5 Hz), 7.46–7.57 (3H, m), 8.23 (1H, m).

mp: 143–146° C.
($R_1$=2-chlorobenzyl, $R_2$=2-n-propyl, $R_3$=—C(O)$NR_4R_5$, $R_4$=2-pyridylmethyl, $R_5$=methyl, n=1, y=0)

Example 38

1-(2-Chlorobenzyl)-6-(Homopiperidinocarbonyl)-2-n-Propylbenzimidazole $^1$H-NMR (CDCl$_3$, δ): 1.03 (3H, t, J=7.5 Hz), 1.46–1.94 (10H, m), 2.80 (2H, t, J=7.5 Hz), 3.32 (2H, brs), 3.64 (2H, t, J=7.5 Hz), 5.41 (2H, s), 6.42 (1H, d, J=7.5 Hz), 7.07 (1H, t, J=7.5 Hz), 7.19–7.29 (3H, m), 7.45 (1H, t, J=7.5 Hz), 7.76 (1H, d, J=7.5 Hz).

mp: 136–137° C. ($R_1$=2-chlorobenzyl, $R_2$=2-n-propyl, $R_3$=—C(O)$NR_4R_5$, $R_4$ and=homopiperidyl, n=1, y=0)

Example 39

1-(3-Methylbenzyl)-2-n-Propyl-6-[(2-Pyridylmethyl)carbamoyl]Benzimidazole $^1$H-NMR (CDCl$_3$, δ): 1.02 (3H, t, J=7.5 Hz), 1.88 (2H, m), 2.26 (3H, s), 2.81 (2H, t, J=7.5 Hz), 4.76 (2H, d, J=5 Hz), 5.36 (2H, s), 6.78–6.84 (2H, m), 7.07 (1H, d, J=7.5 Hz), 7.13–7.22 (2H, m), 7.33 (1H, d, J=7.5 Hz), 7.57–7.72 (2H, m), 7.78 (1H, d, J=7.5 Hz), 7.94 (1H, s), 8.55 (1H, d, J=5 Hz).

mp: 129–131° C. ($R_1$=3-methylbenzyl, $R_2$=2-n-propyl, $R_3$=2-pyridylmethylcarbamoyl, n=1, y=0)

Example 40

2-n-Butyl-1-(2-Fluorobenzyl)-6-[N-Methyl-N-(2-Pyridylmethyl) Carbamoyl]Benzimidazole $^1$H-NMR (CDCl$_3$, δ): 0.92 (3H, t, J=7.5 Hz), 1.45 (2H, m), 1.83 (2H, m), 2.86 (2H, t, J=7.5 Hz), 3.06 (3H, brs), 4.61 (1H, brs), 4.86 (1H, brs), 5.37 (2H, brd), 6.62 (1H, brd), 6.97 (1H, brs), 7.07–7.85 (8H, m), 8.57 (1H, d, J=5 Hz).

mp: 97–100° C.

($R_1$=2-fluorobenzyl, $R_2$=2-n-propyl, $R_3$=—C(O)NR4R$_5$, $R_4$=2-pyridylmethyl, $R_5$=methyl, n=1, y=0)

Example 41

1-(2-Chlorobenzyl)-2-Ethyl-6-[(2-Pyridylmethyl) Carbamoyl]Benzimidazole $^1$H-NMR CDCl$_3$, δ): 1.43 (3H, t, J=7.5 Hz), 2.84 (2H, q, J=7.5 Hz), 4.76 (2H, d, J=5 Hz), 5.45 (2H, s), 6.37 (1H, d, J=7.5 Hz), 7.07 (1H, t, J=7.5 Hz), 7.19–7.28 (2H, m), 7.33 (1H, d, J=7.5 Hz), 7.45 (1H, dd, J=7.5 and 2 Hz), 7.62–7.75 (3H, m), 7.82 (1H, d, J=7.5 Hz), 7.89 (1H, d, J=2 Hz), 8.55 (1H, d, J=5 Hz).

mp: 167–168° C. ($R_1$=2-chlorobenzyl, $R_2$=ethyl, $R_3$=—C(O)NR$_4$R$_5$, $R_4$=2-pyridylmethyl, $R_5$=H, n=1, y=0)

Example 42

2-n-Butyl-1-(2-Chlorobenzyl)-7-[(2-Pyridylmethyl) Carbamoyl]Benzimidazole $^1$H-NMR CDCl$_3$, δ): 0.93 (3H, t, J=7.5 Hz), 1.42 (2H, m), 1.83 (2H, m), 2.81 (2H, t, J=7.5 Hz), 4.44 (2H, d, J=5 Hz), 5.70 (2H, s), 6.13 (1H, dd, J=7.5 and 2 Hz), 6.85–6.97 (3H, m), 7.12–7.28 (4H, m), 7.34 (1H, d, J=7.5 Hz), 7.62 (1H, dt, J=7.5 and 2 Hz), 7.88 (1H, d, J=7.5 Hz), 8.40 (1H, d, J=5 Hz).

mp: 112–114° C. ($R_1$=2-chlorobenzyl, $R_2$=2-n-butyl, $R_3$=—C(O)NR$_4$R$_5$, $R_4$=2-pyridylmethyl, $R_5$=H, n=1, y=0)

Example 43

2-Cyclopropyl-1-(2-Fluorobenzyl)-6-(Piperonylcarbamoyl) Benzimidazole $^1$H-NMR (DMSO-d$_6$, δ): 1.05 (4H, m), 2.27 (1H, m), 4.38 (2H, d, J=5 Hz), 5.71 (2H, s), 5.98 (2H, s), 6.73–6.91 (4H, m), 7.14 (1H, t, J=7.5 Hz), 7.27 (1H, t, J=7.5 Hz), 7.36 (1H, m), 7.55 (1H, d, J=7.5 Hz), 7.73 (1H, dd, J=7.5 and 2 Hz), 8.04 (1H, s), 8.87 (1H, t, J=5 Hz).

mp: 170–173° C.

($R_1$=2-fluorobenzyl, $R_2$=cyclopropyl, $R_3$=—C(O)NR$_4$R$_5$, $R_4$=piperonyl, $R_5$=H, n=1, y=0)

Example 44

2-[[1-(2-Chlorobenzyl)-2-ethylbenzimidazole-6-yl] carbonylaminomethyl]-Pyridine 1-Oxide $^1$H-NMR (CDCl$_3$, δ): 1.42 (3H, t, J=7.5 Hz), 2.82 (2H, q, J=7.5 Hz), 4.81 (2H, d, J=7.5 Hz), 5.43 (2H, s), 6.31 (1H, d, J=7.5 Hz), 7.06 (1H, t, J=7.5 Hz), 7.20–7.31 (3H, m), 7.44 (1H, d, J=7.5 Hz), 7.52 (1H, dd, J=7.5 and 2 Hz), 7.65 (1H, dd, J=7.5 and 2 Hz), 7.77–7.83 (2H, m), 7.96 (1H, t, J=7.5 Hz), 8.23 (1H, dd, J=7.5 and 2 Hz).

mp: 204–207° C. ($R_1$=2-chlorobenzyl, $R_2$=ethyl, $R_3$=—C(O)—NR$_4$R$_5$, $R_4$=pyridyl-oxide-2-methyl, $R_5$=H, n=1)

Example 45

2-n-Butyl-1-(2-Fluorobenzyl)-6-(2-Pyridylmethylcarbamoyl) Benzimidazole $^1$H-NMR (CDCl$_3$, δ): 0.92 (3H, t, J=7.5 Hz), 1.38–1.49 (2H, m), 1.77–1.88 (2H, m), 2.86 (2H, t, J=7.5 Hz), 4.78 (2H, d, J=5 Hz), 5.46 (2H, s), 6.67 (1H, J=9 Hz), 7.00 (1H, t, J=9 Hz), 7.13 (1H, t, J=9 Hz), 7.19–7.31 (2H, m), 7.33 (1H, d, J=9 Hz), 7.60 (1H, br peak), 7.65–7.74 (2H, m), 7.79 (1H, d, J=9 Hz), 7.97 (1H, d, J=2 Hz), 8.58 (1H, d, J=5 Hz).

mp: 154–155 ° C. ($R_1$=2-fluorobenzyl, $R_2$=n-butyl, $R_3$=—C(O)NR$_4$R$_5$, $R_4$=2-pyridylmethyl, $R_5$=H, n=1, y=0)

Example 46

1-(2-Chlorobenzyl)-6-Cyano-2-n-Propylbenzimidazole

Dichloromethane solution (1 molar, 0.14 ml) of titanium tetrachloride and triethylamine (0.36 ml) are added to a tetrahydrofuran solution (4 ml) of 6-carbamoyl-1-(2-chlorobenzyl)-2-n-propylbenzimidazole (200 mg) at 0 ° C., and the solution is stirred for two hours at 20° C. The reaction mixture is separated into layers using ethyl acetate and water. The organic layer is washed with water, dried and concentrated under reduced pressure. The residue is developed and purified using column chromatography with ethyl acetate/hexane (1/10~1/3). The material is re-crystallized using ethyl acetate/hexane and 1-(2-chlorobenzyl)-6-cyano-2-n-propylbenzimidazole (140 ing) is obtained. (Colorless crystal) $^1$H-NMR (CDCl$_3$, δ): 1.05 (3H, t, J=8 Hz), 1.90 (2H, sextet, J=8 Hz), 2.85 (2H, t, J=8 Hz), 5.45 (2H, s), 6.42, (1H, dd, J=1, 8 Hz), 7.15 (1H, dt, J=1, 8 Hz), 7.28 (1H, dt, J=1, 8Hz), 7.48 (1H, s), 7.50 (1H, d, J=10 Hz), 7.54 (1H, dd, J=1, 8 Hz), 7.85 (1H, d, J=10 Hz).

mp: 124–126 ° C. ($R_1$=2-Chlorobenzyl, $R_2$=n-propyl, $R_3$=cyano, n=1, y=0)

Example 47

1-(2-Chlorobenzyl)-6-Ethoxycarbonyl-2-Methylbenzimidazole

A.) 3-Acetylamino-4-nitro-ethylbenzoate

Acetyl chloride (9 ml) is added to a mixture of 3-amino-4-nitro-ethylbenzoate (18.4 g) and N,N-dimethylaniline (200 ml) under ice-chilled conditions, and the solution is stirred for 2 hours at room temperature. It is stirred for another 2 hours at 50° C. The reaction solution is poured into the cold 1N-hydrochloric acid, and then extraction is performed with ethyl acetate twice. After the organic layer is washed with 1N-hydrochloric acid, then with water, and dried, the solvent is removed through evaporation under reduced pressure. The residue is purified using silica gel column chromatography (eluate: ethyl acetate/hexane=1/10~1/4) and thus, 3-acetylamino-4-nitro-ethylbenzoate (19.6 g) is obtained. $^1$H-NMR (CDCl$_3$, δ): 1.42 (3H, t, J=7.1 Hz), 2.32 (3H, s), 4.43 (2H, q, J=7.1 Hz), 7.82 (1H, dd, J=1.8 and 8.7 Hz), 8.25 (1H, d, J=8.7 Hz), 9.35 (1H, d, J=1.8 Hz), 10.19 (1H, s).

B.) 3-[N-(2-Chlorobenzyl)acetylamino]-4-nitro-ethylbenzoate

60% sodium hydride (0.406 g) is added to an N,N-dimethylformamide (12 ml) solution of 3-acetylamino-4-nitro-ethylbenzoate (1.706 g) in an ice bath, and the solution is stirred for 40 minutes at room temperature. Then an N,N-dimethylformamide (10 ml) solution of 2-chlorobenzyl bromide (1.806 g) is added and the solution is stirred for three hours at room temperature. The reaction mixture is poured into cold 1N-hydrochloric acid, then extraction is performed using ethyl acetate twice. The organic layer is washed with 1N-hydrochloric acid, and then with water. After the solution is dried, the solvent is removed through evaporation under reduced pressure. The residue is purified using silica gel column chromatography (eluate: ethyl acetate/hexane=1/10~1/4), and oily 3-[N-(2-chlorobenzyl) acetylamino]-4-nitro-ethylbenzoate (2.08 g) is obtained. $^1$H-NMR (CDCl$_3$, δ): 1.38 (3H, t, J=7.1 Hz), 1.92 (3H, s), 4.28–4.45 (2H, m), 4.72 (1H, d, J=14.5 Hz), 5.34 (1H, d, J=14.5 Hz), 7.16–7.44 (4H, m), 7.69(1H, d, J=1.7 Hz), 7.94 (1H, d, J=8.4 Hz), 8.13 (1H, dd, J=1.7 and 8.4 Hz).

C.) 1-(2-Chlorobenzyl)-6-ethoxycarbonyl-2-methylbenzimidazole

Ethanol (20 ml), acetic acid (11 ml), and reduced iron (3.07 g) are added into 3-[N-(2-chlorobenzyl)acctylamino]-4-nitro-ethylbenzoate (2.07 g), and the solution is refluxed for four hours. Solid are separated through filtration, and washed with ethanol. After the filtrate is concentrated, a sodium bicarbonate aqueous solution is added to the residue, and extraction is performed with ethyl acetate. After it is dried, the solvent is removed through evaporation under reduced pressure. The residue is purified using silica gel column chromatography (eluate: hexane/ethyl acetate=100/0~70/30) and thus, 1-(2-chlorobenzyl)-6-ethoxycarbonyl-2-methylbenzimidazole (1.46 g) is obtained. $^1$H-NMR (CDCl$_3$, δ): 1.39 (3H, t, J=7.1 Hz), 2.57 (3H, s), 4.37 (2H, q, J=7.1 Hz,), 5.46 (2H, s), 6.41 (1H, d, J=7.8 Hz), 7.10 (1H, t, J=7.8 Hz), 7.25 (1H, t), 7.47 (1H, d, J=8.0 Hz), 7.75 (1H, d, J=8.4 Hz), 7.94 (1H, s), 8.00 (1H, dd, J=1.5 and 8.4 Hz). ($R_1$=2-Chlorobenzyl, $R_2$=methyl, $R_3$=ethoxycarbonyl, n=1, y=0)

Example 48

6-Ethoxycarbonyl-1-Methyl-2-n-Propylbenzimidazolc

By using the method of example 47, part A, a preliminarily purified material of 3-(N-methylbutyrylamino)-4-nitro-ethylbenzoate (1.00 g) is obtained from 3-butyrylamino-4-nitro-ethylbenzoate (1.00 g) and methyl iodide (0.843 g). Subsequently, by using the method of example 47, parts B and C, 6-ethoxycarbonyl-1-methyl-2-n-propylbenzimidazole (0.56 g) is obtained. $^1$H-NMR (CDCl$_3$, δ): 1.08 (3H, t, J=7.4 Hz), 1.43 (3H, t, J=7.0 Hz), 1.89–1.97 (2H, m), 2.89 (2H, t, J=7.7 Hz), 3.79 (3H, s), 4.38–4.44 (2H, m), 7.71 (1H, d, J=8.4 Hz), 7.96 (1H, dd, J=8.4 and 1.5 Hz,), 8.05 (1H, d, J=1.4 Hz).
($R_1$=methyl, $R_2$=n-propyl, $R_3$=ethoxycarbonyl, n=1, y=0)

Example 49

1-n-Butyl-6-Ethoxycarbonyl-2-n-Propylbenzimidazole

Under room temperature, an N,N-dimethylformamide (10 ml) solution of 3-butyrylamino-4-nitro-ethylbenzoate (1.86 g) is dripped into a slurry of 60% sodium hydride (0.428 g) and N,N-dimethylformamide (10 ml), and the solution is stirred for 30 minutes at room temperature. Then, an N,N-dimethylformamide (10 ml) solution of n-butyl iodide (1.97 g) is dripped into the solution and the solution is heated for 13 hours at 50° C. The reaction solution is poured into a mixture solution of diluted hydrochloric acid (70 g) and ethyl acetate (70 g) and extraction is performed. The obtained organic layer is washed with water (twice), dried, concentrated under reduced pressure, and a preliminarily purified material (2.59 g) of 3-(N-n-butylbutyrylamino)-4-nitro-ethylbenzoate is obtained. Subsequently, by using the method of example 47, 1-n-butyl-6-ethoxycarbonyl-2-n-propylbenzimidazole (0.81 g) is obtained. $^1$H-NMR (CDCl$_3$, δ): 0.98 (3H, t, J=7.4 Hz), 1.08 (3H, t, J=7.4 Hz), 1.43 (3H, t, J=7.1 Hz), 1.75–1.83 (2H, m), 1.91–1.98 (2H, m), 2.88 (2H, t, J=7.6 Hz), 4.15 (2H, t, J=7.5 Hz), 4.42 (2H, q, J=7.2 Hz), 7.73 (1H, d, J=8.4 Hz), 7.96 (1H, dd, J=8.5 and 1.5 Hz), 8.06 (1H, d, J=1.4 Hz).
($R_1$=n-butyl, $R_2$=n-propyl, $R_3$=ethoxycarbonyl, n=1, y=0)

Example 50

1-(3-Chlorobenzyl)-6-Ethoxycarbonyl-2-n-Propylbenzimidazole

By using the method of example 47, part A, a preliminarily purified material of 3-[N-(3-chlorobenzyl) butyrylamino]-4-nitro-ethylbenzoate isobtained from 3-butyrylamino-4-nitro-ethylbenzoate (1.86 g) and 3-chlorobenzyl bromide (1.64 g). Without purification, this material is changed to 1-(3-chlorobenzyl)-6-ethoxycarbonyl-2-n-propylbenzimidazole (0.57 g) by using the method of example 47, parts B and C. $^1$H-NMR CDCl$_3$, δ): 1.02 (3H, t, J=7.4 Hz), 1.39 (3H, t, J=7.1 Hz), 1.85–1.92 (2H, m), 2.80 (2H, t, J=7.5 Hz), 4.38 (2H, q, J=7.1 Hz), 5.37 (2H, s), 6.86 (1H, d, J=7.4 Hz), 7.04 (1H, s), 7.21–7.29 (2H, m), 7.77 (1H, d, J=8.4 Hz), 7.96 (1H, d, J=1.2 Hz), 7.99 (1H, dd, J=8.5 and 1.5 Hz).
($R_1$=3-chlorbenzyl, $R_2$=n-propyl, $R_3$=ethoxycarbonyl, n=1, y=0)

Example 51

1-Benzyl-6-Ethoxycarbonyl-2-n-Propylbenzimidazole

By using the method of example 47, part A, 3-[N-benzylbutyrylamino]-4-nitro-ethylbenzoate is obtained from 3-butyrylamino-4-nitro-ethylbenzoate (1.86 g) and benzyl bromide (1.36 g). Without purification, this material is changed to 1-benzyl-6-ethoxycarbonyl-2-n-propylbenzimidazole (0.97 g) by using the method of example 47, parts B and C.

$^1$H-NMR (CDCl$_3$, δ): 1.01 (3H, t, J=7.4 Hz), 1.39 (3H, t, J=7.1 Hz), 1.83–1.9 (2H, m), 2.81 (2H, t, J=7.5 Hz), 4.37 (2H, q, J=7.1 Hz), 5.40 (2H, s), 7.03 (1H, d, J=6.4 Hz), 7.28–7.33 (3H, m), 7.76 (1H, d, J=8.4 Hz), 7.98 (1H, dd, J=8.4 and 1.2 Hz), 8.00 (1H, s). ($R_1$=benzyl, $R_2$=n-propy ethoxycarbonyl, n=1, y=0)

Example 52

1-(4-Chlorobenzyl)-6-Ethoxycarbonyl-2-n-Propylbenzimidazole

By using the method of example 47, part A, 3-[N-(4-chlorobenzyl) butyrylamino]-4-nitro-ethylbenzoate is obtained from 3-butyrylamino-4-nitro-ethylbenzoate (1.86 g) and 4-chlorobenzyl bromide (1.64 g). Without purification, this material is changed to 1-(4-chlorobenzyl)-6-ethoxycarbonyl-2-n-propyl benzimidazole (1.06 g) by using the method of example 47, parts B and C. $^1$H-NMR (CDCl$_3$, δ): 1.02 (3H, t, J=7.4 Hz), 1.39 (3H1, t, J=7.1 Hz), 1.83–1.92 (2H, t, J=7.8 Hz), 4.38 (2H, q, J=7.5 Hz), 5.36 (2H, s), 6.96 (2H, d, J=8.2 Hz), 7.29 (2H, d, J=8.3 Hz), 7.76 (1H, d, J=8.4 Hz), 7.96 (111, d, J=1.2 Hz), 7.99 (1H, dd, J=8.3 and 1.2 Hz). ($R_1$=4-chlorbenzyl, $R_2$=n-propyl, $R_3$=ethoxycarbonyl, n=1, y=0)

Example 53

6-Ethoxycarbonyl-2-Methyl-1-[2-(Trifluoromethyl)benzyl]Benzimidazole

By using the method of example 47, parts B and C, 6-ethoxycarbonyl-2-methyl-1-[2-(trifluoromethyl)benzyl] benzimidazole (1.32 g) is obtained from 4-nitro-3-[N-[2-(trifluoromethyl)benzyl]acetylamino]ethylbenzoate (1.82 g). $^1$H-NMR (CDCl$_3$, δ): 1.38 (3H, t, J=7.1 Hz), 2.53 (3H, s), 4.37 (2H, q, J=7.1 Hz), 5.58 (2H, s), 6.47 (1H, d, J=7.1 Hz), 7.36 (1H, t, J=7.5 Hz), 7.41 (1H, t, J=7.5 Hz), 7.75–7.97 (2H, m), 7.94 (1H, d, J=1.0 Hz), 8.02 (1H, dd, J=1.6 and 8.6 Hz).

($R_1$=2-(trifluoromethyl)benzyl, $R_2$=methyl, $R_3$=ethoxycarbonyl, n=1, y=0)

Example 54

6-Ethoxycarbonyl-2-methyl-1-[4-(trifluoromethyl)benzyl]benzimidazole

By using the method of example 47, parts B and C, 6-ethoxycarbonyl-2-methyl-1-[4-(trifluoromethyl)benzyl] benzimidazole (1.22 g) is obtained from 4-nitro-3-[N-[4-(trifluoromethyl)benzyl]acetylamino]ethylbenzoate (1.52 g). $^1$H-NMR (CDCl$_3$, δ): 1.39 (3H, t, J=7.1 Hz), 2.58 (3H, s), 4.38 (2H, q, J=7.1 Hz), 5.44 (2H, s), 7.15 (2H, d, J=8.2 Hz), 7.59 (2H, d, J=8.2 Hz), 7.75 (1H, d, J=8.3 Hz), 7.97 (1H, s), 8.00 (1H, dd, J=1.5 and 8.5 Hz).

($R_1$=4-(trifluoromethyl)benzyl, $R_2$=methyl, $R_3$=ethoxycarbonyl, n=1, y=0)

Example 55

1-(3,4-Dichlorobenzyl)-6-Ethoxycarbonyl-2-Methylbenzimidazole

By using the method of example 47, part A, 3-[N-(3,4-dichlorobenzyl)acetylamino]-4-nitro-ethylbenzoate is obtained from 3-acctylamino-4-nitro-ethylbenzoate (1.50 g) and 3,4-dichlorobenzyl bromide (1.74 g). Without purification, this material is changed to 1-(3,4-dichlorobenzyl)-6-ethoxycarbonyl-2-methylbenzimidazole (0.76 g) by using the method of example 47, parts B and C. $^1$H-NMR (CDCl$_3$, δ): 1.40 (3H, t, J=7.1 Hz), 2.58 (3H, s), 4.39 (2H, q, J=7.2 Hz), 5.33 (2H, s), 6.84 (1H, dd, J=8.4 and 2.3 Hz), 7.16 (2H, d, J=2.0 Hz), 7.39 (1H, d, J=8.3 Hz), 7.74 (1H, d, J=8.4 Hz), 7.96 (1H, d, J=1.2 Hz), 8.00 (1H, dd, J=8.4 and 1.5 Hz).

($R_1$=3,4-dichlorobenzyl, $R_2$=methyl, $R_3$=ethoxycarbonyl, n=1, y=0)

Example 56

1-(Biphenyl-4-ylmethyl)-6-Ethoxycarbonyl-2-Methylbenzimidazole

By using the method of example 47, part A, a preliminarily purified material (1.44 g) of 3-[N-(biphenyl-4-ylmethyl)acetylamino]-4-nitro-ethylbenzoate is obtained from 3-acetylamino-4-nitro-ethylbenzoate (1.51 g) and 4-chloromethylbiphenyl (1.46 g). Then by using the method of example 47, parts B and C, 1-(biphenyl-4-ylmethyl)-6-ethoxycarbonyl-2-methylbenzimidazole (1.13 g) is obtained. $^1$H-NMR CDCl$_3$, δ): 1.39 (3H, t, J=7.1 Hz), 2.62 (3H, s), 4.38 (2H, q, J=7.1 Hz), 5.42 (2H, s), 7.11 (2H, d, J=8.2 Hz), 7.34 (1H, m), 7.42 (2H, m), 7.54 (4H, m), 7.74 (1H, d, J=8.4 Hz), 7.99 (1H, dd, J=1.5 and 8.4 Hz), 8.06 (1H, d, J=1.5 Hz).

($R_1$=biphenyl-4-ylmethyl, $R_2$=methyl, $R_3$=ethoxycarbonyl, n=1, y=0)

Example 57

6-Ethoxyvcarbonyl-2-Methyl-1-(2-Methylbenzyl)Benzimidazole

By using the method of example 47, part A, 3-[N-(2-methylbenzyl)acetylamino]-4-nitro-ethylbenzoate is obtained from 3-acetylamino-4-nitro-ethylbenzoate (1.50 g) and 2-methylbenzyl bromide (1.65 g). Without purification, this material is changed to 6-ethoxycarbonyl-2-methyl-1-(2-methylbenzyl) benzimidazole (0.81 g) by using the method of example 47, parts B and C. $^1$H-NMR (CDCl$_3$, δ): 1.38 (3H, t, J 7.2 Hz), 2.43 (3H, s), 2.54 (3H, s), 4.36 (2H, q, J=7.2 Hz), 5.33 (2H, s), 6.35 (1H, d, J=7.7 Hz), 7.03 (1H, t, J=8.2 Hz), 7.18–7.25 (2H, m), 7.75 (1H, d, J=8.5 Hz), 7.91 (1H, d, J=1.2 Hz), 7.98 (1H, dd, J=8.5 and 1.5 Hz).

($R_1$=2-methylbenzyl, $R_2$=methyl, $R_3$=ethoxycarbonyl, n=1, y=0)

Example 58

6-Ethoxycarbonyl-1-(2-Methoxybenzyl)-2-Methylbenzimidazole

By using the method of example 47, part A, a preliminarily purified material of 3-[N-(2-methoxybenzyl)acetylamino]-4-nitro-ethylbenzoate is obtained from 3-acetylamino-4-nitro-ethylbenzoate (1.16 g) and 2-methoxybenzyl chloride (1.44 g). Then by using the method of example 47, parts B and C, 6-ethoxycarbonyl-1-(2-methoxybenzyl)-2-methylbenzimidazole (1.18 g) is obtained. $^1$H-NMR (CDCl$_3$, δ): 1.39 (3H, t, J=7.2Hz), 2.60 (3H, s), 3.90 (3H, s), 4.37 (2H, q, 7.2 Hz), 5.36 (2H, s), 6.61 (1H, d, J=7.4 Hz), 6.82 (1H, t, J=7.5 Hz), 6.92 (1H, d, J=8.3 Hz), 7.27 (1H, m), 7.71 (1H, d, J=8.4 Hz), 7.96 (1H, dd, J=1.5 and 8.4 Hz), 8.03 (1H, d, J=1.3 Hz).

($R_1$=2-methoxybenzyl, $R_2$=methyl, $R_3$=ethoxycarbonyl, n=1, y=0)

Example 59

6-Ethoxycarbonyl-1-(4-Methoxybenzyl)-2-Methylbenzimidazole

By using the method of example 47, part A, a preliminarily purified material of 3-[N-(4-methoxybenzyl)acetylamino]-4-nitro-ethylbenzoate is obtained from 3-acetylamino-4-nitro-ethylbenzoate (1.60 g) and 4-methoxybenzyl chloride (1.49 g). Then by using the method of example 47, parts B and C, 6-ethoxycarbonyl-1-(4 -methoxybenzyl)-2-methylbenzimidazole (1.27 g) is obtained. $^1$H-NMR (CDCl$_3$, δ): 1.40 (3H, t, J=7.1H), 2.59 (3H, s), 3.77 (3H, s), 4.38 (2H, q, J=7.1 Hz), 5.31 (2H, s), 6.84 (2H, m), 7.00 (2H, m), 7.71 (1H, d, J=8.4 Hz), 7.97 (1H, dd, J=1.4 and 8.4 Hz), 8.03 (1H, d, J=1.3 Hz).

($R_1$=4-methoxybenzyl, $R_2$=methyl, $R_3$=ethoxycarbonyl, n=1, y=0)

Example 60

1-[2-(Benzenesulfonylmethyl)benzyl]-6-Ethoxycarbonyl-2-Methylbenzimidazole

By using the method of example 47, part A, 3-[N-[2-(benzenesulfonylmethyl)benzyl]acetylamino]-4-nitro-ethylbenzoate is obtained from 3-acetylamino-4-nitro-ethylbenzoate (1.00 g) and 2-(benzenesulfonylmethyl)benzyl bromide (1.93 g). Without purification, this material is changed to 1-[2-(benzene-sulfonylmethyl)benzyl]-6-ethoxycarbonyl-2-methylbenzimidazole (0.89 g) by using the method of example 47, parts B and C. $^1$H-NMR (CDCl$_3$, δ): 1.37 (3H, t, J=7.1 Hz), 2.57 (3H, s), 4.36 (2H, q, J=7.1 Hz), 4.50 (2H, s), 5.60 (2H, s), 6.38 (1H, d, J=6.7 Hz), 6.88 (1H, dd, J=1.5 and 7.3 Hz), 7.10–7.18 (2H, m), 7.57 (2H, t, J=7.6 Hz), 7.69–7.78 (2H, m), 7.79 (1H, dd, J=0.8 and 8.1 Hz), 7.92 (1H, d, J=1.2 Hz), 7.99 (1H, dd, J=1.5 and 8.4 Hz). ($R_1$=2-(benzenesulfonylmethyl)benzyl, $R_2$=methyl, $R_3$=ethoxycarbonyl, n=1, y=0)

Example 61

1-(2-Cyanobenzyl)-6-(2-Cyanobenzyloxycarbonyl)-2-Methylbenzimidazole

By using the method of example 47, parts B and C, 1-(2-cyanobenzyl)-6-(2-cyanobenzyloxycarbonyl)-2-methylbenzimidazole (1.75 g) is obtained from 3-[N-(2-cyanobenzyl)acetylamino]-4-nitro-benzoic acid 2-cyanobenzyl ester (3.33 g). $^1$H-NMR CDCl$_3$, δ): 2.60 (3H, s), 5.55 (2H, s), 5.60 (2H, s), 6.68 (1H, d, J=7.3 Hz), 7.41–7.48 (3H, m), 7.61 (2H, m), 7.72 (1H, d, J=7.6 Hz), 7.76(1H, d, J=7.6 Hz), 7.77 (1H, d, J=8.6 Hz), 8.02 (1H, s), 8.05 (1H, dd, J=8.4 and 1.5 Hz).
($R_1$=2-cyanobenzyl, $R_2$=methyl, $R_3$=2-cyanobenzyloxycarbonyl, n=1, y=0)

Example 62

1-(Biphenyl-2-ylmethyl)-6-Ethoxycarbonyl-2-Methylbenzimidazole

By using the method of example 47, part A, 3-[N-(biphenyl-2-ylmethyl)acetylamino]-4-nitro-ethylbenzoate is obtained from 3-acetylamino-4-nitro-ethylbenzoate (1.00 g) and 2-bromomethylbiphenyl (1.47 g). Without purification, this material is changed to 1-(biphenyl-2-ylmethyl)-6-ethoxycarbonyl-2-methylbenzimidazole (1.31 g) by using the method of example 47, parts B and C. $^1$H-NMR (CDCl$_3$, δ): 1.41 (3H, t, J=7.3 Hz), 2.39 (3H, s), 4.38 (2H, q, J=7.3 Hz), 5.27 (2H, s), 6.68 (1H, d, J=7.9 Hz), 7.21 (1H, dt, J=9.0 and 2.1 Hz), 7.32–7.39 (4H, m), 7.43 (1H, dd, J=7.3 and 1.9 Hz), 7.46–7.51 (2H, m), 7.68 (1H, d, J=8.4 Hz), 7.87 (1H, d, J=1.3 Hz), 7.95 (1H, dd, J=8.4 and 1.6 Hz).
($R_1$=biphenyl-2-ylmethyl, $R_2$=methyl, $R_3$=ethyoxycarbonyl, n=1, y=0)

Example 63

1-Benzyl-6-Ethoxycarbonyl-2-Methylbenzimidazole

By using the method of example 47, part A, 3-(N-benzylacetylamino)-4-nitro-ethylbenzoate is obtained from 3-acetylamino-4-nitro-ethylbenzoate (1.00 g) and benzyl bromide (1.02 g). Without purification, this material is changed to 1-benzyl-6-ethoxycarbonyl-2-methylbenzimidazole (108) (0.71 g) by using the method of example 47, parts B and C. $^1$H-NMR CDCl$_3$, δ):1.39 (3H, t, J=7.1 Hz), 2.58 (3H, s), 4.38 (2H, q, J=7.1 Hz), 5.38 (2H, s), 7.05 (2H, dd, J=8.3 and 1.8 Hz), 7.28–7.33 (3H, m), 7.72 (1H, d, J=8.4 Hz), 7.98 (1H, dd, J=8.4 and 1.5 Hz), 8.02 (1H, d, J=1.2 Hz).
($R_1$=benzyl, $R_2$=methyl, $R_3$=ethyoxycarbonyl, n=1, y=0)

Example 64

1-(4-t-Butylbenzyl)-6-Ethoxycarbonyl-2-Methylbenzimidazole

By using the method of example 47, part A, 3-[N-(4-t-butylbenzyl)acetylamino]-4-nitro-ethylbenzoate is obtained from 3-acetylamino-4-nitro-ethylbenzoate (1.00 g) and 4-t-butylbenzyl bromide (1.35 g). Without purification of this material, a preliminarily purified material (1.60 g) of 1-(4-t-butylbenzyl)-6-ethoxycarbonyl-2-methylbenzimidazole is obtained by using the method of example 47, parts B and C.
($R_1$=4-t-butylbenzyl, $R_2$=methyl, $R_3$=ethyoxycarbonyl, n=1, y=0)

Example 65

6-Ethoxycarbonyl-2-Methyl-1-(2-Naphthylmethyl)Benzimidazole

By using the method of example 47, part A, 3-[N-(2-naphthylmethyl)acetylamino]-4-nitro-ethylbenzoate is obtained from 3-acetylamino-4-nitro-ethylbenzoate (1.00 g) and 2-naphthylmethyl bromide (1.32 g). Without purification of this material, a preliminarily purified material (1.28 g) of 6-ethoxycarbonyl-2-methyl-1-(2-naphthylmethyl)benzimidazole is obtained by using the method of example 47, parts B and C.
($R_1$=2-naphthylmethyl, $R_2$=methyl, $R_3$=ethyoxycarbonyl, n=1, y=0)

Example 66

1-(Biphenyl-4-ylmethyl)-6-Ethoxycarbonyl-2-Ethylbenzimidazole

By using the method of example 47, part A, 3-[N-(biphenyl-4-ylmethyl)propionylamino]-4-nitro-ethylbenzoate is obtained from 4-nitro-3-propionylamino-ethylbenzoate (2.00 g) and 4-chloromethylbiphenyl (2.28 g). Without purification, this material is changed to 1-(biphenyl-4-ylmethyl)-6-ethoxycarbonyl-2-ethylbenzimidazole (2.07 g) by using the method of example 47, parts B and C. $^1$H-NMR (CDCl$_3$, δ): 1.39 (3H, t, J=7.2 Hz), 1.45 (3H, t, J=7.5 Hz), 2.90 (2H, q, J=7.5 Hz), 4.38 (2H, q, J=7.2 Hz), 5.43 (2H, s), 7.10 (2H, d, J=8.3 Hz), 7.33–7.36 (1H, m), 7.43 (2H, t, J=7.4 Hz), 7.51–7.56 (4H, m), 7.79 (1H, d, J=8.5 Hz), 7.80 (1H, dd, J=1.5 and 8.4 Hz), 8.05 (1H, d, J=1.3 Hz).
($R_1$=biphenyl-4-ylmethyl, $R_2$=ethyl, $R_3$=ethyoxycarbonyl, n=1, y=0)

Example 67

1-(2-Chlorobenzyl)-5-ethoxycarbonyl-2-methylbenzimidazole

By using the method of example 47, part A, 4-[N-(2-chlorobenzyl)acetylamino]-3-nitro-ethylbenzoate is obtained from 4-acetylamino-3-nitro-ethylbenzoate (3.15 g) and 2-chlorobenzyl bromide (3.85 g). Without purification, this material is changed to 1-(2-chlorobenzyl)-5-ethoxycarbonyl-2-methyl-benzimidazole (2.54 g) by using the method of example 47, parts B and C. $^1$H-NMR (CDCl$_3$, δ): 1.41 (3H, t, J=7.1 Hz), 2.59 (3H, s), 4.40 (2H, q, J=7.1 Hz), 5.43 (1H, s), 6.43 (1H, d, J=7.8 Hz), 7.10 (1H, t, J=7.5 Hz), 7.19 (1H, d, J=8.5 Hz), 7.25 (1H, m), 7.46 (1H, d, J=8.1 Hz), 7.95 (1H, dd, J=1.4 and 8.4 Hz), 8.47 (1H,s). ($R_1$=2-chloro-benzyl, $R_2$=methyl, $R_3$=ethyoxycarbonyl, n=1, y=0)

Example 68

1-(2,6-Dichlorobenzyl)-6-Ethoxycarbonyl-2-Methylbenzimidazole

By using the method of example 47, part A, 3-[N-(2,6-dichlorobenzyl)acetylamino]-4-nitro-ethylbenzoate is obtained from 3-acetylamino-4-nitro-ethylbenzoate (1.50 g)

and 2,6-dichlorobenzyl bromide (2.14 g). Without purification, this material is changed to 1-(2,6-dichlorobenzyl)-6-etboxycarbonyl-2-methylbenzimidazole (0.91 g) by using the method of example 47, parts B and C.
$^1$H-NMR CDCl$_3$, δ): 1.38 (3H, t, J=7.1 Hz), 2.64 (3H, s), 4.34 (2H, q, J=7.1 Hz), 5.61 (2H, s), 7.30 (1H, dd, J=7.6 and 8.5 Hz), 7.40 (2H, d, J=8.0 Hz), 7.66 (1H, d, J=8.4 Hz), 7.87 (1H, d, J=1.1 Hz), 7.91 (1H, dd, J=8.4 and 1.5 Hz). (R$_1$=2,6-dichlorobenzyl, R$_2$=methyl, R$_3$=ethyoxycarbonyl, n=1, y=0)

Example 69

6-Ethoxycarbonyl-2-n-Propyl-1-i-Propylbenzimidazole

A.) 4-Amino-3-(N-i-propylbutyrylamino)-ethylbenzoate

At room temperature, an N,N-dimethylfoimamide (10 ml) solution of 3-butyrylamino-4-nitro-ethylbenzoate (2.00 g) is dripped into a slurry of 60% sodium hydride (0.428 g) and N,N-dimethylformamide (10 ml), and the mixture is stirred for 30 minutes. Then, an N,N-dimethylformamide (10 ml) solution of isopropyl iodide (1.46 g) is dripped into the solution, and the solution is stirred for 5 days at 100° C. The reaction solution is poured into a mixture solution of diluted hydrochloric acid (80 g) and ethyl acetate (80 g), then separated into layers. The obtained organic layer is washed with water (50 g), and concentrated under reduced pressure. The residue is purified using silica gel column chromatography (eluate: hexane/ethyl acetate=4/1) and a preliminarily purified material (0.260 g) of 4-nitro-3-(N-i-propylbutyrylamino)-ethylbenzoate is obtained. Subsequently, under room temperature, ethanol (3 ml) and acetic acid (2 ml) are added to the 3-(N-i-propylbutyrylamino)-4-nitro-ethylbenzoate (0.260 g). Further, reduced iron (0.519 g) is added to the solution, and the solution is refluxed by heating for four hours. Using filter aid, solids are removed, and the filtrate is concentrated. Ethyl acetate (30 ml) and diluted hydrochloric acid (30 ml) are added to the residue, and the solution is separated into layers. Its organic layer is washed with water and concentrated under reduced pressure. The residue is purified using fractional thin film silica gel column chromatography (developing solvent: hexane/ethyl acetate=1/1), and 4-amino-3-(N-i-propyl-butyrylamino)ethylbenzoate (0.06 g) is obtained. $^1$H-NMR (CDCl$_3$, δ): 0.82 (3H, t, J=7.4 Hz), 1.01 (3H, d, J=6.9 Hz), 1.24 (3H, d, J=6.6 Hz), 1.38 (3H, t, J=7.0 Hz), 1.54–1.62 (2H, m), 1.87–2.04 (2H, m), 4.34 (2H, q, J=7.0 Hz), 4.45 (2H, s), 4.88–4.96 (1H, m), 6.78 (1H, d, J=8.4 Hz), 7.64 (1H, d, J=1.9 Hz), 7.87 (1H, dd, J=8.84 and 1.9 Hz).

B.) 6-Ethoxycarbonyl-2-n-propyl-1-i-propylbenzimidazole

Acetic acid (2 ml) is added to 4-amino-3-(N-i-propylbutyrylamino)-ethylbenzoate (0.06 g), and the solution is stirred for 14 hours at 90° C. The reaction solution is concentrated under reduced pressure, and 6-ethoxycarbonyl-2-n-propyl-1-i-propyl-benzimidazole (0.05 g) is obtained. $^1$H-NMR CDCl$_3$, δ): 1.07 (3H, t, J=7.4 Hz), 1.43 (3H, t, J=7.0 Hz), 1.69 (6H, d, J=6.9 Hz), 1.85–1.92 (2H, m), 2.91 (2H, t, J=7.7 Hz), 4.41 (2H, q, J=7.3 Hz), 4.67–4.76 (1H, m), 7.72 (1H, d, J=8.3 Hz), 7.94 (1H, dd, J=8.7 and 1.5 Hz), 8.25 (1H, d, J=1.2 Hz).
(R$_1$=isopropyl, R$_2$=n-propyl, R$_3$=ethyoxycarbonyl, n=1, y=0)

Example 70

1-(2,4-Dichlorobenzyl)-6-Ethoxycarbonyl-2-Methylbenzimidazole>

Under room temperature, an N,N-dimethylformamide (8 ml) solution of 3-acetylamido-4-nitro-ethylbenzoate (1.50 g) is dripped into the slurry of 60% sodium hydride (0.357 g) and N,N-dimethylformamide (8 ml), and the solution is stirred for 30 minutes. Next, an N,N-dimethylformamide (8 ml) solution of 2,4-dichlorobenzyl chloride (1.74 g) is dripped into the solution, and the solution is stirred for 30 minutes. The reaction solution is poured into the mixture solution of diluted hydrochloric acid (50 g) and ethyl acetate (60 g), and its layers are separated. Obtained organic layer is washed with water (50 g) twice. The organic layer is concentrated under reduced pressure, and preliminarily purified material of 3-[N-(2,4-dichlorobenzyl)acetylamino]-4-nitro-ethylbenzoate (3.5 g) is obtained. Without purification, this material is dissolved with ethanol (23 ml) and acetic acid (12 ml), then reduced iron (3.32 g) is added to the solution, and the solution is refluxed by heating for 6 hours. Using filter aid, the solids are removed, and the filtrate is concentrated under reduced pressure. Ethyl acetate (60 ml) and diluted hydrochloric acid (50 ml) are added to the obtained residue, and its layers are separated. The organic layer is washed with saturated sodium bicarbonate aqueous solution (50 g), then washed with water (50 g) twice, and concentrated under reduced pressure. The obtained residue is purified using silica gel column chromatography (eluate: hexane/ethyl acetate=4/1~1/1) and, 1-(2,4-dichlorobenzyl)-6-ethoxycarbonyl-2-methylbenzimidazole (0.94 g) is obtained. $^1$H-NMR(CDCl$_3$, δ): 1.40 (3H, t, J=7.1 Hz), 2.56 (3H, s), 4.38 (2H, q, J=7.1 Hz), 5.41 (2H, s), 6.34 (1H, d, J=8.4 Hz), 7.09 (1H, dd, J=8.4 and 2.0 Hz), 7.49 (1H, d, J=2.0 Hz), 7.75 (1H, d, J=8.4 Hz), 7.92 (1H, s), 8.00 (1H, dd, J=8.5 and 1.4 Hz)
(R$_1$=2,4-dichlorobenzyl, R$_2$=methyl, R$_3$=ethyoxycarbonyl, n=1, y=0)

Example 71

6-Carboxy-1-(4-Chlorobenzyl)-2-n-Propylbenzimidazole

10% sodium hydroxide aqueous solution (3.57 g), ethanol (5 ml) and water (3.57 g) are added to 1-(4-chlorobenzyl)-6-ethoxycarbonyl-2-n-propylbenzimidazole (1.06 g) (example 51), and the solution is refluxed by heating for 1 hour. The acidity of the reaction solution is adjusted to pH 6 with 10% hydrochloric acid. The solution is concentrated under reduced pressure, ethanol is added to its obtained residue, and the inorganic acid (MU KI ENN) is separated through filtration. The filtrate is concentrated under reduced pressure, and residue (0.80 g) is obtained. The residue is purified with silica gel column chromatography (eluate: ethyl acetate/methanol=4/1), and 6-carboxy-1-(4-chlorobenzyl)-2-n-propylbenzimidazole (0.63 g) is obtained. $^1$H-NMR (DMSO-d$_6$, δ): 0.96 (3H, t, J=7.3 Hz), 1.76–1.88 (2H, m), 3.10–3.23 (2H, m), 5.83 (2H, s), 7.27 (2H, d, J=8.4 Hz), 7.44 (2H, d, J=8.4 Hz), 7.89 (1H, d, J=8.4 Hz), 7.89 (1H, d, J=8.5 Hz), 8.28 (1H, s)
(R$_1$=4-chlorobenzyl, R$_2$=n-propyl, R$_3$=carboxyl, n=1, y=0)

Example 72

6-Carboxy1-Methyl-2-n-Propylbenzimidazole

By using the method of example 71, 6-carboxy-1-methyl-2-n-propylbenzimidazole (0.46 g) is obtained from 6-ethoxycarbonyl-1-methyl-2-n-propylcarbonylbenzimidazole (0.56 g). $^1$H-NMR (DMSO-d$_6$, δ): 1.00 (3H, t, J=7.3 Hz), 1.79–1.93 (2H, m), 3.06 (3H, t, J=7.4 Hz), 3.92 (3H, s), 7.76 (1H, d, J=8.4 Hz), 7.97 (1H, d, J=8.4 Hz), 8.31 (1H, s).
(R$_1$=methyl, R$_2$=n-propyl, R$_3$=carboxyl, n=1, y=0)

Example 73

6-Carboxy-2-n-Propyl-1-i-Propylbenzimidazole

By using the method of example 71, 6-carboxy-2-n-propyl-1-i-propylbenzimidazole (0.045 g) is obtained from 6-ethoxycarbonyl-2-n-propyl-1-i-propylbenzimidazole (0.045 g). $^1$H-NMR (CD$_3$OD, δ): 0.98 (3H, t, J=7.4 Hz), 1.61 (6H, d, J=6.9 Hz), 1.74–1.82 (2H, m), 2.89 (2H, t, J=7.5 Hz), 3.21–3.24 (2H, m), 4.78–4.83 (1H, m), 7.51 (1H, d, J=8.3 Hz), 7.84 (1H, dd, J=8.4 and 1.5 Hz), 8.26 (1H, s). (R$_1$=i-propyl, R$_2$=n-propyl, R$_3$=carboxyl, n=1, y=0)

Example 74

1-n-Butyl-6-Carboxy-2-n-Propylbenzimidazole

By using the method of example 71, 1-n-butyl-6-carboxy-2-n-propylbenzimidazole (0.60 g) is obtained from 1-n-butyl-6-ethoxycarbonyl-2-n-propylbenzimidazole (0.81 g). $^1$H-NMR (DMSO-d$_6$, δ): 1.02 (3H, t, J=7.3 Hz), 1.17 (3H, t, J=7.3 Hz), 1.33–1.41 (2H, m), 1.70–1.77 (2H, m), 1.85–1.93 (2H, m), 3.07 (2H, t, J=7.6 Hz), 4.42 (2H, t, J=7.4 Hz), 7.78 (1H, d, J=8.5 Hz), 7.99 (1H, dd, J=8.5 and 1.0 Hz), 8.35 (1H, s), 13.13 (1H, s).
(R$_1$=n-butyl, R$_2$=n-propyl, R$_3$=carboxyl, n=1, y=0)

Example 75

6-Carboxy-1-(2-Chlorobenzyl)-2-Methylbenzimidazole

Ethanol (80 ml) and 10% sodium hydroxide aqueous solution (37 g) are added to 1-(2-chlorobenzyl)-6-ethoxycarbonyl-2-methylbenzimidazole (10.0 g) (example 47), and the solution is refluxed for 4 hours. After the reaction solution is cooled, its acidity is adjusted to pH 6 with 10% hydrochloric acid. The sediment is gathered, washed with water, dried under reduced pressure, and thus, (8.30 g) is obtained.
(R$_1$=2-chlorobenzyl, R$_2$=methyl, R$_3$=carboxyl, n=1, y=0)

Example 76

6-Carboxy-1-(2,6-Dichlorobenzyl)-2-Methylbenzimidazole

By using the method of example 75, 6-carboxy-1-(2,6-dichlorobenzyl)-2-methylbenzimidazole (0.72 g) is obtained from 1-(2,6-dichlorobenzyl)-6-ethoxycarbonyl-2-methylbenzimidazole (0.90 g) (example 67). $^1$H-NMR (DMSO-d$_6$, δ): 2.60 (3H, s), 5.71 (2H, s), 7.46 (1H, t, J=7.9 Hz), 7.57 (3H, t, J=8.2 Hz), 7.73 (2H, m), 12.57 (1H, s).
(R$_1$=2,6-dichlorobenzyl, R$_2$=methyl, R$_3$=carboxyl, n=1, y=0)

Example 77

6-Carboxy-2-Methyl-1-[2-(Trifluoromethyl) Benzyl] Benzimidazole

By using the method of example 75, 6-carboxy-2-methyl-1-[2-(trifluoromethyl)benzyl]benzimidazole (0.98 g) is obtained from 6-ethoxycarbonyl-2-methyl-1-[2-(trifluoromethyl)benzyl]benzimidazole (1.17 g) (example 53). $^1$H-NMR (DMSO-d$_6$, δ): 2.49 (3H, s), 5.70 (2H, s), 6.46–6.51 (1H, mn), 7.51 (2H, m), 7.65 (1H, d, J=8.4 Hz), 7.81 (1H, dd, J=1.4 and 8.4 Hz), 7.82–7.87 (1H, mn), 7.91 (1H, s).
(R$_1$=2-(trifluoromethyl) benzyl, R$_2$=methyl, R$_3$=carboxyl, n=1, y=0)

Example 78

6-Carboxy-2-Methyl-1-[4-(Trifluoromethyl)Benzyl] Benzimidazole

By using the method of example 75, 6-carboxy-2-methyl-1-[4-(trifluoromethyl)benzyl]benzimidazole (1.07 g) is obtained from 6-ethoxycarbonyl-2-methyl-i-[4-(trifluoromethyl)benzyl]benzimidazole (1.22 g) (example 54).
$^1$H-NMR (DMSO-d$_6$, δ): 2.85 (3H, s), 5.92 (2H, s), 7.50 (2H, d, J=8.1 Hz), 7.74 (2H, d, J=8.1 Hz), 7.88 (1H, d, J=8.5 Hz), 8.07 (1H, d, J=8.5 Hz), 8.31 (1H, s), 13.3 (1H, br s).
(R$_1$=4-(trifluoromethyl) benzyl, R$_2$=methyl, R$_3$=carboxyl, n=1, y=0)

Example 79

6-Carboxy-1-(3,4-Dichlorobenzyl)-2-Methylbenzimidazole

By using the method of example 75, 6-carboxy-1-(3,4-dichlorobenzyl)-2-methylbenzimidazole (0.55 g) is obtained from 1-(3,4-dichlorobenzyl)-6-ethoxycarbonyl-2-methylbenzimidazole (0.76 g) (example 55). $^1$H-NMR (DMSO-d$_6$, δ): 2.56 (3H, s), 5.61 (2H, s), 6.98 (1H, dd, J=8.4 and 1.9 Hz), 7.46 (1H, d, J=1.9 Hz), 7.59 (1H, d, J=8.3 Hz), 7.63 (1H, d, J=8.4 Hz), 7.81 (1H, dd, J=8.4 and 1.4 Hz), 8.07 (1H, s), 12.76 (1H, s).
(R$_1$=3,4-dichlorobenzyl, R$_2$=methyl, R$_3$=carboxyl, n=1, y=0)

Example 80

1-Benzyl-6-Carboxy-2-n-Propylbenzimidazole

10% sodium hydroxide aqueous solution (3.61 g), ethanol (5 ml), and water (3 ml) are added to 1-benzyl-6-ethoxycarbonyl-2-n-propylbenzimidazole (0.97 g) (example 51), and the solution is refluxed by heating for one hour. The acidity of the reaction solution is adjusted to pH 6 with 10% hydrochloric acid. The solution is concentrated under reduced pressure, ethanol is added to the obtained residue, and the inorganic salt is separated through filtration. The filtrate is concentrated under reduced pressure, and 1-benzyl-6-carboxy-2-n-propylbenzimidazole (0.85 g) (example 80) is obtained. $^1$H-NMR (DMSO-d$_6$, δ): 0.94 (3H, t, J=7.4 Hz), 1.73–1.81 (2H, m), 2.85 (2H, t, J=7.3 Hz), 5.59 (2H, s), 7.07 (2H, dd, J=1.1 and 8.3 Hz), 7.27 (1H, t, J=7.3 Hz), 7.33 (2H, t, J=7.4 Hz), 7.65 (1H, d, J=8.4 Hz), 7.79 (1H, dd, J=1.5 and 8.4 Hz), 8.04 (1H, s).
(R$_1$=benzyl, R$_2$=n-propyl, R$_3$=carboxyl, n=1, y=0)

Example 81

6-Carboxy-1-(3-Chlorobenzyl)-2-n-Propylbenzimidazole

By using the method of example 80, 6-carboxy-1-(3-chlorobenzyl)-2-n-propylbenzimidazole (0.35 g) is obtained from 1-(3-chlorobenzyl)-6-ethoxycarbonyl-2-n-propylbenzimidazole (0.57 g) (example 50). $^1$H-NMR (DMSO-d$_6$, δ): 0.94 (3H, t, J=7.3 Hz), 1.70–1.79 (2H, m), 2.83 (2H, t, J=7.4 Hz), 5.59 (2H, s), 6.94 (1H, s), 7.15 (1H, s), 7.34 (2H, d, J=4.4 Hz), 7.59 (1H, d, J=8.4 Hz), 7.81 (1H, d, J=8.1 Hz), 8.02 (1H, s).
(R$_1$=3-chlorobenzyl, R$_2$=n-propyl, R$_3$=carboxyl, n=1, y=0)

Example 82

5-Ethoxycarbonyl-2-methylbenzimidazole

Reduced iron (6.64 g), ethanol (48 ml) and acetic acid (24 ml) are added to 3-acetylamino-4-nitro-ethylbenzoate (3.00 g), and the solution is refluxed by heating for 12 hours. Solid materials are removed using filter aid, and the filtrate is concentrated under reduced pressure. Ethanol (100 ml) and 35% hydrochloric acid (5.2 g) are added to the residue and the solution is refluxed by heating for five hours. The reaction solution is neutralized with sodium bicarbonate (6.3 g). The filtrate obtained through filtration is concentrated under reduced pressure. Ethyl acetate (70 ml) and water (70 ml) are added to the obtained residue, and the solution is separated. The organic layer is washed with water three times and extraction is performed on the aqueous layer using ethyl acetate three times. By concentrating the obtained organic layer under reduced pressure, 5-ethoxycarbonyl-2-methylbenzimidazole (1.53 g ) powder is obtained. $^1$H-NMR (CDCl$_3$, δ): 1.41 (3H, t, J=6.9 Hz), 2.67 (3H, s), 4.40 (2H, q, J=7.1 Hz), 7.55 (1H, d, J=8.4 Hz), 7.96 (1H, dd, J=8.4 and 1.5 Hz), 8.27 (1H, d, J=1.4 Hz).
($R_2$=methyl, $R_3$=ethoxycarbonyl, n=1, y=0)

Examples 83 and 84

6-Ethoxycarbonyl-2-Methyl-1-(2-Nitrobenzyl) Benzimidazole and 5-Ethoxycarbonyl-2-Methyl-1-(2-Nitrobenzyl) Benzimidazole N,N-dimethylformamide (15 ml), 2-nitrobenzyl bromide (1.59 g) and sodium bicarbonate (1.23 g) are added to 5-ethoxycarbonyl-2-methylbenzimidazole (1.00 g) and the solution is heated for one hour at 60° C. After adding ethyl acetate (70 ml) and water (70 ml) and separating the solution, the organic layer is washed with water three times and extraction is performed on the aqueous layer using ethyl acetate three times. By concentrating the obtained organic layer under reduced pressure, a mixture of 6-ethoxycarbonyl-2-methyl-1-(2-nitrobenzyl) benzimidazole and 5-ethoxycarbonyl-2-methyl-1-(2-nitrobenzyl)benzimidazole is obtained. Purification using medium pressure silica gel column chromatography (eluate: hexane/etlhyl acetate=1/4~0/100) produced 6-ethoxycarbonyl-2-methyl-1-(2-nitrobenzyl) benzimidazole (83) (0.614 g) and 5-ethoxycarbonyl-2-methyl-1-(2-nitrobenzyl)benzimidazole (84) (0.259 g). $^1$H-NMR CDCl$_3$, δ): 1.38 (3H, t, J=7.2 Hz), 2.56 (3H, s), 4.37 (2H, q, J=7.1 Hz), 5.84 (2H, s), 6.41 (1H, d, J=6.8 Hz), 7.44–7.53 (2H, m), 7.78 (1H, d, J=8.6 Hz), 7.88 (1H, s), 8.02 (1H, dd, J=8.3 and 1.5 Hz), 8.30 (1H, dd, J=7.9 and 1.5 Hz).
($R_1$=2-nitrobenzyl, $R_2$=methyl, $R_3$=ethoxycarbonyl, n=1, y=0)

Example 84: $^1$H-NMR CDCl$_3$, δ): 1.42 (3H, t, J=7.0 Hz), 2.56 (3H, s), 4.40 (2H, q, J=7.0 Hz), 5.80 (2H, s), 6.43 (1H, dd, J=7.6 and 1.0 Hz), 7.14 (1H, d, J=8.3 Hz), 7.45–7.53 (2H, m), 7.95 (1H, dd, J=8.4 and 1.5 Hz), 8.27 (1H, dd, J=8.0 and 1.7 Hz), 8.48 (1H, d, J=1.2 Hz).
($R_1$=2-nitrobenzyl, $R_2$=methyl, $R_3$=cthoxycarbonyl, n=1, y=0)

Example 85

6-Carboxy-2-Methyl-1-(2-Nitrobenzyl) Benzimidazole

By using the method of example 80, 6-carboxy-2-methyl-1-(2-nitrobenzyl)benzimidazole (0.35 g) is obtained from 6-ethoxycarbonyl-2-methyl-1-(2-nitrobenzyl) benzimidazole (0.61 g). $^1$H-NMR (DMSO-d$_6$, δ): 2.51 (3H, s), 5.96 (2H, s), 6.33 (1H, d, J=7.0 Hz), 7.55–7.62 (2H, m), 7.66 (1H, d, J=8.3 Hz), 7.81 (1H, d, J=8.4 Hz), 8.06 (1H, s), 8.24 (1H, d, J=7.0 Hz), 12.66 (1H, s).
($R_1$=2-nitrobenzyl, $R_2$=methyl, $R_3$=carboxyl, n=1, y=0)

Example 86

6-Carboxy-1-(2-Chlorobenzyl)-2-Methylbenzimidazole

Ethanol (15 ml) and 5% sodium hydroxide aqueous solution (10.6 g) are added to 1-(2-chlorobenzyl)-6-ethoxycarbonyl-2-methylbenzimidazole (1.456 g) (example 47), and the solution is refluxed for I hour. After the reaction solution is cooled, its acidity is adjusted to pH 6 with 10% hydrochloric acid. The sediment is gathered, washed with water, dried under reduced pressure, and thus, 6-carboxy-1-(2-chlorobenzyl)-2-methylbenzimidazole (0.645 g) is obtained.
($R_1$=2-chlorobenzyl, $R_2$=methyl, $R_3$=carboxyl, n=1, y=0)

Example 87

6-Carboxy-1-(2,4-Dichlorobenzyl)-2-Methylbenzimidazole

10% sodium hydroxide aqueous solution (3.10 g) and ethanol (10 ml) are added to 1-(2,4-dichlorobenzyl)-6-ethoxycarbonyl-2-methylbenzimidazole (0.94 g) (example 70), and the solution is refluxed by heating for 1 hour. Its acidity is adjusted to pH 6 with 10% hydrochloric acid. The precipitated crystals are separated through filtration, dried, and thus, 6-carboxy-1-(2,4-dichlorobenzyl)-2-methylbenzimidazole (0.68 g) is obtained. $^1$H-NMR (DMSO-d$_6$, δ): 2.52 (3H, s), 5.61 (2H, s), 6.54 (1H, d, J=8.4 Hz), 7.33 (1H, dd, J=8.4 and 2.1 Hz), 7.64 (1H, d, J=8.4 Hz), 7.74 (1H, d, J=2.1 Hz), 7.81 (1H, dd, J=8.4 and 1.5 Hz), 7.98 (1H, s), 12.72 (1H, s).
($R_1$=2,4-dichlorobenzyl, $R_2$=methyl, $R_3$=carboxyl, n=1, y=0)

Example 88

1-(Biphenyl-4-ylmethyl)-6-Carboxy-2-Methylbenzimidazole

By using the method of example 75, 1-(biphenyl-4-ylmethyl)-6-carboxy-2-methylbenzimidazole (0.83 g) is obtained from 1-(biphenyl-4-ylmethyl)-6-ethoxycarbonyl-2-methylbenzimidazole (1.10 g) (example 56). $^1$H-NMR (DMSO-d$_6$, δ): 2.53 (3H, s), 5.61 (2H, s), 7.18 (2H, d, J=8.2 Hz), 7.34 (1H, m), 7.43 (2H, m), 7.62 (5H, m), 7.79 (1H, dd, J=1.6 and 8.5 Hz), 8.09 (1H, d, J=1.0 Hz), 12.72 (1H, br s).
($R_1$=4-biphenyl, $R_2$=methyl, $R_3$=carboxyl, n=1, y=1)

Example 89

1-(4-t-Butylbenzyl)-6-Carboxy-2-Methylbenzimidazole

By using the method of example 75, 1-(4-t-butylbenzyl)-6-carboxy-2 -methylbenzimidazole (0.55 g) is obtained from 1-(4-t-butylbenzyl)-6-ethoxycarbonyl-2-methylbenzimidazole (1.34 g) (example 63). $^1$H-NMR (DMSO-d$_6$, δ): 1.22 (9H, s), 2.57 (3H, s), 5.52 (2H, s), 7.03 (2H, d, J=8.2 Hz), 7.35 (1H, d, J=8.3 Hz), 7.60 (1H, d, J=8.4 Hz), 7.78 (1H, dd, J=8.4 and 1.5 Hz), 8.06 (1H, s), 12.71 (1H, s).
($R_1$=4-t-butylbenzyl, $R_2$=methyl, $R_3$=carboxyl, n=1, y=0)

Example 90

6-Carboxy-2-Methyl-1-(2-Methylbenzyl) Benzimidazole

By using the method of example 75, 6-carboxy-2-methyl-1-(2-methylbenzyl)benzimidazole (0.49 g) is obtained from 6-ethoxycarbonyl-2-methyl-1-(2-methylbenzyl) benzimidazole (0.81 g) (example 57). $^1$H-NMR (DMSO-$d_6$, δ): 2.41 (3H, s), 2.48 (3H, s), 5.55 (2H, s), 6.14 (1H, d, J=7.6 Hz), 7.02 (1H, t, J=7.4 Hz), 7.17 (1H, t, J=7.3 Hz), 7.26 (1H, d, J=7.4 Hz), 7.65 (1H, d, J=8.4 Hz), 7.81 (1H, dd, J=8.4 and 1.4 Hz), 7.97 (1H, d, J=1.1 Hz), 12.71 (1H, s).
($R_1$=2-methylbenzyl, $R_2$=methyl, $R_3$=carboxyl, n=1, y=0)

Example 91

6-Carboxy-1-(2-Methoxybenzyl)-2-Methylbenzimidazole

By using the method of example 75, 6-carboxy-1-(2-methoxybenzyl)-2-methylbenzimidazole (1.00 g) is obtained from 6-ethoxycarbonyl-1-(2-methoxybenzyl)-2-methylbenzimidazole (1.63 g) (example 58). $^1$H-NMR (DMSO-$d_6$, δ): 2.55 (3H, s), 3.81 (3H, s), 5.42 (2H, s), 6.77 (1H, m), 6.85 (1H, m), 7.05 (1H, m), 7.28 (1H, m), 7.58 (1H, m), 7.76 (1H, m), 7.99 (1H, s), 12.65 (1H, br s).
($R_1$=2-methoxybenzyl, $R_2$=methyl, $R_3$=carboxyl, n=1, y=0)

Example 92

6-Carboxy-1-(4-Methoxybenzyl)-2-Methylbenzimidazole

By using the method of example 75, 6-carboxy-1-(4-methoxybenzyl)-2-methylbenzimidazole (0.99 g) is obtained from 6-ethoxycarbonyl- I -(4-methoxybenzyl)-2-methylbenzimidazole (1.27 g) (example 59). $^1$H-NMR (DMSO-$d_6$, δ): 2.86 (3H, s), 3.71 (3H, s), 5.69 (2H, s), 6.92 (2H, d, J=8.4 Hz), 7.27 (2H, d, J=8.4 Hz), 7,84 (1H, d, J=8.5 Hz), 8.04 (1H, d, J=8.5 Hz), 8.33 (1H, s), 13.25 (1H, br t).
($R_1$=4-methoxybenzyl, $R_2$=methyl, $R_3$=carboxyl, n=1, y=0)

Example 93

6-Carboxy-2-Methyl-1-[2-(Benzenesulifonylmethyl)Benzyl]Benzimidazole

By using the method of example 75, 6-carboxy-2-methyl-1-[2-(benzenesulfonylmethyl)benzyl]benzimidazole (0.74 g) is obtained from 6-ethoxycarbonyl-2-methyl-1-[2-(benzenesulfonylmethyl)benzyl]benzimidazole (0.89 g). $^1$H-NMR (DMSO-$d_6$, δ): 2.44 (3H, s), 4.99 (2H, s), 5.71 (2H, s), 6.08 (1H, d, J=6.5 Hz), 7.12–7.20 (3H, m), 7.64–7.70 (3H, m), 7.77–7.83 (2H, m), 7.89 (2H, s), 7.90 (1H, s), 12.71 (1H, s).
($R_1$=2-(benzenesulfonylmethyl)benzyl, $R_2$=methyl, $R_3$=carboxyl, n=1, y=0)

Example 94

6-Carboxy-1-(2-Cyanobenzyl)-2-Methylbenzimidazole

By using the method of example 75, 6-carboxy-1-(2-cyanobenzyl)-2-methylbenzimidazole (1.14 g) is obtained from 1-(2-cyanobenzyl)-6-(2-cyanobenzyloxycarbonyl)-2-methylbenzimidazole (2.04 g) (example 61). $^1$H-NMR (DMSO-$d_6$, δ): 2.54 (3H, s), 5.80 (2H, s), 6.78 (1H, d, J=7.8 Hz), 7.51 (1H, t, J=7.4 Hz), 7.61 (1H, dt, J=7.8 and 1.2 Hz), 7.64 (1H, d, J=8.4 Hz), 7.80 (1H, dd, J=8.4 and 1.5 Hz), 7.94 (1H, d, J=6.7 Hz), 8.00 (1H, d, J=1.1 Hz), 12.70 (1H, s).
($R_1$=2-cyanobenzyl, $R_2$=methyl, $R_3$=carboxyl, n=1, y=0)

Example 95

6-Carboxy-1-(Biphenyl-2-ylmethyl)-2-Methylbenzimidazole

By using the method of example 75, 6-carboxy-1-(biphenyl-2-ylmethyl)-2-methylbenzimidazole (1.07 g) is obtained from 1-(biphenyl-2-ylmethyl)-6-ethoxycarbonyl-2-methylbenzimidazole (1.31 g) (example 62). $^1$H-NMR (DMSO-$d_6$, δ): 2.32 (3H, s), 5.45 (2H, s), 6.61 (1H, d, J=7.7 Hz), 7.26 (1H, dt, J=7.7 and 1.4 Hz), 7.31 (1H, dd, J=7.5 and 1.3 Hz), 7.36 (1H, dt, J=7.5 and 0.7 Hz), 7.40–7.46 (1H, m), 7.46–7.52 (4H, m), 7.57 (1H, d, J=8.4 Hz), 7.76 (1H, dd, J=7.9 and 1.5 Hz), 7.86 (1H, d, J=1.2 Hz), 12.72 (1H, s).
($R_1$=2-biphenyl, $R_2$=methyl, $R_3$=carboxyl, n=1, y=1)

Example 96

1-Benzyl-6-Carboxy-2-Methylbenzimidazole

By using the method of example 75, 1-benzyl-6-carboxy-2-methylbenzimidazole (0.59 g) is obtained from 1-benzyl-6-ethoxycarbonyl-2-methylbenzimidazole (0.71 g) (example 63). $^1$H-NMR (DMSO-$d_6$, δ): 2.56 (3H, s), 5.57 (2H, s), 7.11 (1H, d, J=8.0 Hz), 7. 27 (1H, t, J=7.2 Hz), 7.32–7.35 (2H, m), 7.61 (1H, d, J=8.3 Hz), 7.79 (1H, dd, J=8.4 and 1.3 Hz), 8.06 (1H, s), 12.75 (1H, s).
($R_1$=benzyl, $R_2$=methyl, $R_3$=carboxyl, n=1, y=0)

Example 97

6-Carboxy-2-Methyl-1-(2-Naphthylmethyl)Benzimidazole

By using the method of example 75, 6-carboxy-2-methyl-1-(2-naphthylmethyl)benzimidazole (0.80 g) is obtained from 6-ethoxycarbonyl-2-methyl-1-(2-naphthylmethyl)benzimidazole (1.28 g) (example 65). $^1$H-NMR (DMSO-$d_6$, δ): 2.61 (3H, s), 5.74 (2H, s), 7.29 (1H, d, J=8.6 Hz), 7.46–7.52 (2H, m), 7.59 (1H, s), 7.63 (1H), d, J=8.3 Hz), 7.78–7.92 (4H, m), 8.09 (1H, s), 12.68 (1H, s).
($R_1$=2-naphthyl, $R_2$=methyl, $R_3$=carboxyl, n=1, y=1)

Example 98

1-(Biphenyl-4-ylmethyl)-6-Carboxy-2-Ethylbenzimidazole

By using the method of example 75, 1-(biphenyl-4-ylmethyl)-6-carboxy-2-ethylbenzimidazole (1.70 g) is obtained from 1-(biphenyl-4-ylmethyl)-6-ethoxycarbonyl-2-ethylbenzimidazole (2.07 g) (example 66). $^1$H-NMR (DMSO-$d_6$, δ): 1.32 (3H, t, J=7.4 Hz), 2.94 (2H, q, J=7.5 Hz), 5.63 (2H, s), 7.16 (2H, d, J=8.2 Hz), 7.34 (1H, t, J=7.4 Hz), 7.44 (2H, t, J=7.5 Hz), 7.60–7.78 (5H, m), 7.81 (1H, dd, J=1.4 and 8.4 Hz), 8.10 (1H, d, J=1.2 Hz), 12.73 (1H, s).
($R_1$=4-biphenyl, $R_2$=ethyl, $R_3$=carboxyl, n=1, y=1)

Example 99

5-Carboxy-1-(2-Chlorobenzyl)-2-Methylbenzimidazole

By using the method of example 75, 5-carboxy-1-(2-chlorobenzyl)-2-methylbenzimidazole (2.48 g) is obtained from 1-(2-chloro-benzyl)-5-ethoxycarbonyl-2-methylbenzimidazole (3.70 g) (example 67). $^1$H-NMR (DMSO-$d_6$, δ): 2.49 (3H, s), 5.57 (2H, s), 6.53 (1H, d, J=7.8 Hz), 7.22 (1H, d, J=7.6 Hz), 7.33 (1H, t, J=7.6 Hz), 7.44 (1H, d, J=8.4 Hz), 7.54 (1H, d, J=8.0 Hz), 7.77 (1H, dd, J=1.6 and 8.5 Hz), 8.16 (1H, d, J=1.3 Hz), 12.71 (1H, br s).
($R_1$=2-chlorobenzyl, $R_2$=methyl, $R_3$=carboxyl, n=1, y=0)

Example 100

5-Carboxy-2-methyl-1-(2-nitrobenzyl)benzimidazole

By using the method of example 75, 5-carboxy-2-methyl-1-(2-nitrobenzyl)benzimidazole (0.15 g) is obtained from 5-ethoxycarbonyl-2-methyl-1-(2-nitrobenzyl) benzimidazole (0.26 g)(example 84). $^1$H-NMR (DMSO-d$_6$, δ): 2.49 (3H, s), 5.91 (2H. s), 6.36 (1H, dd, J=7.2 and 1.8 Hz), 7.52 (1H, d, J=8.5 Hz), 7.55–7.62 (2H, m), 7.77 (1H, dd, J=8.5 and 1.5 Hz), 8.18 (1H, d, J=1.3 Hz), 8.24 (1H, dd, J=7.4 and 1.6 Hz), 12.69 (1H, s).
(R$_1$=2-nitrobenzyl, R$_2$=methyl, R$_3$=carboxyl, n=1, y=0)

Example 101

2-Benzyl-5-Carboxy-1-(2-Chlorobenzyl) Benzimidazole

A.) 3-Acetylamino-4-nitro-ethylbenzoate

Phenylacetyl chloride (3.74 g) is added to a mixture of 4-amino-3-nitro-ethylbenzoate (4.04 g) and N,N-dimethylaniline (200 ml) under ice-chilled conditions, and the solution is stirred for 2 hours at room temperature. It is stirred for another 2 hours at 50° C. The reaction solution is poured into the cold 1N-hydrochloric acid, and then extraction is performed with ethyl acetate twice. After the organic layer is washed with 1N-hydrochloric acid, then with water, and dried, the solvent is removed through evaporation under reduced pressure. The residue is purified using silica gel column chromatography (eluate: ethyl acetate/hexane=1/10~1/4) and thus 3-nitro-4-phenylacetylamino-ethylbenzoate (6.00 g) is obtained.

B.) 2-Benzyl-5-ethoxycarbonylbenzimidazole

A mixture of 3-nitro-4-phenylacetylamino-ethylbenzoate (3.60 g), ethanol (47 ml), acetic acid (23 ml) and iron (6.4 g) is refluxed by heating for four hours. Solids are separated through filtration and the filtrate is concentrated. Ethanol (50 ml) and 35% hydrochloric acid (5 g) are added to the residue and the solution is stirred for 40 hours as it is refluxed by heating. The solution is neutralized with sodium bicarbonate and chloroform extraction is performed. The organic layer is concentrated under reduced pressure and then purified using silica gel column chromatography. Thus, 2-benzyl-5-ethoxy-carbonylbenzimidazole (2.30 g) is obtained. $^1$H-NMR (CDCl$_3$, δ): 1.39 (3H, t, J =7.1Hz), 4.26 (2H, s), 4.37 (2H, q, J=7.1Hz), 7.22–7.36 (5H, m), 7.50 (1H, d, J=8.6Hz), 7.94 (1H, dd, J=1.5 and 8.6Hz), 8.23 (1H, d, J=1.3Hz).

C.) 2-Benzyl-1-(2-chlorobenzyl)-6-ethoxycarbonylbenzimidazole and 2-Benzyl-1-(2-chlorobenzyl)-5-ethoxycarbonylbenzimidazole By using the method of examples 83 and 84, 2-benzyl-1-(2-chlorobenzyl)-6-ethoxycarbonylbenzimidazole (1.06 g) and 2-benzyl-1-(2-chlorobenzyl)-5-ethoxycarbonylbenzimidazole (0.640 g) are obtained from 2-benzyl-5-ethoxycarbonylbenzimidazole (2.37 g) and 2-chlorobenzyl bromide (3.94 g). $^1$H-NMR (CDCl$_3$, δ): 1.83 (3H, t, J=7.1Hz), 4.23 (2H, s), 4.35 (2H, q, J=7.1Hz), 5.36 (2H, s), 6.23 (1H, d, J=7.8Hz), 6.97 (1H, d, J=7.6Hz), 7.11–7.45 (7H, m), 7.85 (1H, d, J=8.5Hz), 7.91 (1H, s), 8.02 (1H, dd, J=1.2 and 8.6Hz).

H-NMR (CDCl$_3$, δ): 1.41 (3H, t, J=7.1Hz), 4.25 (2H, s), 4.41 (2H, q, J=7.1Hz) 5.33 (2H, s), 6.22 (1H, d, J=6.9Hz), 6.97 (1H, t, J=7.6Hz), 7.12–7.28 (7H, m), 7.40 (1H, d, J=8.0Hz), 7.95 (1H, dd, J=1.6 and 8.6Hz), 8.60 (1H, d, J=1.4Hz).

D.) 2-Benzyl-5-carboxy-1-(2-chlorobenzyl)benzimidazole

By using the method of example 75, 2-benzyl-5-carboxy-1-(2-chlorobenzyl)benzimidazole (0.488 g) is obtained from 2-benzyl-1-(2-chlorobenzyl)-5-ethoxycarbonylbenzimidazole (0.635 g). $^1$H-NMR (DMSO-d$_6$, δ): 4.27 (2H, s), 5.57 (2H. s), 6.27 (1H, d, J=7.1Hz), 7.06 (1H, t), 7.10–7.29 (6H, m), 7.39 (1H, d, J=8.6Hz), 7.47 (1H, d, J=7.9Hz), 7.78 (1H, dd, J=1.4 and 8.6Hz), 8.21 (1H, d, J=1.2Hz), 12.71 (1H, br s).
(R$_1$=2-chlorobenzyl, R$_2$=benzyl, R$_3$=carboxyl, n=1, y=0)

Example 102

2-Benzyl-6-carboxy-1-(2-chlorobenzyl) benzimidazole

By using the method of example 75, 2-benzyl-6-carboxy-1-(2-chlorobenzyl)benzimidazole (0.780 g) is obtained from 2-benzyl-1-(2-chlorobenzyl)-6-ethoxycarbonylbenzimidazole (1.00 g) (example 101, part C). $^1$H-NMR (DMSO-d$_6$, δ): 4.29 (2H, s), 5.63 (2H. s), 6.28 (1H, d, J=7.8Hz), 7.07 (1H, t, J=7.6Hz), 7.15 (1H, m), 7.19–7.29 (5H, m), 7.49 (1H, d, J=7.4Hz), 7.70 (1H, d, J=8.4Hz), 7.81 (1H, d, J=8.4Hz), 7.91 (1H, s), 12.73 (1H, br s).
(R$_1$=2-chlorobenzyl, R$_2$=benzyl, R$_3$=carboxyl, n=1, y=0)

Example 103

5-Ethoxycarbonyl-2-Trifluoromethylbenzimidazole

To a methanol (100 ml) solution of 3-amino-4-nitro-ethylbenzoate (4.00 g), 5% palladium/carbon (0.50 g) is added, and the solution is stirred for 12 hours at 50° C. under a nitrogen environment. Solids are separated through filtration. Concentration of the filtrate produced 3,4-diamino-ethylbenzoate. Trifluoroacetic acid (20 ml) is added to this material, and the solution is stirred for two hours at 60° C. The reaction solution is concentrated and chloroform is added. Precipitated crystals are separated through filtration and dried. Thus, 5-ethoxycarbonyl-2-trifluoromethylbenzimidazole (4.46 g) (157) is obtained. $^1$H-NMR (DMSO-d$_6$, δ): 1.36 (3H, t, J=7.0Hz), 4.36 (2H, q, J=7.0Hz), 7.82 (1H, d, J=8.5Hz), 7.99 (1H, dd, J=1.5 and 8.7Hz), 8.33 (1H, s),
(R$_1$=H, R$_2$=trifluoromethyl, R$_3$=ethoxycarbonyl, n=1, y=0)

Examples 104 and 105

1-(Biphenyl-4-ylmethyl)-6-Ethoxycarbonyl-2-Trifluoromethylbenzimidazole and 1-(Biphenyl-4-ylmethyl)-5-Ethoxycarbonyl-2-Trifluoromethylbenzimidazole By using the method of examples 83 and 84, 1-(biphenyl-4-ylmethyl)-6-ethoxycarbonyl-2-trifluoromethylbenzimidazole (104) (0.69 g) and 1-(biphenyl-4-ylmethyl)-5-ethoxycarbonyl-2-triflutoromethylbenzimidazole (105) (0.38 g) are obtained from 5-ethoxycarbonyl-2-trifluoromethylbenzimidazole (2.00 g) and 4-bromomethylbiphenyl (10.08 g). $^1$H-NMR (CDCl$_3$, δ): 1.39 (3H, t), 4.38 (2H, q), 5.64 (2H, s), 7.18 (2H, d, J=8.2Hz), 7.34 (1H, t, J=7.4Hz), 7.42 (2H, t, J=7.4Hz), 7.52–7.57 (4H, m), 7.95 (1H, d, J=8.8Hz), 8.09 (2H, dd, J=1.4 and 8.8Hz), 8.14 (1H, d, J=1. I Hz).
(R$_1$=4-biphenyl, R$_2$=trifluoromethyl, R$_3$=ethoxycarbonyl, n=1, y=1)

Example 105: $^1$H-NMR (CDCl$_3$, δ): 1.40 (3H, t), 4.40 (2H, q), 5.59 (2H. s), 7.16 (2H, d, J=8.1Hz), 7.34 (2H, t, J=6.2Hz), 7.41 (2H, t, J=7.5Hz), 7.53 (4H, m), 8.08 (1H, dd, J =1.3 and 9.1Hz), 8.65 (1H, s).
(R$_1$=4-biphenyl, R$_2$=trifluoromethyl, R$_3$=ethoxycarbonyl, n=1, y=1)

Example 106

1-(Biphenyl-4-ylmethyl)-6-Carboxy-2-Trifluoromethylbenzimidazole

By using the method of example 75, 1-(biphenyl-4-ylmethyl)-6-carboxy-2-trifluoromethylbenzimidazole (0.483 g) is obtained from 1-(biphenyl-4-ylmethyl)-6-ethoxycarbonyl-2-trifluoromethylbenzimidazole (0.690 g) (example 104). $^1$H-NMR (DMSO-d$_6$, δ): 5.87 (2H, s), 7.18 (2H, d, J=8.2Hz), 7.35 (1H, t, J=7.4Hz), 7.44 (2H, t, J=7.5Hz), 7.60–7.67 (4H, m), 7.98 (2H, d, J=0.7Hz), 8.32 (1H, s), 13.15 (1H,
(R$_1$=4-biphenyl, R$_2$=trifluoromethyl, R$_3$=carboxyl, n=1, y=1)

Example 107

1-(Biphenyl-4-ylmethyl)-5-Carboxy-2-Trifluoromethylbenzimidazole

By using the method of example 75, 1-(biphenyl-4-ylmethyl)-5-carboxy-2-trifluoromethylbenzimidazole (0.270 g) is obtained from 1-(biphenyl-4-ylmethyl)-5-ethoxycarbonyl-2-trifluoromethylbenzimidazole (0.38 g) (example 105). $^1$H-NMR (DMSO-d$_6$, δ): 5.80 (2H, s), 7.19 (2H, d, J=6.3Hz), 7.35 (1H, t, J=7.2Hz), 7.43 (2H, t, J=7.3Hz), 7.82 (1H, d, J=8.7Hz), 8.04 (1H, d, J=8.7Hz), 8.45 (11H, s).
(R$_1$=4-biphenyl, R$_2$=trifluoromethyl, R$_3$=carboxyl, n=1, y=1)

Example 108

1-(2-Chlorobenzyl)-2-Methylbenzimidazole-6-Acetic Acid

To 1-(2-chlorobenzyl)-2-methylbenzimidazole-6-acetonitrile (0.500 g), 10% hydrochloric acid is added, and the solution is refluxed by heating for 15 hours. It is neutralized with a saturated sodium bicarbonate aqueous solution, and chloroform extraction is performed. The organic layer is concentrated and purified using silica gel column chromatography (eluate: chloroform/ethanol=9/1~4/1). Thus, 1-(2-chlorobenzyl)-2-methylbenzimidazole-6-acetic acid (0.170 g) is obtained. $^1$H-NMR (CDCl$_3$, δ): 2.42 (3H, s), 3.56 (2H, s), 5.15 (2H, s), 6.33 (1H, d), 6.96 (1H, t), 7.03 (1H, s), 7.13 (2H, m), 7.35 (1H, d, J=7.9Hz), 7.62 (1H, d), 8.90 (1H, bra s).
(R$_1$=2-chlorobenzyl, R$_2$=methyl, R$_3$=carboxymethyl, n=1, y=0)

Example 109

1-(2-Chlorobenzyl)-2-Methylbenzimidazole-6-Methyl Acrylate

Triphenylphosphoranyl-methyl acetate (4.49 g) is added to a 1,4-dioxane (50 ml) solution of 1-(2-chlorobenzyl)-6-formyl-2-methylbenzimidazole (2.73 g), and the solution is stirred for six hours as it is refluxed by heating. After the reaction solution is cooled, the solvent is removed through evaporation under reduced pressure and the residue is purified using silica gel chromatography (eluate: chloroform/methanol=9/1). Thus a preliminarily purified material of 1-(2-chlorobenzyl)-2-methylbenzimidazole-6methyl acrylate (7.43 g) is obtained. This preliminarily purified material is immediately used for the following reaction.
(R$_1$=2-chlorobenzyl, R$_2$=methyl, R$_3$=methoxycarbonyl-2-ethenyl, n=1, y=0)

Example 110

1-(2-Chlorobenzyl)-2-Methylbenzimidazole-6-Acrylic Acid

The above-mentioned (example 109) preliminarily purified material, 1-(2-chlorobenzyl)-2-methylbenzimidazole-6-methyl acrylate (3.29 g) is dissolved in ethanol (20 ml), 5% sodium hydroxide aqueous solution (10.1 g) is added, and the solution is refluxed for two hours. The reaction solution is neutralized with a hydrochloric acid aqueous solution, and a residue is obtained by concentrating the solvent under reduced pressure. The residue is purified using silica gel chromatography (eluate: chloroform/methanol =9/1~6/1), and thus, 1-(2-chlorobenzyl)-2-methylbenzimidazole-6-acrylic acid (1.10 g) is obtained. $^1$H-NMR (DMSO-d$_6$, δ): 2.56 (3H, s), 5.65 (2H, s), 6.54 (1H, d, J=15.9 Hz), 6.62 (1H, d, J=7.6 Hz), 7.25 (1H, t), 7.35 (1H, t), 7.56 (1H, d, J=8.1 Hz), 7.60–7.70 (3H, m), 7.99 (1H, s), 12.35 (1H, br s).
(R$_1$=2-chlorobenzyl, R$_2$=methyl, R$_3$=carboxyl-2-ethenyl, n=1, y=0)

Example 111

6-Benzenesulfonylcarbamoyl-1-(2-Chlorobenzyl)-2-Methylbenzimidazole

N,N'-carbonyldiimidazole (45.8 g) is added all at once to an N,N-dimethyl-formamide (950 ml) solution of 6-carboxy-1-(2-chlorobenzyl)-2-methylbenzimidazole (45.0 g) (example 75), and the solution is stirred for one hour at room temperature. Subsequently, benzenesulfonamide (47.1 g) and diazabicycloundecene (35.0 g) are added, and the solution is stirred for 70 hours at 100° C. The reaction solution is cooled and the solvent is removed through evaporation under reduced pressure. Water (300 ml) and methanol (200 ml) are added to the residue, and moreover, 35% hydrochloric acid is added to adjust the acidity of the solution to pH 5.5. Precipitated crystals are separated through filtration, washed with a mixture solution (200 ml) of methanol and water (1/1), dried and thus, 6-benzenesulfonylcarbamoyl-1-(2-chlorobenzyl)-2-methylbenzimidazole (38.4 g) is obtained. In addition, water is added to filtrates and crystals precipitated. The crystals are separated through filtration, washed with water, dried and thus, of the material (13.3 g) is obtained. Both sets of crystals are gathered and dissolved by adding acetone (3300 ml) and water (900 ml) and by heating. The solvent is removed through evaporation as this solution is heated. Then the solution is cooled. Precipitated crystals are separated through filtration, dried, and thus, of 6-benzenesulfonylcarbamoyl-1-(2-chlorobenzyl)-2-methylbenzimidazole (33.8 g) is obtained. $^1$H-NMR (DMSO-d6δ): 2.53 (3H, s), 5.46 (2H, s), 6.34 (1H, d, J=7.8 Hz), 7.11 (1H, m), 7.27 (1H, m), 7.48 (1H, m), 7.52 (2H, m), 7.60 (1H, m), 7.69 (1H, d, J=8.6Hz), 7.90 (1H, m), 8.09 (2H, m), 8.11 (1H, s), 11.84 (1H, br s).
IR(KBr): 1684, 1448 cm$^{-1}$.
Mass(FAB): m/e 440(M+1).
mp: 273.5–274.3° C.
(R$_1$=2-chlorobenzyl, R$_2$=methyl, R$_3$=—C(O)NR$_4$R$_5$, R$_4$=SO$_2$R$_6$, R$_5$=H, R$_6$=phenyl, n=1, y=0)

Example 112

6-Benzenesulfonylcarbamoyl-1-(Biphenyl-4-ylmethyl)-2-Methylbenzimidazole

By using the method of example 111, 6-benzenesulfonyl-carbamoyl-1-(biphenyl-4-ylmethyl)-2-methylbenzimidazole (0.473 g) is obtained from 1-(biphenyl-4-ylmethyl)-2-ethyl-6-carboxybenzimidazole (0.600 g), N,N'-carbonyldiimidazole (0.546 g), benzene-sulfonamide (0.529 g) and diazabicycloundecene (0.512 g).
$^1$H-NMR (DMSO-d6, δ): 1.29 (3H, t, J=7.4 Hz), 2.88 (2H, q, J=7.4 Hz), 5.59 (2H, s), 7.16 (2H, d, J=8.2 Hz), 7.33–7.37 (1H, m), 7.44 (2H, t, J=7.5 Hz), 7.59–7.71 (8H, m), 7.74 (1H, dd, J=8.4 and 1.4 Hz), 7.98–8.02 (2H, m), 8.21 (1H, s), 12.43 (1H, br s).

IR(KBr): 1684cm$^{-1}$.

mp: 149.5–157.0° C.

($R_1$=4-biphenyl, $R_2$=methyl, $R_3$=—C(O)NR$_4$R$_5$, $R_4$=SO$_2$R$_6$, $R_5$=H, $R_6$=phenyl, n=1, y =1)

Example 113

5-Benzenesulfonylcarbamoyl-1-(2-Chlorobenzyl)-2-Methylbenzimidazole

By using the method of example 111, 5-benzenesulfonyl-carbamoyl-1-(2-chlorobenzyl)-2-methylbenzimidazole (0.480 g) is obtained from 5-carboxy-1-(2-chlorobenzyl)-2-methylbenzimidazole (0.450 g) (example 99), N,N'-carbonyl-diimidazole (0.485 g), benzenesulfonamide (0.470 g) and diazabicycloundccene (0.456 g). $^1$H-NMR (DMSO-d6, δ): 2.53 (3H,s), 5.61 (2H, s), 6.57 (1H, d, J=7.4 Hz), 7.22 (1H, t), 7.33 (1H, t), 7.50 (1H, d, J=8.6 Hz), 7.54 (11H, dd, J=7.9 and 0.9 Hz), 7.63 (2h, t), 7.71 (2H, m), 8.00 (2H, d, J=7.3 Hz), 8.21 (1H, d, J=1.4 Hz), 12.50 (1H, br,s).

IR(KBr): 1685 cm$^{-1}$.

mp: 137.0–138.5° C.

($R_1$=2-chlorobenzyl, $R_2$=methyl, $R_3$=—C(O)NR$_4$R$_5$, $R_4$=SO$_2$R$_6$, $R_5$=phenyl, n=1, y=0)

Example 114

5-(4-Chlorobenzenesulfonylcarbamoyl)-1-(2-Chlorobenzyl)-2-Methylbenzimidazole

By using the method of example 111, 5-(4-benzenesulfonyl-carbamoyl)-1-(2-chlorobenzyl)-2-methylbenzimidazole (0.520 g) is obtained from 5-carboxy-1-(2-chlorobenzyl)-2-methylbenzimidazole (0.450 g) (example 99, N,N'-carbonyldiimidazole (0.485 g), 4-chlorobenzenesulforamide (0.573 g) and diazabicycloun-decene (0.456 g). $^1$H-NMR (DMSO-d6, δ): 2.49 (3H, s), 5.58 (2H, s), 6.51 (1H, d, J=7.6 Hz), 7.21 (1H, t), 7.32 (1H, t), 7.45 (1H, d, J=8.6 Hz), 7.53 (1H, d, J=7.8 Hz), 7.69 (3H, d, J=8.6 Hz), 7.99 (2H, d, J=8.6 Hz), 8.18 (1H, s), 12.58 (1H, br s).

IR(KBr): 1619 cm$^{-1}$.

mp: 261.5–263.0° C.

($R_1$=2-chlorobenzyl, $R_2$=methyl, $R_3$=—C(O)NR$_4$R$_5$, $R_4$=SO$_2$R$_6$, $R_5$=H, $R_6$=4-chlorophenyl, n=1, y=0)

Example 115

1-(2-Chlorobenzyl)-2-Methyl-5-(2-Naphthalenesulfonylcarbamoyl)Benzimidazole

By using the method of example 111, 1-(2-chlorobenzyl)-2-methyl-5-(2-naphthalenesulfonylcarbaamoyl) benzimidazole (0.352 g) is obtained from 5-carboxy-1-(2-chlorobenzyl)-2-methylbenzimidazole (0.450 g) (example 99), N,N'-carbonyldiimidazole (0.485 g), 2-naphthalenesulfonamide (0.620 g) and diazabicyclo-undecene (0.456 g). $^1$H-NMR (DMSO-d6, δ): 2.48 (3H, s), 5.56 (2H, s), 6.49 (1H, d, J=7.7 Hz), 7.20 (1H, t, J=7.6 Hz), 7.31 (1H, t, J=7.7 Hz), 7.44 (1H, d, J=8.6Hz), 7.52 (1H, d, J=8.0 Hz), 7.66–7.75 (3H, m), 7.97 (1H, d, J=8.8 Hz), 8.04 (1H, d, J=8.0 Hz), 8.14 (1H, d, J=8.8 Hz), 8.19 (1H, s), 8.23 (1H, d, J=8.0 Hz), 8.68 (1H, s), 12.55 (1H, br s).

IR(KBr): 1685 cm$^{-1}$.

mp: 236.5–238.0° C.

($R_1$=2-chlorobenzyl, $R_2$=methyl, $R_3$=—C(O)NR$_4$R$_5$, $R_4$=SO$_2$R$_6$, $R_5$=H, $R_6$=2-naphthyl, n=1, y=0)

Example 116

1-(2-Chlorobenzyl)-6-Methanesulfonylcarbamoyl-2-Methylbenzimidazole

By using the method of example 111, 1-(2-chlorobenzyl)-6-methanesulfonylcarbamoyl-2-methylbenzimidazole (0.564 g) is obtained from 6-carboxy-1-(2-chlorobenzyl)-2-methylbenzimidazole (0.500 g) (example 75), N,N'-carbonyldiimidazole (0.539 g), methanesulfonamide (0.316 g) and diazabicyclo-undecene (0.506 g). $^1$H-NMR (DMSO-d6, δ): 2.49 (3H, s), 3.35 (3H, s), 5.60 (2H, s), 6.43 (1H, d, J=7.8 Hz), 7.23 (1H, t), 7.34 (1H, t, J=7.7 Hz), 7.57 (1H, d, J=8.0 Hz), 7.68 (1H, d, J=8.5 Hz), 7.81 (1H, dd, J=1.7 and 8.5 Hz), 8.13 (1H, d, J=1.5 Hz), 11.94 (1H, br s).

IR(KBr): 1670 cm$^{-1}$.

mp: 302.0–303.0° C.

($R_1$=2-chlorobenzyl, $R_2$=methyl, $R_3$=—C(O)NR$_4$R$_5$, R=SO$_2$R$_6$, $R_5$=H, $R_6$=methyl, n=1, y=0)

Example 117

6-(Butanesulfonylcarbamoyl)-1-(2-Chlorobenzyl)-2-Methylbenzimidazole

By using the method of example 111, 6-(butanesulfonyl-carbamoyl)-1-(2-chlorobenzyl)-2-methylbenzimidazole (0.595 g) is obtained from 6-carboxy-1-(2-chlorobenzyl)-2-methylbenzimidazole (0.500 g) (example 75), N,N'-carbonyldiimidazole (0.539 g), 1-butanesulfonamide (0.456 g) and diaza-bicycloundecene (0.506 g). $^1$H-NMR (DMSO-d6δ): 0.84 (3H, t, J=7.4 Hz), 1.38 (2H, m), 1.65 (2H, m), 2.49 (3H, s), 3.49 (2H, m), 5.60 (2H, s), 6.44 (1H, d, J=7.6 Hz), 7.23 (1H, t, J=7.6 Hz), 7.35 (1H, t), 7.56 (1H, d, J=8.0 Hz), 7.68 (1H, d, J=8.4 Hz), 7.80 (1H, dd, J=1.6 and 8.4 Hz), 8.11 (1H, d, J=1.4 Hz), 11.86 (1H, br s).

IR(KBr): 1684 cm$^{-1}$.

mp: 214–217.0° C.

($R_1$=2-chlorobenzyl, $R_2$=methyl, $R_3$=—C(O)NR$_4$R$_5$, $R_4$=SO$_2$R$_6$, $R_5$=H, $R_6$=butyl, n=1, y=0)

Example 105

1-(2-Chlorobenzyl)-2-Methyl-6-(1-Butanesulfonylcarbamoyl) Benzimidazole

By using the method of example 111, 1-(2-chlorobenzyl)-2-methyl-6-(1-octanesulfonylcarbamoyl)benzimidazole (0.309 g) is obtained from 6-carboxy-1-(2-chlorobenzyl)-2-methylbenzimidazole (0.400 g) (example 75), N,N'-carbonyldiimidazole (0.431 g), 1-octanesulfonamide (0.406 g) and diazabicyclo-undecene (0.404 g). $^1$H-NMR (DMSO-d6, δ): 0.82 (3H, t, J=7.3 Hz), 1.13–1.28 (8H, m), 1.32–1.41 (2H, m), 1.62–1.71 (2H, m), 2.50 (3H, s), 3.50 (2H, t, J=8.5 Hz), 5.61 (2H, s), 6.45 (1H, d, J=7.7Hz). 7.24 (1H, t, J=7.5 Hz), 7.35 (1H, t, J=7.5 Hz), 7.58 (1H, d, J=8.0 Hz), 7.69 (1H, d, J=8.4 Hz), 7.81 (1H, d, J=8.5 Hz), 8.12 (1H, s), 11.86 (1H, s).

IR(KBr): 1674 cm$^{-1}$.

mp: 180.0–183.0° C.

($R_1$=2-chlorobenzyl, $R_2$=methyl, $R_3$=—C(O)NR$_4$R$_5$, $R_4$=SO$_2$R$_6$, $R_5$=H, $R_6$=octyl, n=1 , y=0)

Example 119

1-(2-Chlorobenzyl)-2-Methyl-6-(2-Propanesulfonylcarbamoyl) Benzimidazole

By using the method of example 111, 1-(2-chlorobenzyl)-2-methyl-6-(2-propanesulfonylcarbamoyl)benzimidazole (0.417 g) is obtained from 6-carboxy-1-(2-chlorobenzyl)-2-methylbenzimidazole (0.400 g) (example 75), N,N'-carbonyldiimidazole (0.431 g), 1-propanesulfonamide (0.328 g) and diazabicycloundecene (0.404 g). $^1$H-NMR (DMSO-d6, δ): 1.30 (6H, d, J=6.9 Hz), 2.50 (3H, s), 3.81–3.87 (1H, m), 5.62 (2H, s), 6.46 (1H, d, J=7.7 Hz), 7.25 (1H, t, J=7.5Hz), 7.35 (1H, t, J=7.5 Hz), 7.62 (1H, d, J=7.9 Hz), 7.69 (1H, d, J=8.5 Hz), 7.81 (1H, d, J=8.6 Hz), 8.12 (1H, s), 11.8 (1H, s).

IR(KBr): 1670 cm$^{-1}$.

mp: 215.0–217.5° C.

($R_1$=2-chlorobenzyl, $R_7$=methyl, $R_3$=—C(O)NR$_4$R$_5$, $R_4$=SO$_2$R$_6$, $R_5$=H, $R_6$=propyl, n=1, y=0)

Example 120

1-(Biphenyl-4-ylmethyl)-6-(1-Butanesulfonylcarbamoyl)-2-Methlybenzimidazole

By using the method of example 111, 1-(biphenyl-4-ylmethyl)-6-(1-butanesulfonylcarbamoyl)-2-methylbenzimidazole (0.349 g) is obtained from 1-(biphenyl-4-ylmethyl)-6-carboxy-2-methylbenzimidazole (0.300 g) (example 88), N,N'-carbonyldiimidazole (0.323 g), 1-butanesulfonamide (0.273 g) and diazabicycloundecene (0.303 g). $^1$H-NMR (DMSO-d$_6$, δ): 0.85 (3H, t, J=7.4 Hz), 1.36–1.43 (2H, m), 1.63–1.72 (2H, m), 2.57 (3H, s), 3.52 (2H, t, J=7.7 Hz), 5.60 (2H, s), 7.21 (2H, d, J=8.2 Hz), 7.35 (1H, t, J=7.3 Hz), 7.44 (2H, t, J=7.5Hz), 7.60–7.68 (5H, m), 7.81(1H, dd, J=1.6 and 8.4 Hz), 8.26 (1H, d, J=1.4 Hz), 11.97 (1H, s).

IR(KBr): 1676 cm$^{31\ 1}$.

mp: 219.5–222.5° C.

($R_1$=4-biphenyl, $R_2$=methyl, $R_3$=—C(O)NR$_4$R$_5$, $R_4$=SO$_2$R$_6$, $R_5$=butyl, n=1, y=1)

Example 121

6-(1-Butanesulfonylcarbamoyl)-1-(2,4-Dichlorobenzyl)-2-Methylbenzimidazole

By using the method of example 111 , 6-(1-butanesulfony-1carbamoyl)-1-(2,4-dichlorobenzyl)-2-methylbenzimidazole (0.459 g) is obtained from 6-carboxy-1-(2,4-dichlorobenzyl)-2-methylbenzimidazole (0.400 g) (example 87), N,N'-carbonyldiimidazole (0.431 g), 1-butanesulfonamide (0.364g) and diazabicycloundecene (0.404 g). $^1$H-NMR (DMSO-d6, δ): 0.85 (3H, t, J=7.3Hz), 1.36–1.42 (2H, m), 1.63–1.70 (2H, m), 2.50 (3H, s), 3.51 (2H, t, J=7.7 Hz), 5.59 (2H, s), 6.45 (1H, d, J=8.4 Hz), 7.33 (1H, dd, J=2.1 and 8.4 Hz), 7.69 (1H, t, J=8.4Hz), 7.76 (1H, d, J=2.0 Hz), 7.81 (1H, dd, J=1.7 and 8.5 Hz), 8.11 (1H, d, J=1.3 Hz), 11.90 (1H, s).

IR(KBr): 1670 cm$^{-1}$.

mp: 222.0–223.0° C.

($R_1$=2,4-dichlorobenzyl, $R_2$=methyl, $R_3$=—C(O)NR$_4$R$_5$, $R_4$=SO$_2$R$_6$, $R_5$=H, $R_6$=butyl, n=1, y=0)

Example 122

1-(Biphenyl-4-ylmethyl)-6-(1-Butanesulfonylcarbamoyl)-2-Ethylbenzimidazole

By using the method of example 111, 1-(biphenyl-4-ylmethyl)-6-(1-butanesulfonylcarbamoyl)-2-ethylbenzimidazole (0.300 g) is obtained from 1-(biphenyl-4-ylmethyl)-6-carboxy-2-ethylbenzimidazole (0.300 g) (example 98), N,N'-carbonyldiimidazole (0.340 g), 1-butanesulfonamide (0.300 g) and diazabicycloundecene (0.320 g). $^1$H-NMR (DMSO-d6, δ): 0.85 (3H, t, J 7.3Hz), 1.30 (3H, t, J=7.5 Hz), 1.35–1.44 (2H, m), 1.64–1.72 (2H, m), 2.90 (2H, q, J=7.4Hz), 3.52 (2H, t, J=7.7Hz) 5.61 (2H, s), 7.19 (2H, d, J=8.3 Hz), 7.35 (1H, t, J=7.3Hz), 7.44 (2H, t, J=7.5 Hz), 7.61–7.67(4H, m), 7.71 (1H, d, J=8.5 Hz), 7.82 (1H, dd, J=1.6 and 8.5 Hz), 8.27 (1H, d J=1.3 Hz), 12.01 (1H, s).

IR(Nujol): 1687, 1682 cm$^{-1}$.

mp: 171.8–173.0° C.

($R_1$=4-biphenyl, $R_2$=ethyl, $R_3$=—C(O)NR$_4$R$_5$, $R_4$=SO$_2$R$_6$, $R_5$=H, $R_6$=butyl, n=1, y=1)

Example 123

6-Benzenesulfonylcarbamoyl-1-(Biphenyl-4-ylmethyl)-2-Trifluoromethylbenzimidazole By using the method of example 111, 6-benzenesulfonylcarbamoyl-1-(biphenyl-4-ylmethyl)-2-trifluoromethylbenzimidazole (0.508 g) is obtained from 1-(biphenyl-4-ylmethyl)-6-carboxy-2-trifluoromethylbenzimidazole (0.483 g) (example 106), N,N'-carbonyldiimidazole (0.396 g), benzenesulfonamide (0.383 g) and diazabicyclo-undecene (0.371 g). $^1$H-NMR (DMSO-d6, δ): 5.81 (2H, s), 7.15 (2H, d, J=8.3 Hz), 7.35 (1H, t, J=7.5 Hz), 7.44 (2H, t, J=7.5Hz), 7.60–7.66 (6H, m), 7.70 (1H, t, J=7.4 Hz), 7.91 (1H, dd, J=8.7 and 1.4 Hz), 7.96–8.01 (3H, m), 8.42 (1H, s), 12.65 (1H, s).

IR(KBr): 1685 cm$^{-1}$.

mp: 164.5–167.0° C.

($R_1$=4-biphenyl, $R_2$=trifluoromethyl, $R_3$=—C(O)NR$_4$R$_5$, $R_4$=SO$_2$R$_6$, $R_5$=H, $R_6$=phenyl, n=1, y=1)

Example 124

5-Benzenesulfonylcarbamoyl-1-(Biphenyl-4-ylmethyl)-2-Trifluoromethylbenzimidazole By using the method of example 111, 5-benzenesulfonylcarbamoyl-1-(biphenyl-4-ylmethyl)-2-trifluoromethylbenzimidazole (0.286 g) is obtained from 1-(biphenyl-4-ylmethyl)-5-carboxy-2-trifluoromethylbenzimidazole (0.270 g) (example 107), N,N'-carbonyldiimidazole (0.221 g), benzenesulfonamide (0.214 g) and diazabicycloundecene (0.207 g). $^1$H-NMR (DMSO-d6, δ): 5.79 (2H, s), 7.15 (2H, d, J=8.1 Hz), 7.35 (1H, t, J=7.5 Hz), 7.43 (2H, t, J=7.5 Hz), 7.59 –7.67 (6H, m), 7.72 (1H, t, J=7.6 Hz), 7.83 (1H, d, J=8.8 Hz), 7.94 (1H, d, J=8.9 Hz), 8.02 (2H, d, J=7.4 Hz), 8.49 (1H, s), 12.69 (1H, s).

IR(KBr): 1699 cm$^{-1}$.

mp: 248.5–251.0° C.

($R_1$=4-biphenyl, $R_2$=trifluoromethyl, $R_3$=—C(O)NR$_4$R$_5$, $R_4$=SO$_2$R$_6$, $R_5$=H, $R_6$=phenyl, n=1, y=1)

Example 125

6-Benzenesulfonylcarbamoyl-2-Cyclopropyl-1-(2-Fluorobenzyl)Benzimidazole

By using the method of example 111, 6-benzenesulfonylcarbamoyl-2-cyclopropyl-1-(2-fluorobenzyl)benzimidazole (0.730 g) is obtained from 6-carboxy-2-cyclopropyl-1-(2-fluorobenzyl)benzimidazole (0.930 g) (example 18), N,N'-carbonylduimidazole (0.972 g), benzenesulfonamide (0.942 g) and diazabicycloundecene (0.906 g). $^1$H-NMR (DMSO-d6, δ): 1.04 (4H, m), 2.15 (1H, m), 5.70 (2H, s), 6.85 (1H, t, J=7.5 Hz), 7.12 (1H, t, J=7.5 Hz), 7.22–7.38 (2H, m), 7.54–7.70 (5H, m), 7.99 (2H, d, J=7.5 Hz), 8.11 (1H, s). White Powder
($R_1$=2-fluorobenzyl, $R_2$=cyclopropyl, $R_3$=—C(O)$NR_4R_5$, $R_4$=$SO_2R_6$, $R_5$=H, $R_6$=phenyl, n=1, y=0)

Example 126

N-Benzenesulfonyl-3-[1-(2-Chlorobenzyl)-2-Methylbenzimidazole-6-yl]Acrylamide By using the method of example 111, N-benzenesulfonyl-3-[1-(2-chlorobenzyl)-2-methylbenzimidazole-6-yl]acrylamide (1.05 g) is obtained from 1-(2-chlorobenzyl)-2-methylbenzimidazole-6-acrylic acid (1.10 g) (example 110), N,N'-carbonyldiimidazole (1.09 g), benzenesulfonamide (1.06 g) and diazabicycloundecene (1.02 g). $^1$H-NMR (DMSO-$d_6$, δ): 2.47 (3H, s), 5.55 (2H, s), 6.46–6.55 (2H, m), 7.22 (1H, t, J=7.6 Hz), 7.32 (1H, t, J=7.7 Hz), 7.40 (1H, d, J=8.4 Hz), 7.52–7.66 (6H, m), 7.69 (1H, t), 7.93 (2H, d, J=7.9 Hz), 12.17 (1H, br s).

IR(KBr): 1687 $cm^{-1}$.

Mass(FAB): m/e 466(M+1).

mp: 243.1–244.3° C.

($R_1$=2-chlorobenzyl, $R_2$=methyl, $R_3$=benzenesulfonylcarbamoylethenyl, n=1, y=0)

Example 127

1-(2,4-Dichlorobenzyl)-2-Methyl-6-[(2-pyridylmethyl) carbamnoyl]benzimidazole Dichloromethane (150 ml) and a few drops of N-dimethylformamide are added to 6-carboxy-1-(2,4-dichlorobenzyl)-2-methylbenzimidazole (9.00 g) (example 87), and the solution is chilled with ice. Oxalyl chloride (6.84 g) is dripped into the solution, which is then stirred for a few minutes. After the solution is further stirred for 1.5 hours at room temperature, the solution is concentrated under reduced pressure to a third of its original volume. Precipitants are collected and added to a dichloromethane (200 ml) solution of 2-aminomethylpyridine (2.69 g) and triethylamine (7.34 g) over a few doses while it is chilled with ice. After the solution is stirred for 15 hours, the reaction solution is washed with water three times, and is further washed with a saturated sodium bicarbonate aqueous solution. The organic layer is concentrated under reduced pressure, and crystals are formed using ethyl acetate. When crystals are separated through filtration and dried, 1-(2,4-dichlorobenzyl)-2-methyl-6-[(2-pyridylmethyl)carbamoyl]benzimidazole (4.35 g) is obtained. $^1$H-NMR (CDCl$_3$, δ): 2.56 (3H, s), 4.76 (2H, d, J=4.8 Hz), 5.40 (2H, s), 6.33 (1H, d, J=8.4 Hz), 7.07 (1H, dd, J=8.4 and 2.0 Hz), 7.22 (1H, dd, J=7.4 and 4.9 Hz), 7.33 (1H, d, J=7.9 Hz), 7.48 (1H, d, J =2.1 Hz), 7.62 –7.79 (4H, m), 7.86 (1H, d, J=1.1Hz), 8.57 (1H, d, J=4.9Hz).

IR(KBr): 1645 $cm^{-1}$.

mp: 204.5–206.5° C.

($R_1$=2,4-dichlorobenzyl, $R_2$=cyclopropyl, $R_3$=—C(O)$NR_4R_5$, $R_4$=2-pyridylmethyl, $R_5$=H, n=1, y=0)

Example 128

1-Methyl-2-n-Propyl-6-[(2-Pyridylmethyl) Carbamoyl]Benzimidazole

By using the method of example 127, 1-methyl-2-n-propyl-6-[(2-pyridylmethyl)carbamoyl]benzimidazole (0.213 g) is obtained from 6-carboxy-1-methyl-2-n-propylbenzimidazole (0.402 g), oxalyl chloride (0.468 g), 2-aminomethylpyridine (0.199 g) and triethylamine (0.559 g). $^1$H-NMR (CDCl$_3$, δ): 1.08 (3H, t, J=7.4 Hz), 1.92 (2H, m), 2.88 (2H, m), 3.76 (3H, s), 4.80 (2H, d, J=4.8 Hz), 7.22 (1H, dd, J=2.5 and 7.5 Hz), 7.35 (1H, d, J=7.8 Hz), 7.67–7.77 (4H, m), 7.80 (1H, s), 8.58 (1H, dd, J=4.9 and 0.9Hz).

IR(KBr): 1647 $cm^{-1}$.

mp: 140.5–141.5° C.

($R_1$=methyl, $R_2$=n-propyl, $R_3$=—C(O)$NR_4R_5$, $R_4$=2-pyridylmethyl, $R_5$=H, n=1, y=0)

Example 129

1-(2-Chlorobenzyl)-2-Methyl-6-[(2-Pyridylmethyl) Carbamoyl]Benzimidazole

By using the method of example 127, 1-(2-chlorobenzyl)-2-methyl-6-[(2-pyridylmethyl)carbamoyl]benzimidazole (0.164 g) is obtained from 6-carboxy-1-(2-chlorobenzyl)-2-methylbenzimidazole (0.300 g) (example 75), oxalyl chloride (0.253 g), 2-aminomethylpyridine (0.108 g) and triethylamine (0.302 g). $^1$H-NMR (CDCl$_3$, δ): 2.56 (3H, s), 4.76 (2H, d, J=4.8 Hz), 5.45 (2H, s), 6.40 (1H, d, J=7.8 Hz), 7.08 (1H,t, J=7.6 Hz), 7.20–7.27 (2H, m), 7.33 (1H, d, J=7.8 Hz), 7.45 (1H, dd, J=0.9 and 8.1 Hz), 7.64 (1H, s), 7.65–7.69 (1H, m), 7.72 (1H, dd, J=1.5 and 8.4 Hz), 7.77 (1H, d, J=8.4 Hz), 7.88 (1H, d, J=1.2 Hz), 8.56 (1H, d, J=4.7Hz).

IR(KBr): 1646 $cm^{-1}$.

mp: 156.5–157.5° C.

($R_1$=2-chlorobenzyl, $R_2$=methyl, $R_3$=—C(O)$NR_4R_5$, $R_4$=2-pyridylmethyl, $R_5$=H, n=1, y=0)

Example 130

2-n-Propyl-1-i-Propyl-6-[(2-Pyridylmethyl) Carbamoyl]Benzimidazole

By using the method of example 127, 2-n-propyl-1-i-propyl-6-[(2-pyridylmethyl)carbamoyl]benzimidazole (0.020g) is obtained from 6-carboxy-2-n-propyl-1-i-propylbenzimidazole (0.095 g) (example 73), oxalyl chloride (0.100 g), 2-aminomethylpyridine (0.039 g) and triethylamine (0.097 g). $^1$H-NMR (CDCl$_3$, δ): 1.08 (3H, t, J=7.4 Hz), 1.69 (6H, d, J=7.1 Hz), 1.87–1.93 (2H, m), 2.90 (2H, t, J=7.8 Hz), 4.69–4.75 (1H, m), 4.80 (2H, d, J=4.9 Hz), 7.23 (1H, dd, J=7.3 and 2.1 Hz), 7.37 (1H, d, J=7.7 Hz), 7.62–7.77 (4H, m), 8.21 (1H, s), 8.58 (1H, d, J=4.5Hz).

IR(KBr): 1631 $cm^{-1}$.

mp: 155.0–156.9° C.

($R_1$=i-propyl, $R_2$=n-propyl, $R_3$=—C(O)$NR_4R_5$, $R_4$=2-pyridylmethyl, $R_5$=H, n=1,y=0)

Example 131

1-n-Butyl-2-n-Propyl-6-[(2-Pyridylmethyl) Carbamoyl]Benzimidazole

By using the method of example 127, 1-n-butyl-2-n-propyl-6-[(2-pyridylmethyl)carbamoyl]benzimidazole (0.283 g) is obtained from 1-n-butyl-6-carboxy-2-n-propylbenzimidazole (0.500 g), oxalyl chloride (0.487 g), 2-aminomethylpyridine (0.208 g) and triethylamine (0.582 g). $^1$H-NMR (CDCl$_3$, δ): 0.97 (3H, t, J=7.3 Hz), 1.08 (3H, t, J=7.4 Hz), 1.37–1.46 (2H, m), 1.76–1.83 (2H, m), 1.92–2.00 (2H, m) 2.86 (2H, t, J=7.8 Hz), 4.15 (2H, t, J=7.6 Hz), 4.81 (2H, d, J=4.8 Hz), 7.23 (1H, dd, J=7.3 and 2.4 Hz), 7.36 (1H, d, J=7.8 Hz), 7.63–7.76 (4H, m), 8.02 (1H, s), 8.58 (1H, d, J=4.7Hz).
IR(KBr): 1631 cm$^{-1}$.
mp: 105.8–107.2° C.
($R_1$=n-butyl, $R_2$=n-propyl, $R_3$=—C(O)$NR_4R_5$, $R_4$=2-pyridylmethyl, $R_5$=H, n=1, y=0)

Example 132

1-(3-Chlorobenzyl)-2-n-Propyl-6-[(2-Pyridylmethyl) Carbamoyl]Benzimidazole

By using the method of example 127), 1-(3-chlorobenzyl)-2-n-propyl-6-[(2-pyridylmethyl)carbamoyl] benzimidazole (0.311 g) is obtained from 6-carboxy-1-(3-chlorobenzyl)-2-n-propylbenzimidazole (0.580 g) (example 81), oxalyl chloride (0.407 g), 2-aminomethylpyridine (0.173 g) and triethylamine (0.486 g). 1H-NMR (CDCl$_3$, δ): 1.03 (3H, t, J=7.4 Hz), 1.85–1.93 (2H, m), 2.80 (2H, t, J=7.5 Hz), 4.77 (2H, d, J=4.8 Hz), 5.36 (2H, s), 6.86 (1H, d, J=7.4 Hz), 7.02 (1H, s), 7.20–7.28 (3H, m), 7.33 (1H, d, J=7.8 Hz), 7.63–7.73 (3H, m), 7.79 (1H, d, J=8.4 Hz), 7.91 (1H, d, J=1.3 Hz), 8.57 (1H, d, J=4.7Hz).
IR(KBr): 1643 cm$^{-1}$.
mp: 157.7–158.8° C.
($R_1$=3-chlorobenzyl, $R_2$=n-propyl, $R_3$=—C(O)$NR_4R_5$, $R_4$=2-pyridylmethyl, $R_5$=H, n=1, y=0)

Example 133

1-Benzyl-2-n-Propyl-6-[(2-Pyridylmethyl) Carbamoyl]Benzimidazole

By using the method of example 127, 1-benzyl-2-n-propyl-6-[(2-pyridylmethyl)carbamoyl]benzimidazole (0.350 g) is obtained from 1-benzyl-6-carboxy-2-n-propylbenzimidazole (0.850 g) (example 80), oxalyl chloride (0.949 g), 2-aminomethylpyridine (0.404 g) and triethylamine (1.132 g). $^1$H-NMR (CDCl$_3$, δ): 1.01 (3H, t, J=7.4 Hz), 1.83–1.92 (2H, m), 2.82 (2H, t, J=7.6 Hz), 4.77 (2H, d, J=4.8 Hz), 5.40 (2H, s), 7.03 (2H, d, J=6.5 Hz), 7.21 (1H, dd, J=7.1 and 2.1 Hz), 7.18–7.34 (4H, m), 7.60 (1H, s), 7.65–7.72 (2H, m), 7.78 (1H, d, J=8.4 Hz), 7.94 (1H, d, J=1.2 Hz), 8.56 (1H, d, J=4.2Hz).
IR(KBr): 1642 cm$^{31\ 1}$.
mp: 121.9–123.1° C.
($R_1$=benzyl, $R_2$=n-propyl, $R_3$=—C(O)$NR_4R_5$, $R_4$=2-pyridylmethyl, $R_5$=H, n=1, y=0)

Example 134

2-Benzyl-6-Carboxy-1-Methylbenzimidazole Hydrochloride

To an ethanol (4 ml) solution of 2-benzyl-6-ethoxycarbonyl-1-methylbenzimidazole (0.340 g), 5% sodium hydroxide aqueous solution (2.8 g) is added, and the solution is refluxed by heating for 1.5 hours. The solution is made acidic using 1N hydrochloric acid and concentrated under reduced pressure. Ethanol is added to the residue and organic materials are extracted. The ethanol is removed under reduced pressure and thus, 2-benzyl-6-carboxy-1-methylbenzimidazole hydrochloride (0.300 g) is obtained.
$^1$H-NMR (DMSO-d6, δ): 4.00 (3H, s), 4.62 (2H, s), 7.33 (1H, m), 7.35–7.45 (4H, m), 7.83 (1H, d, J=8.4 Hz), 8.06 (1H, d, J=8.4 Hz), 8.42 (1H, s), 13.3 (1H, br s).
($R_1$=benzyl, $R_2$=methyl, $R_3$=carboxyl, n=1, y=0)

Example 135

1-(4-Chlorobenzyl)-2-Propyl-6-[(2-Pyridylmethyl) Carbamoyl] Benzimidazole

By using the method of example 127, 1-(4-chlorobenzyl)-2-propyl-6-[(2-pyridylmethyl)carbamoyl]benzimidazole (0.089 g) is obtained from 6-carboxy-1-(4-chlorobenzyl)-2-propylbenzimidazole (0.547 g) (example 71), oxalyl chloride (0.384 g), 2-aminomethylpyridine (0.163 g) and triethylamine (0.458 g). $^1$H-NMR (CDCl$_3$, δ): 1.02 (3H, t, J=7.4 Hz), 1.84–1.92 (2H, m), 2.77–2.83 (2H, m), 4.76 (2H, d, J=4.8 Hz), 5.36 (2H, s), 6.96 (2H, d, J=8.3 Hz), 7.22 (1H, dd, J=6.4 and 0.4 Hz), 7.27 (2H, dd, J=8.3 and 1.3 Hz), 7.33 (1H, d, J=7.8 Hz), 7.62–7.73 (3H, m), 7.78 (1H, d, J=8.4 Hz), 7.91 (1H, d, J=0.9 Hz), 8.56 (1H, dd, J=4.9 and 0.8Hz).
IR(KBr): 1643 cm$^{-1}$.
mp: 158.8–161.0° C.
($R_1$=3-chlorobenzyl, $R_2$=propyl, $R_3$=—C(O)$NR_4R_5$, $R_4$=2-pyridylmethyl, $R_5$=H, n=1, y=0)

Example 136

1-(2,6-Dichlorobenzyl)-2-methyl-6-[(2-pyridylmethyl) carbamoyl]benzimidazole

By using the method of example 127, 1-(2,6-dichlorobenzyl)-2-methyl-6-[(2-pyridylmethyl)carbamoyl] benzimidazole (0.040 g) is obtained from 6-carboxy-1-(2,6-dichlorobenzyl)-2-methylbenzimidazole (0.600 g) (example 76), oxalyl chloride (0.472 g), 2-aminomethylpyridine (0.201 g) and triethylamine (0.188 g). $^1$H-NMR (CDCl$_3$, δ): 2.62 (3H, s), 4.76 (2H, d, J=4.7 Hz), 5.62 (2H, s), 7.23 (1H, dd, J=7.1 and 2.2 Hz), 7.28 (1H, d, J=7.8 Hz), 7.32 (1H, d, J=7.9 Hz), 7.39 (2H, d, J=8.1 Hz), 7.54 (1H, s), 7.66–7.71 (3H, m), 7.78 (1H, s), 8.60 (1H, d, J=4.6Hz).
IR(KBr): 1635 cm$^{-1}$.
mp: 225.7–226.9° C
($R_1$=2,6-dichlorobenzyl, $R_2$=propyl, $R_3$=—C(O)$NR_4R_5$, $R_4$=2-pyridylmethyl, $R_5$=H, n=1, y=0)

Example 137

2-Methyl-6-[(2-Pyridylmethyl)Carbamoyl]-1-[2-(Trifluoromethyl)Benzyl]Benzimidazole By using the method of example 127, 2-methyl-6-[(2-pylidylmethyl)carbamoyl]-1-[2-(trifluoromethyl)benzyl] benzimidazole (0.713 g) is obtained from 6-carboxy-2-methyl-1-[2-(trifluoromethyl)benzyl]benzimidazole (0.970 g) (example 77), oxalyl chloride (0.736 g), 2-aminomethylpyridine (0.261 g) and triethylamine (0.726 g). $^1$H-NMR (CDCl$_3$, δ): 2.54 (3H, s), 4.76 (2H, d, J=4.8 Hz), 5.59 (2H, s), 6.45 (1H, d, J=7.9 Hz), 7.22 (1H, dd, J=5.8 Hz), 7.34 (2H, t, J=8.8 Hz), 7.40 (1H, t, J=7.5 Hz), 7.62 (1H, br s), 7.68 (1H, dt, J=1.7 and 7.7 Hz), 7.72–7.82 (3H, m), 7.87 (1H, s), 8.56 (1H, d, J=4.9Hz).
IR(KBr): 1648 cm$^{-1}$.
mp: 172–174° C.
($R_1$=2-trifluoromethylbenzyl, $R_2$=methyl, $R_3$=—C(O) $NR_4R_5$, $R_4$=2-pyridylmethyl, $R_5$=H, n=1,y=0)

Example 138

2-Methyl-6-[(2-Pyridylmethyl)Carbamoyl]-1-[4-(Trifluoromethyl)benzyl]Benzimidazole By using the method of example 127, 2-methyl-6-[(2-pyridylmethyl)carbamoyl]-1-[4-(trifluoromethyl)benzyl] benzimidazole (0.194 g) is obtained from 6-carboxy-2-methyl-1-[4-(trifluoromethyl)benzyl]benzimidazole (0.970 g) (example 78), oxalyl chloride (0.736 g), 2-aminomethylpyridine (0.261 g) and triethylamine (0.726 g). $^1$H-NMR (CDCl$_3$, δ): 2.59 (3H, s), 4.77 (2H, d, J=4.7

Hz), 5.45 (2H, s), 7.15 (2H, d, J=8.2 Hz), 7.23 (1H, m), 7.33 (1H, d, J=7.9 Hz), 7.58 (2H, d, J=8.2 Hz), 7.63 (1H, br s), 7.67–7.74 (2H, m), 7.77 (1H, d, J=8.3 Hz), 7.93 (1H, s), 8.57 (1H, d, J=4.9 Hz),

IR(KBr): 1637 cm$^{-1}$.

mp: 188.5–190.0° C.

($R_1$=2-trifluoromethylbenzyl, $R_2$=methyl, $R_3$=—C(O)$NR_4R_5$, $R_4$=2-pyridylmethyl, $R_5$=H, n=1, y=0)

Example 139

1-(3,4-Dichlorobenzyl)-2-methyl-6-[(2-pyridylmethyl) carbamoyl]benzimidazole

By using the method of example 127, 1-(3,4-dichlorobenzyl)-2-methyl-6-[(2-pyridylmethyl)carbamoyl] benzimidazole (0.264 g) is obtained from 6-carboxy-1-(3, 4-dichlorobenzyl)-2-methylbenzimidazole (0.500 g) (example 79), oxalyl chloride (0.393 g), 2-aminomethylpyridine (0.167 g) and triethylamine (0.469 g). $^1$H-NMR (CDCl$_3$, δ): 2.58 (3H, s), 4.77 (2H, d, J=4.8 Hz), 5.33 (2H, s), 6.85 (1H, dd, J=8.3 and 2.2 Hz), 7.14 (1H, d, J=2.1 Hz), 7.22 (1H, dd, J=7.3 and 5.6 Hz), 7.33 (1H, d, J=7.8 Hz), 7.38 (1H, d, J=8.3 Hz), 7.65–7.77 (4H, m), 7.92 (1H, d, J=1.2 Hz), 8.57 (1H, d, J=4.8Hz).

IR(KBr): 1638 cm$^{-1}$.

mp: 219.0–220.7° C.

($R_1$=3,4-dichlorobenzyl, $R_2$=methyl, $R_3$=—C(O)$NR_4R_5$, $R_4$=2-pyridylmethyl, $R_5$=H, n=1, y=0)

Example 140

2-Methyl-1-(2-Methylbenzyl)-6-[(2-Pyridylmethyl) Carbamoyl] Benzimidazole

By using the method of example 127, 2-methyl-1-(2-methylbenzyl)-6-[(2-pyridylmethyl)carbamoyl] benzimidazole (0.100 g) is obtained from 6-carboxy-2-methyl-1-(2-methylbenzyl)benzimidazole (0.453 g) (example 90), oxalyl chloride (0.411 g), 2-aminomethylpyridine (0.175 g) and triethylamine (0.490 g). $^1$H-NMR (CDCl$_3$, δ): 2.42 (3H, s), 2.54 (3H, s), 4.75 (2H, d, J=4.9 Hz), 5.32 (2H, s), 6.33 (1H, d, J=7.8 Hz), 7.01 (1H, t, J=7.8 Hz), 7.17–7.24 (3H, m), 7.33 (1H, d, J=7.8 Hz), 7.60 (1H, s) 7.63–7.73 (2H, m), 7.76 (1H, d, J=8.4 Hz), 7.84 (1H, d, J=1.4 Hz), 8.56 (1H, d, J=4.9Hz).

IR(KBr): 1635 cm$^{-1}$.

mp: 154.0–157.0° C.

($R_1$=2-methylbenzyl, $R_2$=methyl, $R_3$=—C(O)$NR_4R_5$, $R_4$=2-pyridylmethyl, $R_5$=H, n=1, y=0)

Example 141

1-(2-Methoxybenzyl)-2-Methyl-6-[(2-Pyridylmethyl) Carbamoyl]Benzimidazole

By using the method of example 127, 1-(2-methoxybenzyl)-2-methyl-6-[(2pyridylmethyl)carbamoyl] benzimidazole (0.918 g) is obtained from 6-carboxy-1-(2-methoxybenzyl)-2-methylbenzimidazole (0.997 g) (example 91), oxalyl chloride (0.858 g), 2-aminomethylpyridine (0.309 g) and triethylamine (1.02 g). $^1$H-NMR (CDCl$_3$, δ): 2.60 (3H, s), 3.89 (3H, s), 4.77 (2H, d, J=4.8 Hz), 5.36 (2H, s), 6.60 (1H, d, J=7.4 Hz), 6.79 (1H, dt, J=0.8 and 7.4 Hz), 6.91 (1H, d, J=7.4 Hz), 7.20–7.28 (2H, m), 7.34 (1H, d, J=7.9 Hz), 7.56 (1H, br t), 7.66–7.75 (3H, m), 7.95 (1H, m), 8.57 (1H, d, J=4.9Hz).

IR(KBr): 1652 cm$^{-1}$.

mp: 136–138.5° C.

($R_1$=2-methoxybenzyl, $R_2$=methyl, $R_3$=—C(O)$NR_4R_5$, $R_4$=2-pyridylmethyl, $R_5$=H, n=1, y=0)

Example 142

1-(4-Methoxybenzyl)-2-Methyl-6-[(2-Pyridylmethyl) Carbamoyl]Benzimidazole

By using the method of example 127, 1-(4-methoxybenzyl)-2-methyl-6-[(2-pyridylmethyl)carbamoyl] benzimidazole (0.697 g) is obtained from 6-carboxy-1-(4-methoxybenzyl)-2-methylbenzimidazole (0.985 g) (example 92), oxalyl chloride (0.858 g), 2-aminomethylpyridine (0.309 g) and triethylamine (1.02 g). $^1$H-NMR (CDCl$_3$, δ): 2.59 (3H, s), 3.76 (3H, s), 4.78 (2H, d, J=4.8 Hz), 5.32 (2H, s), 6.83 (2H, m), 7.00 (2H, m), 7.22 (1H, dd, J=5.1 and 6.8 Hz), 7.34 (1H, d, J=7.8 Hz), 7.60 (1H, br t), 7.67–7.76 (3H, m), 7.97 (1H, d, J=1.2 Hz), 8.57 (1H, d, J=4.9Hz).

IR(KBr): 1652 cm$^{-1}$.

mp: 191.5–192.2° C.

($R_1$=4-methoxybenzyl, $R_2$=methyl, $R_3$=—C(O)$NR_4R_5$, $R_4$=2-pyridylmethyl, $R_5$=H, n=1, y=0)

Example 143

1-[2-(Benzenesulfonylmethyl)Benzyl]-2-Methyl-6-[(2-Pyridylmethyl) Carbamoyl] Benzimidazole By using the method of example 127, 1-[2-(benzenesulfonylmethyl)benzyl]-2-methyl-6-[(2-pyridylmethyl)carbamoyl]benzimidazole (0.64 g) is obtained from 1-[2-(benzenesulfonylmethyl)benzyl]-6-carboxy-2-methylbenzimidazole (0.74 g), oxalyl chloride (0.45 g), 2-aminomethylpyridine (0.19 g) and triethylamine (0.53 g). $^1$H-NMR (CDCl$_3$, δ): 2.57 (3H, s), 4.50 (2H, s), 4.74 (2H, d, J=4.9 Hz), 5.59 (2H, s), 6.63 (1H, d, J=7.7 Hz), 6.87 (1H, d, J=7.4 and 1.5 Hz), 7.09–7.19 (3H, m), 7.31 (1H, d, J=7.8 Hz), 7.53–7.61 (3H, m), 7.64 (1H, dt, J=7.6 and 1.6 Hz), 7.68–7.79 (5H, m), 7.84 (1H, s), 8.52 (1H, d, J=4.8Hz).

IR(neat): 1646 cm$^{-1}$. Liquid.

($R_1$=2-(benzenesulfonylmethyl)benzyl, $R_2$=methyl, $R_3$=—C(O)$NR_4R_5$, $R_4$=2p-yridylmethyl, $R_5$=H, n=1, y=0)

Example 144

1-(2-Cyanobenzyl)-2-Methyl-6-[(2-Pyridylmethyl) Carbamoyl]Benzimidazole

By using the method of example 127, 1-(2-cyanobenzyl)-2-methyl-6-[(2-pyridylmethyl)carbamoyl]benzimidazole (1.03 g) is obtained from 6-carboxy-1-(2-cyanobenzyl)-2-methylbenzimidazole (1.14 g) (example 94), oxalyl chloride (0.998 g), 2-aminomethylpyridine (0.425 g) and triethylamine (1.19 g). $^1$H-NMR (CDCl$_3$, δ): 2.58 (3H, s), 4.76 (2H, d, J=4.8 Hz), 5.59 (2H, s), 6.64 (1H, d, J=7.4 Hz), 7.21 (1H, dt, J=5.6 and 1.8 Hz), 7.33 (1H, d, J=7.9 Hz), 7.39–7.47 (2H, m), 7.65–7.79 (5H, m), 7.89 (1H, s), 8.56 (1H, dd, J=4.9 and 0.9Hz).

IR(KBr): 2223, 1642 cm$^{-1}$.

mp: 150.5–151.4° C.

($R_1$=2-cyanobenzyl, $R_2$=methyl, $R_3$=—C(O)$NR_4R_5$, $R_4$=2-pyridylmethyl, $R_5$=H, n=1, y=0)

Example 145

1-(Biphenyl-2-ylmethyl)-2-Methyl-6-[(2-Pyridylmethyl) Carbamoyl]Benzimidazole

By using the method of example 127, 1-(biphenyl-2-ylmethyl)-2-methyl-6-[(2-pyridylmethyl)carbamoyl]

benzimidazole (0.672 g) is obtained from 1-(biphenyl-2-ylmethyl)-6-carboxy-2-methylbenzimidazole (1.07 g), oxalyl chloride (0.796 g), 2-aminomethylpyridine (0.339 g) and triethylamine (0.950 g). $^1$H-NMR (CDCl$_3$, δ): 2.38 (3H, s), 4.78 (2H, d, J=4.8 Hz), 5.27 (2H, s), 6.64 (1H, d, J=8.0 Hz), 7.17–7.24 (2H, m), 7.29–7.43 (6H, m), 7.48 (2H, t, J=5.5 Hz), 7.49 (1H, s), 7.57–7.73 (3H, m), 7.80 (1H, d, J=1.0 Hz), 8.58 (1H, d, J=4.9Hz).

IR(KBr): 1630, 1619 cm$^{-1}$.

mp: 179.8–180.8° C.

($R_1$=2-biphenyl, $R_2$=methyl, $R_3$=—C(O)NR$_4$R$_5$, $R_4$=2-pyridylmethyl, $R_5$=H, n=1, y=1)

Example 146

1-Benzyl-2-methyl-6-[(2-pyridylmethyl)carbamoyl]benzimidazole

By using the method of example 127, 1-benzyl-2-methyl-6-[(2-pyridylmethyl)carbamoyl]benzimidazole (0.66 g) is obtained from 1-benzyl-6-carboxy-2-methylbenzimidazole (0.59 g) (example 96), oxalyl chloride (0.56 g), 2-aminomethylpyridine (0.24 g) and triethylamine (0.67 g). $^1$H-NMR (CDCl$_3$, 6): 2.58 (3H, s), 4.76 (2H, d, J=4.9 Hz), 5.36 (2H, s), 7.02–7.06 (2H, m), 7.21 (1H, dd, J=6.9 and 5.0 Hz), 7.27–7.35 (4H, m), 7.65–7.75 (4H, m), 7.96 (1H, d, J=0.8 Hz), 8.56 (1H, d, J=4.8Hz).

IR(KBr): 1640 cm$^{-1}$.

mp: 124.0–124.9° C.

($R_1$=benzyl, $R_2$=methyl, $R_3$=—C(O)NR$_4$R$_5$, $R_4$=2-pyridylmethyl, $R_5$=H, n=1, y=0)

Example 147

1-(4-t-Butylbenzyl)-2-Methyl-6-[(2-Pyridylmethyl) Carbamoyl]Benzimidazole

By using the method of example 127, 1-(4-t-butylbenzyl)-2-methyl-6-[(2-pyridylmethyl)carbamoyl]benzimidazole (0.47 g) is obtained from 1-(4-t-butylbenzyl)-6-6-carboxy-2-methylbenzimidazole (0.544 g) (example 89), oxalyl chloride (0.428 g), 2-aminomethylpyridine (0.183 g) and triethylamine (0.511 g). $^1$H-NMR (CDCl$_3$, δ): 1.27 (9H, s), 2.60 (3H, s), 4.77 (2H, d, J=4.9 Hz), 5.34 (2H, s), 6.98 (2H, d, J=d, J=8.3 Hz), 7.21 (1H, dd, J=7.3 and 5.1 Hz), 7.29–7.35 (3H, m), 7.62 (1H, br.s), 7.65–7.75 (3H, m), 7.96 (1H, d, J=1.1 Hz), 8.57 (1H, d, J=4.7Hz).

IR(KBr): 1646 cm$^{-1}$.

mp: 140.4–142.8° C.

($R_1$=4-t-butylbenzyl, $R_2$=methyl, $R_3$=carboxyl, n=1, y=0)

Example 148

2-Methyl-1-(2-Naphthylmethyl)-6-[(2-Pyridylmethyl) Carbamoyl]Benzimidazole

By using the method of example 127, 2-methyl-1-(2-naphthylmethyl)-6-[(2-pyridylmethyl)carbamoyl]benzimidazole (0.47 g) is obtained from 6-carboxy-2-methyl-1-(2-naphthylmethyl)benzimidazole (0.80 g) (example 97), oxalyl chloride (0.64 g), 2-aminomethylpyridine (0.27 g) and triethylamine (0.77 g). $^1$H-NMR (CDCl$_3$, δ): 2.60 (3H, s), 4.75 (2H, d, J=4.9 Hz), 5.52 (2H, s), 7.17–7.23 (2H, m), 7.31 (1H, d J=7.8Hz 7.8 Hz), 7.38 (1H, s), 7.43–7.48 (2H, m), 7.60–7.82 (7H, m), 8.00 (1H, d, J=1.0 Hz), 8.53 (1H, d, J=4.7Hz).

IR(KBr): 1640 cm$^{-1}$.

mp: 143.0–144.5° C.

($R_1$=2-naphthylmethyl, $R_2$=methyl, $R_3$=—C(O)NR$_4$R$_5$, $R_4$=2-pyridylmethyl, $R_5$=H, n=1, y=0)

Example 149

1-(Biphenyl-4-ylmethyl)-2-Ethyl-6-[(2-Pyridylmethyl) Carbamoyl]Benzimidazole By using the method of example 127, 1-(biphenyl-4-ylmethyl)-2-ethyl-6-[(2pyridylmethyl)carbamoyl]benzimidazole (0.410 g) is obtained from 1-(biphenyl-4-ylmethyl)-6-carboxy-2-ethylbenzimidazole (0.500 g) (example 98), oxalyl chloride (0.356 g), 2-aminomethylpyridine (0.151 g) and triethylamine (0.424 g). $^1$H-NMR (CDCl$_3$, δ): 1.45 (3H, t, J=7.7 Hz), 2.90 (2H, q, J=7.4 Hz), 4.77 (2H, d, J=4.7 Hz), 5.43 (2H, s), 7.10 (2H, d, J=8.2 Hz), 7.20 (1H, dt, J=4.9 and 7.7 Hz), 7.33 (2H, t, J=7.4 Hz), 7.42 (2H, t, J=7.5 Hz), 7.49–7.55 (4H, m), 7.61 (1H, br t), 7.67 (1H, dt, J=7.8 and 1.8 Hz), 7.72 (1H, d, J=8.4 Hz), 7.81 (1H, d, J=8.4 Hz), 7.99 (1H, s), 8.56 (1H, d, J=4.9Hz).

IR(KBr): 1640 cm$^{-1}$.

mp: 123.0–124.0° C.

($R_1$=4-biphenyl, $R_2$=ethyl, $R_3$=—C(O)NR$_4$R$_5$, $R_4$=2-pyridylmethyl, $R_5$=H, n=1, y=1)

Example 150

1-(2-Chlorobenzyl)-6-[(2-Pyridylmethyl)Carbamoyl] Benzimidazole

By using the method of example 127, 1-(2-chlorobenzyl)-6-[(2-pyridylmethyl)carbamoyl]benzimidazole (0.110 g) is obtained from 6-carboxy-1-(2-chlorobenzyl)benzimidazole (0.461 g), oxalyl chloride (0.728 g), 2-aminomethylpyridine (0.174 g) and triethylamine (0.486g). $^1$H-NMR (CDCl$_3$, δ): 4.78 (2H, t, J=4.8 Hz), 5.51 (2H, s), 6.92 (1H, d, J=6.5 Hz), 7.17–7.31 (3H, m), 7.34 (1H, d, J=7.8 Hz), 7.45 (1H, dd, J=1.1 and 8.0 Hz), 7.69 (1H, dt, J=1.8 and 7.7 Hz), 7.67–7.73 (1H, br s), 7.76 (1H, dd, J=1.5 and 8.4 Hz), 7.87 (1H, d, J=8.4 Hz), 8.05 (2H, s), 8.57 (1H, d, J=4.9Hz).

IR(KBr): 1646 cm$^{31\ 1}$.

mp: 144.0–145.0° C.

($R_1$=2-chlorobenzyl, $R_2$=H, $R_3$=—C(O)NR$_4$R$_5$, $R_4$=2-pyridylmethyl, $R_5$=H, n=1, y 0)

Example 151

2-Methyl-1-(2-Nitrobenzyl)-6-[(2-Pyridylmethyl) Carbamoyl]Benzimidazole

By using the method of example 127, 2-methyl-1-(2-nitrobenzyl)-6-[(2-pyridylmethyl)carbamoyl]benzimidazole (0.241 g) is obtained from 6-carboxy-2-methyl-1-(2-nitrobenzyl)benzimidazole (0.367 g) (example 85), oxalyl chloride (0.299 g), 2-aminomethylpyridine (0.217 g) and triethylamine (0.360 g). $^1$H-NMR (CDCl$_3$, 6): 2.56 (3H, s), 4.75 (2H, t, J=4.8 Hz), 5.83 (2H, s), 6.41 (1H, d, J=7.8 and 1.2 Hz), 7.22 (1H, dt, J=5.0 and 1.7 Hz), 7.32 (1H, d, J=7.9 Hz), 7.43–7.52 (2H, m), 7.64 (1H, s), 7.68 (1H, dt, J=7.6 and 1.7 Hz), 7.75 (1H, dd, J=8.4 and 1.5 Hz), 7.80 (1H, d, J=8.4 Hz), 7.82 (1H, d, J=1.3 Hz), 8.28 (1H, dd, J=8.0 and 1.7 Hz), 8.56 (1H, d, J=4.9Hz).

IR(KBr): 1645 cm$^{31\ 1}$.

mp: 194.8–196.7° C.

($R_1$=2-nitrobenzyl, $R_2$=methyl, $R_3$=—C(O)NR$_4$R$_5$, $R_4$=2-pyridylmethyl, $R_5$=H, n=1, y=0)

Example 152

2-Methyl-1-(2-nitrobenzyl)-5-[(2-pyridylmethyl)carbamoyl]benzimidazole

By using the method of example 127, 2-methyl-1-(2-nitrobenzyl)-5-[(2-pyridylmethyl)carbamoyl]benzimidazole (0.079 g) is obtained from 5-carboxy-2-methyl-1-(2-nitrobenzyl)benzimidazole (0.096 g), oxalyl chloride (0.078g), 2-aminomethylpyridine (0.048 g) and triethylamine (0.093 g). $^1$H-NMR (CDCl$_3$, δ): 2.57 (3H, s), 4.80 (2H, d, J=4.7 Hz), 5.80 (2H, s), 6.43 (1H, d, J=7.4 and 0.8 Hz), 7.17 (1H, d, J=8.4 Hz), 7.22 (1H, dt, J=5.5 and 1.8 Hz), 7.35 (1H, d, J=7.8 Hz), 7.44–7.52 (2H, m), 7.67 (1H, s), 7.69 (1H, dt, J=7.8 and 1.9 Hz), 7.82 (1H, dd, J=8.4 and 1.5 Hz), 8.27 (1 H, dd, J=8.0 and 1.6 Hz), 8.28 (1H, d, J=1.4 Hz), 8.56 (1H, d, J=4.9 Hz).

IR(KBr): 1645 cm$^{-1}$.

mp: ~96° C. (accompanied with decomposition).
($R_1$=2-nitrobenzyl, $R_2$=methyl, $R_3$=—C(O)NR$_4$R$_5$, $R_4$=2-pyridylmethyl, $R_5$=H, n=1, y=0)

Example 153

1-(2-Chlorobenzyl)-2-Methyl-6-(2-Naphthalenesulfonylcarbamoyl]Benzimidazole Sodium Salt N,N'-carbonyldiimidazole (0.541 g) is added all at once to an N,N-dimethylformamide (20 ml) solution of 6-carboxy-1-(2-chlorobenzyl)-2-methylbenzimidazole (0.500 g) (example 75), and the solution is stirred for one hour at room temperature. Subsequently, an N,N-dimethylfonnamide (5 ml) solution of 2-naphthalenesulfonamide (0.689 g) and diazabicycloundecene (0.506 g) is added, and the solution is stirred for 48 hours at 100° C. The reaction solution is cooled and the solvent is removed through evaporation under reduced pressure. Water and chloroform are added to the residue. 10% hydrochloric acid is added until the aqueous layer became acidic. Chloroform extraction is performed (twice) and to the resultant organic layer, a saturated sodium bicarbonate aqueous solution is added. The solution is stirred. Precipitated crystals are separated through filtration and are dissolved in a small amount of methanol. Further, ethyl acetate is added and crystallization is performed. The crystals are separated through filtration, dried, and thus, 1-(2-chlorobenzyl)-2-methyl-6-(2-naphthalenesulfonylcarbamoyl]benzimidazole sodium salt (206) (0.508 g) is obtained.

$^1$H-NMR (DMSO-d6, δ): 2.46 (3H, s), 5.51 (2H, s), 6.38 (1H, d, J=7.9 Hz), 7.17 (1H, t, J=7.5 Hz), 7.30 (1H, t), 7.45 (1H, d, J=8.5 Hz), 7.51 -7.57 (3H, m), 7.77–7.93 (5H, m), 7.99 (1H, m), 8.35 (1H, s).

IR(KBr): 1594 cm$^{-1}$.

Mass(FAB): m/e 512(M+1).

mp: 352.0–354.5° C.
($R_1$=2-chlorobenzyl, $R_2$=methyl, $R_3$=—C(O)NR$_4$R$_5$, $R_4$=SO$_2$R$_6$, $R_5$=H, $R_6$=2-naphthyl, n=1, y=0)

Example 154

1-(2-Chlorobenzyl)-2-Methyl-6-(1-Naphthalenesulfonylcarbamoyl]Benzimidazole Sodium Salt By using the method of example 153, 1-(2-chlorobenzyl)-2-methyl-6-(1-naphthalenesulfonylcarbamoyl]benzimidazole sodium salt (0.390 g) is obtained from 6-carboxy-1-(2-chlorobenzyl)-2-methylbenzimidazole (0.600 g) (example 75), N,N'-carbonyldiimidazole (0.647 g), 1-naphthalenesulfonamide (0.829 g) and diazabicycloundecene (0.608 g). $^1$H-NMR (DMSO-d6, δ): 2.46 (3H, s), 5.49 (2H, s), 6.39 (1H, d, J=7.8 Hz), 7.16 (1H, t, J=7.5 Hz), 7.31 (1H, t, J=7.3 Hz), 7.36 (1H, t), 7.40–7.45 (2H, m), 7.50 (1H, t, J=7.7 Hz), 7.54 (1H, d, J=8.0 Hz), 7.75–7.81 (2H, m), 7.87 (1H, d, J=7.9 Hz), 7.93 (1H, d, J=8.2 Hz), 8.09 (1H, d, J=7.3 Hz), 8.86 (1H, d, J=8.5 Hz).

IR(KBr): 1633 cm$^{-1}$.

Mass(FAB): m/e 512(M+1).

mp: 265° C. (accompanied with decomposition).
($R_1$=2-chlorobenzyl, $R_2$=methyl, $R_3$=—C(O)NR$_4$R$_5$, $R_4$=SO$_2$R$_6$, $R_5$=H, $R_6$=2-naphthyl, n=1, y=0)

Example 155

6-(4-Chlorobenzenesulfonylcarbamoyl)-1-(2-Chlorobenzyl)-2-Methylbenzimidazole Sodium Salt By using the method of example 153, 6-(4-chlorobenzenesulfonylcarbamoyl)-1-(2-chlorobenzyl)-2-methylbenzimidazole sodium salt (0.270 g) is obtained from 6-carboxy-1-(2-chlorobenzyl)-2-methyl-benzimidazole (0.400 g) (example 75), N,N'-carbonyldiimidazole (0.432 g), 4-chlorobenzenesulfonamide (0.510 g) and diazabicycloundecene (0.404 g). $^1$H-NMR (DMSO-d6, δ): 2.46 (3H, s), 5.52 (2H, s), 6.38 (1H, d, J=7.4 Hz), 7.19 (1H, t, J=7.6 Hz), 7.31 (1H, t, J=7.6 Hz), 7.39 (2H, d, J=8.5 Hz), 7.45 (1H, d, J=8.9 Hz), 7.54 (1H, d, J=8.0 Hz), 7.76–7.82 (4H, m).

IR(KBr): 1592 cm$^{-1}$.

Mass(FAB): m/e 496(M+1).

mp: 360–362° C. (decomposition).
($R_1$=2-chlorobenzyl, $R_2$=methyl, $R_3$=—C(O)NR$_4$R$_5$, $R_4$=SO$_2$R$_6$, $R_5$=H, $R_6$=4-chlorophenyl, n=1, y=0)

Example 156

6-(3-Chlorobenzenesulfonylcarbamoyl)-1-(2-Chlorobenzyl)-2-Methylbenzimidazole By using the method of example 153, 6-(3-chlorobenzenesulfonylcarbamoyl)-1-(2-chlorobenzyl)-2-methylbenzimidazole sodium salt is obtained from 6-carboxy-1 -(2-chlorobenzyl)-2-methylbenzimidazole (0.450 g) (example 75), N,N'-carbonyldiimidazole (0.486 g), 3-chlorobenzene-sulfonamide (0.573 g) and diazabicycloundecene (0.456 g). This material is dissolved in a mixture solution of methanol and water. Its acidity is adjusted to pH5~6 using 10% hydrochloric acid. Precipitated crystals are separated through filtration, dried and thus, 6-(3-chlorobenzenesulfonylcarbamoyl)-1-(2-chlorobenzyl)-2-methylbenzimidazole (0.420 g) is obtained. $^1$H-NMR (DMSO-d6, δ): 2.51 (3H, s), 5.63 (2H, s), 6.48 (1H, d, J=7.7 Hz), 7.22 (1H, t, J=7.6 Hz), 7.34 (1H, t, J=7.7 Hz), 7.56 (1H, t, J=8.0 Hz), 7.64 (1H, t, J=8.0 Hz), 7.68 (1H, d, J=8.5 Hz), 7.78 (2H, t, J=8.6 Hz), 7.91 (1H, d, J=7.6 Hz), 7.95 (1H, d, J=1.6 Hz), 8.10 (1H, s).

IR(KBr): 1687 cm$^{-1}$.

Mass(FAB): m/e 474(M+1).

mp: 254.5–257.5° C. (accompanied with decomposition).
($R_1$=2-chlorobenzyl, $R_2$=methyl, $R_3$=—C(O)NR$_4$R$_5$, $R_4$=SO$_2$R$_6$, $R_5$=2-chlorophenyl, n=1, y=0)

Example 157

1-(Biphenyl-4-ylmethyl)-2-Methyl-6-[(2-Pyridylmethyl)Carbamoyl]Benzimidazole Oxalyl chloride (0.655 g) is added to a dichloromethane (13 ml) solution of 1-(biphenyl-4-ylmethyl)-6-carboxy-2-methylbenzimidazole (0.886 g) (example 88), and N,N-dimethylformamide (one drop) under ice-chilled conditions, and the solution is stirred for 15 hours at room temperature. Precipitated crystals are separated through filtration, washed with methylene chloride and dried under reduced pressure. These crystals are added to a dichloromethane (15 ml) solution of 2-aminomethylpyridine (0.235 g) and triethylamine (0.653 g) under ice-chilled conditions, and the solution is stirred for one hour. Water is added to the reaction solution and the reaction is halted. After the solution is washed with water (twice) and washed with a saturated sodium bicarbonate aqueous solution, the organic layer is dried. Then, the solvent is concentrated under reduced pressure. Recrystallization of the residue in a mixed solvent of ethyl acetate and ethanol produced 1-(biphenyl-4-ylmethyl)-2-methyl-6-[(2-pyridylmethyl)carbamoyl]benzimidazole (0.774 g). $^1$H-NMR (CDCl$_3$, δ): 2.62 (3H, s), 4.77 (2H, d, J=4.8 Hz), 5.42 (2H, s), 7.12 (2H, d, J=8.5 Hz), 7.21 (1H, m), 7.34 (2H, m), 7.42 (2H, m), 7.51–7.55 (4H, m), 7.62 (1H, br t), 7.67 (1H, dt, J=1.7 and 7.7 Hz), 7.71 (1H, dd, J=1.6 and 8.4 Hz), 7.76 (1H, d, J=8.4 Hz), 8.00, (1H, d, J=1.2 Hz), 8.56 (1H, d, J=4.8 Hz).

IR(KBr): 1642 cm$^{-1}$.

mp: 205.0–206.5° C.

($R_1$=4-biphenyl, $R_2$=methyl, $R_3$=—C(O)NR$_4$R$_5$, $R_4$=pyridylmethyl, $R_5$ H, n=1, y=1)

Example 158

6-Benzenesulfonylcarbamoyl-1-(Biphenyl-4-ylmethyl)-2-Methylbenzimidazole Sodium Salt By using the method of example 153, 6-benzenesulfonylcarbamoyl-1-(biphenyl-4-ylmethyl)-2-methylbenzimidazole sodium salt (0.365 g) is obtained from 6-carboxy-1-(biphenyl-4-ylmethyl)-2-methylbenzimidazole (0.637 g), N,N'-carbonyldiimidazole (0.533 g), benzenesulfonamide (0.516 g) and diazabicycloundecene (0.500 g). $^1$H-NMR (DMSO-d6, δ): 2.52 (3H, s), 5.52 (2H, s), 7.13 (2H, d, J=8.1 Hz), 7.31–7.37 (4H, m), 7.39–7.45 (3H, m), 7.58 -7.63 (4H, m), 7.78–7.82 (3H, m), 7.97 (1 H, s).

IR(KBr): 1591 cm$^{-1}$.

mp: 289.0–290.0° C. (accompanied with decomposition).
($R_1$=4-biphenyl, $R_2$=methyl, $R_3$=benzenesulfonylcarbamoyl, n=1, y=1)

Example 159

1-(2-Chlorobenzyl)-2-Methyl-6-Trifluoromethanesulfonylcarbamoyl-Benzimidazole Hydrochloride N,N'-carbonyldiimidazole (0.647 g) is added all at once to an N,N-dimethylformamide (20 ml) solution of 6-carboxy-1-(2-chlorobenzyl)-2-methylbenzimidazole (0.600 g) (example 75), and the solution is stirred for one hour at room temperature. Subsequently, an N,N-dimethylformamide (5 ml) solution of trifluoromethanesulfonamide (0.596 g) and diazabicycloundecene (0.609 g) is added, and the solution is stirred for 72 hours at 100° C. The reaction solution is cooled and the solvent is removed through evaporation under reduced pressure. Water and ethyl acetate are added to the residue. While being stirred, 10% hydrochloric acid is added until the aqueous layer became acidic. Precipitated crystals are washed with a mixture solvent of ethanol (25 ml) and methanol (25 ml). The crystals are dried and thus, 1-(2-chlorobenzyl)-2-methyl-6-trifluoromethanesulfonylcarbamoylbenzimidazole hydrochloride (214) (0.420 g) is obtained. $^1$H-NMR (DMSO-d6, δ): 2.84 (3H, s), 5.82 (2H, s), 7.08 (1H, d, J=7.5 Hz), 7.30 (1H, t), 7.40 (1H, t, J=7.7 Hz), 7.58 (1H, d, J=8.0 Hz), 7.79 (1H, d, J=8.6 Hz), 8.07–8.13 (2H, m).

IR(KBr): 1634 cm$^{-1}$.

Mass(CI): m/e 432(M+1-HCl).

mp: 332–335° C. (accompanied with decomposition).
($R_1$=2-chlorobenzyl, $R_2$=methyl, $R_3$=—C(O)NR$_4$R$_5$, $R_4$=SO$_2$R$_6$, $R_5$=H, $R_6$=trifluoromethyl, n=1, y=0)

Examples 160 and 161

6-Benzenesulfonylcarbamoyl-1-(2,4-Dichlorobenzyl)-2-Methylbenzimidazole Hydrochloride and 6-Benzenesulfonylcarbamoyl-1-(2,4-Dichlorobenzyl)-2-Methylbenzimidazole By using the method of example 159, 6-benzenesulfonylcarbamoyl-1 -(2,4-dichlorobenzyl)-2-methylbenzimidazole hydrochloride (0.540 g) is obtained from 6-carboxy-1-(2,4-dichlorobenzyl)-2-methylbenzimidazole (0.460 g), N,N'-carbonyldiimidazole (0.445 g), benzenesulfonamide (0.431 g) and diazabicycloundecene (0.418 g). $^1$H-NMR (DMSO-d6, δ): 2.71 (3H, s), 5.74 (2H, s), 6.83 (1H, d, J=8.4 Hz), 7.33 (1H, dd, J=2.0 and 8.4 Hz), 7.63 (2H, t), 7.71 (1H, t), 7.78 (1H, d, J=2.0 Hz), 7.86 (1H, d, J=8.7 Hz), 7.95 (1H, dd, J=1.4 and 8.7 Hz), 7.99 (2H, m), 8.29 (1H, s).

IR(KBr): 1686 cm$^{-1}$.

mp: 236.0–238.0° C.

This material is dissolved in a mixture solvent of a potassium bicarbonate aqueous solution and methanol, and its acidity is adjusted to pH5~6 with 10% hydrochloric acid. Precipitated crystals are collected, washed with water, washed with methanol, and then dried. Thus, 6-benzenesulfonylcarbamoyl-1-(2,4-dichlorobenzyl)-2-methylbenzimidazole (216). $^1$H-NMR (DMSO-d6, δ): 2.48 (3H, s), 5.58 (2H, s), 6.42 (1H, d, J=8.4 Hz), 7.31 (1H, dd, J=2.2 and 8.4 Hz), 7.60–7.75 (6H, m), 7.99 (2H, d, J=7.4 Hz), 8.06 (1H, s), 12.40 (1H, s).

IR(KBr): 1540 cm$^{-1}$.

mp: 238.2–239.9° C.
($R_1$=2,4-dichlorobenzyl, $R_2$=methyl, $R_3$=—C(O)NR$_4$R$_5$, $R_4$=SO$_2$R$_6$, $R_5$=H, $R_6$=phenyl, n=1, y=0)

Example 162

1-(2-Chlorobenzyl)-6-(4-Methoxybenzenesulfonylcarbamoy)-2-Methylbenzimidazole

N,N'-carbonyldiimidazole (0.431 g) is added all at once to an N,N-dimethylformamide (15 ml) solution of 6-carboxy-1-(2-chlorobenzyl)-2-methylbenzimidazole (0.400 g) (example 75), and the solution is stirred for one hour at room temperature. Subsequently, an N,N-dimethylformamide (5 ml) solution of 4-methoxybenzenesulfonamide (0.498 g) and diazabicycloundecene (0.405 g) is added, and the solution is stirred for 67 hours at 100° C. The reaction solution is cooled and the solvent is removed through evaporation under reduced pressure. Water and chloroform are added to the residue. While being stirred, 10% hydrochloric acid is added until the aqueous layer became acidic. The organic layer, which is obtained through chloroform extraction (twice), is washed with a saturated sodium bicarbonate aqueous solution, and the solvent is removed through evaporation under reduced pressure. After purification using silica gel column chromatography (eluate: chloroform/methanol=100/2~100/10) and then concentration, crystals are formed in a mixture solution of ethyl acetate and diethylether. The crystals are separated through filtration, dried, and thus, 1-(2-chlorobenzyl)-6-(4-methoxybenzenesulfonylcarbamoyl)-2-methylbenzimidazole (0.450 g) is obtained.

$^1$H-NMR (DMSO-d6, δ): 2.46 (3H, s), 3.83 (2H, s), 5.58 (2H, s), 7.12 (2H, d, J=9.0 Hz), 7.21 (1H, t, J=7.3 Hz), 7.33 (1H, t), 7.56 (1H, d, J=7.0 Hz), 7.63 (1H, d, J=8.5 Hz), 7.71 (1H, dd, J=1.6 and 8.5 Hz), 7.91 (2H, d, J=9.0 Hz), 8.05 (1H, d, J=1.3 Hz).

IR(KBr): 1683 cm$^{-1}$.

Mass(FAB): m/e 470(M+1).

mp: 271.0–274.0° C.

($R_1$=2-chlorobenzyl, $R_2$=methyl, $R_3$=—C(O)NR$_4$R$_5$, $R_4$=SO$_2$R$_6$, $R_5$ H, $R_6$=4-methoxyphenyl, n=1, y=0)

Example 163

1-(2-Chlorobenzyl)-2-Methyl-6-(α-Toluenesulfonylcarbamoyl)Benzimidazole

By using the method of example 162, 1-(2-chlorobenzyl)-2-methyl-6-(α-toluenesulfonylcarbamoyl)benzimidazole (0.350 g) is obtained from 6-carboxy-1-(2-chlorobenzyl)-2-methylbenzimidazole (0.450 g) (example 75), N,N'-carbonyldiimidazole (0.485 g), α-toluenesulfonamide (0.512 g) and diazabicycloundecene (0.456 g). $^1$H-NMR (DMSO-d6, δ): 2.48 (3H, s), 4.36 (2H, s), 5.53 (2H, s), 6.40 (1H, d, J=6.8 Hz), 7.15–7.28 (6H, t), 7.32 (1H, t), 7.49 (1H, d, J=8.3 Hz), 7.55 (1H, d), 7.83–7.87 (2H, m).

IR(KBr): 1593 cm$^{-1}$.

Mass(FAB): m/e 454(M+1).

mp: 193–196° C. (foam).

($R_1$=2-chlorobenzyl, $R_2$=methyl, $R_3$=—C(O)NR$_4$R$_5$, $R_4$=SO$_2$R$_6$, $R_5$=H, $R_6$=2-toluene, n=1, y=0)

Example 164

1-(2-Chlorobenzyl)-6-(2,5-Dimethylbenzenesulfonylcarbamoyl)-2-Methylbenzimidazole

By using the method of example 162, 1-(2-chlorobenzyl)-6-(2,5-dimethylbenzenesulfonylcarbamoyl)-2-methylbenzimidazole (0.490 g) is obtained from 6-carboxy-1-(2-chlorobenzyl)-2-methylbenzimidazole (0.500 g) (example 75), N,N'-carbonyldiimidazole (0.539 g), 2,5-xylenesulfonamide (0.616 g) and diazabicycloundecene (0.506 g). $^1$H-NMR (DMSO-d6, δ): 2.35 (3H, s), 2.48 (3H, s), 2.51 (3H, s), 5.58 (2H, s), 6.45 (1H, d, J=7.5 Hz), 7.20–7.27 (2H, m), 7.31–7.39 (2H, m), 7.56 (1H, d, J=8.0 Hz), 7.64 (1H, d, J=8.5 Hz), 7.75 (1H, d, J=8.5 Hz), 7.82 (2H, s), 8.06 (1H, s), 12.45 (1H, br s).

IR(KBr): 1690 cm$^{-1}$.

Mass(FAB): m/e 468(M+1).

mp: 266.5–267.5° C.

($R_1$=2-chlorobenzyl, $R_2$=methyl, $R_3$=—C(O)NR$_4$R$_5$, $R_4$=SO$_2$R$_6$, $R_5$=H, $R_6$=2,5-dimethylphenyl, n=1, y=0)

Example 165

1-(2-Chlorobenzyl)-2-Methyl-6-(4-Nitrobenzenesulfonylcarbamoyl)Benzimidazole

N,N'-carbonyldiimidazole (0.432 g) is added all at once to an N,N-dimethylformamide (15 ml) solution of 6-carboxy-1-(2-chlorobenzyl)-2-methylbenzimidazole (0.432 g) (example 75), and the solution is stirred for one hour at room temperature. Subsequently, an N,N-dimethylformamide (5 ml) solution of 4-nitrobenzenesulfonamide (0.538 g) and diazabicyclotindecene (0.405 g) is added, and the solution is stirred for 84 hours at 100° C. The reaction solution is cooled and the solvent is removed through evaporation under reduced pressure. When chloroform and hydrochloric acid are added to the residue and the solution is stirred, crystals precipitated. The crystals are separated through filtration, dried, and thus, 1-(2-chlorobenzyl)-2-methyl-6-(4-nitrobenzenesulfonylcarbamoyl)benzimidazole (0.300 g) is obtained.

$^1$H-NMR (DMSO-d6, δ): 2.56 (3H, s), 5.65 (2H, s), 6.54 (1H, d, J=7.6 Hz), 7.23 (1H, t, J=7.6 Hz), 7.34 (1H, t, J=7.6 Hz), 7.56 (1H, t, J=8.0 Hz), 7.68 (1H, d, J=8.5 Hz), 7.83 (1H, d, J=8.3 Hz), 8.07 (1H, s), 8.16 (2H, d, J=8.7 Hz), 8.37 (2H, d, J=8.7 Hz).

IR(KBr): 1621 cm$^{-1}$.

Mass(FAB): m/e 485(M+1).

mp: 330–332° C.

($R_1$=2-chlorobenzyl, $R_2$=methyl, $R_3$=—C(O)NR$_4$R$_5$, $R_4$=SO$_2$R$_6$, $R_5$=H, $R_6$=4-nitrophenyl, n=1, y=0)

Example 166

1-(2-Chlorobenzyl)-2-Methyl-6-[4(Trifluoromethyl)Benzenesulfonylcarbamoyl]Benzimidazole

By using the method of example 162, 1-(2-chlorobenzyl)-2-methyl-6-[4-(trifluoromethyl)benzenesulfonylcarbamoyl]benzimidazole (0.390 g) is obtained from 6-carboxy-1-(2-chlorobenzyl)-2-methylbenzimidazole (0.450 g) (example 75), N,N'-carbonyldiimidazole (0.486 g), 4-(trifluoromethyl)benzenesulfonamide (0.676 g) and diazabicycloundecene (0.457 g). $^1$H-NMR (DMSO-d6, δ): 2.52 (3H, s), 5.62 (2H, s), 6.47 (1H, d, J=7.2 Hz), 7.22 (1H, t, J=7.5 Hz), 7.34 (1H, t), 7.56 (1H, d, J=8.0 Hz), 7.66 (1H, d, J=8.5 Hz), 7.78 (1H, d), 7.97 (2H, d, J=8.3 Hz), 8.06 (1H, s), 8.15 (2H, d, J=8.3 Hz).

IR(KBr): 1620 cm$^{-1}$.

Mass(FAB): m/e 508(M+1).

mp: 288.0–292.0° C.

($R_1$=2-chlorobenzyl, $R_2$=methyl, $R_3$=—C(O)NR$_4$R$_5$, $R_4$=SO$_2$R$_6$, $R_5$=H, $R_6$4-trifluoromethylphenyl, n=1, y=0)

Example 167

6-(2-Chlorobenzenesulfonylcarbamoyl)-1-(2-Chlorobenzyl)-2-Methylbenzimidazole Ammonium Salt

N,N'-carbonyldiimidazole (0.485 g) is added all at once to an N,N-dimethylformamide (15 ml) solution of 6-carboxy-1-(2-chlorobenzyl)-2-methylbenzimidazole (0.450 g) (example 75), and the solution is stirred for one hour at room temperature. Subsequently, an N,N-dimethylformamide (5 ml) solution of trifluoromethanesulfonamide (0.575 g) and diazabicycloundecene (0.457 g) is added, and the solution is stirred for 72 hours at 100° C. The reaction solution is cooled and the solvent is removed under reduced pressure. Water and ethyl acetate are added to the residue. As it is being stirred, 10% hydrochloric acid is added until the water layer became acidic. Precipitated crystals are separated through filtration. The crystals are then dissolved in ethanol and then aqueous ammonia is added to adjust the acidity to pH 7. Furthermore, diisopropyl ether is added. Precipitated crystals are separated through filtration, then dried and thus, 6-(2-chlorobenzenesulfonylcarbamoyl)-1-(2-chlorobenzyl) 2-methylbenzimidazole ammonium salt (0.360 g) is obtained. $^1$ $^1$H-NMR (DMSO-d6, δ): 2.47 (3H, s), 5.51 (2H, s), 6.43 (1H, d, J=7.5 Hz), 7.12 (4H, br s), 7.19 (1H, t, J=7.6 Hz), 7.28–7.38 (4H, m), 7.46 (1H, d, J=8.3 Hz), 7.53 (1H, d, J=7.9 Hz), 7.78–7.82 (2H, m), 7.97 (1H, m).

IR(KBr): 1590 cm$^{-1}$.

Mass (FAB): m/e 474(M+1-NH3).

mp: 264.0–267.0° C.

($R_1$=2-chlorobenzyl, $R_2$=methyl, $R_3$=—C(O)$NR_4R_5$, $R_4$=$SO_2R_6$, $R_5$=H, $R_6$2-chlorophenyl, n=1, y=0)

Example 168

6-Carbamoyl-1-(2,4-Dichlorobenzyl)-2-Methylbenzimidazole

Oxylyl chloride (0.437 g) is added to a methylene chloride (8 ml) solution of 6-carboxy-1-(2,4-dichlorobenzyl)-2-methylbenzimidazole (0.490 g) and N,N-dimethylformamide (1 drop) under ice-chilled conditions, and the solution is stirred for 1.5 hours at room temperature. Then, 28% aqueous ammonia (4 ml) is added and the solution is stirred for 12 hours at room temperature. Water and methylene chloride are added to the reaction solution for extraction. After the organic layer is concentrated, precipitated crystals are collected, dried and 6-carbamoyl-1-(2,4-dichlorobenzyl)-2-methylbenzimidazole (0.240 g) is obtained. $^1$H-NMR (DMSO-d6, δ): 2.48 (3H, s), 5.54 (2H, s), 6.41 (1H, d, J=8.4 Hz), 7.21–8.02 (3H, m), 7.31 (1H, dd, J=2.2 and 8.4 Hz), 7.60 (1H, d, J=8.4 Hz), 7.75 (1H, m), 7.93 (1H, s).

IR(KBr): 1666 cm$^{-1}$.

mp: 112.0–114.0° C.

($R_1$=2,4-dichlorobenzyl, $R_2$=methyl, $R_3$ carbamoyl, n=1, y=0)

Example 169

6-Benzenesulfonylcarbamoyl-1-(Biphenyl-4-ylmethyl)-2-Methoxybenzimidazole

A.) N-Benzenesulfonyl-4-amino-3-(biphenyl-4-ylmethylamino)benzamide Potassium Salt 5% Palladium/carbon (0.64 g) is added to a mixture of N-benzenesulfonyl-3-(biphenyl-4-ylmethylamino)-4-nitrobenzamide potassium salt (4.27 g), 20% potassium bicarbonate aqueous solution (10.7 g), and methanol (200 ml). The solution is then stirred for 14 hours at 35° C. under a hydrogen environment. The precipitated crystals are dissolved when a mixture solution of acetone and water (acetone/water=5/2, 400 ml) is added and its solids are separated through filtration. The filtrate is concentrated, the precipitated crystals are separated through filtration and dried, and thus, N-benzenesulfonyl-4-amino-3-(biphenyl-4-ylmethylamino)benzamide potassium salt (3.15 g) is obtained. $^1$H-NMR (DMSO-d6, δ): 4.31 (2H, d, J=5.7 Hz), 4.85 (2H, s), 4.91 (1H, br t, J=5.7 Hz), 6.45 (1H, d, J=7.9 Hz), 7.07 (1H, s), 7.13 (1H, d, J=7.9 Hz), 7.29–7.36 (4H, m), 7.43–7.47 (4H, m), 7.60 (2H, d, J=8.1 Hz), 7.65 (2H, d, J=7.6 Hz), 7.73–7.76 (2H, m).

IR (Nujol): 1574 cm$^{-1}$.

B.) 6-Benzenesulfonylcarbamoyl-1-(Biphenyl-4-ylmethyl)-2-Methoxybenzimidazole

Tetramethoxymethane (0.250 g) is added to an acetic acid solution (3 ml) of N-benzenesulfonyl-4-amino-3-(biphenyl-4-ylmethylamino)benzamide (0.400 g), and the solution is stirred for two hours at 80° C. Methanol is added to the reaction solution, and precipitated crystals are collected. The crystals are washed in a mixture solvent of acetone (1 ml) and methanol (8 ml), separated through filtration, dried and thus, 6-benzenesulfonylcarbamoyl-1-(biphenyl-4-ylmethyl)-2-methoxybenzimidazole (0.280 g) is obtained. $^1$H-NMR (DMSO-d6, δ): 4.17 (3H, s), 5.33 (2H, s), 7.30 (2H, d, J=8.2 Hz), 7.35 (1H, t, J=7.4 Hz), 7.44 (2H, t, J=7.5 Hz), 7.50 (1H, d, J=8.4 Hz), 7.60–7.65 (6H, m), 7.68–7.72 (2H, m), 7.98–8.01 (2H, m), 8.05 (1H, d, J=1.5 Hz), 8.18 (1H, s), 12.50 (1H, s).

IR(KBr): 1690 cm$^{-1}$.

mp: 136.0–138.5° C.

($R_1$=4-biphenyl, $R_2$=methoxy, $R_3$=—C(O)$NR_4R_5$, $R_4$=$SO_2R_6$, $R_5$=H, $R_6$=phenyl, n=1, y=1)

Example 170

6-Benzenesulfonylcarbamoyl-1-(Biphenyl-4-ylmethyl)-2-carboxybenzimidazole

Triethylamine (0.080 g) and methyloxalyl chloride (0.148 g) are added to an N,N-dimethylformamide (3 ml) solution of N-benzenesulfonyl-4-amino-3-(biphenyl-4-ylmethylamino)benzamide (0.400 g) (example 169, part A), and the solution is stirred for two hours at room temperature. The reaction solution is concentrated and the residue is purified using silica gel column chromatography (eluate: ethyl acetate/methanol=9/1) and preliminarily purified 6-benzenesulfonylcarbamoyl-1-(biphenyl-4-ylmethyl)-2-carboxybenzimidazole is obtained. This is dissolved in acetic acid (1 ml) and methanol (5 ml) and the solution is stirred for 15 hours at 60° C. The solution is neutralized with a potassium hydroxide aqueous solution. Precipitated crystals are separated through filtration, dried and thus, 6-benzenesulfonylcarbamoyl-1-(biphenyl-4-ylmethyl)-2-carboxybenzimidazole (0.245 g) is obtained. $^1$H-NMR (DMSO-d6, δ): 5.44 (2H, s), 7.23 (1H, d, J=8.4 Hz), 7.36 (1H, t, J=7.6 Hz), 7.41 (2H, d, J=8.1 Hz), 7.45 (2H, t, J=7.5 Hz), 7.58 (2H, t, J=7.8 Hz), 7.60–7.71 (7H, m), 7.94 (2H, d, J=8.3 Hz), 12.38 (1H, s), 12.52 (1H, s).

IR(KBr): 1670 cm$^{-1}$.

mp: 247.5–250.0° C.

($R_1$=4-biphenyl, $R_2$=carboxyl, $R_3$=—C(O)$NR_4R_5$, $R_4$=$SO_2R_6$, $R_5$=H, $R_6$=phenyl, n=1, y=1)

Example 171

6-Benzenesulfonylcarbamoyl-1-(Biphenyl-4-ylmethyl)-2-Methylaminobenzimidazole A mixture of N-benzenesulfonylcarbamoyl-4-amino-3-(biphenyl-4-ylmethylamino)benzamide (0.300 g), methylisothiocyanate (0.200 g), methanol (5 ml) and acetone (5 ml) is stirred for twelve hours at room temperature. Furthermore, 97% sulfuric acid (1 ml) is added and the solution is stirred for 43 hours at room temperature. After the reaction solution is made basic by adding 20% potassium bicarbonate aqueous solution, the solution is concentrated and the residue is extracted with ethyl acetate and water. An organic layer is concentrated and dissolved in chloroform. Hexane is added to the solution. Precipitated crystals are separated through filtration, dried and thus, 6-benzenesulfonylcarbamoyl-1-(biphenyl-4-ylmethyl)-2-methylaminobenzimidazole 0.140 g) is obtained. $^1$H-NMR (DMSO-d6, δ): 2.98 (3H, d, J=4.4 Hz), 5.34 (2H, s), 7.22 (2H, d, J=8.2 Hz), 7.26 (1H, d, J=8.4 Hz), 7.34 (1H, t, J=7.3 Hz), 7.44 (2H, t, J=7.5 Hz), 7.57 (2H, t, J=7.6 Hz), 7.59–7.68 (6H, m), 7.76 (1H, s), 7.95 (2H, d, J=7.4 Hz), 12.28 (1H, s).

IR(KBr): 1672 cm$^{-1}$.

mp: 225.0–228.0° C.

($R_1$=4-biphenyl, $R_2$=methylamino, $R_3$=—C(O)NR$_4$R$_5$, $R_4$=SO$_2$R$_6$, $R_5$=H, $R_6$=phenyl, n=1, y=1)

Example 172

2-Amino-6-Benzenesulfonylcarbamoyl-1-(Biphenyl-4-ylmethyl)Benzimidazole

Methanol (10 ml), acetone (10 ml), and bromocyanogen (0.395 g) are added to N-benzenesulfonylcarbamoyl-4-amino-3-(biphenyl-4-ylmethylamino)benzaamide (0.395 g). The solution is stirred for 100 hours at room temperature and 30 hours at 50° C. Chloroform and water are added and an extraction is performed. An organic layer is washed with water (6 times), and concentrated. The residue is purified using silica gel column chromatography (eluate: ethyl acetate/methanol=9/1) and thus, 2-amino-6-benzenesulfonylcarbamoyl-1-(biphenyl-4-ylmethyl) benzimidazole (0.135 g) is obtained. $^1$H-NMR (DMSO-d6, δ): 5.32 (2H, s), 6.77 (2H, s), 7.05 (1H, d, J=8.8 Hz), 7.21 (2H, d, J=8.3 Hz), 7.31–7.38 (4H, m), 7.43 (2H, t, J=7.5 Hz), 7.58–7.65 (6H, m), 7.79–7.82 (2H, m).

IR(KBr): 1684 cm$^{-1}$.

Mass(FAB): m/e 483(M+1).

mp: 352.5–355.0° C.

($R_1$=4-biphenyl, $R_2$=amino, $R_3$=—C(O)NR$_4$R$_5$, $R_4$=SO$_2$R$_6$, $R_5$=H, $R_6$=phenyl, n=1, y=1)

Example 173

6-Benzenesulfonylcarbamoyl-1-(Biphenyl-4-ylmethyl)-2-n-Propylbenzimidazole Potassium Salt Triethylamine (0.060 g) and butyryl chloride (0.084 g) are added to an N,N-dimethylformamide (2 ml) solution of N-benzenesulfonyl-4-amino-3-(biphenyl-4-ylmethylamino) benzamide (0.300 g). The solution is stirred for 1.5 hours at room temperature. The reaction solution is purified of itself using silica gel column chromatography Chloroform and N-benzenesulfonyl-3-(biphenyl-4-ylmethylamino)-4-butyrylaminobenzamide (0.250 g) is obtained. Methanol (5 ml) and 35% hydrochloric acid (0.50 g) are added to this and the solution is stirred for three hours at 60° C. The reaction is halted by adding 20% potassium bicarbonate. Extraction is performed with ethyl acetate and water. An organic layer is concentrated and the formed material is dissolved in a small amount of chloroform. By adding ether, crystallization is performed. The crystals are separated through filtration, dried and thus, 6-benzenesulfonyl-carbamoyl-1-(biphenyl-4-ylmethyl)-2-n-propylbenzimidazole Potassium Salt (0.157 g) is obtained. $^1$H-NMR (DMSO-d6, δ): 0.95 (3H, t, J=7.4 Hz), 1.77 (2H, q, J=7.5 Hz), 2.82 (2H, t, J=7.5 Hz), 5.55 (2H, s), 7.11 (2H, d, J=8.2 Hz), 7.32–7.38 (4H, m), 7.43 (2H, t, J=7.5 Hz), 7.47 (1H, d, J=8.4 Hz), 7.58–7.64 (4H, m), 7.79–7.83 (3H, m), 7.96 (1H, s).

IR(Nujol): 1592 cm$^{-1}$.

Mass(FAB): m/e 548(M+1).

mp: 279.0–282.0° C.

($R_1$=4-biphenyl, $R_2$=n-propyl, $R_3$=—C(O)NR$_4$R$_5$, $R_4$=SO$_2$R$_6$, $R_5$=H, $R_6$=phenyl, n=1,y=1)

Example 174

6-Benzenesulfonylcarbamoyl-1-(Biphenyl-4-ylmethyl)-2-n-Butylbenzimidazole

By using the method of of example 173, 6-benzenesulfonylcarbamoyl-1-(biphenyl-4-ylmethyl)-2-n-butylbenzimidazole (0.232 g) is obtained from N-benzenesulfonyl-4-amino-3-(biphenyl-4-ylmethylamino) benzamide (0.400 g), triethylamine (0.080 g), and oxtanoyl chloride (0.170 g). $^1$H-NMR (DMSO-d6, δ): 0.79 (3H, t, J=7.3 Hz), 1.12–1.24 (6H, m), 1.24–1.31 (2H, m), 1.66–1.73 (2H, m), 2.84 (2H, t, J=7.6 Hz), 5.58 (2H, s), 7.14 (2H, d, J=8.1 Hz), 7.34 (2H, t, J=7.6 Hz), 7.43 (2H, t, J=7.4 Hz), 7.52–7.66 (7H, m), 7.75 (1H, d, J=8.8 Hz), 7.95 (2H, d, J=7.6 Hz), 8.15 (1H, s), 12.45 (1H, s).

IR(KBr): 1688 cm$^{-1}$.

mp: 112.0–117.5° C.

($R_1$=4-biphenyl, $R_2$=n-butyl, $R_3$=—C(O)NR$_4$R$_5$, $R_4$=SO$_2$R$_6$, $R_5$=H, $R_6$=phenyl, n=1, y=1)

Example 175

6-Benzenesulfonylcarbamoyl-1-(Biphenyl-4-ylmethyl)-2-Chloromethylbenzimidazole

By using the method of of example 173, 6-benzenesulfonylcarbamoyl-1-(biphenyl-4-ylmethyl)-2-chloromethylbenzimidazole (0.193 g) is obtained from N-benzenesulfonyl-4-amino-3-(biphenyl-4-ylmethylamino) benzamide (0.300 g), triethylamine (0.060 g), and chloro-acetyl chloride (0.102 g). $^1$H-NMR (DMSO-d6, δ): 5.10 (2H, s), 5.71 (2H, s), 7.23 (2H, d, J=8.3 Hz), 7.23 (2H, d, J=8.3 Hz), 7.35 (1H, t, J=7.3 Hz), 7.44 (2H, t, J=7.5 Hz), 7.60–7.66 (6H, m), 7.69 (1H, t, J=7.5 Hz), 7.75–7.81 (2H, m), 7.98–8.01 (2H, m), 8.16 (1H, s), 12.52 (1H, s).

IR(KBr): 1700 cm$^{-1}$.

mp: 220.5–223.5° C.

($R_1$=4-biphenyl, $R_2$=chloromethyl, $R_3$=—C(O)NR$_4$R$_5$, $R_4$=SO$_2$R$_6$, $R_5$=H, $R_6$=phenyl, n=1, y=1)

Example 176

6-Benzenesulfonylcarbamoyl-1-(Biphenyl-4-ylmethyl)-2-Methoxymethylbenzimidazole

By using the method of of example 173, 6-benzenesulfonylcarbamoyl-1-(biphenyl-4-ylmethyl)-2-methoxymethylbenzimidazole (0.183 g) is obtained from N-benzenesulfonyl-4-amino-3-(biphenyl-4-ylmethylamino) benzamide (0.400 g), triethylamine (0.115 g), and methoxy-acetyl chloride (0.131 g). $^1$H-NMR (DMSO-d6, δ): 3.31 (3H, s), 4.72 (2H, s), 5.63 (2H, s), 7.23 (2H, d, J=8.3 Hz), 7.35 (1H, t, J=7.4 Hz), 7.44 (2H, t, J=7.5 Hz), 7.60–7.65 (6H, m), 7.70 (1H, t, J=7.5 Hz), 7.72–7.79 (2H, m), 7.98–8.01 (2H, m), 8.18 (1H, s), 12.50 (1H, s).

IR(KBr): 1690 cm$^{-1}$.

mp: 195.0–198.0° C.

($R_1$=4-biphenyl, $R_2$=methoxymethyl, $R_3$=—C(O)NR$_4$R$_5$, $R_4$=SO$_2$R$_6$, $R_5$=H, $R_6$=phenyl, n=1, y=1)

Example 177

6-Benzenesulfonylcarbamoyl-1-(Biphenyl-4-ylmethyl)-2-i-Propylbenzimidazole Potassium Salt By using the method of of example 173, N-benzenesulfonyl-4-amino-3-(biphenyl-4-ylmethylamino) benzamide (0.400 g), triethylamine (0.080 g), and isobutyryl chloride (0.121 g) are reacted as source materials. The preliminarily purified material is dissolved in a mixture solvent of methanol and 20% potassium bicarbonate aqueous solution. The solution's acidity is adjusted to pH 7 with 10% hydrochloric acid. Precipitated crystals are found to be 6-benzenesulfonylcarbamoyl-1-(biphenyl-4-ylmethyl)-2-i- propylbenzimidazole Potassium Salt (0.167 g). $^1$H-NMR (DMSO-d6, δ): 1.26 (6H, d, J=6.8 Hz), 3.25–3.40 (1H, m), 5.58 (2H, s), 7.09 (2H, d, J=8.3 Hz), 7.32–7.37 (4H, m), 7.43 (2H, t, J=7.5 Hz), 7.48 (1H, d, J=8.4 Hz), 7.58–7.64 (4H, m), 7.79–7.83 (3H, m), 7.95 (1H, s).

IR(Nujol): 1592 cm$^{-1}$.

Mass(FAB): m/e 548(M+1).

mp: 310.1–312.7° C.

($R_1$=4-biphenyl, $R_2$=i-propyl, $R_3$=—C(O)NR$_4$R$_5$, $R_4$=SO$_2$R$_6$, $R_5$=H, $R_6$=phenyl, n=1,y=1)

Example 178

6-Benzenesulfonylcarbamoyl-1-(Biphenyl-4-ylmethyl)Benzimidazole

A mixture of N-benzenesulfonyl-4-amino-3-(biphenyl-4-ylmethylamino) benzamide (0.400 g) and formic acid (2 ml) is stirred for three hours at 90° C. The reaction solution is concentrated. The crystals which precipitated by adding methanol are separated through filtration, dried and thus, 6-benzenesulfonylcarbamoyl-1-(biphenyl-4 -ylmethyl)benzimidazole (0.243 g) is obtained. $^1$H-NMR (DMSO-d6, δ): 5.60 (2H, s), 7.35 (1H, t, J=7.2 Hz), 7.39 (2H, d, J=8.2 Hz), 7.44 (2H, t, J=7.6 Hz), 7.61–7.77 (9H, m), 8.00 (2H, d, J=7.7 Hz), 8.26 (1H, s), 8.66 (1H, s), 12.5 (1H, s).

IR(KBr): 1683 cm$^{-1}$.

mp: 141.5–143.6° C.

($R_1$=4-biphenyl, $R_2$=H, $R_3$=—C(O)NR$_4$R$_5$, $R_4$=SO$_2$R$_6$, $R_5$=H, $R_6$=phenyl, n=1, y=1)

Example 179

1-(4-Benzyloxybenzyl-2-Methyl-6-[(2-Pyridylmethyl)Carbamoyl]Benzimidazole

Acetic acid (4 ml) and ethanol (8 ml) are added to an N-(2-pyridylmethyl)-4-acetylamino-3-(4-benzyloxybenzylamino)benzamide (0.434 g) and the solution is stirred for seven hours at 90° C. Residue is obtained by reduced pressure condensation. By adding ethyl acetate and ether to the residue, crystallization is performed. The crystals are separated through filtration, dried and thus, 1-(4-benzyloxybenzyl)-2-methyl-6-[(2-pyridylmethyl)carbamoyl]benzimidazole (0.375 g) is obtained. $^1$H-NMR (DMSO-d6, δ): 2.59 (3H, s), 4.78 (2H, d, J=4.8 Hz), 5.01 (2H, s), 5.31 (2H, s), 6.89 (2H, d, J=8.7 Hz), 6.99 (2H, d, J=8.6 Hz), 7.21 (1H, dd, J=5.1 and 7.4 Hz), 7.29–7.42 (6H, m), 7.62 (1H, br t), 7.65–7.75 (3H, m), 7.98 (1H, s), 8.57 (1H, d, J=4.1 Hz).

IR(KBr): 1640 cm$^{-1}$.

mp: 169.0–170.0° C.

($R_1$=4-benzyloxybenzyl, $R_2$=methyl, $R_3$=—C(O)NR$_4$R$_5$, $R_4$=pyridylmethyl, $R_5$=H, n=1, y=0)

Example 180

2-Methyl-1-(3,4-Methylenedioxybenzyl)-6-[(2-Pyridylmethyl)Carbamoyl]Benzimidazole Acetic acid (2 ml) and ethanol (5 ml) are added to an N-(2-pyridylmethyl)-4-acetylamino-3-(3,4-methylenedioxybenzylamino)benzamide (0.490 g) and the solution is stirred for eight hours at 70° C. The residue obtained by reduced pressure condensation is purified using silica gel column chromatography (eluate: ethyl acetate/ methanol=9/1), and crystallization is performed in ethyl acetate. The crystals are separated through filtration, dried and thus, 2-methyl-1-(3,4-methylenedioxybenzyl)-6-[(2-pyridylmethyl)carbamoyl]benzimidazole (0.270 g) is obtained. $^1$H-NMR (CDCl$_3$, δ): 2.59 (3H, s), 4.78 (2H, d, J=4.8 Hz), 5.28 (2H, s), 5.93 (2H, s), 6.51 (1H, d, J=1.6 Hz), 6.55 (1H, dd, J=1.4 and 7.9 Hz), 6.72 (2H, d, J=8.0 Hz), 7.22 (1H, dd, J=6.7 and 5.0 Hz), 7.34 (1H, d, J=7.7 Hz), 7.62 (1H, br t), 7.67–7.75 (3H, m), 7.96 (1H, d, J=1.1 Hz), 8.58 (1H, d, J=4.9 Hz).

IR(KBr): 1637 cm$^{-1}$.

mp: 190.5–192.0° C.

($R_1$=3,4-methylenedioxybenzyl, $R_2$=methyl, $R_3$=—C(O)NR$_4$R$_5$, $R_4$=2-pyridylmethyl, $R_5$=H, n=1, y=0)

Example 181

2-Methyl-6-[(2-Pyridylmethyl)Carbamoyl]-1-[4-(1,2,3-Thiadiazole-4-yl)Benzyl]Benzimidazole By using the method of example 179, 2-methyl-6-[(2-pyridylmethyl)carbamoyl]-1-[4-(1,2,3-thiadiazole-4-yl) benzyl]benzimidazole (0.33 g) is obtained from N-(2-pyridylmethyl)-4-acetylamino-3-[4-(1,2,3-thiadiazole-4-yl) benzylamino]benzamide (0.50 g). $^1$H-NMR (CDCl$_3$, δ): 2.58 (3H, s), 4.58 (2H, d, J=5.9 Hz), 5.62 (2H, s), 7.24 (1H, dd, J=7.3 and 5.0 Hz), 7.28–7.33 (3H, m), 7.64 (1H, d, J=8.4 Hz), 7.73 (1H, dd, J=7.7 and 1.6 Hz), 7.81 (1H, dd, J=8.4 and 1.3 Hz), 8.10 (1H, d, J=8.2 Hz), 8.13 (1H, s), 8.49 (1H, d, J=4.2 Hz), 9.04 (1H, t, J=5.9 Hz), 9.58 (1H, s).

IR(KBr): 1642 cm$^{-1}$.

mp: 216.0–217.0° C.

($R_1$=4-(1,2,3-thiadiazole-4-yl)benzyl, $R_2$=methyl, $R_3$=—C(O)NR$_4$R$_5$, $R_4$=pyridylmethyl, $R_5$=H, n=1, y=0)

Example 182

6-Benzenesulfonylcarbamoyl-1-(2,4-Difluorobenzyl)-2-Methylbenzimidazole

N-benzenesulfonyl-4-acetylamino-3-(2,4-difluorobenzylamino)benzamide (0.370 g) is added to a mixture solvent of 10% hydrochloric acid (3.3 g), methanol (6 ml), and water (4 ml). Furthermore, 35% hydrochloric acid (0.5 g) is added and the solution is stirred for three hours at 60° C. After 20% potassium bicarbonate aqueous solution is added to turn the reaction solution into a basic, its acidity is adjusted to pH 5~6 with 10% hydrochloric acid. Precipitated crystals are separated through filtration, dried and thus, 0.182 g of 6-benzenesulfonylcarbamoyl-1-(2,4-difluorobenzyl)-2-methyl-benzimidazole is obtained. $^1$H-NMR (DMSO-d6, δ): 2.53 (3H, s), 5.56 (2H, s), 6.95–7.01 (1H, m), 7.04 (1H, dt, J=8.7 and 1.4 Hz), 7.32 (1H, dt, J=10.7 and 2.1 Hz), 7.59–7.66 (3H, m), 7.68–7.74 (2H, m), 8.00 (2H, d, J=8.1 Hz), 8.13 (1H, s), 12.43 (1H, s).

IR(KBr): 1686 cm$^{-1}$.

mp: 234.5–235.5° C. (accompanied by decomposition).

($R_1$=2,4-difluorobenzyl, $R_2$=methyl, $R_3$=—C(O)NR$_4$R$_5$, $R_4$=SO$_2$R$_6$, $R_5$=H, $R_6$=phenyl, n=1, y=0)

Example 183

6-Benzenesulfonylcarbamoyl-2-Methyl-1-(2-Nitrobenzyl)Benzimidazole

By using the method of example 182, 6-benzenesulfonyl-carbamoyl-2-methyl-1-(2-nitrobenzyl)benzimidazole (0.237 g) is obtained from N-benzenesulfonyl-4-acetylamino-3-(2-nitrobenzylamino)benzamide (0.79 g). $^1$H-NMR (DMSO-d6, δ): 2.48 (3H, s), 5.01 (2H, s), 5.93 (2H, s), 6.28–6.30

(1H, m), 7.55–7.62 (4H, m), 7.64–7.74 (3H, m), 7.97 (2H, d, J=8.0 Hz), 8.10 (1H, s), 8.22–8.28 (1H, m), 12.39 (1H, s).

IR(KBr): 1686 cm$^{-1}$.

mp: 269.5–272.5° C. (accompanied by decomposition).

($R_1$=2-nitrobenzyl, $R_2$=methyl, $R_3$=—C(O)NR4R$_5$, $R_4$=SO$_2$R$_6$, $R_5$=H, $R_6$=phenyl, n=1, y=0)

Example 184

6-Benzenesulfonylcarbamoyl-2-Methyl-1-Benzylbenzimidazole

By using the method of example 182, 6-benzenesulfonyl-carbamoyl-2-methyl-1-benzylbenzimidazole (0.222 g) is obtained from N-benzenesulfonyl-4-acetylamino-3-benzylaminobenzamide (0.38 g). $^1$H-NMR (DMSO-d6, δ): 2.54 (3H, s), 5.55 (2H, s), 7.12 (2H, d, J=7.9 Hz), 7.28 (1H, t, J=7.3 Hz), 7.34 (2H, t, J=7.0 Hz), 7.61–7.66 (3H, m), 7.69–7.76 (2H, m), 8.00 (2H, d, J=7.9 Hz), 8.18 (1H, s), 12.43 (1H, s).

IR(KBr): 1695 cm$^{-1}$.

mp: 260.0–262.0° C. (accompanied by decomposition).

($R_1$=benzyl, $R_2$=methyl, $R_3$=—C(O)NR$_4$R$_5$, $R_4$=SO$_2$R$_6$, $R_5$=H, $R_6$=phenyl, n=1, y=0)

Examples 185 and 186

6-Benzenesulfonylcarbamoyl-2-Methyl-1-(4-Nitrobenzyl)Benzimidazole and 6-Benzenesulfonylcarbamoyl-2-Methyl-1-(4-Nitrobenzyl)Benzimidazole Potassium Salt By using the method of example, 6-benzenesulfonyl-carbamoyl-2-methyl-1-(4-nitrobenzyl)benzimidazole (0.255 g) (185) is obtained in a crystal form from N-benzenesulfonyl-4-acetylamino-3-(4-nitrobenzylamino) benzamide (0.505 g). Furthermore, the filtrate is concentrated and thus, crystals of 6-benzenesulfonylcarbamoyl-2-methyl-1-(4-nitrobenzyl)benzimidazole potassium salt (250) (0.136 g) (186) are obtained. $^1$H-NMR (DMSO-d6, δ): 2.50 (3H, s), 5.70 (2H, s), 7.30 (2H, d, J=8.7 Hz), 7.52 (2H, t, J=7.6 Hz), 7.57 (2H, d, J=8.3 Hz), 7.76 (1H, dd, J=8.4 and 1.4 Hz),. 7.92 (2H, d, J=7.3 Hz), 8.05 (1H, s), 8.20 (2H, d, J=8.7 Hz), 12.43 (1H, s).

IR(KBr): 1686 cm$^{-1}$.

mp: 164.5–167.0° C.

Example 186: $^1$H-NMR (DMSO-d6, δ): 2.51 (3H, s), 5.68 (2H, s), 7.28 (2H, d, J=8.5 Hz), 7.32–7.41 (3H, m), 7.46 (1H, d, J=8.4 Hz), 7.78–7.86 (3H, m), 7.91 (1H, s), 8.20 (2H, d, J=8.5 Hz).

IR(KBr): 1594 cm$^{-1}$.

mp: 326.0–328.0° C. (accompanied by decomposition).

($R_1$=4-nitrobenzyl, $R_2$=methyl, $R_3$=—C(O)NR$_4$R$_5$, $R_4$=SO$_2$R$_6$, $R_5$=H, $R_6$=phenyl, n=1, y=0)

Example 187

6-Benzenesulfonylcarbamoyl-1-(4-Benzyloxybenzyl)-2-Methylbenzimidazole

A mixture of N-benzenesulfonyl-3-amino-4-acetylaminobenzamide potassium salt (0.500 g), 4-benzyloxybenzyl bromide (0.470 g), 20% potassium bicarbonate aqueous solution (0.925 g) and N,N-dimethylformamide (3 ml) is stirred for one hour at 90° C. The reaction solution is concentrated and purified through silica gel column chromatography (eluate: ethyl acetate/methanol=9/1) to obtain preliminarily purified N-benzenesulfonyl-4-acetylamino-3-(4-benzyloxybenzylamino)benzamide. This material underwent cyclization and thus, 6-benzenesulfonylcarbamoyl-1-(4-benzyloxybenzyl)-2-methylbenzimidazole (0.160 g) is obtained. $^1$H-NMR (DMSO-d6, δ): 2.54 (3H, s), 5.05 (2H, s), 5.44 (2H, s). 7.09 (2H, d, J=8.7 Hz), 7.32 (2H, d, J=7.0 Hz), 7.29–7.44 (5H, m), 7.58–7.67 (3H, m), 7.68–7.75 (2H, m), 7.79–8.02 (2H, m), 8.18 (1H, s), 12.46 (1H, s).

IR(KBr): 1685 cm$^{-1}$.

mp: 111.0–114.0° C.

($R_1$=4-benzyloxybenzyl, $R_2$=methyl, $R_3$=—C(O)NR$_4$R$_5$, $R_4$=SO$_2$R$_6$, $R_5$=H, $R_6$=phenyl, n=1, y=0)

Example 188

2-Methyl-5-[(2-Pyridylmethyl)Carbamoyl]Benzimidazole

5% palladium/carbon (0.10 g) is added to a mixture of preliminarily purified N-(pyridylmethyl)-4-acetylamino-3-nitrobenzamide (1.00 g), acetic acid (8 ml), and ethanol (12 ml), and then solution is stirred for seven hours at 80° C. under a nitrogen environment. The solids are separated through filtration and the filtrate is then concentrated. Ethyl acetate is added to the residue and crystals are formed. The crystals are separated through filtration, then dried and thus, 2-methyl-5-[(2-pyridylmethyl) carbamoyl]benzimidazole (0.57 g) is obtained. $^1$H-NMR (CDCl$_3$, δ): 2.52 (3H, s), 4.59 (2H, d, J=5.9 Hz), 7.26 (1H, dd, J=7.1 and 5.1 Hz), 7.33 (1H, d, J=7.8 Hz), 7.50 (1H, d, J=8.4 Hz), 7.72–7.78 (2H, m), 8.08(1H, s), 8.51 (1H, d, J=4.8 Hz), 9.04 (1H, t, J=5.8 Hz), 12.44 (1H, s).

IR(KBr): 1641 cm$^{-1}$.

mp: 212.0–215.0° C.

($R_1$=H, $R_2$=methyl, $R_3$=—C(O)NR$_4$R$_5$, $R_4$=SO$_2$R$_6$, $R_5$=H, $R_6$=phenyl, n=1, y=0)

Examples 189 and 190

1-Benzenesulfonyl-2-Methyl-6-[(2-Pyridylmethyl)Carbamoyl]Benzimidazole and 1-Benzenesulfonyl-2-Methyl-5-[(2-Pyridylmethyl)Carbamoyl]Benzimidazole Dichloromethane (10 ml) and triethylamine (0.760 g) are added to 1-methyl-5-[(2-pyridylmethyl)carbamoyl]benzimidazole (1.00 g). Furthermore, benzenesulfonyl chloride (0.994 g) is dripped into the solution. After stirring for three hours, the reaction solution is washed with water three times, and once more washed with a sodium bicarbonate aqueous solution. An organic layer is concentrated under reduced pressure, purified through silica gel column chromatography (eluate: ethyl acetate/ethanol=9/1) and thus, a mixture of 1-benzenesulfonyl-2-methyl-6-[(2-pyridylmethyl)carbamoyl]benzimidazole and 1-benzenesulfonyl-2-methyl-5-[(2-pyridylmethyl) carbamoyl]benzimidazole (1.38 g) is obtained. Further, this mixture is purified through medium pressure silica gel column chromatography (eluate: ethyl acetate/methanol= 100/3) and thus, 0.550 g of oily 1-benzenesulfonyl-2-Methyl-6-[(2-pyridylmethyl)carbamoyl]benzimidazole (189) and 0.540 g of oily 1-benzenesulfonyl-2-methyl-5-[(2-pyridylmethyl)carbamoyl]benzimidazole (190) are obtained. The oily materials are dissolved using methylene chloride (1.5 ml), and then crystallized by adding diethyl-ether. $^1$H-NMR (CDCl$_3$, δ): 2.84 (3H, s), 4.81 (2H, d, J=4.8 Hz), 7.24 (1H, dd, J=5.1 and 7.3 Hz), 7.37 (1H, d, J=7.7 Hz), 7.53 (2H, dd, J=7.9 and 7.5 Hz), 7.63–7.74 (2H, m), 7.85 (1H, dd, J=8.4 and 1.2 Hz), 7.97 (2H, dd, J=9.6 and 1.1 Hz), 8.58–8.61 (2H, m).

IR(KBr): 1636 cm$^{-1}$.

mp: 163.4–164.3° C.

($R_1$=benzenesulfonyl, $R_2$=methyl, $R_3$=—C(O)NR$_4$R$_5$, $R_4$=SO$_2$R$_6$, $R_5$=H, $R_6$=phenyl, n=1,y=0)

Example 190: $^1$H-NMR (CDCl$_3$, δ): 2.83 (3H, s), 4.78 (2H, d, J=4.7 Hz), 7.23 (1H, dd, J=4.9 and 8.6 Hz), 7.34 (1H, d, J=7.9 Hz), 7.53 (2H, dd, J=7.5 and 8.4 Hz), 7.64–7.75 (3H, m), 7.91–7.96 (3H, m), 8.10 (1H, d, J=9.1 Hz), 8.14 (1H, d, J=1.3 Hz), 8.56 (1H, dd, J=4.9 and 1.0 Hz).

IR(KBr): 1657 cm$^{-1}$.

mp: 88.3–91.3° C.

($R_1$=benzenesulfonyl, $R_2$=methyl, $R_3$=—C(O)NR$_4$R$_5$, $R_4$=SO$_2$R$_6$, $R_5$=H, $R_6$=phenyl, n=n=1, y=0)

Examples 191 and 192

2-Methyl-1-(4-Nitrobenzyl)-6-[(2-Pyridylmethyl) Carbamoyl]Benzimidazole and 2-Methyl-1-(4-Nitrobenzyl)-5-[(2-Pyridylmethyl)Carbamoyl] Benzimidazole N,N-dimethylformamide (10 ml), 4-nitrobenzyl bromide (3.24 g), and sodium bicarbonate (2.52 g) are added to 2-methyl-5-[(2-pyridylmethyl)carbamoyl]benzimidazole (3.56 g), and the solution is heated for two hours at 80° C. Chloroform and water are added to the reaction solution and layers are separated. After the organic layer is concentrated under reduced pressure, it is purified through silica gel column chromatography (eluate: ethyl acetate/methanol=4/1), and a mixture of 2-methyl-1-(4-nitrobenzyl)-6-[(2-pyridylmethyl)carbamoyl]benzimidazole and 2-methyl-1-(4-nitrobenzyl)-5-[(2-pyridylmethyl)carbamoyl] benzimidazole is obtained. Further, the position isomers in this mixture are separated through medium pressure silica gel column chromatography (eluate: ethyl acetate/methanol=85/15). Each is recrystallized in a mixed solvent of chloroform and diethylether, and thus, 2-methyl-1-(4-nitrobenzyl)-6-[(2-pyridylmethyl)carbamoyl]benzimidazole (1.37 g) (191) and 2-methyl-1-(4-nitrobenzyl)-5-[(2-pyridylmethyl)carbamoyl]benzimidazole (1.19 g) (192) are obtained.

$^1$H-NMR (CDCl$_3$, δ): 2.59 (3H, s), 4.77 (2H, d, J=4.8 Hz), 5.48 (2H, s), 7.09 (2H, d, J=8.7 Hz), 7.22 (1H, dd, J=7.2 and 4.9 Hz), 7.33 (1H, d, J=7.8 Hz), 7.66–7.70 (2H, m), 7.73 (1H, dd, J=8.4 and 1.5 Hz), 7.78 (1H, d, J=8.4 Hz), 7.91 (1H, d, J=1.2 Hz), 8.15–8.19 (2H, m), 8.56 (1H, d, J=4.6 Hz).

IR(KBr): 1652 cm$^{-1}$.

mp: 116.1–119.1° C.

($R_1$=4-nitrobenzyl, $R_2$=methyl, $R_3$=—C(O)NR$_4$R$_5$, $R_4$=SO$_2$R$_6$, $R_5$=H, $R_6$=phenyl, n=1, y=0)

Example 192: $^1$H-NMR (CDCl$_3$, δ): 2.59 (3H, s), 4.79 (2H, d, J=4.8 Hz), 5.46 (2H, s), 7.17–7.24 (4H, m), 7.35 (1H, d, J=7.8 Hz), 7.69 (2H, dt, J=7.6 and 1.7 Hz), 7.83 (1H, d, J=8.4 Hz), 8.19 (2H, d, J=8.6 Hz), 8.26 (1H, d, J=1.3 Hz), 8.57 (1H, d, J=4.8 Hz).

IR(KBr): 1634 cm$^{-1}$.

mp: 203.7–206.3° C.

($R_1$=4-nitrobenzyl, $R_2$=methyl, $R_3$=—C(O)NR4R$_5$, $R_4$=SO$_2$R$_6$, $R_5$ xH, $R_6$=phenyl, n=1, y=0)

Examples 193 and 194

2-Methyl-1-(2-Phenylethyl)-6-[(2-Pyridylmethyl) Carbamoyl]Benzimidazole and 2-Methyl-1-(2-Phenylethyl)-5-[(2-Pyridylmethyl)Carbamoyl] Benzimidazole By using the method of examples 191 and 192, 2-methyl-1-(2-phenylethyl)-6-[(2-pyridylmethyl)carbamoyl] benzimidazole (0.30 g) (193) and 2-methyl-1-(2-phenylethyl)-5-[(2-pyridylmethyl)carbamoyl] benzimidazole (0.23 g) (194) are obtained from 2-methyl-5-[(2-pyridylmethyl)carbamoyl]benzimidazole (2.00 g) and phenethyl iodide (15.0 g). $^1$H-NMR (CDCl$_3$, δ): 2.17 (3H, s), 3.10 (2H, t, J=6.8 Hz), 4.35 (2H, t, J=6.8 Hz), 4.82 (2H, d, J=4.8 Hz), 6.92–6.97 (2H, m), 7.21–7.28 (4H, m), 7.38 (1H, d, J=7.8 Hz), 7.78(1H, d, J=7.8 Hz), 7.78(1H,brt), 7.68–7.73(3H, m), 7.98(1H, d, J=0.9 Hz), 8.60 (1H, dd, J=1.0 and 4.9 Hz).

IR(neat): 1633 cm$^{-1}$. Liquid.

($R_1$=2-phenylethyl, $R_2$=methyl, $R_3$=—C(O)NR$_4$R$_5$, $R_4$=SO$_2$R$_6$, $R_5$ =H, $R_6$=phenyl, n=1, y=0)

Example 194: $^1$H-NMR (CDCl$_3$, δ): 2.19 (3H, s), 3.08 (2H, t, J=6.8 Hz), 4.35 (2H, t, J=6.8 Hz), 4.81 (2H, d, J=4.8 Hz), 6.91–6.96 (2H, m), 7.19–7.26 (4H, m), 7.31 (1H, d, J=8.4 Hz), 7.36 (1H, d, J=7.8 Hz), 7.64–7.73 (2H, m), 7.85 (1H, dd, J=1.7 and 8.4 Hz), 8.19 (1H, d, J=1.3 Hz), 8.58 (1H, d, J=4.0 Hz).

IR(neat): 1643 cm$^{-1}$. Liquid.

($R_1$=2-phenylethyl, $R_2$=methyl, $R_3$=—C(O)NR$_4$R$_5$, $R_4$=SO$_2$R$_6$, $R_5$=H, $R_6$=phenyl, n=1, y=0)

Examples 195 and 196

1-(2,4-Difluorobenzyl)-2-Methyl-6-[(2-Pyridylmethyl)Carbamoyl]Benzimidazole and 1-(2,4-Difluorobenzyl)-2-Methyl-5-[(2-Pyridylmethyl) Carbamoyl]Benzimidazole By using the method of examples 191 and 192, 1-(2,4-difluorobenzyl)-2-methyl-6-[(2-pyridylmethyl)carbamoyl] benzimidazole (0.25 g) (195) and 1-(2,4-difluorobenzyl)-2-methyl-5-[(2-pyridylmethyl)carbamoyl]benzimidazole (0.25 g) (196) are obtained from 2-methyl-5-[(2-pyridylmethyl)carbamoyl]benzimidazole (1.00 g) and 2,4-difluorobenzyl bromide (1.0 g). $^1$H-NMR (CDCl$_3$, δ): 2.62 (3H, s), 4.78 (2H, d, J=4.7 Hz), 5.38 (2H, s), 6.73–6.79 (2H, m), 6.88 (1H, t, J=10.0 Hz), 7.24 (1H, dd, J=7.3 and 5.1 Hz), 7.35(1H, d, J=7.8 Hz), 7.67–7.76 (4H, m), 7.97 (1H, s), 8.58 (1H, d, J=4.4 Hz).

IR(KBr): 1642 cm$^{-1}$.

mp: 98.0–104.0° C.

($R_1$=2,4-difluorobenzyl, $R_2$=methyl, $R_3$=—C(O)NR$_4$R$_5$, $R_4$=2-pyridylmethyl, $R_5$=H, n=1,y=0)

$^1$H-NMR (CDCl$_3$, δ): 2.62 (3H, s), 4.79 (2H, d, J=4.7 Hz), 5.35 (2H, s), 6.72–6.81 (2H, m), 6.89 (1H, t, J=9.8 Hz), 7.22 (1H, t, J=6.2 Hz), 7.28 (1H, d, J=8.4 Hz), 7.34 (1H, d, J=7.8 Hz), 7.63–7.71 (2H, m), 7.83 (1H, d, J=8.4 Hz), 7.97 (1H, s), 8.57 (1H, d, J=4.7 Hz).

IR(KBr): 1647 cm$^{-1}$.

mp: 143.5–144.0° C.

($R_1$=2,4-difluorobenzyl, $R_2$=methyl, $R_3$=—C(O)NR$_4$R$_5$, $R_4$=2-pyridylmethyl, $R_5$=H, n=1, y=0)

Examples 197 and 198

1-(4-Aminobenzyl)-2-Methyl-6-[(2-Pyridylmethyl) Carbamoyl]Benzimidazole and 1-(4-Aminobenzyl)-2-Methyl-5-[(2-Pyridylmethyl)Carbamoyl] Benzimidazole Methanol (30 ml) and 5% palladium/carbon (0.20 g) are added to a mixture (2.32 g) of 2-methyl-1-(4-nitrobenzyl)-6-[(2-pyridylmethyl)carbamoyl]benzimidazole and 2-methyl-1-(4-nitrobenzyl)-5-[(2-pyridylmethyl) carbamoyl]benzimidazole, and the solution is stirred at room temperature under a nitrogen environment until the raw materials dissolved. Solid materials are separated through filtration. The filtrate is concentrated and a residue is obtained. The residue is purified through medium pressure silica gel column chromatography (eluate: ethyl acetate/methanol=85/15), and 1-(4-aminobenzyl)-2-methyl-6-[(2-pyridylmethyl)carbamoyl]benzimidazole and 1-(4-aminobenzyl)-2-methyl-5-[(2-pyridylmethyl)carbamoyl]benzimidazole are separated. These materials are crystallized in mixed solvents of chloroform and diethylether. The crystals are separated through filtration, dried and thus, 1-(4-aminobenzyl)-2-methyl-6-[(2-pyridylmethyl)carbamoyl]benzimidazole (0.354 g) (197) and 1-(4-aminobenzyl)-2-methyl-5-[(2-pyridylmethyl)carbamoyl]benzimidazole (0.330 g) (198) are obtained. $^1$H-NMR (CDCl$_3$, δ): 3.00 (3H, s), 4.98 (2H, s), 5.88 (2H, s), 7.55 (2H, d, J=8.6 Hz), 7.69 (2H, d, J=8.6 Hz), 7.90 (1H, d, J=8.6 Hz), 7.96 (1H, dt, J=7.1 and 0.6 Hz), 8.12 (1H, J=8.0 Hz), 8.18 (1H, dd, J=8.5 and 1.4 Hz), 8.55 (1H, dt, J=8.0 and 1.7 Hz), 8.62 (1H, d,J=1.1 Hz), 8.77(1H, dd, J=5.9 and 1.1 Hz).

IR(KBr): 1643 cm$^{-1}$.

mp: 180.0–181.0° C.

($R_1$ 32 4-aminobenzyl, $R_2$=methyl, $R_3$=—C(O)NR$_4$R$_5$, $_4$=2-pyridylmethyl, $R_5$=H, n=1, y=0)

Example 198: $^1$H-NMR (CDCl$_3$, δ): 3.00 (3H, s), 5.01 (2H, s), 5.83 (2H, s), 7.47 (2H, d, J=8.5 Hz), 7.78 (2H, d, J=8.5 Hz), 7.78 (1H, d, J=8.9 Hz), 7.97 (1H, dt, J=7.2 and 0.7 Hz), 8.13 (1H, J=8.1 Hz), 8.15 (1H, d, J=8.9Hz), 8.51 (1H, s), 8.55 (1H, dt, J=7.9 and 1.6 Hz), 8.77 (1H, d, J=5.8 Hz).

IR(KBr): 1639, 1612 cm$^{-1}$.

mp: 168.0–171.0° C.

($R_1$=4-aminobenzyl, $R_2$=methyl, $R_3$=—C(O)NR$_4$R$_5$, $R_4$=2-pyridylmethyl, $R_5$=H, n=1, y=0)

Example 199

1-[4-(Benzenesulfonylamino)Benzyl]-2-Methyl-6-[(2-Pyridylmethyl)Carbamoyl]Benzimidazole Triethylamine (0.185 g) and benzenesulfonyl chloride (0.210 g) are added to a chloroform (10 ml) solution of 1-(4-aminobenzyl)-2-methyl-6-[(2-pyridylmethyl)carbamoyl]benzimidazole (0.340 g), and the solution is stirred for eight hours at room temperature. Water is added and the reaction is halted. A chloroform extraction is performed. An organic layer is washed with water (three times), and dried. After concentration, the residue is purified through silica gel column chromatography (eluate: ethyl acetate/methanol=100/0~4/1), and thus, 1-[4-(benzenesulfonylamino)benzyl]-2-methyl-6-[(2-pyridylmethyl)carbamoyl]benzimidazole (263) (0.300 g) is obtained. $^1$H-NMR (CDCl$_3$, δ): 2.53 (3H, s), 4.78 (2H, d, J=4.8 Hz), 5.28 (2H, s), 6.90 (2H, t, J=8.6 Hz), 6.99 (2H, d, J=8.5 Hz), 7.11 (1H, s), 7.23 (1H, dd, J=5.5 and 7.2 Hz), 7.34 (1H, d, J=7.7 Hz), 7.40 (2H, t, J=8.1 Hz), 7.50 (1H, t, J=7.5 Hz), 7.66–7.74 (6H, m), 7.92 (1H, s), 8.56 (1H, d, J=4.8 Hz).

IR(KBr): 1642 cm$^{-1}$.

mp: 204.4–206.5° C.

($R_1$=4-(benzenesulfonylamino)benzyl, $R_2$=methyl, $R_3$=—C(O)NR$_4$R$_5$, $R_4$=2-pyridylmethyl, $R_5$=H, n=1, y=0)

Example 200

N-Benzenesulfonyl-3-[1-(2-chlorobenzyl)-2-methylbenzimidazole-6-yl]propionamide

To an ethanol (150 ml) solution of N-benzenesulfonyl-1-(2-chlorobenzyl)-2-methylbenzimidazole-6-acrylamide (0.607 g), 5% palladium/carbon (0.500 g) is added, and the solution is stirred for 43 hours at room temperature under a hydrogen environment. Solid materials are separated through filtration. The filtrate is concentrated and then dissolved in a mixture solution of 20% potassium bicarbonate aqueous solution and methanol. The solution's acidity is adjusted to pH 5~with 10% hydrochloric acid. Precipitated crystals are separated through filtration and thus, N-benzenesulfonyl-3-[1-(2-chlorobenzyl)-2-methylbenzimidazole-6-yl]propionamide (0.250 g) is obtained. $^1$H-NMR (DMSO-d6, δ): 2.45 (3H, s), 2.52 (2H, t), 2.78 (2H, t), 5.37 (2H, s), 6.88 (1H, d, J=8.4 Hz), 7.08 (2H, d, J=7.4 Hz), 7.22–7.34 (3H, m) 7.36 (1H, t, J=8.1 Hz), 7.55 (2H, t), 7.67 (1H, t), 7.84 (2H, d, J=7.6 Hz), 12.04 (1H, br s).

IR(KBr): 1715 cm$^{-1}$.

Mass(FAB): m/e 468(M+1)

mp: 229.8–233.0° C.

($R_1$=2-chlorobenzyl, $R_2$=methyl, $R_3$=—C(O)NR$_4$R$_5$, $R_4$=SO$_2$R$_6$, $R_5$=H, $R_6$=phenyl, n=1, y=0)

Example 201

6-Benzenesulfonylcarbamoyl-2-Methyl-1-[4-(1,2,3-Thiadiazole-4-yl)Benzyl]Benzimidazole By using the method of example 182, 6-benzenesulfonyl carbamoyl-2-methyl-1-[4-(1,2,3-thiadiazole-4-yl)benzyl]benzimidazole (0.279 g) is obtained from N-benzenesulfonyl-4-acetylamino-3-[4-(1,2,3-thadiazole-4-yl)benzylamino]benzimidazole (0.382 g). $^1$H-NMR (DMSO-d6, δ): 2.56 (3H, s), 5.62 (2H, s), 7.28 (2H, d, J=8.2 Hz), 7.58–7.63 (3H, m), 7.67 (1H, t, J=7.3 Hz), 7.74 (1H, dd, J=8.5 and 1.2 Hz), 7.99 (2H, dd, J=8.4 and 1.2 Hz) 8.10 (2H, d, J=8.2 Hz), 8.19 (1H, s), 9.58 (1H, s), 12.47 (1H, s).

IR(KBr): 1617, 1556 cm$^{-1}$.

mp: 258.5–260.0° C. (accompanied by decomposition).

($R_1$=4-(1,2,3-thiadiazole-4-yl)benzyl, $R_2$=methyl, $R_3$==C(O)NR$_4$R$_5$, $R_4$=SO$_2$R$_6$, $R_5$=H, $R_6$=phenyl, n=1, y=0)

Example 202

1-(2-Chlorobenzyl)-2-Methyl-6-(8-Quinolinesulfonylcarbamoyl)Benzimidazole Sodium Salt By using the method of example 153, 1-(2-chlorobenzyl)-2-methyl-6-(8-quinolinesulfonylcarbamoyl)benzimidazole sodium salt (0.400 g) is obtained from 6-carboxy-1-(2-chlorobenzyl)-2-methylbenzimidazole (0.450 g) (example 75), N,N'-carbonyldiimidazole (0.485 g), 8-quinolinesulfonamide (0.625 g) and diazabicycloundecene (0.457 g). $^1$H-NMR (DMSO-d6, δ): 2.42 (3H, s), 5.48 (2H, s), 6.32 (1H, d, J=7.7 Hz), 7.17 (1H, t, J=7.5 Hz), 7.30 (1H, t, J=7.7 Hz), 7.42 (1H, d, J=8.4 Hz), 7.48 (1H, dd, J=4.2 and 8.2 Hz) 7.53 (1H, d, J=8.0 Hz), 7.64 (1H, t, J=7.7 Hz), 7.79 (1H, d, J=8.5 Hz), 7.88 (1H, s), 8.04 (1H, d, J=8.1 Hz), 8.33–8.37 (2H, m), 8.85 (1H, dd).

IR(KBr): 1594 cm$^{-1}$.

Mass(FAB): m/e 513(M+1).

mp: 348–352° C. (accompanied by decomposition).

($R_1$=2-chlorobenzyl, $R_2$=methyl, $R_3$=—C(O)NR$_4$R$_5$, $R_4$=SO$_2$R$_6$, $R_5$=H, $R_6$=8-quinoline, n=1, y=0)

Example 203

6-(4-t-Butylbenzenesulfonylcarbamoyl)-1-(2-Chlorobenzyl)-2-Methylbenzimidazole Sodium Salt By using the method of example 153, 6-(4-t-butylbenzene sulfonyl carbamoyl)-1-(2-chlorobenzyl)-2- methylbenzimidazole sodium salt (0.280 g) is obtained from 6-carboxy-1-(2-chlorobenzyl)-2-methylbenzimidazole (0.450 g) (example 75), N,N'-carbonyldiimidazole (0.486 g), 2-t-benzenesulfonamide (0.640 g) and diazabicycloundecene (0.657 g). $^1$H-NMR (DMSO-d6, δ): 1.25 (9H, s), 2.46 (3H, s), 5.51 (2H, s), 6.37 (1H, d, J=7.7 Hz), 7.18 (1H, t), 7.31 (1H, t), 7.34 (2H, d, J=8.4 Hz), 7.44 (1H, d, J=8.4 Hz), 7.54 (1H, d, J=8.0 Hz), 7.69 (2H, d, J=8.5 Hz), 7.78–7.82 (2H, m).

IR(KBr): 1596 cm$^{-1}$.

Mass(FAB): m/e 518(M+1).

mp: 359.5–362° C.

($R_1$=2-chlorobenzyl, $R_2$=methyl, $R_3$=—C(O)NR$_4$R$_5$, $R_4$=SO$_2$R$_6$, $R_5$=H, $R_6$4-t-butylphenyl, n=1, y=0)

Example 204

6-Benzenesulfonylcarbamoyl-2-Methyl-1-[4-(Trifluoromethyl)Benzyl]Benzimidazole A methanol (7 ml) solution of N-benzenesulfonyl-4-acetylamino-3-aminobenzamide (0.50 g), 4-(trifluoromethyl)benzyl bromide (0.418 g) and potassium bicarbonate (0.423 g) is stirred for 1 hour at 60° C. to give preliminarily purified N-benzenesulfonyl-4-acetylamino-3-[4-(trifluoromethyl)benzylamino]benzamide (0.30 g). This is dissolved in methanol. When it is left undisturbed crystals precipitated. The crystals are separated through filtration, dried and thus, 6-benzenesulfonylcarbamoyl-2-methyl-1-[4-(trifluoromethyl)benzyl]benzimidazole (0.160 g)is obtained.

$^1$H-NMR (DMSO-d6, δ): 2.51 (3H, s), 5.66 (2H, s), 7.28 (2H, d, J=8.1 Hz), 7.59–7.65 (3H, m), 7.67–7.75 (4H, m), 7.99 (2H, d, J=7.5 Hz), 8.14 (1H, d, J=1.0 Hz), 12.43 (1H, s).

IR(KBr): 1618,1550 cm$^{-1}$.

mp: 278.5–280.0° C.

($R_1$=4-trifluoromethylbenzyl, $R_2$=methyl, $R_3$=—C(O)NR$_4$R$_5$, $R_4$=SO$_2$R$_6$, $R_5$=H, $R_6$=phenyl, n=1, y=0)

Example 205

5-Benzenesulfonylcarbamoyl-2-Methylbenzimidazole

A mixture of N-benzenesulfonyl-4-acetylamino-3-aminobenzamide (0.500 g), 35% hydrochloric acid (3.9 g), methanol (15 ml), and water (12 ml) is stirred for one hour at 60° C. The solution is neutralized with a potassium bicarbonate aqueous solution. Precipitated crystals are separated through filtration, dried, and thus, 5-benzenesulfonylcarbamoyl-2-methylbenzimidazole (0.404 g) is obtained. $^1$H-NMR (DMSO-d6, δ): 2.79 (3H, s), 7.64–7.68 (2H, m), 7.72–7.76 (1H, m), 7.81 (1H, d, J=8.7 Hz), 7.94 (1H, dd, J=1.6 and 8.7 Hz), 8.02–8.05 (2H, m), 8.30 (1H, s).

IR(KBr): 1701 cm$^{-1}$.

mp: 223.0–227.5° C.

($R_{1=H,\ R2}$=methyl, $R_3$=—C(O)NR$_4$R$_5$, $R_4$=SO$_2$R$_6$, $R_5$=H, $R_6$=phenyl, n=1, y=0)

Example 206

1-(Biphenyl-4-ylmethyl)-6-Ethoxycarbonyl-2-Methoxymethylbenzimidazole

By using the method of example 47, part B, preliminarily purified 3-[N-(biphenyl-4-ylmethyl)methoxyacetylamino]-4-nitro-ethylbenzoate (2.02 g) is obtained from 3-methoxyacetylamino-4-nitro-ethylbenzoate (2.00 g) and 4-biphenylmethyl bromide (2.98 g). Subsequently, by using the method of example 47, preliminarily purified 1-(biphenyl-4-ylmethyl)-6-ethoxycarbonyl-2-methoxymethylbenzimidazole (1.44 g) is obtained.

($R_1$=4-biphenyl, $R_2$=methoxymethyl, $R_3$=ethoxycarbonyl, n=1, y=1)

Example 207

1-(Biphenyl-4-ylmethyl)-6-Carboxy-2-Methoxymethylbenzimidazole

By using the method of example 75, 1-(biphenyl-4-ylmethyl)-6-carboxy-2-methoxymethylbenzimidazole (0.864 g) is obtained from the preliminarily purified 1-(biphenyl-4-ylmethyl)-6-ethoxycarbonyl-2-methoxymethyl-benzimidazole (1.44 g). $^1$H-NMR (DMSO-d6, 67 ): 3.35 (3H, s), 4.77 (2H. s), 5.68 (2H, s), 7.25 (2H, d, J=8.3 Hz), 7.35 (1H, t, J=7.4 Hz), 7.44 (2H, t, J=7.5 Hz), 7.61–7.66 (4H, m), 7.74 (1H, d, J=8.6 Hz), 7.83 (1H, dd, J=1.6 and 8.5 Hz), 8.08 (1H, d, J=1.2 Hz), 12.83 (1H, s).

($R_1$=4-biphenyl, $R_2$=methoxymethyl, $R_3$=-carboxyl, n=1, y=1)

Example 208

1-(Biphenyl-4-ylmethyl)-6-(Butanesulfonylcarbamoyl)-2-Methoxymethylbenzimidazole By using the method of example 111, 1-(biphenyl-4-ylmethyl)-6-(butanesulfonylcarbamoyl)-2-methoxymethylbenzimidazole (0.429 g) is obtained from 1-(biphenyl-4-ylmethyl)-6-carboxy-2-methoxymethylbenzimidazole (0.400 g), N,N'-carbonyldiimidazole (0.348 g), 1-butanesulfonamide (0.294 g) and diazabicycloundecene (0.327 g). $^1$H-NMR (DMSO-d6, δ): 0.84 (3H, t, J=7.4 Hz), 1.35–1.42 (2H. m), 1.62–1.70 (2H, m), 3.33(3H, s), 3.51 (2H, t, J=7.6 Hz), 4.74 (2H, s), 5.65 (2H, s), 7.26 (2H, d, J=8.3 Hz), 7.35 (1H, t, J=7.3 Hz), 7.44 (2H, t, J=7.5 Hz), 7.62–7.67 (4H, m), 7.78 (1H, d, J=8.6 Hz), 7.84 (1H, dd, J=1.5 and 8.4 Hz), 8.24 (1H, d, J=1.5 Hz), 12.01 (1H, s).

IR(KBr): 1684 cm$^{-1}$.

mp: 176.0–178.5° C.

($R_1$=4-biphenyl, $R_2$=methoxymethyl, $R_3$=—C(O)NR$_4$R$_5$, $R_4$=SO$_2$R$_6$, $R_5$=H, $R_6$=butyl, n=1, y=1)

Example 209

1-(4-Benzyloxybenzyl)-6-ethoxycarbonyl-2-methoxymethylbenzimidazole

By using the method of example 47, part B, preliminarily purified 3-[N-(4-benzyloxybenzyl)methoxyacetylamino]-4-nitro-ethylbenzoate (2.14 g) is obtained from 3-methoxyacetylamino-4-nitro-ethylbenzoate (2.00 g) and 4-benzyloxybenzyl chloride (3.30 g). Subsequently, by using the method of Example 24, preliminarily purified 1-(4-benzyloxybenzyl)-6-ethoxycarbonyl-2-methoxymethylbenzimidazole (1.66 g) is obtained.

($R_1$=4-benzyloxybenzyl, $R_2$=methoxymethyl, $R_3$=ethoxycarbonyl, n=1, y=0)

Example 210

1-(4-Benzyloxybenzyl)-6-Carboxy-2-Methoxymethylbenzimidazole

By using the method of example 75, 1-(4-benzyloxybenzyl)-6-carboxy-2-methoxymethylbenzimidazole (2.64 g) is obtained from the preliminarily purified 1-(4-benzyloxybenzyl)-6-ethoxycarbonyl-2-methoxymethyl-benzimidazole (3.75 g). $^1$H-NMR (DMSO-d6, δ): 3.34 (3H, s), 4.74 (2H. s), 5.05 (2H, s), 5.53 (2H, s), 6.97 (2H, d, J=8.7 Hz), 7.15 (2H, d, J=8.7 Hz), 7.31 (1H, t, J=7.2 Hz), 7.41 (2H, d, J=7.2 Hz), 7.71 (1H, d, J=8.4 Hz), 7.81 (1H, dd, J=1.5 and 7.4 Hz), 8.04 (1H, d, J=1.1 Hz), 12.81 (1H, s).
($R_1$=4-benzyloxybenzyl, $R_2$=methoxymethyl, $R_3$=carboxyl, n=1, y=0)

Example 211

1-(4-Benzyloxybenzyl)-6-(1-Butanesulfonylcarbamoyl)-2-Methoxymethylbenzimidazole By using the method of example 162, 1-(4-benzyloxybenzyl)-6-(1-butanesulfonylcarbamoyl)-2-methoxymethylbenzimidazole (0.321 g) is obtained from 1-(4-benzyloxybenzyl)-6-carboxy-2-methoxymethyl-benzimidazole (0.400 g), N,N'-carbonyldiimidazole (0.322 g), 1-butanesulfonamide (0.272 g) and diazabicycloundecene (0.302 g). $^1$H-NMR (DMSO-d6, δ): 0.86 (3H, t, J=7.4 Hz), 1.37–1.44 (2H, m), 1.65–1.71 (2H, m), 3.32 (3H, s), 3.52 (2H, t, J=7.6 Hz), 4.71 (2H, s), 5.05 (2H, s), 5.51 (2H, s), 6.98 (2H, d, J=8.7 Hz), 7.15 (2H, d, J=8.3 Hz), 7.31 (1H, t, J=7.2 Hz), 7.37 (2H, t, J=7.2 Hz), 7.41 (2H, d, J=7.1 Hz), 7.74, (1H, d, J=8.5 Hz), 7.82 (1H, dd, J=1.5 and 8.5 Hz), 8.21 (1H, s), 11.98 (1H, s).
IR(KBr): 1685 cm$^{-1}$.
mp: 72.0–74.0° C.
($R_1$=4-benzyloxybenzyl, $R_2$=methoxymethyl, $R_3$=—C(O)NR$_4$R$_5$, $R_4$=SO$_2$R$_6$, $R_5$=H, $R_6$=butyl, n=1, y=1)

Example 212

1-(2,4-Dichlorobenzyl)-6-Ethoxycarbonyl-2-Methoxymethylbenzimidazole

By using the method of example 47, part B, preliminarily purified 3-[N-(2,4-dichlorobenzyl)methoxyacetylamino]-4-nitro-ethylbenzoate is obtained from 3-methoxyacetylamino-4-nitro-ethylbenzoate (2.00 g) and 2,4-dichlorobenzyl chloride (2.08 g). Subsequently, by using the method of example 47, preliminarily purified 1-(2,4-dichlorobenzyl)-6-ethoxycarbonyl-2-methoxymethylbenzimidazole (3.15 g) is obtained.
($R_1$=2,4-dichlorobenzyl, $R_2$=methoxymethyl, $R_3$=ethoxycarbonyl, n=1, y=0)

Example 213

6-Carboxy-1-(2,4-Dichlorobenzyl)-2-Methoxymethylbenzimidazole

By using the method of example 75, 6-carboxy-1-(2,4-dichlorobenzyl)-2-methoxymethylbenzimidazole (1.46 g) is obtained from the preliminarily purified 1-(2,4-dichlorobenzyl)-6-ethoxycarbonyl-2-methoxymethyl-benzimidazole (3.15 g) (example 212). $^1$H-NMR (DMSO-d6, δ): 3.23 (3H, s), 4.70 (2H, s), 5.68 (2H, s), 6.54 (1H, d, J=8.5 Hz), 7.31 (1H, dd, J=2.2 and 8.5 Hz), 7.73 (1H, d, J=2.1 Hz), 7.76 (1H, d, J=8.5 Hz), 7.86 (1H, dd, J=1.5 and 8.5 Hz), 8.00 (1H, d, J=1.1 Hz), 12.85 (1H, s).
($R_1$=2,4-dichlorobenzyl, $R_2$=methoxymethyl, $R_3$=carboxyl, n=1, y=0)

Example 214

6-(1-Butanesulfonylcarbamoyl)-1-(2,4-Dichlorobenzyl)-2-Methoxymethylbenzimidazole By using the method of example 111, 6-(1-butanesulfonyl-carbamoyl)-1-(2,4-dichlorobenzyl)-2-methoxymethylbenzimidazole (0.430 g) is obtained from 6-carboxy-1-(2,4-dichlorobenzyl)-2-methoxymethylbenzimidazole (0.400 g), N,N'-carbonyldiimidazole (0.355 g), 1-butanesulfonamide (0.300 g) and diazabicycloundecene (0.333 g). $^1$H-NMR (DMSO-d6, δ): 0.85 (3H, t, J=7.3 Hz), 1.37–1.42 (2H. m), 1.63–1.69 (2H, m), 3.21 (3H, s), 3.51 (2H, t, J=7.6 Hz), 4.68 (2H, s), 5.65 (2H, s), 6.46 (1H, d, J=8.5 Hz), 7.31 (1H, dd, J=2.0 and 8.4 Hz), 7.75 (1H, d, J=2.1 Hz), 7.80 (1H, d, J=8.5 Hz), 7.86 (1H, dd, J=1.7 and 8.6 Hz), 8.14 (1H, d, J=1.2 Hz), 12.00 (1H, s).
IR(KBr): 1694 cm$^{-1}$.
mp: 168.5–170.5° C.
($R_1$=2,4-dichlorobenzyl, $R_2$=methoxymethyl, $R_3$=—C(O)NR$_4$R$_5$, R4=SO$_2$R$_6$, $R_5$=H, $R_6$=butyl, n=1, y=0)

Example 215

1-(2-Chlorobenzyl)-2-Methyl-6-(1-Propanesulfonylcarbamoyl)Benzimidazole

By using the method of example 1 1 , 1-(2-chlorobenzyl)-2-methyl-6-(1-propanesulfonylcarbamoyl)benzimidazole (0.459 g) is obtained from 6-carboxy-1-(2-chlorobenzyl)-2-methylbenzimidazole (0.400 g), N,N'-carbonyl-diimidazole (0.431 g), 1-propanesulfonamide (0.328 g) and diazabicycloundecene (0.404 g). $^1$H-NMR (DMSO-d6, δ): 0.98 (3H, t, J=7.4 Hz), 1.67–1.75 (2H. m), 2.50 (3H, s), 3.49 (2H, t, J=7.7 Hz), 5.61 (2H, s), 6.45 (1H, d, J=7.0 Hz), 7.24 (1H, dt, J=0.8 and 7.8 Hz), 7.35 (1H, dt, J=1.4 and 7.4 Hz), 7.63 (1H, dd, J=0.9 and 7.9 Hz), 7.69 (1H, d, J=8.5 Hz), 7.81 (1H, dd, J=1.6 and 8.5 Hz), 8.12 (1H, d, J=1.6 Hz), 11.90 (1H, s).
IR(KBr): 1676 cm$^{-1}$.
mp: 217.5–218.5° C.
($R_1$=2-chlorobenzyl, $R_2$=methyl, $R_3$=—C(O)NR$_4$R$_5$, $R_4$=SO$_2$R$_6$, $R_5$=H, $R_6$=propyl, n=1,y=0)

Example 216

6-Ethanesulfonylcarbamoyl-1-(2-Chlorobenzyl)-2-Methylbenzimidazole

By using the method of example 111, 6-ethanesulfonyl-carbamoyl-1-(2-chlorobenzyl)-2-methylbenzimidazole (0.459 g) is obtained from 6-carboxy-1-(2-chlorobenzyl)-2-methylbenzimidazole (0.400 g), N,N'-carbonyldiimidazole (0.431 g), ethanesulfonamide (0.290 g) and diazabicycloundecene (0.404 g). $^1$H-NMR (DMSO-d6, δ): 1.23 (3H, t, J=7.3 Hz), 2.50 (3H. s), 3.50 (2H, q, J=7.3 Hz), 5.61 (2H, s), 6.45 (1H, d, J=6.7 Hz), 7.24 (1H, dt, J=0.9 and 7.5 Hz), 7.35 (1H, dt, J=1.4 and 7.5 Hz), 7.58 (1H, dd, J=1.0 and 8.0 Hz), 7.69 (1H, d, J=8.5 Hz), 7.81 (1H, dd, J=1.6 and 8.4 Hz), 8.13 (1H, d, J=1.5 Hz), 11.86 (1H, s).
IR(KBr): 1673 cm$^{-1}$.
mp: 256.5–258.5° C.
($R_1$=2-chlorobenzyl, $R_2$=methyl, $R_3$=—C(O)NR$_4$R$_5$, $R_4$=SO$_2$R$_6$, $R_5$=H, $R_6$=ethyl, n=1, y=0)

Example 217

6-(Propanesultam-1-ylcarbonyl)-1-(2-Chlorobenzyl)-2-Methylbenzimidazole

By using the method of example 111, 6-(propanesultam-1-ylcarbonyl)-1-(2-chlorobenzyl)-2-methylbenzimidazole (0.323 g) is obtained from 6-carboxy-1-(2-chlorobenzyl)-2-methylbenzimidazole (0.400 g), N,N'-carbonyldiimidazole (0.431 g), 1-(3-chloropropane)sulfonamide (0.420 g) and diazabicycloundecene (0.404 g). ¹H-NMR (DMSO-d6, δ): 2.27–2.33 (2H, m), 2.52 (3H. s), 3.52 (2H, t, J=7.0 Hz), 3.87 (2H, t, J=6.6 Hz), 5.59 (2H, s), 6.57 (1H, d, J=7.7 Hz), 7.23 (1H, t, J=7.6 Hz), 7.34 (1H, t, J=6.4 Hz), 7.53–7.58 (2H, m), 7.67 (1H, d, J=8.4 Hz), 7.79 (1H, d, J=1.1 Hz).

IR(KBr): 1648 cm⁻¹.

mp: 165.5–166.6° C.

($R_1$=2-chlorobenzyl, $R_2$=methyl, $R_3$=—C(O)NR₄R₅, $R_4$ and $R_5$=propansultamyl, n=1,y=0)

Example 218

6-Benzenesulfonylcarbamoyl-1-(Biphenyl-4-ylmethyl)-2-Cyclopropylbenzimidazole By using the method of example 173, from N-benzenesulfonyl-4-amino-3-(biphenyl-4-ylmethylamino)benzamide (0.400 g) and cyclopropanecarbonyl chloride (0.101 g), first N-benzenesulfonyl-3-(biphenyl-4-ylmethylamino)-4-cyclopropanecarbonylaminobenzamide is obtained and then 6-benzenesulfonylcarbamoyl-1-(biphenyl-4-ylmethyl)-2-cyclopropylbenzimidazole (0.196 g) is obtained. ¹H-NMR (DMSO-d6, δ): 1.00–1.15 (4H, m), 2.23–2.31 (1H. m), 5.66 (2H, s), 7.21 (2H, m, J=9.1 Hz), 7.32–7.45 (7H, m), 7.59–7.63 (4H, m), 7.78–7.83 (3H, m), 7.97 (1H, s).

IR(Nujol): 1540 cm⁻¹.

Mass(FAB): m/e 546(M+1).

mp: 220.8–224.8° C.

($R_1$=4-biphenyl, $R_2$=cyclopropyl, $R_3$=—C(O)NR₄R₅, $R_4$=SO₂R₆, $R_5$=H, $R_6$=phenyl, n=1, y=1)

Example 219

1-(2-Chlorobenzyl)-2-Methyl-6-(1-Pentanesulfonylcarbamoyl)Benzimidazole

By using the method of example 111, 1-(2-chlorobenzyl)-2-methyl-6-(1-pentanesulfonylcarbamoyl)benzimidazole (0.491 g) is obtained from 6-carboxy-1-(2-chlorobenzyl)-2-methylbenzimidazole (0.400 g), N,N'-carbonyldiimidazole (0.431 g), 1-pentanesulfonamide (0.402 g) and diazabicycloundecene (0.404 g). ¹H-NMR (DMSO-d6, δ): 0.81 (3H, t, J=7.2 Hz), 1.23–1.28 (2H, m), 1.32–1.37 (2H. m), 1.65–1.69 (2H, m), 3.50 (2H, t, J=7.8 Hz), 5.61 (2H, s), 6.45 (1H, d, J=7.5 Hz), 7.24 (1H, t, J=7.6 Hz), 7.35 (1H, t, J=7.5 Hz), 7.57 (1H, d, J=7.9 Hz), 7.69 (1H, d, J=8.5 Hz), 7.81 (1H, dd, J=1.7 and 8.4 Hz), 8.12 (1H, d, J=1.2 Hz), 12.25 (1H, s).

IR(KBr): 1684 cm⁻¹.

mp: 173.3–179.8° C.

($R_1$=2-chlorobenzyl, $R_2$=methyl, $R_3$=—C(O)NR₄R₅, $R_4$=SO₂R₆, $R_5$=H, $R_6$=pentyl, n=1, y=0)

Example 220

1-(2-Chlorobenzyl-2-Methyl-6-[(3-Methylbutane)Sulfonylcarbamoyl]Benzimidazole By using the method of example 111, 1-(2-chlorobenzyl)-2-methyl-6-[(3-methylbutane)sulfonylcarbamoyl]benzimidazole (0.284 g) is obtained from 6-carboxy-1-(2-chlorobenzyl)-2-methylbenzimidazole (0.300 g), N,N'-carbonyldiimidazole (0.323 g), 1-(3-methyl)butanesulfonamide (0.302 g) and diazabicycloundecene (0.303 g). ¹H-NMR (DMSO-d6, δ): 0.84 (6H, d, J=6.5 Hz), 1.52–1.59 (2H, m), 1.61–1.70 (1H. m), 3.44 (2H, t, J=7.9 Hz), 5.60 (2H, s), 6.45 (1H, d, J=7.8 Hz), 7.24 (1H, t, J=7.6 Hz), 7.35 (1H, t, J=7.4 Hz), 7.57 (1H, d, J=7.9 Hz), 7.66 (1H, d, J=8.5 Hz), 7.81 (1H, dd, J=1.6 and 8.6 Hz), 8.09 (1H, s), 11.87 (1H, s).

IR(KBr): 1682 cm⁻¹.

mp: 201.0–204.1° C.

($R_1$=2-chlorobenzyl, $R_2$=methyl, $R_3$=—C(O)NR₄R₅, $R_4$=SO₂R₆, $R_5$=H, $R_6$=3-methylbutyl, n=1, y=0)

Example 221

1-(2-Chlorobenzyl)-6-(1-Hexanesulfonylcarbamovyl-2-Methylbenzimidazole

By using the method of example 111, 1-(2-chlorobenzyl)-6-(1-hexanesulfonylcarbamoyl)-2-methylbenzimidazole (0.379 g) is obtained from 6-carboxy-1-(2-chlorobenzyl)-2-methylbenzimidazole (0.300 g), N,N'-carbonyldiimidazole (0.323 g), 1-hexanesulfonamide (0.335 g) and diazabicycloundecene (0.303 g). ¹H-NMR (DMSO-d6, δ): 0.81 (3H, t, J=7.0 Hz), 1.18–1.28 (4H, m), 1.32–1.41 (2H. m), 1.63–1.71 (2H, m), 2.53 (3H, s), 3.50 (2H, t, J=7.7 Hz), 5.64 (2h, s), 6.51 (1H, d, J=7.7 Hz), 7.25 (1H, dt, J=1.2 and 7.8 Hz), 7.36 (1H, dt, J=1.4 and 7.7 Hz), 7.58 (1H, dd, J=1.0 and 8.0 Hz), 7.72 (1H, d, J=8.5 Hz), 7.84 (1H, dd, J=1.6 and 8.5 Hz), 8.15 (1H, d, J=1.3 Hz), 11.87 (1H, s).

IR(KBr): 1682 cm³¹ ¹.

mp: 141.2–143.5° C.

($R_1$=2-chlorobenzyl, $R_2$=methyl, $R_3$=—C(O)NR₄R₅, $R_4$=SO₂R₆, $R_5$=H, $R_6$=hexyl, n=1, y=0)

Example 222

1-(2,4-Dichlorobenzyl)-7-Ethoxycarbonyl-2-Methylbenzimidazole

A.) 2-[N-(2,4-Dichlorobenzyl)acetylamino]-3-nitro-methylbenzoate

By using the method of example 47, part B, 2-[N-(2,4-dichlorobenzyl)acetylamino]-3-nitro-methylbenzoate (0.250 g) is obtained from 2-acetylamino-3-nitro-methylbenzoate (1.00 g) and 2,4-dichlorobenzyl chloride (0.985 g).

¹H-NMR (CDCl₃, δ): 1.99 (3H, s), 3.71 (3H, s), 4.85 (1H, d, J=4.5 Hz), 4.98 (1H, d, J=4.5 Hz), 7.17–7.22 (2H, m), 7.46 (1H, d, J=7.9 Hz), 7.63 (1H, t, J=7.9 Hz), 7.63 (1H, t, J=7.9 Hz), 7.98 (1H, d, J=8.0 Hz), 8.09 (1H, d, J=7.9 Hz).

B.) 1-(2,4-Dichlorobenzyl)-7-ethoxycarbonyl-2-methylbenzimidazole

By using the method of example 47, 1-(2,4-dichlorobenzyl)-7-ethoxycarbonyl-2-methylbenzimidazole (5.15 g) is obtained from 2-[N-(2,4-dichlorobenzyl)acetylamino]-3-nitro-methylbenzoate (6.50 g). ¹H-NMR (CDCl₃, δ): 2.53 (3H, s), 3.70 (3H, s), 5.72 (2H, s), 6.26 (1H, d, J=8.4 Hz), 7.04 (1H, dd, J=2.0 and 8.4 Hz), 7.28 (1H, t, J=7.9 Hz), 7.45 (1H, d, J=2.0 Hz), 7.75 (1H, d, J=7.8 Hz), 7.93 (1H, d, J=7.9 Hz).

($R_1$=2,4-dichlorobenzyl, $R_2$=methyl, $R_3$=ethoxycarbonyl, n=1, y=0)

Example 223

7-Carboxy-1-(2,4-dichlorobenzyl)-2-methylbenzimidazole

By using the method of example 75, 7-carboxy-1-(2,4-dichlorobenzyl)-2-methylbenzimidazole (1.76 g) is obtained from 1-(2,4-dichlorobenzyl)-7-ethoxycarbonyl-2-methylbenzimidazole (2.00 g). ¹H-NMR(DMSO-d6, δ): 2.49 (3H, s), 5.81 (2H, s), 6.09 (1H, d, J=8.4 Hz), 7.21–7.28 (2H, m), 7.62 (1H, d, J=7.8 Hz), 7.67 (1H, d, J=2.2 Hz), 7.83 (1H, d, J=8.0 Hz), 13.04 (1H, br s).

($R_1$=2,4-dichlorobenzyl, $R_2$=methyl, $R_3$=carboxyl, n=1, y=0)

Example 224

7-(1-Butanesulfonylcarbamoyl)-1-(2,4-Dichlorobenzyl)-2-Methylbenzimidazole

By using the method of example 111, 7-(1-butanesulfonylcarbamoyl)-1-(2,4-dichlorobenzyl)-2-methylbenzimidazole (0.325 g) is obtained from 7-carboxy-1-(2,4-dichlorobenzyl)-2-methylbenzimidazole (0.463 g), N,N'-carbonyldiimidazole (0.448 g), 1-butanesulfonamide (0.379 g) and diazabicycloundecene (0.421 g). $^1$H-NMR (DMSO-d6, δ): 0.84 (3H, t, J=7.3 Hz), 1.33 (2H, m), 1.44 (2H, m), 2.53 (3H, s), 3.16 (2H, m), 5.64 (2H, s), 6.03 (1H, d, J=8.4 Hz), 7.25 (1H, dd, J=2.1 and 8.4 Hz), 7.30 (1H, t, J=7.8 Hz), 7.44 (1H, d, J=7.4 Hz), 7.68 (1H, d, J=2.1 Hz), 7.87 (1H, d, J=7.8 Hz), 12.18 (1H, br s).

IR(KBr): 1690 cm$^{-1}$.

mp: 98.5–102.0° C.

($R_1$=2-chlorobenzyl, $R_2$=methyl, $R_3$=—C(O)NR$_4$R$_5$, $R_4$=SO$_2$R$_6$, $R_5$=H, $R_6$=butyl, n=1, y=0)

Example 225

1-(2-Chlorobenzyl)-2-Methyl-6-[1-[3-(Trimethylsilyl)Propane]Sulfonylcarbamoyl] Benzimidazole

By using the method of example 111, 1-(2-chlorobenzyl)-2-methyl-6-[1-[3-(trimethylsilyl)propane]sulfonylcarbamoyl]benzimidazole (0.604 g) is obtained from 6-carboxy-1-(2-chlorobenzyl)-2-methylbenzimidazole (0.400 g), N,N'-carbonyldiimidazole (0.431 g), 1-[3-(trimethylsilyl)propane]sulfonamide (0.520 g), and diazabicycloundecene (0.404 g).

$^1$H-NMR (DMSO-d6, δ): −0.06 (9H, s), 0.61 (2H, t, J=8.6 Hz), 1.66–1.73 (2H, m), 2.50 (3H, s), 3.51 (2H, t, J=7.7 Hz), 5.61 (2H, s), 6.46 (1H, d, J=7.8 Hz), 7.24 (1H, t, J=7.6 Hz), 7.35 (1H, t, J=7.6 Hz), 7.57 (1H, dd, J=7.9 and 0.9 Hz), 7.70 (1H, d, J=8.5 Hz), 7.81 (1H, dd, J=1.5 and 8.5 Hz), 8.12 (1H, d, J=1.4 Hz), 11.98 (1H, s).

IR(KBr): 1688 cm$^{-1}$.

mp: 197.0–203.9° C.

($R_1$=2-chlorobenzyl, $R_2$=methyl, $R_3$=—C(O)NR$_4$R$_5$, $R_4$=SO$_2$R$_6$, $R_5$=H, $R_6$=3-trimethylsilyl-propyl, n=1, y=0)

Example 226

4-Ethoxycarbonyl-2-Methylbenzimidazole

A mixture of 2-acetylamino-3nitromethylzenzoate (8.03 g), reduced iron (18.8 g), acetic acid (20 ml), and ethanol (40 ml) is refluxed by heating for 18 hours. After the solvent is concentrated, chloroform and 10% hydrochloric acid is added to the residue and extraction is performed. After a saturated sodium bicarbonate aqueous solution is added to the water layer to turn it basic, chloroform extraction is performed. The chloroform is removed under reduced pressure and thus, 4-ethoxycarbonyl-2-methylbenzimidazole (1.61 g) is obtained. $^1$H-NMR (CDCl$_3$, δ): 1.43 (3H, t), 2.66 (3H, s), 4.45 (2H, q), 7.24–7.28 (1H, m), 7.84–7.89 (2H, m), 10.26 (1H, br s).

($R_1$=H, $R_2$=methyl, $R_3$=-ethoxycarbonyl, n=1, y=0)

Example 227

1-(2,4-Dichlorobenzyl)-4-Ethoxycarbonyl-2-Methylbenzimidazole

A mixture of 4-ethoxycarbonyl-2-methylbenzimidazole (1.61 g), 2,4-dichlorobenzyl chloride (3.08 g), potassium iodide (1.51 g), potassium carbonate (1.05 g) and N,N-dimethylformamide (4 ml) is stirred for 16 hours at 80° C. Chloroform and water are added and extraction is performed. The chloroform layer is washed with water, dried, and concentrated. The residue is purified using silica gel column chromatography (eluate: hexane/ethyl acetate=2/8) and thus, 1-(2,4-dichlorobenzyl)-4-ethoxycarbonyl-2-methylbenzimidazole (0.730 g) is obtained. $^1$H-NMR (CDCl$_3$, δ): 1.47 (3H, t, J=7.1 Hz), 2.63 (3H, s), 4.52 (2H, q, J=7.1 Hz), 5.39 (2H, s), 6.30 (1H, d, J=7.06 (1H, dd, J=2.1 and 8.4 Hz), 7.25 (1H, t, J=7.9 Hz), 7.32 (1H, dd, J=1.0 and 7.9 Hz), 7.48 (1H, d, J=2.0 Hz), 7.93 (1H, dd, J=1.0 and 7.7 Hz).

($R_1$=2,4-dichlorobenzyl, $R_2$=methyl, $R_3$=-ethoxycarbonyl, n=1, y=0)

Example 228

4-Carboxy-1-(2,4-Dichlorobenzyl)-2-Methylbenzimidazole

By using the method of example 75, 4-carboxy-1-(2,4-dichlorobenzyl)-2-methylbenzimidazole (0.575 g) is obtained from 1-(2,4-dichlorobenzyl)-4-ethoxycarbonyl-2-methylbenzimidazole (0.730 g). $^1$H-NMR (DMSO-d6, δ): 2.65 (3H, s), 5.67 (2H, s), 6.73 (1H, d, J=8.3 Hz), 7.33 (1H, dd, J=2.2 and 8.4 Hz), 7.39 (1H, t, J=7.9 Hz), 7.74 (1H, d, J=2.2 Hz), 7.76 (1H, d, J=8.2 7.7 Hz), 7.85 (1H, d, J=7.5 Hz), ($R_1$=2,4-dichlorobenzyl, $R_2$=methyl, $R_3$=carboxyl, n=1, y=0)

Example 229

4-(1-Butanesulfonylcarbamoyl)-1-(2,4-dichlorobenzyl)-2-methylbenzimidazole

By using the method of example 111, 4-(1-butanesulfonyl-carbamoyl)-1-(2,4-dichlorobenzyl)-2-methylbenzimidazole (0.275 g) is obtained from 4-carboxy-1-(2,4-dichlorobenzyl)-2-methylbenzimidazole (0.350 g), N,N'-carbonyldiimidazole (0.339 g), 1-butanesulfonamide (0.287 g) and diazabicycloundecene (0.318 g). $^1$H-NMR (DMSO-d6, δ): 0.86 (3H, t, J=7.3 Hz), 1.42 (2H, m), 1.73 (2H, m), 2.61 (3H, s), 3.61 (2H, m), 5.65 (2H, s), 6.67 (1H, d, J=8.4 Hz), 7.32 (1H, dd, J=2.1 and 8.4 Hz), 7.39 (1H, t, J=7.9 Hz), 7.73 (1H, d, J=2.1 Hz), 7.78 (1H, d, J=8.0 Hz), 7.91 (1H, d, J=7.7 Hz), 12.66 (1H, br s).

IR(KBr): 1699 cm$^{-1}$.

mp: 180.7–183.6° C.

($R_1$=2,4-dichlorobenzyl, $R_2$=methyl, $R_3$=—C(O)NR$_4$R$_5$, $R_4$=S0$_2$R$_6$, $R_5$=H, $R_6$=butyl, n=1, y=0)

Example 230

1-(4-Benzyloxybenzyl)-6-Ethoxycarbonyl-2-Methylbenzimidazole

By using the method of example 47, part B, preliminarily purified 3-[N-(4-benzyloxybenzyl)acetylamino]-4-nitroethylzenzoate is obtained from 3-acetylamino-4-nitro-ethylbenzoate (2.00 g) and 4-chlorobenzyl chloride (3.69 g). Subsequently, by using the method of example 47, part C, preliminarily purified 1-(4-benzyloxybenzyl)-6-ethoxycarbonyl-2-methylbenzimidazole (4.09 g) is obtained.

($R_1$=4-benzyloxybenzyl, $R_2$=methyl, $R_3$=-ethoxycarbonyl, n=1, y=0)

Example 231

1-(4-Benzyloxybenzyl)-6-Carboxy-2-Methylbenzimidazole

By using the method of example 75, 1-(4-benzyloxybenzyl)-6-carboxy-2-methylbenzimidazole (1.13 g) is obtained from 1-(4-benzyloxy-benzyl)-6-ethoxycarbonyl-2-methylbenzimidazole (4.09 g). $^1$H-NMR (DMSO-d6, δ): 2.57 (3H, s), 5.05 (2H, s), 5.48 (2H, s), 6.97 (2H, d, J=8.6 Hz), 7.08 (2H, d, J=8.5 Hz), 7.28–7.43 (5H, m), 7.60 (1H, d, J=8.3 Hz), 7.78 (1H, d, J=7.5 Hz), 8.07 (1H, s), 12.72 (1H, s).
($R_1$=4-benzyloxybenzyl, $R_2$=methyl, $R_3$=-carboxyl, n=1, y=0)

Example 232

1-(4-Benzyloxybenzyl)-6-(1-Butanesulfonylcarbamoyl)-2-Methylbenzimidazole

By using the method of example 111, 1-(4-benzyloxybenzyl)-6-(1-butanesulfonylcarbamoyl)-2-methylbenzimidazole (0.206 g) is obtained from 6-carboxy-1-(2-benzyloxybenzyl)-2-methylbenzimidazole (0.300 g), N,N'-carbonyldiimidazole (0.242 g), 1-butanesulfonamide (0.204 g), and diazabicyclo-undecene (0.227 g). $^1$H-NMR (DMSO-d6, δ): 0.87 (3H, t, J=7.3 Hz), 1.38–1.43 (2H, m), 1.64–1.71 (2H, m), 2.54 (3H, s), 3.49 (2H, t, J=6.8 Hz), 5.05 (2H, s), 5.45 (2H, s), 6.98 (2H, d, J=7.10 (2H, d, J=8.7 Hz), 7.31 (1H, t, J=7.2 Hz), 7.37 (2H, t, J=7.2 Hz), 7.41 (2H, d, J=7.3 Hz), 7.62 (1H, d, 8.5 Hz), 7.79 (1H, dd, J-1.5 and 8.4 Hz), 8.23 (1H, s), 11.93 (1H, s).
IR(KBr): 1684 cm$^{-1}$.
mp: 132.4–137.7° C.
($R_1$=4-benzyloxybenzyl, $R_2$=methyl, $R_3$=—C(O)NR$_4$R$_5$, $R_4$=SO$_2$R$_6$, $R_5$=H, $R_6$=butyl, n=1, y=0)

Example 233

6-Ethoxycarbonyl-1-[(2'-Cyanobiphenyl-4-yl)Methyl]-2-Methylbenzimidazole

By using the method of example 47, part B, preliminarily purified 3-[N-[(2'-cyanobiphenyl-4-yl)methyl]acetylamino]-4-nitroethyl-benzoate (0.750 g) is obtained from 3-acetylamino-4-nitro-ethylbenzoate (1.00 g) and 4'-bromomethyl-2-cyanobiphenyl (1.30 g). Subsequently, by using the method of example 47, part C, 6-ethoxycarbonyl-1-[(2'-cyanobiphenyl-4-yl)methyl]-2-methylbenzimidazole (0.410 g) is obtained. $^1$H-NMR (CDCl$_3$, δ): 1.40 (3H, t), 2.63 (3H, s), 4.39 (2H, q), 5.46 (2H, s), 7.17 (7.40–7.66 (5H, m), 7.73–7.78 (2H, m), 8.00 (1H, dd, J=1.5 and 8.5 Hz), 8.05 (1H, d, J=1.2 Hz).
($R_1$=2'-cyano-4-biphenyl, $R_2$=methyl, $R_3$=-ethoxycarbonyl, n=1, y=1)

Example 234

6-Carboxy-1-[(2'-Cyanobiphenyl-4-yl)Methyl]-2-Methylbenzimidazole

By using the method of example 75, 6-carboxy-1-[(2'-cyanobiphenyl-4-yl)methyl]-2-methylbenzimidazole (0.190 g) is obtained from 6-ethoxycarbonyl-1-[(2'-cyanobiphenyl-4-yl)methyl]-2-methylbenzimidazole (0.410 g).
$^1$H-NMR (DMSO-d6, δ): 2.59 (3H, s), 5.67 (2H, s), 7.24 (2H, d, J=8.1 Hz), 7.53–7.64 (5H, m), 7.75 (1H, t, J=7.7 Hz), 7.80 (1H, d), 7.92 (1H, d, J=7.7 Hz), 8.12 (1H, s), 12.74 (1H, br s).
($R_1$=2'-cyano-4-biphenyl, $R_2$=methyl, $R_3$=-carboxyl, n=1, y=1)

Example 235

6-(1-Butanesulfonylcarbamoyl-1-[(2'-Cyanobiphenyl-4-yl)Methyl]-2-Methyl-Benzimidazole By using the method of example 162, 6-(1-butanesulfonyl-carbamoyl-1-[(2'-cyanobiphenyl-4-yl)methyl]-2-methylbenzimidazole (0.155 g) is obtained from 6-carboxy-1-[(2'-cyanobiphenyl-4-yl)methyl]-2-methylbenzimidazole (0.187 g), N,N'-carbonyldiimidazole (0.160 g), 1-butanesulfonamide (0.135 g) and diazabicycloundecene (0.150 g) through purification using silica gel column chromatography (eluate: chloroform/methanol=20/1). $^1$H-NMR (DMSO-d6, δ): 0.83 (3H, t, J=7.4 hz), 1.34 (2H, m), 1.60 (2H,m), 2.56 (3H, s), 3.27 (2H, m), 5.62 (2H, s), 7.23 (2H, d, J=8.2 Hz), 7.53–7.57 (4H, m), 7.60 (1H, d, J=7.8 Hz), 7.75 (1H, dt, J=1.0 and 7.8 Hz), 7.83 (1H, dd, J=1.5 and 8.4 Hz), 7.92 (1H. d), 8.13 (1H, s), 11.92 (1H, br s).
IR(KBr): 2223 cm$^{-1}$.
mp: 115–118° C.
($R_1$=2'-cyano-4-biphenyl, $R_2$=methyl, $R_3$=—C(O)NR$_4$R$_5$, $R_4$=SO$_2$R$_6$, $R_5$=H, $R_6$=butyl, n=1, y=1)

Example 236

6-Ethoxycarbonyl-1-[(2'-Fluorobiphenyl-4-yl)Methyl]-2-Methylbenzimidazole

A.) 2-Fluoro-4'-methylbiphenyl 1.6M-n-Butyllithiumhexane solution (30 ml) is added to tetrahydrofuran (30 ml), the tetrahydrofuran is chilled to −78° C. under a nitrogen environment beforehand. Subsequent to this addition, a tetrahydrofuran (30 ml) solution of 4-bromotoluene (8.33 g) is added. Then, the solution is stirred for one hour at −78° C. A tetrahydrofuran (30 ml) solution of zinc chloride (6.64 g), which had been heat-dissolved and dehydrated under reduced pressure, is added to the solution at −78° C. and the solution is stirred for one hour at room temperature. This solution is added to a tetrahydrofuran (30 ml) solution of 2-fluoroiodobenzene (7.22 g) and tetrakis(triphenylphosphyne)palladium (0.52 g) at room temperature, and the solution is stirred for a day and a night. The reaction solution is diluted with ethyl acetate (300 ml), 10% hydrochloric acid is added, and extraction is performed. After the organic layer is washed with a saturated saline solution and dried, it is concentrated. The residue is purified using silica gel column chromatography (eluate: hexane) and thus, oily 2-fluoro-4'-methylbiphenyl (6.05 g) is obtained. $^1$H-NMR (CDCl$_3$, δ): 2.39 (3H, s), 7.10–7.30 (5H, m), 7.39–7.49 (3H, m).

B.) 2-Fluoro-4'-bromomethylbiphenyl

A mixture of 2-fluoro-4'-methylbiphenyl (8.70 g), N-bromosuccinimide (8.32 g), 2,2'-azobisisobutyronitrile (0.10 g) and carbon tetrachloride (150 ml) is refluxed by heating for five hours. The reaction solution is washed with water. The residue, which is obtained by concentrating the organic layer, is purified using silica gel column chromatography (eluate: hexane/ethyl acetate=9/1) and thus, preliminarily purified 2-fluoro-4'-bromomethylbiphenyl is obtained. Furthermore, crystallization using hexane produced 2-fluoro-4'-bromomethylbiphenyl (4.93 g). $^1$H-NMR (CDCl$_3$, δ): 4.55 (2H, s), 7.13–7.23 (2H, m), 7.33 (1H, m), 7.43 (1H, m), 7.47 (2H, d, J=8.1 Hz), 7.54 (2H, d, J=8.1 Hz).

C.) 3-[N-[(2'-Fluorobiphenyl-4-yl)methyl]acetylamino]-4-nitro-ethylbenzoate

By using the method of example 47, part B, 3-[N-[(2'-fluorobiphenyl-4-yl)methyl]acetylamino]-4-nitro-ethylbenzoate (1.90 g) is obtained from 3-acetylamino-4-nitro-ethylbenzoate (1.54 g) and 2-fluoro-4'-bromomethylbiphenyl (2.26 g). $^1$H-NMR (CDCl$_3$, δ): 1.33 (3H, t, J=7.1 Hz), 1.92 (3H, s), 4.36 (2H, m), 4.44 (1H, d, J=4.4 Hz), 5.32 (1H, d, J=4.4 Hz), 7.13 (1H, m), 7.18–7.22 (3H, m), 7.31 (1H, m), 7.40 (1H, dt, J=1.6 and 7.7 Hz), 7.44 (2H, d), 7.67 (1H, d, J=1.6 Hz), 7.94 (1H, d, J=8.4 Hz), 8.15 (1H, dd, J=1.8 and 8.4 Hz).

D.) 6-Ethoxycarbonyl-1-[(2'-fluorobiphenyl-4-yl)methyl]-2-methylbenzimidazole

By using the method of example 47, part C, 6-ethoxycarbonyl-1-[(2'-fluorobiphenyl-4-yl)methyl]-2-methylbenzimidazole (1.53 g) is obtained from 3-[N-[(2'-fluorobiphenyl-4-yl)methyl]acetylamino]-4-nitro-ethylbenzoate (1.90 g). $^1$H-NMR (CDCl$_3$, δ): 1.40 (3H, t, J=7.1 Hz), 2.62 (3H, s), 4.38 (2H, q, J=7.1 Hz), 5.43 (2H, s), 7.10–7.17 (3H, m), 7.19 (1H, dt, J=1.0 and 7.5 Hz), 7.31 (1H, m), 7.38 (1H, dt, J=1.8 and 7.8 Hz), 7.50 (2H, dd), 7.74 (1H, d, J=8.5 Hz), 8.00 (1H, dd, J=1.4 and 8.4 Hz), 8.06 (1H, s).
($R_1$=2'-fluoro-4-biphenyl, $R_2$=methyl, $R_3$=ethoxycarbonyl, n=1, y=1)

Example 237

6-Carboxy-1-[(2'-Fluorobiphenyl-4-yl)Methyl]-2-Methylbenzimidazole

By using the method of example 75, 6-carboxy-1-[(2'-fluorobiphenyl-4-yl)methyl]-2-methylbenzimidazole (1.24 g) is obtained from 6-ethoxycarbonyl-1-[(2'-fluorobiphenyl-4-yl)methyl]-2-methylbenzimidazole (1.50 g).

$^1$H-NMR (DMSO-d6, δ): 2.59 (3H, s), 5.63 (2H, s), 7.19 (2H, d, J=8.1 Hz), 7.24–7.31 (2H, m), 7.39 (1H, m), 7.46–7.53 (3H, m), 7.62 (1H, d, J=8.4 Hz), 7.80 (1H, dd, J=1.3 and 8.4 Hz), 8.10 (1H, s).
($R_1$=2'-fluoro-4-biphenyl, $R_2$=methyl, $R_3$=ethoxycarbonyl, n=1, y=1)

Example 238

6-(1-Ethanesulfonylcarbamoyl)-1-[(2'-Fluorobiphenyl-4-yl)Methyl]-2-Methylbenzimidazole By using the method of example 111, 6-(1-ethanesulfonyl-carbamoyl)-1-[(2'-fluorobiphenyl-4-yl)methyl]-2-methylbenzimidazole (0.340 g) is obtained from 6-carboxy-1-[(2'-fluorobiphenyl-4-yl)methyl]-2-methylbenzimidazole (0.455 g), N,N'-carbonyldiimidazole (0.409 g), 1-butanesulfonamide (0.346 g) and diazabicycloundecene (0.384 g). $^1$H-NMR (DMSO-d6, δ): 0.84 (3H, t, J=7.3 Hz), 1.39 (1H, m), 1.67 (1H, m), 2.57 (3H, s), 3.51 (1H, t), 5.60 (2H, s), 7.21 (2H, d, J=8.0 Hz), 7.24–7.30 (2H, m), 7.39 (1H, m), 7.48 (1H, t), 7.52 (2H, d, J=8.0 Hz), 7.66 (1H, d, J=8.5 Hz), 7.80 (1H, d, J=8.5 Hz), 8.25 (1H,s), 11.93 (1H, br s).
($R_1$=2'-fluoro-4-biphenyl, $R_2$=methyl, $R_3$=—C(O)NR$_4$R$_5$, R$_4$=SO$_2$R$_6$, R$_5$=H, R$_6$=ethyl, n=1, y=1)

Example 239

6-Ethoxycarbonyl-1-[(3-Fluorobiphenyl-4-yl)Methyl]-2-Methylbenzimidazole

A.) 3-Fluoro-4-methylbiphenyl 1.6M-n-Butyllithiumhexane solution (30 ml) is added to tetrahydrofuran (30 ml) the tetrahydrofuran is chilled to −78° C. under a nitrogen environment beforehand. Subsequent to this addition, a tetrahydrofuran (30 ml) solution of 4-bromo-2-fluorotoluene (9.21 g) is added. Then, the solution is stirred for one hour at −78° C. A tetrahydrofuran (30 ml) solution of zinc chloride (6.64 g), which had been heat-dissolved and dehydrated under reduced pressure, is added to the solution at −78° C. and the solution is stirred for one hour at room temperature. This solution is added to a tetrahydrofuran (30 ml) solution of iodobenezen (6.63 g) and tetrakis(triphenylphosphyne)palladium (0.52 g) at room temperature, and the solution is stirred for a day and a night. The reaction solution is diluted with ethyl acetate (300 ml), 10% hydrochloric acid is added, and extraction is performed. After the organic layer is washed with a saturated saline solution and dried, it is concentrated. The residue is purified using silica gel column chromatography (eluate: hexane) and thus, oily 3-fluoro-4-methylbiphenyl (6.00 g) is obtained. $^1$H-NMR (CDCl$_3$, δ): 2.31 (3H, d, J=1.8 Hz), 7.20–7.28 (3H, m), 7.34 (1H, m), 7.43 (2H, t), 7.55 (2H, d).

B.) 4-Bromomethyl-3-fluorobiphenyl

A mixture of 3-fluoro-4-methylbiphenyl (6.00 g), N-bromosuccinimide (5.73 g), 2,2'-azobisisobutyronitrile (0.075 g) and carbon tetrachloride (120 ml) is refluxed by heating for five hours. The reaction solution is washed with water. The residue, which is obtained by concentrating the organic layer, is purified using silica gel column chromatography (eluate: hexane/ethyl acetate=9/1) and thus, oily 4-bromomethyl-3-fluorobiphenyl (8.30 g) is obtained. $^1$H-NMR (CDCl$_3$, δ): 4.57 (2H, s), 7.30 (1H, d, J=11.0 Hz), 7.34–7.40 (2H, m), 7.45 (3H, m), 7.56 (2H, d).

C.) 3-[N-[(3-Fluorobiphenyl-4-yl)methyl]acetylamino]-4-nitro-ethylbenzoate

By using the method of example 47, part B, 2.68 g of a preliminarily purified material of 3-[N-[(3-fluorobiphenyl-4-yl)methyl]acetylamino]-4-nitro-ethylbenzoate is obtained from 3-acetylamino-4-nitro-ethylbenzoate (1.54 g) and 3-fluoro-4-bromomethylbiphenyl (2.26 g).

D.) 6-Ethoxycarbonyl-1-[(3-fluorobiphenyl-4-yl)methyl]-2-methylbenzimidazole

By using the method of example 47, part C, 6-ethoxycarbonyl-1-[(3-fluorobiphenyl-4-yl)methyl]-2-methylbenzimidazole (1.34 g) is obtained from the preliminarily purified material (2.68 g) of 3-[N-[(3-fluorobiphenyl-4-yl)methyl]acetylamino]-4-nitro-ethylbenzoate. $^1$H-NMR (CDCl$_3$, δ): 1.40 (3H, t, J=7.1 Hz), 2.65 (3H, s), 4.39 (2H, q, J=7.1 Hz), 5.46 (2H, s), 6.79 (1H, t, J=8.0 Hz), 7.25 (1H, m), 7.34–7.40 (2H, m), 7.41–7.47 (2H, m), 7.50–7.54 (2H, m), 7.74 (1H, d, J=8.5 Hz), 7.99 (1H, dd, J=1.5 and 8.4 Hz), 8.07 (1H, d, J=1.3 Hz).
($R_1$=2'-fluoro-4-biphenyl, $R_2$=methyl, $R_3$=-ethoxycarbonyl, n=1, y=1)

Example 240

6-Carboxy-1-[(3-Fluorobiphenyl-4-yl)Methyl]-2-Methylbenzimidazole

By using the method of example 75, 6-carboxy-1-[(3-fluorobiphenyl-4-yl)methyl]-2-methylbenzimidazole (1.15 g) is obtained from 6-ethoxycarbonyl-1-[(3-fluorobiphenyl-4-yl)methyl]-2-methylbenzimidazole (1.34 g).

$^1$H-NMR (DMSO-d6, δ): 2.59 (3H, s), 5.64 (2H, s), 7.03 (1H, t, J=8.0 Hz), 7.37 (1H, t, J=7.3 Hz), 7.42–7.48 (3H, m), 7.56–7.68 (4H, m), 7.79 (1H, dd, J=1.4 and 8.4 Hz), 8.11 (1H, s), 12.7 (1H, br s).
($R_1$=2'-fluoro-4-biphenyl, $R_2$=methyl, $R_3$=-carboxyl, n=1, y=1)

Example 241

6-(1-Butanesulfonylcarbamoyl)-1-[(3-Fluorobiphenyl-4-yl)Methyl]-2-Methylbenzimidazole By using the method of example 111, 6-(1-butanesulfonyl-carbamoyl)-1-[(3-fluorobiphenyl-4-yl)methyl]-2-methylbenzimidazole (0.236 g) is obtained from 6-carboxy-1-[(3-fluorobiphenyl-4-yl)methyl]-2- methylbenzimidazole (0.390 g), N,N'-carbonyldiimidazole (0.351 g), 1-butanesulfonamide (0.297 g) and diazabicycloundecene (0.329 g). $^1$H-NMR (DMSO-d6, δ): 0.84 (3H, t), 1.38 (2H, m), 1.65 (2H, m), 2.57 (3H, s), 3.48 (2H, m), 5.63 (2H, s), 6.93 (1H, t, J=8.1 Hz), 7.37 (1H, m), 7.42–7.47 (3H, m), 7.60 (1H, dd, J=1.7 and 11.8 Hz), 7.62–7.68 (3H, m), 7.80 (1H, dd, J=1.5 and 8.4 Hz), 8.21 (1H, d, J=1.3 Hz), 11.90 (1H, br s).

IR(Nujol): 1681 cm$^{-1}$.

mp: 227–230° C.

($R_1$=3-fluoro-4-biphenyl, $R_2$=methyl, $R_3$=—C(O)NR$_4$R$_5$, $R_4$=SO$_2$R$_6$, $R_5$=H, $R_6$=butyl, n=1, y=1)

Example 242

1-(2-Chlorobenzyl)-6-[(2-Methoxyethane) Sulfonylcarbamoyl]-2-Methylbenzimidazole By using the method of example 111, 1-(2-chlorobenzyl)-6-[(2-methoxyethane)sulfonylcarbamoyl]-2-methylbenzimidazole (0.149 g) is obtained from 1-(biphenyl-4-ylmethyl)-6-carboxy-2-ethylbenzimidazole (0.300 g), N,N'-carbonyldiimidazole (0.272 g), (2-ethoxyethane)sulfonamide (0.258 g) and diazabicycloundecene (0.256 g). $^1$H-NMR (DMSO-d6, δ): 0.87 (3H, t, J=6.9 Hz), 1.30 (3H, t, J=8.0 Hz), 2.89 (2H, q, J=7.6 Hz), 3.25–3.35 (2H, m), 3.63–3.74 (2H, m), 5.59 (2H, s), 7.17 (2H, d, J=8.1 Hz), 7.34 (1H, t, J=7.0 Hz), 7.44 (2H, t, J=7.6 Hz), 7.58–7.68 (5H, m), 7.82 (1H, d, J=8.4 Hz), 8.23 (1H, s), 11.88 (1H, s).

IR(Nujol): 1681 cm$^{-1}$.

mp: 78–81° C.

($R_1$=2-chlorobenzyl, $R_2$=methyl, $R_3$=—C(O)NR$_4$R$_5$, $R_4$=SO$_2$R$_6$, $R_5$=H, $R_6$2-methoxyethyl, n=1, y=0)

Example 243

1-(2,4-Dichlorobenzyl)-2-Methyl-6-(1-Pentanesulfonylcarbamoyl)Benzimidazole By using the method of example 111, 1-(2,4-dichlorobenzyl)-2-methyl-6-(1-pentanesulfonylcarbamoyl)benzimidazole (0.196 g) is obtained from 6-carboxy-1-(2,4-dichlorobenzyl)-2-methylbenzimidazole (0.300 g), N,N'-carbonyldiimidazole (0.323 g), 1-pentanesulfonamide (0.301 g) and diazabicyclo-undecene (0.303 g). $^1$H-NMR (DMSO-d6, δ): 0.81 (3H, t, J=7.3 Hz), 1.22–1.30 (2H, m), 1.32–1.39 (2H, m), 1.64–1.71 (2H, m), 2.50 (3H, s), 3.50 (2H, t, J=7.8 Hz), 5.59 (2H, s), 6.45 (1H, d, J=8.4 Hz), 7.33 (1H, dd, J=2.2 and 8.5 Hz), 7.69 (1H, t, J=8.5 Hz), 7.76 (1H, d, J=2.1 Hz), 7.80(1H, dd, J=1.6and8.5 Hz), 8.10 (1H, s), 11.89 (1H, s).

IR(Nujol): 1682 cm$^{-1}$.

mp: 213.2–214.6° C.

($R_1$=2,4-dichlorobenzyl, $R_2$=methyl, $R_3$=—C(O)NR$_4$R$_5$, $R_4$=SO$_2$R$_6$, $R_5$=H, $R_6$=pentyl, n=1, y=0)

Example 244

1-(Biphenyl-4-ylmethyl)-2-Ethyl-6-[1-[3-(Metbylthio)Propane]Sulfonylcarbamoyl] Benzimidazole By using the method of example 111, 1-(biphenyl-4-ylmethyl)-2-ethyl-6-[1-[3-(methylthio)propane]sulfonylcarbamoyl]benzimidazole (0.178 g) is obtained from 6-carboxy-1-(biphenyl-4-ylmethyl)-2-ethylbenzimidazole (0.300 g), N,N'-carbonyldiimidazole (0.272 g), 1-[(3-methylthio)propane]sulfonamide (0.285 g) and diazabicycloundecene (0.256 g). $^1$H-NMR (DMSO-d6, δ): 1.30 (3H, t, J=7.5 Hz), 1.91–1.99 (2H, m), 1.97 (3H, s), 2.58 (2H, t, J=7.2 Hz), 2.90 (2H, q, J=7.6 Hz), 3.55–3.61 (2H, m), 5.60 (2H, s), 7.18 (2H, d, J=8.2 Hz), 7.35 (1H, t, J=7.3 Hz), 7.44 (2H, t, J=7.5 Hz), 7.60–7.66 (4H, m), 7.69 (1H, d, J=8.5 Hz), 7.82 (1H, dd, J=1.8 and 8.5 Hz), 8.24 (1H, s), 11.98 (1H, s).

IR(Nujol): 1671 cm$^{-1}$.

mp: 89.9–91.2° C.

($R_1$=4-biphenyl, $R_2$=ethyl, $R_3$=—C(O)NR$_4$R$_5$, $R_4$=SO$_2$R$_6$, $R_5$=H, $R_6$=3-methylthiopropyl, n=1, y=1)

Example 245

1-(4-Biphenylmethyl)-2-Ethyl-6-(1-Pentanesulfonylcarbamoyl)Benzimidazole

By using the method of example 111, 1-(4-biphenylmethyl)-2-ethyl-6-(1-pentanesulfonylcarbamoyl) benzimidazole (0.258 g) is obtained from 6-carboxy-1-(4-biphenylmethyl)-2-ethylbenzimidazole (0.300 g), N,N'-carbonyldiimidazole (0.272 g), 1-pentanesulfonamide (0.254 g) and diazabicyclo-undecene (0.256 g). $^1$H-NMR (DMSO-d6, δ): 0.87 (3H, t, J=7.2 Hz), 1.22–1.39 (4H, m), 1.30 (3H, t, J=7.5 Hz), 1.66–1.73 (2H, m), 2.90 (2H, q, J=7.4 Hz), 3.51 (2H, t, J=7.7 Hz), 5.60 (2H, s), 7.18 (2H, d, J=8.2 Hz), 7.34 (1H, t, J=7.4 Hz), 7.44 (2H, t, J=7.6Hz), 7.60–7.67 (4H, m), 7.71 (1H, d, J=8.4 Hz), 7.81 (1H, dd, J=1.6 and 8.4 Hz), 8.27 (1H, d, J=1.1 Hz), 11.92 (1H, s).

IR(Nujol): 1682 cm$^{-1}$.

mp: 175.3–178.4° C.

($R_1$=4-biphenyl, $R_2$=ethyl, $R_3$=—C(O)NR$_4$R$_5$, $R_4$=SO$_2$R$_6$, $R_5$=H, $R_6$=3-pentyl, n=1, y=1)

Example 246

6-(1-Butanesulfonylcarbamoyl)-1-(2,4-Dichlorobenzyl)-2-Ethylbenzimidazole

By using the method of example 111, 6-(1-butanesulfonyl-carbamoyl)-1-(2,4-dichlorobenzyl)-2-ethylbenzimidazole (0.253 g) is obtained from 6-carboxy-1-(2,4-dichlorobenzyl)-2-ethylbenzimidazole (0.300 g), N,N'-carbonyldiimidazole (0.258 g), 1-butanesulfonamide (0.217 g) and diazabicycloundecene (0.262 g). $^1$H-NMR (DMSO-d6, δ): 0.85 (3H, t, J=7.4 Hz), 1.27 (3H, t, J=7.4 Hz), 1.35–1.43 (2H, m), 1.63–1.70 (2H, m), 2.81 (2H, q, J=7.4 Hz), 3.51 (2H, t, J=7.7 Hz), 5.59 (2H, s), 6.41 (1H, d, J=8.4 Hz), 7.32 (1H, dd, J=2.0 and 8.4 Hz), 7.73 (1H, d, J=8.4 Hz), 7.76 (1H, d, J=2.0 Hz), 7.81 (1H, dd, J=1.5 and 8.5 Hz), 8.12 (1H, d, J=1.6 Hz), 11.87 (1H, s).

IR(Nujol): 1694 cm$^{-1}$.

mp: 175.7–176.9° C.

($R_1$=2,4-dichlorobenzyl, $R_2$=ethyl, $R_3$=—C(O)NR$_4$R$_5$, $R_4$=SO$_2$R$_6$, $R_5$=H, $R_6$=butyl, n=1, y=0)

Example 247

1-(4-Biphenylmethyl)-2-Ethyl-6-[1-(3-Methyl) Butanesulfonylcarbamoyl]Benzimidazole By using the method of example 111, 1-(4-biphenylmethyl)-2-ethyl-6-[1-(3-methyl)butanesulfonylcarbamoyl]benzimidazole (0.273 g) is obtained from 1-(4-biphenylmethyl)-6-carboxy-2-ethylbenzimidazole (0.300 g), N,N'-carbonyldiimidazole (0.272 g), 1-(3-methyl)butanesulfonamide (0.254 g) and diazabicycloundecene (0.256 g).

¹H-NMR (DMSO-d6, δ): 0.85 (6H, d, J=6.5 Hz), 1.30 (3H, t, J=7.4 Hz), 1.55–1.62 (2H, m), 1.63–1.70 (1H, m), 2.90 (2H, q, J=7.4 Hz), 3.52 (2H, t, J=7.9 Hz), 5.61 (2H, s), 7.19 (2H, d, J=8.3 Hz), 7.35 (1H, t, J=7.4 Hz), 7.44 (2H, t, J=7.5 Hz), 7.61–7.66 (4H, m), 7.71 (1H, d, J=8.5 Hz), 7.81 (1H, dd, J=1.6 and 8.4 Hz), 8.27 (1H, s), 11.95 (1H, s).
IR(Nujol): 1682 cm⁻¹.
mp: 102.8–104.5° C.
($R_1$=4-biphenyl, $R_2$=ethyl, $R_3$=—C(O)NR₄R₅, $R_4$=SO₂R₆, $R_5$=H, $R_6$=3-methylbutyl, n=1, y=1)

Example 248

1-(2,4-Dichlorobenzyl)-5-Ethoxycarbonyl-2-Methylbenzimidazole

By using the method of example 47, part B, 4-[N-[(2,4-dichlorobenzyl)acetylamino]-3-nitro-ethylbenzoate is obtained from 4-acetylamino-3-nitro-ethylbenzoate (1.525 g) and 2,4-dichlorobenzyl chloride (1.42 g). By using the method of example 47, part C, without purification, this material is altered to 1-(2,4-dichlorobenzyl)-5-ethoxycarbonyl-2-methylbenzimidazole (1.476 g). ¹H-NMR (CDCl₃, δ): 1.42 (3H, t, J=7.1 Hz), 2.57 (3H, s), 4.41 (2H, q, J=7.1 Hz), 5.38 (2H, s), 6.35 (1H, d, J=8.4 Hz), 7.09 (1H, dd, J=2.0 and 8.4 Hz), 7.16 (1H, d, J=8.9 Hz), 7.49 (1H, d, J=2.0 Hz), 7.96 (1H, dd, J=1.5 and 8.5 Hz), 8.46 (1H, s).
($R_1$=2,4-dichlorobenzyl, $R_2$=methyl, $R_3$=-ethoxycarbonyl, n=1, y=0)

Example 249

5-Carboxy-1-(2,4-Dichlorobenzyl)-2-Methylbenzimidazole

By using the method of example 75, 5-carboxy-1-(2,4-dichlorobenzyl)-2-methylbenzimidazole (1.195 g) is obtained from 1-(2,4-dichlorobenzyl)-5-ethoxycarbonyl-2-methylbenzimidazole (1.465 g). ¹H-NMR (DMSO-d6, δ): 2.48 (3H, s), 5.56 (2H, s), 6.53 (1H, d, J=8.4 Hz), 7.32 (1H, dd, J=2.1 and 8.4 Hz), 7.44 (1H, d, J=8.4 Hz), 7.73 (1H, d, J=2.2 Hz), 7.78 (1H, dd, J=1.5 and 8.4 Hz), 8.15 (1H, d, J=1.3 Hz).
($R_1$=2,4-dichlorobenzyl, $R_2$=methyl, $R_3$=-carboxyl, n=1, y=0)

Example 250

5-(1-Butanesulfonylcarbamoyl)-1-(2,4-Dichlorobenzyl)-2-Methylbenzimidazole

By using the method of example 111, 5-(1-butanesulfonyl-carbamoyl)-1-(2,4-dichlorobenzyl)-2-methylbenzimidazole (0.690 g) is obtained from 5-carboxy-1-(2,4-dichlorobenzyl)-2-methylbenzimidazole (0.565 g), N,N'-carbonyldiimidazole (0.504 g), 1-butanesulfonamide (0.427 g) and diazabicycloundecene (0.473 g). ¹H-NMR (DMSO-d6, δ): 0.87 (3H, t, J=7.3 Hz), 1.41 (2H, m), 1.68 (2H, m), 2.49 (3H, s), 3.52 (2H, m), 5.58 (2H, s), 6.53 (1H, d, J=8.4 Hz), 7.33 (1H, dd, J=2.1 and 8.4 Hz), 7.50 (1H, d, J=8.5 Hz), 7.73 (1H, d, J=2.1 Hz), 7.78 (1H, dd, J=1.5 and 8.5 Hz), 8.24 (1H, s), 11.97 (1H, br s).
IR(Nujol): 1674 cm⁻¹.
mp: 135.4–139.2° C.
($R_1$=2,4-dichlorobenzyl, $R_2$=methyl, $R_3$=—C(O)NR₄R₅, $R_4$=SO₂R₆, $R_5$=H, $R_6$=butyl, n=1, y=0)

Example 251

1-(4-Biphenylmethyl)-5-Ethoxycarbonyl-2-Ethylbenzimidazole

By using the method of example 47, part B, 4-[N-[(4-biphenylmethyl)propionylamino]-3-nitro-ethylbenzoate is obtained from 4-propionylamino-3-nitro-ethylbenzoate (1.50 g) and 4-bromomethylbiphenyl (1.67 g). By using the method of example 47, part C, without purification, this material is altered to 1-(4-biphenylmethyl)-5-ethoxycarbonyl-2-ethylbenzimidazole (1.23 g). ¹H-NMR (CDCl₃, δ): 1.40 (3H, t, J=7.1 Hz), 1.45 (3H, t, J=7.6 Hz), 2.90 (2H, q, J=7.6 Hz), 4.39 (2H, q, J=7.1 Hz), 5.40 (2H, s), 7.09 (2H, d, J=8.2 Hz), 7.27 (1H, d, J=8.8 Hz), 7.34 (1H, m), 7.42 (2H, t), 7.55–7.51 (4H, m), 7.97 (1H, dd, J=1.5 and 8.4 Hz), 8.52 (1H, d, J=1.2 Hz).
($R_1$=4-biphenyl, $R_2$=ethyl, $R_3$=-ethoxycarbonyl, n=1, y=1)

Example 260

1-(4-Biphenylmethyl)-5-Carboxy-2-Ethylbenzimidazole

By using the method of example 75, 1-(4-biphenylmethyl)-5-carboxy-2-ethylbenzimidazole (0.870 g) is obtained from 1-(4-biphenylmethyl)-5-ethoxycarbonyl-2-ethylbenzimidazole (1.00 g). ¹H-NMR (DMSO-d6, δ): 1.30 (3H, t, J=7.4 Hz), 2.90 (2H, q, J=7.4 Hz), 5.57 (2H, s), 7.17 (2H, d, J=8.3 Hz), 7.33 (1H, m), 7.42 (2H, t), 7.63–7.57 (5H, m), 7.81 (1H, dd, J=1.6 and 8.6 Hz), 8.18 (1H, d, J=1.3 Hz), 12.67(1H, br s). (
$R_1$=4-biphenyl, $R_2$=ethyl, $R_3$=-carboxyl, n=1, y=1)

Example 261

1-(4-Biphenylmethyl)-5-(1-Butanesulfonylcarbamoyl)-2-Ethylbenzimidazole

By using the method of example 111, 1-(4-biphenylmethyl)-5-(1-butanesulfonylcarbamoyl)-2-ethylbenzimidazole (0.305 g) is obtained from 1-(4-biphenylmethyl)-5-carboxy-2-ethylbenzimidazole (0.400 g), N,N'-carbonyl-diimidazole (0.364 g), 1-butanesulfonamide (0.308 g) and diazabicycloundecene (0.342 g). ¹H-NMR (DMSO-d6, δ): 0.86 (3H, t, J=7.4 Hz), 1.30 (3H, t, J=7.5 Hz), 1.41 (2H, m), 1.68 (2H, m), 2.91 (2H, q, J=7.4 Hz), 3.52 (2H, m), 5.59 (2H, s), 7.16 (2H, d, J=8.2 Hz), 7.34 (1H, t, J=7.4 Hz), 7.43 (2H, t), 7.59–7.65 (5H, m), 7.80 (1H, dd, J=1.6 and 8.6 Hz), 8.24 (1H, d, J=1.6 Hz), 11.97 (1H, br s).
IR(Nujol): 1682 cm⁻¹.
mp: 142.9–144.4° C.
($R_1$=4-biphenyl, $R_2$=ethyl, $R_3$=—C(O)NR₄R₅, $R_4$=SO₂R₆, $R_5$=H, $R_6$=butyl, n=1, y=1)

Example 254

1-(4-Bilphenylmethyl)-2-Ethyl-6-(2-Methoxyethanesulfonylcarbamoyl)Benzimidazole

By using the method of example 111, 1-(4-biphenylmethyl)-2-ethyl-6-(2-methoxyethanesulfonylcarbamoyl)benzimidazole (0.487 g) is obtained from benzimidazole (0.513 g), N,N'-carbonyldiimidazole (0.464 g), 2-methoxyethanesulfonamide (0.420 g) and diazabicycloundecene (0.438 g). ¹H-NMR (DMSO-d6, δ): 1.30 (3H, t, J=7.5 Hz), 2.90 (2H, 1, J=7.4 Hz), 3.13 (3H, s),3.70–3.77 (4H, m), 5.60 (2H, s), 7.18 (2H, d, J=8.2 Hz), 7.35 (1H, t, J=7.1 Hz), 7.44 (2H, t, J=7.5 Hz), 7.60–7.67 (4H, m), 7.70 (1H, d, J=8.5 Hz), 7.80 (1H, dd, J=7.4 and 1.3 Hz), 8.25 (1H, s), 11.97 (1H, s).
IR(Nujol): 1684 cm⁻¹.
mp: 94.6–97.2° C.

($R_1$=4-biphenyl, $R_2$=ethyl, $R_3$=—C(O)NP$_4$R$_5$, $R_4$=SO$_2$R$_6$, $R_5$=H, $R_6$=2-methoxyethyl, n=1, y=1)

Example 255

6-Ethoxycarbonyl-2-Ethyl-1-[4-(4-Fluorobenzyloxy) Benzyl]Benzimidazole

A mixture of 4-propionylamino-3-amino-ethylbenzoate (0.534 g), potassium carbonate (0.374 g), 4-(4-fluorobenzyloxy)benzyl bromide (0.800 g), ethyl acetate (5 ml) and water (3 ml) is stirred for 16 hours at 75° C. The organic layer is concentrated, and ethanol and 36% hydrochloric acid (0.46 g) are added to the obtained residue. The residue is stirred for two hours as it is refluxed by heating. After neutralizing it by adding potassium carbonate, the solvent is concentrated under reduced pressure. Ethyl acetate and water are added and extraction is performed. The organic layer is concentrated under reduced pressure, purified using silica gel column chromatography (eluate: hexane/ethyl acetate=1/1), and thus, 6-ethoxycarbonyl-2-ethyl-1-[4-(4-fluorobenzyloxy)benzyl]benzimidazole (0.228 g) is obtained. $^1$H-NMR (CDCl$_3$δ): 1.40 (3H, t, J=7.1 Hz), 1.42 (3H, t, J=7.5 Hz), 2.86 (2H, q, J=7.5 Hz), 4.38 (2H, q, J=7.1 Hz), 4.97 (2H, s), 5.32 (2H, s), 6.88 (2H, q, J=8.7 Hz), 6.98 (2H, d, J=8.7 Hz), 7.05 (2H, t, J=8.7 Hz), 7.37 (2H, m), 7.76 (2H, d, J=8.4 Hz), 7.98 (1H, dd, J=1.5 and 8.5 Hz), 8.02 (1H, s).

($R_1$=4-(4-fluorobenzyloxy)benzyl, $R_2$=ethyl, $R_3$=-ethoxycarbonyl, n=1, y=0)

Example 264

6-Carboxy-2-Ethyl-1-[4-(4-Fluorobenzyloxy)benzyl] Benzimidazole

By using the method of example 75, 6-carboxy-2-ethyl-1-[4-(4-fluorobenzyloxy)benzyl]benzimidazole (0.175 g) is obtained from 6-ethoxycarbonyl-2-ethyl-1-[4-(4-fluorobenzyloxy)benzyl]benzimidazole (0.225 g). $^1$H-NMR (DMSO-d6, δ): 1.28 (3H, t, J=7.4 Hz), 2.89 (2H, q, J=7.4 Hz), 5.01 (2H, s), 5.47 (2H, s), 6.95 (2H, d), 7.03 (2H, d), 7.18 (2H, t), 7.45 (2H, m), 7.62 (1H, d, J=8.4 Hz), 7.77 (1H, d, J=8.4 Hz), 8.05 (1H, s).

($R_1$=4-(4-fluorobenzyloxy)benzyl, $R_2$=ethyl, $R_3$=-carboxyl, n=1, y=0)

Example 257

6-(1-Butanesulfonylcarbamoyl)-2-Ethyl-1-[4-(4-Fluorobenzyloxy)benzyl]Benzimidazole Ammonium Salt

By using the method of example 111, oily 6-(1-butanesulfonylcarbamoyl)-2-ethyl-1-[4-(4-fluorobenzyloxy)benzyl]benzimidazole is obtained from 6-carboxy-2-ethyl-1-[4-(4-fluorobenzyloxy)benzyl] benzimidazole (0.171 g), N,N'-carbonyldiimidazole (0.137 g), butanesulfonamide (0.116 g) and diazabicycloundecene (0.129 g). This is dissolved in ethyl acetate, and aqueous ammonia is added. Precipitated solids are separated through filtration, dried, and thus, 6-(1-Butanesulfonylcarbamoyl)-2-ethyl-1-[4-(4-fluorobenzyloxy)benzyl]benzimidazole Ammonium Salt (0.140 g) is obtained. $^1$H-NMR (DMSO-d6, δ): 0.83 (3H, t), 1.25 (3H, t), 1.35 (2H, m), 1.61 (2H, m), 2.84 (2H, q), 3.27 (2H, m), 5.01 (2H, s), 5.42 (2H, s), 6.95 (2H, d, J=7.8 Hz), 7.02 (2H, d, J=7.8 Hz), 7.17 (2H, t), 7.44 (2H, m), 7.57 (1H, d, J=8.1 Hz), 7.82 (1H, d, J=8.1 Hz), 8.12 (1H, s).

IR(Nujol): 1614 cm$^{-1}$.

mp: 105–115° C.

($R_1$=4-(4-fluorobenzyloxy)benzyl, $R_2$=ethyl, $R_3$=—C(O) NR$_4$R$_5$, $R_4$=SO$_2$R$_6$, $R_5$=H, $R_6$=butyl, n=1, y=0)

Example 258

1-[4-(3,4-Dichlorobenzyloxy)Benzyl]-6-Ethoxycarbonyl-2-Ethylbenzimidazole

By using the method of example 255, 1-[4-(3,4-dichlorobenzyloxy)benzyl]-6-ethoxycarbonyl-2-ethylbenzimidazole (2.01 g) is obtained from 4-propionylamino-3-amino-ethylbenzoate (1.81 g) and 4-(3,4-dichlorobenzyloxy)benzyl bromide (3.18 g). $^1$H-NMR (CDCl$_3$, δ): 1.40 (3H, t, J=7.1 Hz), 1.42 (3H, t, J=7.5 Hz), 2.86 (2H, q, J=7.5 Hz), 4.38 (2H, q, J=7.1 Hz), 4.97 (2H, s), 5.33 (2H, s), 6.87 (2H, m), 6.98 (2H, m), 7.22 (1H, dd, J=2.0 and 8.3 Hz), 7.44 (1H, d, J=8.3 Hz), 7.50 (1H, d, J=2.0 Hz), 7.76 (1H, d, J=8.6 Hz), 7.97 (1H, dd, J=1.6 and 8.6 Hz), 8.02 (1H, d, J=1.3 Hz).

($R_1$=4-(3,4-dichlorobenzyloxy)benzyl, $R_2$=ethyl, $R_3$=ethoxycarbonyl, n=1, y=0)

Example 259

6-Carboxy-1-[4-(3,4-Dichlorobenzyloxy)benzyl]-2-Ethylbenzimidazole

By using the method of example 75, 6-carboxy-1-[4-(3,4-dichlorobenzyloxy)benzyl]-2-ethylbenzimidazole (1.82 g) is obtained from 6-ethoxycarbonyl-2-ethyl-1-[4-(4-fluorobenzyloxy)benzyl]benzimidazole (2.01 g). $^1$H-NMR (DMSO-d6, δ): 1.28 (3H, t), 2.88 (2H, q), 5.05 (2H, s), 5.47 (2H, s), 6.96 (2H, d), 7.04 (2H, d), 7.39 (1H, m), 7.68–7.59 (3H, m), 7.78 (1H, d, J=8.4 Hz), 8.06 (1H, s).

($R_1$=4-(3,4-dichlorobenzyloxy)benzyl, $R_2$=ethyl, $R_3$=carboxyl, n=1, y=0)

Example 260

6-(1-Butanesulfonylcarbamoyl)-1-[4-(3,4-Dichlorobenzyloxy)benzyl]-2-Ethylbenzimidazole Ammonium Salt

By using the method of example 111, oily 6-(1-butanesulfonylcarbamoyl)-1-[4-(3,4-dichlorobenzyloxy) benzyl]-2-ethylbenzimidazole is obtained from 6-carboxy-1-[4-(3,4-dichlorobenzyloxy)benzyl]-2-ethylbenzimidazole (0.500 g), N,N'-carbonyldiimidazole (0.356 g), butanesufonamide (0.301 g) and diazabicycloundecene (0.334 g). This is dissolved in ethyl acetate, and aqueous ammonia is added. Precipitated solids are separated through filtration, dried, and thus, 6-(1-butanesulfonylcarbamoyl)-1-[4-(3,4-dichlorobenzyloxy)benzyl]-2-ethylbenzimidazole ammonium salt (0.51 g) is obtained. $^1$H-NMR (DMSO-d6, δ): 0.82 (3H, t, J=7.3 Hz), 1.26 (3H, t, J=7.4 Hz), 1.31 (2H, m), 1.54 (2H, m), 2.84 (2H, q, J=7.4 Hz), 3.07 (2H, m), 5.05 (2H, s), 5.41 (2H, s), 6.95 (2H, d, J=8.7 Hz), 7.00 (2H, d, J=8.7 Hz), 7.41 (2H, d, J=8.2 Hz), 7.46 (2H, d, J=8.4 Hz), 7.62 (1H, d, J=8.2 Hz), 7.68 (1H, s), 7.81 (1H, d, J=8.4 Hz), 7.97 (1H, s).

IR(Nujol): 1540 cm$^{-1}$.

mp: 99.5–101.5° C.

($R_1$=4-(3,4-dichlorobenzyloxy)benzyl, $R_2$=ethyl, $R_3$=—C(O)—NR$_4$R$_5$, $R_4$=SO$_2$R$_6$, $R_5$=H, n=1, y=0)

Example 261

1-(4-Biphenylmethyl)-6-(n-Butylcarbamoyl)-2-Ethylbenzimidazole

By using the method of example 26, 1-(4-biphenylmethyl)-6-(n-butylcarbamoyl)-2- ethylbenzimidazole (0.295 g) is obtained from 1-(4-biphenylmethyl)-6-chlorocarbonyl-2-ethylbenzimidazole hydrochloride (0.400 g), n-butylamine (0.233 g) and triethylamine (0.215 g). $^1$H-NMR (DMSO-d6, δ): 0.95 (3H, t, J=7.3 Hz), 1.37–1.48 (2H, m), 1.45 (3H, t, J=7.4 Hz), 1.57–1.63 (2H, m), 2.90 (2H, q, J=7.5 Hz), 3.46 (2H, q, J=7.1 Hz), 5.42 (2H, s), 6.16 (1H, br s), 7.10 (2H, d, J=8.1 Hz), 7.34 (1H, t, J=7.5 Hz), 7.42 (2H, t, J=7.5 Hz), 7.48–7.57 (5H, m), 7.87 (1H, d, J=8.4 Hz), 7.91 (1H, s).

IR(Nujol): 1621 cm$^{-1}$.

mp: 170.5–173.0° C.

($R_1$=4-biphenyl, $R_2$=ethyl, $R_3$=—C(O)—NR$_4$R$_5$, $R_4$=n-butyl, $R_5$=H, n=1, y=1)

Example 262

1-(4-Biphenylmethyl)-2-Ethyl-6-(Thiazole-2-ylcarbamoyl)Benzimidazole

By using the method of example 26, 1-(4-biphenylmethyl)-2-ethyl-6-(thiazole-2-ylcarbamoyl)benzimidazole (0.179 g) is obtained from 1-(4-biphenylmethyl)-6-chlorocarbonyl-2-ethylbenzimidazole hydrochloride (0.400 g), 2-aminothiazole (0.318 g) and triethylamine (0.215 g). $^1$H-NMR (DMSO-d6, δ): 1.48 (3H, t, J=7.5 Hz), 2.95 (2H, q, J=7.5 Hz), 5.41 (2H, s), 6.94 (1H, d, J=3.6 Hz), 7.06 (2H, d, J=8.1 Hz), 7.26 (1H, d, J=3.6 Hz), 7.32 (1H, t, J=7.4 Hz), 7.39 (2H, t, J=7.3 Hz), 7.47–7.51 (4H, m), 7.87 (2H, s), 8.03 (1H, s), 11.15 (1H, s).

IR(Nujol): 1652 cm$^{-1}$.

mp 225.2–227.7° C.

($R_1$=4-biphenyl, $R_2$=ethyl, $R_3$=—C(O)—NR$_4$R$_5$, $R_4$=2-thiazolyl, $R_5$=H, n=1, y=1)

Example 263

1-(4-Biphenylmethyl)-2-Ethyl-6-(2-Pyridylcarbamoyl)Benzimidazole

By using the method of example 111, 1-(4-biphenylmethyl)-2-ethyl-6-(2-pyridylcarbamoyl)benzimidazole (0.116 g) is obtained from 1-(4-biphenylmethyl)-6-carboxy-2-ethylbenzimidazole (0.300 g), N,N'-carbonyldiimidazole (0.272 g), 2-aminopyridine (0.158 g) and diazabicycloundecene (0.256 g). $^1$H-NMR (CDCl$_3$, δ): 1.47 (3H, t, J=7.6 Hz), 2.93 (2H, q, J=7.4 Hz), 5.45 (2H, s), 7.06 (1H, dd, J=7.4 and 4.9 Hz), 7.10 (2H, d, J=8.1 Hz), 7.34 (1H, t, J=7.4 Hz), 7.42 (2H, t, J=7.6 Hz), 7.50–7.55 (4H, m), 7.75 (1H, t, J=7.9 Hz), 7.79 (1H, d, J=8.4 Hz), 7.86 (1H, d, J=8.4 Hz), 7.98 (1H, s), 8.30 (1H, d, J=6.2 Hz), 8.38 (1H, d, J=8.4 Hz), 8.62 (1H, s).

IR(Nujol): 1661 cm$^{-1}$.

mp: 160.9–164.5° C.

($R_1$=4-biphenyl, $R_2$=ethyl, $R_3$=—C(O)—NR$_4$R$_5$, $R_4$=2-pyridyl, $R_5$=H, n=1, y=1)

Example 264

6-(n-Butylcarbamoyl)-1-(2,4-Dichlorobenzyl)-2-Methylbenzimidazole

By using the method of example 26, 6-(n-butylcarbamoyl)-1-(2,4-dichlorobenzyl)-2-methylbenzimidazole (0.156 g) is obtained from 6-chlorocarbonyl-1-(2,4-dichlorobenzyl)-2-ethylbenzimidazole hydrochloride (0.300 g), triethylamine (0.181 g) and n-butylamine (0.196 g). $^1$H-NMR (CDCl$_3$, δ): 0.96 (3H, t, J=7.3 Hz), 1.37–1.43 (2H, m), 1.55–1.62 (2H, m), 2.56 (3H, s), 3.46 (2H, q, J=7.0 Hz), 5.40 (2H, s), 6.15 (1H, br s), 6.32 (1H, d, J=8.5 Hz), 7.07 (1H, d, J=8.4 Hz), 7.48 (1H, d, J=2.0 Hz), 7.55 (1H, d, J=8.4 Hz), 7.74 (1H, d, J=8.4 Hz), 7.79 (1H, s).

IR(Nujol): 1636 cm$^{-1}$.

mp: 146.6–147.5° C.

($R_1$=2,4-dichlorobenzyl, $R_2$=methyl, $R_3$=—C(O)—NR$_4$R$_5$, $R_4$=n-butyl, $R_5$=H, n=1, y=0)

Example 265

1-[sec-(2,4-Dichlorophenethyl)]-6-Ethoxycarbonyl-2-Methylbenzimidazole

A.) 3-[sec-(2,4-Dichlorophenethyl)amino]-4-nitro-ethylbenzoate

A toluene (5 ml) solution of 3-fluoro-4-nitro-benzoic acid (0.877 g) and sec-(2,4-dichlorophenethyl)amine (2.25 g) is refluxed by heating for 15 hours. After the solvent is removed by evaporation, the residue is purified using silica gel column chromatography and thus, a preliminarily purified material of 3-[sec-(2,4-dichlorophenethyl)amino]-4nitro-benzoic acid is obtained. Ethanol (80 ml) and 97% sulfuric acid (3.0 g) are added to this, and the solution is refluxed by heating for 4.5 hours. After removing the ethanol by evaporation under reduced pressure, chloroform and a saturated sodium bicarbonate aqueous solution are added and extraction is performed. After drying the organic layer, a residue is obtained through concentration under reduced pressure. The residue is purified using silica gel column chromatography (eluate: hexane/ethyl acetate=2/1) and thus, 3-[sec-(2,4-dichlorophenethyl)amino]-4-nitro-ethylbenzoate (1.16 g) is obtained. $^1$H-NMR (CDCl$_3$, δ): 1.35 (3H, t, J=7.1 Hz), 1.64 (3H, d, J=6.6 Hz), 4.30 (2H, q, J=7.1 Hz), 5.16 (1H, m), 7.18–7.31 (4H, m), 7.43 (1H, d, J=2.0 Hz), 8.21 (1H, d, J=8.8 Hz), 8.34 (1H, d, J=5 Hz).

B.) 4-Amino-3-[sec-(2,4-dichlorophenethyl)amino] ethylbenzoate

A mixture of 3-[sec-(2,4-dichlorophenethyl)amino]-4-nitro-ethylbenzoate (1.14 g), reduced iron (1.60 g), ethanol (10 ml) and acetic acid (5 ml) is refluxed by heating for three hours. Solids are separated through filtration. The filtrate is concentrated and a residue is formed. Extraction is performed on the residue with chloroform and 10% hydrochloric acid. The organic layer is washed with a saturated sodium bicarbonate aqueous solution and the solvent is removed by evaporation under reduced pressure. The obtained residue is purified using silica gel column chromatography (eluate: hexane/ethyl acetate=2/1) and thus, 4-amino-3-[sec-(2,4-dichlorophenethyl)amino]ethylbenzoate (0.920 g) is obtained. $^1$H-NMR (CDCl$_3$, δ): 1.31 (3H, t, J=7.1 Hz), 1.52 (3H, d, J=6.7 Hz), 3.56 (1H, br s), 3.79 (2H, br s), 4.23 (2H, q, J=7.1 Hz), 4.96 (1H, q, J=6.7 Hz), 6.68 (1H, d, J=8.0 Hz), 7.03 (1H, d, J=1.7 Hz), 7.15 (1H, dd, J=2.1 and 8.4 Hz), 7.35 (1H, d, J=8.4 Hz), 7.39–7.43 (2H, m).

C.) 1-[sec-(2,4-Dichlorophenethyl)]-6-ethoxycarbonyl-2-methylbenzimidazole

Acetyl chloride (0.243 g) is dripped into a pyridine (2.0 ml) solution of 4-amino-3-[sec-(2,4-dichlorophenethyl) amino]ethylbenzoate (0.900 g) at room temperature. After the solution is stirred for one hour at room temperature, ethyl acetate and excessive 10% hydrochloric acid are added and extraction is performed. The organic layer is washed with a saturated sodium bicarbonate aqueous solution. Removal of the solvent through evaporation under reduced pressure produced a preliminarily purified material of 4-4-acetylamino-3-[sec-(2,4-dichlorophenethyl)amino] ethylbenzoate. This is immediately dissolved in ethanol (20 ml). 36% hydrochloric acid (0.4 ml) is added and the solution is refluxed by heating for two hours. Sodium bicarbonate is added and it is neutralized. The solvent is removed through evaporation under reduced pressure. Ethyl acetate and water are added to the residue and extraction is performed. The organic layer is concentrated, purified using silica gel column chromatography (eluate: ethyl acetate/methanol=20/1) and thus, 1-[sec-(2,4-dichlorophenethyl)]-6-ethoxycarbonyl-2-methylbenzimidazole (0.700 g) is obtained. $^1$H-NMR (CDCl$_3$, δ): 1.38 (3H, t, J=7.2 Hz), 2.01 (3H, d, J=7.2 Hz), 2.63 (3H, s), 4.29–4.40 (2H, m), 5.89 (1H, q, J=7.2 Hz), 7.37 (1H, dd J=2.2 and 8.4 Hz), 7.40 (1H, d, J=2.0 Hz), 7.52 (1H, d, J=8.4 Hz), 7.67 (1H, d, J=8.4 Hz), 7.86 (1H, s), 7.91 (1H, dd, J=1.4 and 8.4 Hz).
($R_1$=sec-(2,4-dichlorophenethyl), $R_2$=methyl, $R_3$=-ethoxycarbonyl, n=1, y=0)

Example 266

6-Carboxy-1-[sec-(2,4-Dichlorophenethyl)]-2-Methylbenzimidazole

By using the method of example 75, 6-carboxy-1-[sec-(2,4-dichlorophenethyl)]-2-methylbenzimidazole (0.447 g) is obtained from 1-[sec-(2,4-dichlorophenethyl)]-6-ethoxycarbonyl-2-methylbenzimidazole (0.690 g). $^1$H-NMR (DMSO-d6, δ): 1.88 (3H, d, J=6.8 Hz), 2.57 (3H, s), 6.01 (1H, q), 7.55 (1H, d), 7.60–7.67 (3H, m), 7.71 (1H, d), 7.89 (1H, d), 12.65 (1H, br s).
($R_1$=sec-(2,4-dichlorophenethyl), $R_2$=methyl, $R_3$=-carboxyl, n=1, y=0)

Example 267

6-(1-Butanesulfonylcarbamoyl)-1-[sec-(2,4-Dichlorophenethyl)]-2-Methylbenzimidazole By using the method of example 111, 6-(1-butanesulfonyl-carbamoyl)-1-[sec-(2,4-dichlorophenethyl)]-2-methylbenzimidazole is obtained from 6-carboxy-1-[sec-(2,4-dichlorophenethyl)]-2-methylbenzimidazole (0.433 g), N,N'-carbonyldiimidazole (0.412 g), butanesulfonamide (0.348 g), and diazabicycloundecene (0.386 g). $^1$H-NMR (DMSO-d6, δ): 0.84 (3H, d, J=7.3 Hz), 1.34 (2H, m), 1.57 (2H, m), 1.89 (3H, d, J=7.0 Hz), 2.49 (3H, s), 3.07 (2H, m), 5.954 (1H, q, J=7.0 Hz), 7.41 (1H, d, J=8.7 Hz), 7.56 (1H, dd, J=2.1 and 8.5 Hz), 7.61 (1H, d, J=2.1 Hz), 7.74–7.79 (3H, m).
($R_1$=sec-(2,4-dichlorophenethyl), $R_2$=methyl, $R_3$=—C(O)—NR$_4$R$_5$, R$_4$=SO$_2$R$_6$, R$_5$=H, R$_6$=butyl, n=1, y=0)

Example 268

1-(4-Biphenylmethyl)-2-Ethyl-6-(Phenylcarbamoyl)Benzimidazole

By using the method of example 26, 1-(4-biphenylmethyl)-2-ethyl-6-(phenylcarbamoyl)benzimidazole (0.195 g) is obtained from 1-(4-biphenylmethyl)-6-chlorocarbamoyl-2-ethylbenzimidazole hydrochloride (0.300 g), triethylamine (0.243 g) and aniline (0.224 g). $^1$H-NMR (CDCl$_3$, δ): 1.47 (3H, d, J=7.5 Hz), 2.93 (2H, q, J=7.5 Hz), 5.44 (2H, s), 7.11 (2H, d, J=8.2 Hz), 7.14 (1H, t, J=7.4 Hz), 7.32–7.38 (3H, m), 7.42 (2H, t, J=7.4 Hz), 7.51–7.54 (4H, m), 7.63 (2H, d, J=7.8 Hz), 7.69 (1H, dd, J=8.4 and 1.6 Hz), 7.84 (1H, d, J=8.4 Hz), 7.88 (1H, br s), 7.97 (1H, d, J=1.5 Hz).
IR(Nujol): 1647 cm$^{-1}$.
mp: 171.7–172.1° C.
($R_1$=4-biphenyl, $R_2$=ethyl, $R_3$=—C(O)—NR$_4$R$_5$, R$_4$=phenyl, R$_5$=H, n=1, y=1)

Example 269

1-(4-Biphenylmethyl)-2-Ethyl-6-(1,3,4-Thiadiazole-2-ylcarbamoyl)Benzimidazole

By using the method of example 111, 1-(4-biphenylmethyl)-2-ethyl-6-(1,3,4-thiadiazole-2-ylcarbamoyl)benzimidazole (339) (0.234 g) is obtained from 1-(4-biphenylmethyl)-6-carboxy-2-ethylbenzimidazole (0.300 g), N,N'-carbonyldiimidazole (0.272 g), 2-amino-1,3,4-thiadiazole (0.170 g) and diazabicyclo-undecene (0.256 g). $^1$H-NMR (CDCl$_3$, δ): 1.45 (3H, d, J=7.5 Hz), 2.90 (2H, q, J=7.5 Hz), 5.53 (2H, s), 7.07 (2H, d, J=8.3 Hz), 7.33 (1H, t, J=7.5 Hz), 7.40 (2H, t, J=7.3 Hz), 7.52 (4H, d, J=8.2 Hz), 7.89 (1H, d, J=8.5 Hz), 8.08 (1H, dd, J=8.5 and 1.6 Hz), 8.34 (1H, d, J=1.2 Hz), 7.60 (1H, s), 12.26 (1H, s).
IR(Nujol): 1654 cm$^{-1}$.
mp: 230.1–233.4° C.
($R_1$=4-biphenyl, $R_2$=ethyl, $R_3$=—C(O)—NR$_4$R$_5$, R$_4$=2-(1,3,4-thiadiazolyl), R$_5$=H, n=1, y=1)

Example 270

1-(4-Biphenylmethyl)-2-Ethyl-6-(Tetrazole-5-ylcarbamoyl)Benzimidazole

By using the method of example 111, 1-(4-biphenylmethyl)-2-ethyl-6-(tetrazole-5-ylcarbamoyl)benzimidazole (340) (0.135 g) is obtained from 1-(4-biphenylmethyl)-6-carboxy-2-ethylbenzimidazole (0.300 g), N,N'-carbonyldiimidazole (0.272 g), 5-aminotetrazole (0.143 g) and diazabicycloundecene (0.256 g). $^1$H-NMR (DMSO-d6, δ): 1.32 (3H, t, J=7.5 Hz), 2.93 (2H, q, J=7.5 Hz), 5.61 (2H, s), 7.23 (2H, d, J=8.1 Hz), 7.34 (1H, t, J=7.4 Hz), 7.44 (2H, t, J=7.6 Hz), 7.60–7.67 (4H, m), 7.76 (1H, d, J=8.5 Hz), 7.98 (1H, d, J=8.6 Hz), 8.46 (1H, s), 12.30 (1H, s), 15.95 (1H, s).
IR(Nujol): 1667 cm$^{-1}$.
mp: 273.1–276.0° C.
($R_1$=4-biphenyl, $R_2$=ethyl, $R_3$=—C(O)—NR$_4$R$_5$, R$_4$=5-tetrazolyl, R$_5$=H, n=1, y=1)

Example 271

1-(4-Biphenylmethyl)-2-Ethyl-6-(1,3,4-Triazole-3-ylcarbamoyl)Benzimidazole

By using the method of example 111, 1-(4-biphenylmethyl)-2-ethyl-6-(1,3,4-triazole-3-ylcarbamoyl)benzimidazole (341) (0.224 g) is obtained from 1-(4-biphenylmethyl)-6-carboxy-2-ethylbenzimidazole (0.300 g), N,N'-carbonyldiimidazole (0.272 g), 3-amino-1,3,4-triazole (0.141 g) and diazabicycloundecene (0.256 g). $^1$H-NMR (DMSO-d6, δ): 1.33 (3H, t, J=7.4 Hz), 2.93 (2H, q, J=7.4 Hz), 5.63 (2H, s), 7.17 (2H, d, J=8.3 Hz), 7.35 (1H, t, J=7.4 Hz), 7.44 (2H, t, J=7.5 Hz), 7.60–7.65 (4H, m), 7.78 (1H, d, J=7.4 Hz), 7.83 (1H, dd, J=8.4 and 1.5 Hz), 8.17 (1H, s), 8.77 (2H, s), 12.04 (1H, s).
IR(Nujol): 1675 cm$^{-1}$.
mp: 263.4–266.2° C.
($R_1$=4-biphenyl, $R_2$=ethyl, $R_3$=—C(O)—NR$_4$R$_5$, R$_4$=3-(1,3,4-triazolyl), R$_5$=H, n=1, y=1)

Example 272

1-(4-Biphenylmethyl)-2-Ethyl-6-(1,3,4-Triazole-2-ylcarbamoyl)Benzimidazole

By using the method of example 111, 1-(4-biphenylmethyl)-2-ethyl-6-(1,3,4-triazole-2-ylcarbamoyl)

benzimidazole (342) (0.215 g) is obtained from 1-(4-biphenylmethyl)-6-carboxy-2-ethylbenzimidazole (0.300 g), N,N'-carbonyldiimidazole (0.272 g), 2-amino-1,3,4-triazole (0.141 g) and diazabicycloundecene (0.256 g). $^1$H-NMR (DMSO-d6, δ): 1.31 (3H, t, J=7.4 Hz), 2.92 (2H, q, J=7.4 Hz), 5.60 (2H, s), 7.23 (2H, d, J=7.8 Hz), 7.34 (1H, t, J=7.2 Hz), 7.44 (2H, t, J=7.6 Hz), 7.60–7.66 (4H, m), 7.72 (1H, d, J=8.3 Hz), 7.78 (1H, s), 7.95 (1H, d, J=8.3 Hz), 8.43 (1H, s), 11.85 (1H, s), 13.57 (1H, s).

IR(Nujol): 1659 cm$^{-1}$.

mp: 306° C. (decomposition).

($R_1$=4-biphenyl, $R_2$=ethyl, $R_3$=—C(O)—$NR_5$, $R_4$=3-(1,3,4-triazolyl), $R_5$=H, n=1, y=1)

Example 273

1-(4-Biphenylmethyl)-2-Ethyl-6-(3-Pyridylcarbamoyl)Benzimidazole

By using the method of example 111, 1-(4-biphenylmethyl)-2-ethyl-6-(3-pyridylcarbamoyl) benzimidazole (0.229 g) is obtained from 1-(4-biphenylmethyl)-6-carboxy-2-ethylbenzimidazole (0.300 g), N,N'-carbonyldiimidazole (0.272 g), 3-aminopyridine (0.158 g) and diazabicycloundecene (0.256 g). $^1$H-NMR (CDCl$_3$, δ): 1.47 (3H, t, J=7.6 Hz), 2.93 (2H, q, J=7.4 Hz), 5.45 (2H, s), 7.10 (2H, d, J=8.1 Hz), 7.29–7.36 (2H, m), 7.42 (2H, t, J=7.4 Hz), 7.53 (4H, d, J=8.0 Hz), 7.71 (1H, d, J=8.5 Hz), 7.86 (1H, d, J=8.4 Hz), 7.97 (1H, s), 7.98 (1H, s), 8.27 (1H, d, J=8.4 Hz), 8.38 (1H, d, J=4.7 Hz), 8.68 (1H, d, J=2.5 Hz).

IR(Nujol): 1644 cm$^{-1}$.

mp: 124.4–125.6° C.

($R_1$=4-biphenyl, $R_2$=ethyl, $R_3$=—C(O)—$NR_4R_5$, $R_4$=3-pyridyl, $R_5$=H, n =1, y=1)

Example 274

1-(2,4-Dichlorobenzyl)-2-Ethyl-6-(2-Pyridylcarbamoyl)Benzimidazole

By using the method of example 111, 1-(2,4-dichlorobenzyl)-2-ethyl-6-(2-pyridylcarbamoyl) benzimidazole (0.152 g) is obtained from 6-carboxy-1-(2,4-dichlorobenzyl)-2-ethylbenzimidazole (0.300 g), N,N'-carbonyldiimidazole (0.290 g), 2-aminopyridine (0.168 g) and diazabicycloundecene (0.273 g). $^1$H-NMR (CDCl$_3$, δ): 2.59 (3H, s), 5.43 (2H, s), 6.33 (1H, d, J=8.4 Hz), 7.06–7.10 (2H, m), 7.50 (1H, d, J=2.1 Hz), 7.77 (1H, dt, J=7.8 and 1.9 Hz), 7.83 (2H, s), 7.88 (1H, s), 8.30 (1H, d, J=3.7 Hz), 8.39 (1H, d, J=8.3 Hz), 8.78 (1H, s).

IR(Nujol): 1666 cm$^{-1}$.

mp: 157.4–159.2° C.

($R_1$=2,4-dichlorbenzyl, $R_2$=ethyl, $R_3$=—C(O)—$NR_4R_5$, $R_4$=2-pyridyl, $R_5$=H, n=1, y=0)

Example 275

1-(4-Biphenylmethyl)-2-Ethyl-6-(4-Pyridylcarbamoyl)Benzimidazole

By using the method of example 111, 1-(4-biphenylmethyl)-2-ethyl-6-(4-pyridylcarbamoyl) benzimidazole (0.153 g) is obtained from 1-(4-biphenylmethyl)-6-carboxy-2-ethylbenzimidazole (0.300 g), N,N'-carbonyldiimidazole (0.272 g), 4-aminopyridine (0.158 g) and diazabicycloundecene (0.256 g). $^1$H-NMR (CDCl$_3$, δ): 1.48 (3H, t, J=7.4 Hz), 2.94 (2H, q, J=7.4 Hz), 5.45 (2H, s), 7.10 (2H, d, J=8.1 Hz), 7.35 (1H, d, J=7.4 Hz), 7.42 (2H, t, J=7.4 Hz), 7.50–7.60 (6H, m), 7.691 (1H, d, J=7.8 Hz), 7.86 (1H, d, J=8.3 Hz), 7.95 (1H, s), 7.99 (1H, br s), 8.54 (2H, dd, J=1.5 and 4.7 Hz).

IR(Nujol): 1663 cm$^{-1}$.

mp: 123.8–124.7° C.

($R_1$=4-biphenyl, $R_2$=ethyl, $R_3$=—C(O)—$NR_4R_5$, $R_4$=4-pyridyl, $R_5$=H, n=1, y=1)

Example 276

6-(1-Butanesulfonylcarbamoyl)-1-[4-(2-Pyridyl)benzyl]-2-Methylbenzimidazole

A.) N-(1-Butanesulfonyl)-4-acetylamino-3-nitrobenzamide

N,N'-carbonyldiimidazole (9.40 g) is added to an N,N-dimethylformamide (300 ml) solution of 4-acetylamino-3-nitro-benzoic acid (10.0 g), and the solution is stirred for 1 hour at room temperature. Then, 1-butanesulfonamide (7.92 g) and diazabicycloundecene (8.83 g) are added into the solution, and the solution is stirred for 72 hours at 100° C. After chloroform and water are added into the solution and the solution is separated into layers, the residue, which is obtained by concentrating the organic layer, is purified using silica gel column chromatography (eluate: ethyl acetate/methanol=4/1), and thus, N-(1-butanesulfonyl)-4-acetylamino-3-nitrobenzamide (10.75 g) is obtained. $^1$H-NMR (DMSO-d6, δ): 0.87 (3H, t, J=7.4 Hz), 1.37–1.44 (2H, m), 1.64–1.71 (2H, m), 2.12 (3H, s), 3.52 (2H, t, J=7.7 Hz), 7.83 (1H, d, J=8.6 Hz), 8.21 (1H, dd, J=8.6 and 2.1 Hz), 8.54 (1H, d, J=2.2 Hz), 10.56 (1H, s), 12.32 (1H, s).

B.) N-(1-butanesulfonyl)-3-amino-4-acetylaminobenzamide

N-(1-butanesulfonyl)-4-acetylamino-3-nitrobenzamide (10.75 g) is dissolved with methanol (200 ml) and water (30 ml), and potassium bicarbonate (7.59 g) is added. The solution is hydrogenated with a 5% palladium/carbon (2.53 g) catalyst under a hydrogen environment for 24 hours at 40° C. The solids are separated through filtration, the residue, which is obtained by concentrating the filtrate, is purified using silica gel column chromatography (eluate: ethyl acetate/methanol=4/1), and 6.72 g of N-1-butylsulfonyl-4-acetylamino-3-aminobenzamide is obtained. $^1$H-NMR (DMSO-d6, δ): 0.86 (3H, t, J=7.3 Hz), 1.33–1.43 (2H, m), 1.59–1.67 (2H, m), 2.07 (3H, s), 3.37–3.43 (2H, t), 5.12 (2H, br s), 7.13 (1H, dd, J=8.2 and 2.0 Hz), 7.28 (1H, d, J=1.9 Hz), 7.40 (1H, d, J=8.3 Hz), 9.09 (1H, s).

C.) Production Example 57; Production of N-(1-Butanesulfonyl)-4-acetylamino-3-[4-(2-pyridyl)benzylamino]benzamide By using the method of example 204, a crude product material of N-(1-butanesulfonyl)-4-acetylamino-3-[4-(2-pyridyl)benzylamino]benzamide is obtained from N-(1-butanesulfonyl)-3-amino-4-acetylaminobenzamide (0.400 g) and 2-[(4-brommethyl)phenyl]pyridine (0.477 g). This material is immediately used for the following reaction.

D.) 6-(1-Butanesulfonylcarbamoyl)-1-[4-(2-pyridyl)benzyl]-2-methylbenzimidazole

By using the method of example 182, 6-(1-butanesulfonylcarbamoyl)-1-[4-(2-pyridyl)benzyl]-2-methylbenzimidazole (0.330 g) is obtained from the above-described crude product material of N-(1-butanesulfonyl)-4-acetylamino-3-[4-(2-pyridyl)benzylamino]benzamide.

$^1$H-NMR (DMSO-d6, δ): 0.82 (3H, t), 1.37–1.46 (2H, m), 1.54–1.61 (2H, m), 2.54 (3H, s), 3.10 (2H, t, J=7.8 Hz), 5.57 (2H, s), 7.19 (2H, t, J=7.5 Hz), 7.33 (1H, t, J=5.2 Hz), 7.49 (1H, d, J=8.4 Hz), 7.82–7.87 (2H, m), 7.90 (1H, d, J=8.0 Hz), 8.01–8.04 (3H, m), 8.63 (1H, d, J=4.2 Hz).

IR(Nujol): 1722 cm$^1$.
mp: 292.4–298.4° C.
($R_1$=4-(2-pyridyl)-benzyl, $R_2$=methyl, $R_3$=—C(O)—$NR_4R_5$, $R_4$=$SO_2R_6$, $R_6$=butyl, n=1, y=0)

Example 277

5-Chlorosulfonyl-1-(2,4-Dichlorobenzyl)-2-Methylbenzimidazole and 6-Chlorosulfonyl-1-(2,4-Dichlorobenzyl)-2-Methylbenzimidazole In an ice bath, 1-(2,4-dichlorobenzyl)-2-methylbenzimidazole (4.00 g) is added to chlorosulfonic acid (20 ml) and the solution is stirred for 24 hours at room temperature and at 1.5 hours at 80° C. The reaction solution is poured into ice water, precipitated gummy solids are separated through filtration, and thus, a mixture of 5-chlorosulfonyl-1-(2,4-dichlorobenzyl)-2-methylbenzimidazole and 6-chlorosulfonyl-1-(2,4-dichlorobenzyl)-2-methylbenzimidazole is obtained. This material is immediately used for the following reaction.
($R_1$=2,4-dichlorobenzyl, $R_2$=methyl, $R_3$=chlorosulfonyl, n=1, y=1)

Example 278

5-Aminosulfonyl-1-(2,4-Dichlorobenzyl)-2-Methylbenzimidazole and 6-Aminosulfonyl-1-(2,4-Dichlorobenzyl)-2-Methylbenzimidazole The mixture of 5-chlorosulfonyl-1-(2,4-dichlorobenzyl)-2-methylbenzimidazole and 6-chlorosulfonyl-1-(2,4-dichlorobenzyl)-2-methylbenzimidazole, which is obtained in Example 285, is immediately processed with a 25% aqueous ammonia (100 ml) for one hour at room temperature. Separation of solids through filtration produced a 1/1 mixture (2.68 g) of 5-aminosulfonyl-1-(2,4-dichlorobenzyl)-2-methylbenzimidazole and 6-aminosulfonyl-1-(2,4-dichlorobenzyl)-2-methylbenzimidazole. $^1$H-NMR (CD$_3$OD, δ): 2.52 (3/2H, s), 2.54 (3/2H, s), 5.54 (2H, s), 6.55 (1H, d, J=6.9 Hz), 7.17 (1H, d, J=8.0 Hz), 7.52 (1H, s), 7.65–7.78 (2H, m), 7.82 (1/2H, s), 8.11 (1/2H, s).
($R_1$=2,4-dichlorobenzyl, $R_2$=methyl, $R_3$=-aminosulfonyl, n=1, y=0)

Example 287

6-(n-Valerylaminosulfonyl)-1-(2,4-Dichlorobenzyl)-2-Methylbenzimidazole and 5-n-Valerylaminosulfonyl)-1-(2,4-Dichlorobenzyl)-2-Methylbenzimidazole Chloroform (1 ml), triethylamine (0.56 ml) and n-valeryl chloride (0.500 g) are added to the mixture (0.500 g) of 5-aminosulfonyl-1-(2,4-dichlorobenzyl)-2-methylbenzimidazole and 6-aminosulfonyl-1-(2,4-dichlorobenzyl)-2-methyl-benzimidazole, and the solution is stirred for 48 hours at room temperature. Water is added, the reaction is halted, and chloroform extraction is performed. The organic layer is dried, concentrated and purified using silica gel column chromatography (eluate: chloroform/methanol=95/5). Thus, a mixture (0.360 g) of 5-(n-valerylaminosulfonyl)-1-(2,4-dichlorobenzyl)-2-methylbenzimidazole and 6-(n-valerylaminosulfonyl)-1-(2,4-dichlorobenzyl)-2-methylbenzimidazole is obtained. Further, purification of the material using medium pressure silica gel column chromatography (eluate: hexane/ethyl acetate=1/1~1/4) produced 6-(n-valerylaminosulfonyl)-1-(2,4-dichlorobenzyl)-2-methylbenzimidazole (0.95 g) and 5-(n-valerylaminosulfonyl)-1-(2,4-dichlorobenzyl)-2-methylbenzimidazole (0.45 g). $^1$H-NMR (DMSO-d6, δ): 0.74 (3H, t, J=7.3 Hz), 1.09 (2H, m), 1.31 (2H, m), 2.10 (2H, t, J=7.3 Hz), 2.53 (3H, s), 5.63 (2H, s), 6.60 (1H, d, J=8.4 Hz), 7.32 (1H, d, J=8.3 Hz), 7.67–7.77 (3H, m), 7.93 (1H, s).

IR(KBr): 1726 cm$^{-1}$.
mp: 207.5–210.0° C.
Mass(FD): m/e 454(M+1).
$^1$H-NMR (DMSO-d6, δ): 0.75 (3H, t, J=7.3 Hz), 1.11 (2H, m), 1.34 (2H, m), 2.13 (2H, t, J=7.4 Hz), 2.51 (3H, s), 5.59 (2H, s), 6.57 (1H, d, J=8.5 Hz), 7.32 (1H, dd, J=2.2 and 8.4 Hz), 7.57 (1H, d, J=8.6 Hz), 7.67 (1H, dd, J=1.6 and 8.6 Hz), 7.73 (1H, d, J=2.1 Hz), 8.08 (1H, d, J=1.6 Hz).
IR(KBr): 1706 cm$^1$.
mp: 213.0–216.0° C.
($R_1$=2,4-dichlorobenzyl, $R_2$=methyl, $R_3$=-valerylaminosulfonyl, n=1, y=0)

Example 280

1-(2,4-Dichlorobenzyl)-2,4-Dimethyl-6-Methoxycarbonylbenzimidazole

A mixture of 2,4-dimethyl-6-methoxycarbonylbenzimidazole (0.900 g), 2,4-dichlorobenzyl chloride (1.20 g), sodium iodide (0.200 g), potassium carbonate (0.610 g) and N,N-dimethylformamide (4 ml) is stirred for 16 hours at 80° C. After removing the organic solvent through evaporation under reduced pressure, ethyl acetate and water are added and extraction is performed. The organic layer is concentrated, hexane is added and it is crystallized. The crystals are separated through filtration, dried and thus, 1-(2,4-dichlorobenzyl)-2,4-dimethyl-6-methoxycarbonylbenzimidazole (1.08 g) is obtained. $^1$H-NMR (CDCl$_3$, δ): 2.58 (3H, s), 2.71 (3H, s), 3.90 (3H, s), 5.39 (2H, s), 6.30 (1H, d, J=8.4 Hz), 7.07 (1H, dd, J=8.4 and 2.0 Hz), 7.49 (1H, d, J=2.0 Hz), 7.75 (1H, s), 7.81 (1H, s).
($R_1$=2,4-dichlorobenzyl, $R_2$=methyl, $R_3$=-methoxycarbonyl, methyl, n=2, y=0)

Example 281

6-Carboxy-1-(2,4-dichlorobenzyl)-2,4-dimethylbenzimidazole

By using the method of example 75, 6-carboxy-1-(2,4-dichlorobenzyl)-2,4-dimethylbenzimidazole (0.435 g) is obtained from 1-(2,4-dichlorobenzyl)-2,4-dimethyl-6-methoxycarbonylbenzimidazole (0.510 g). $^1$H-NMR (DMSO-d6, δ): 2.51 (3H, s), 2.55 (3H, s), 5.57 (2H, s), 6.49 (1H, d, J=8.4 Hz), 7.31 (1H, dd, J=8.4 and 2.2 Hz), 7.62 (1H, s), 7.72 (1H, d, J=2.0 Hz), 7.78 (1H, s), 12.64 (1H, br s).
($R_1$=2,4-dichlorobenzyl, $R_2$=methyl, $R_3$=-methoxycarbonyl, methyl, n=2, y=0)

Example 282

6-(1-Butanesulfonylcarbamoyl)-1-(2,4-Dichlorobenzyl)-2,4-Dimethylbenzimidazole

By using the method of example 111, 6-(1-butanesulfonylcarbamoyl)-1-(2,4-dichlorobenzyl)-2,4-dimethylbenzimidazole (0.468 g) is obtained from 6-carboxy-1-(2,4-dichlorobenzyl)-2,4-dimethylbenzimidazole (0.417 g), N,N'-carbonyldiimidazole (0.290 g), 1-butanesulfonamide (0.246 g) and diazabicycloundecene (0.273 g). $^1$H-NMR (DMSO-d6, δ): 0.84 (3H, t, J=7.4 Hz), 1.38 (2H, m), 1.64 (2H, m), 2.49 (3H, s), 2.56 (3H, s), 3.48 (2H, t), 5.55 (2H, s), 6.40 (1H, d, J=8.5 Hz), 7.31 (1H, dd, J=2.1 and 8.4 Hz), 7.64 (1H, s), 7.75 (1H, d, J=2.1 Hz), 7.90 (1H, s), 11.79 (1H, br s).
IR(Nujol): 1682 cm$^{-1}$.
mp: 180.0–181.5° C.
($R_1$=2,4-dichlorobenzyl, $R_2$=methyl, $R_3$=—C(O)NR$_4$R$_5$, methyl, $R_4$=SO$_2$R$_6$, $R_5$=H, $R_6$=butyl, n=2, y=0)

Example 283

6-Ethoxycarbonyl-2-Methyl-1-(4-Phenoxybenzyl)Benzimidazole

By using the method of example 255, 4-acetylamino-3-[(4-phenoxy)benzylamino]ethylbenzoate (0.49 g) is obtained from 4-acetylamino-3-amino-ethylbenzoate (0.56 g), sodium carbonate (0.33 g), sodium iodide (0.12 g) and 4-phenoxybenzyl chloride (0.66 g). Subsequently, this material is altered to 6-ethoxycarbonyl-2-methyl-1-(4-phenoxybenzyl)benzimidazole (0.44 g). $^1$H-NMR (CDCl$_3$, δ): 1.40 (3H, t, J=7.1 Hz), 2.61 (3H, s), 4.39 (2H, q, J=7.1 Hz), 5.35 (2H, s), 6.92–6.95 (2H, m), 6.97–7.00 (2H, m), 7.02 (2H, d, J=8.7 Hz), 7.09–7.13 (1H, m), 7.31–7.34 (2H, m), 7.72 (1H, d, J=8.6 Hz), 7.98 (1H, dd, J=1.5 and 8.4 Hz), 8.04 (1H, d, J=1.2 Hz).
($R_1$=4-phenoxybenzyl, $R_2$=methyl, $R_3$=-ethoxycarbonyl, n=1, y=0)

Example 284

6-Carboxy-2-methyl-1-(4-phenoxybenzyl)benzimidazole

By using the method of example 75, 6-carboxy-2-methyl-1-(4-phenoxybenzyl)benzimidazole (0.37 g) is obtained from 6-ethoxycarbonyl-2-methyl-1-(4phenoxy)benzylbenzimidazole (0.44 g). $^1$H-NMR (DMSO-d6, δ): 2.57 (3H, s), 5.54 (2H, s), 6.95–6.97 (4H, m), 7.09–7.13 (3H, m), 7.33–7.37 (2H, m), 7.60 (1H, d, J=8.4 Hz), 7.78 (1H, d, J=8.4 Hz), 8.07 (1H, s), 12.72 (1H, br s).
($R_1$=4-phenoxybenzyl, $R_2$=methyl, $R_3$=-carboxyl, n=1, y=0)

Example 285

6-(1-Butanesulfonylcarbamoyl)-2-Methyl-1-(4-Phenoxybenzyl)Benzimidazole

By using the method of example 111, 6-(1-butanesulfonylcarbamoyl)-2-methyl-1-(4-phenoxybenzyl)benzimidazole (0.19 g) is obtained from 6-carboxy-2-methyl-1-(4-phenoxybenzyl)benzimidazole (0.36 g), N,N'-carbonyldiimidazole (0.24 g), 1-butanesulfonamide (0.21 g) and diazabicycloundecene (0.23 g). $^1$H-NMR (DMSO-d6, δ): 0.85 (3H, t, J=7.4 Hz), 1.40 (2H, m), 1.68 (2H, m), 2.54 (3H, s), 3.52 (2H, t, J=7.8 Hz), 5.51 (2H, s), 6.96–6.98 (4H, m), 7.11 (1H, t, J=7.4 Hz), 7.17 (2H, d, J=8.6 Hz), 7.34–7.37 (2H, m), 7.64 (1H, d, J=8.5 Hz), 7.79 (1H, dd, J=1.5 and 8.5 Hz), 8.24 (1H, s), 11.92 (1H, br s).
IR(Nujol): 1632 cm$^{-1}$.
mp: 183.4–184.4° C.
($R_1$=4-phenoxybenzyl, $R_2$=methyl, $R_3$=—C(O)NR$_4$R$_5$, $R_4$=SO$_2$R$_6$, $R_5$=H, $R_6$=butyl, n=1, y=0)

Example 286

6-Ethoxycarbonyl-2-Methyl-1-(2-Pyridylmethyl)Benzimidazole

By using the method of example 255, 6-ethoxycarbonyl-2-methyl-1-(2-pyridylmethyl)benzimidazole (0.656 g) is obtained from 4-acetylamino-3-amino-ethylbenzoate (0.600 g), potassium carbonate (0.450 g), sodium iodide (0.121 g) and 2-chloromethylpyridine (0.413 g). This material is immediately used for the following reaction.
($R_1$=2-pyridylmethyl, $R_2$=methyl, $R_3$=-ethoxycarbonyl, n=1, y=0)

Example 287

6-Carboxy-2-Methyl-1-(2-Pyridylmethyl)Benzimidazole

By using the method of example 75, 6-carboxy-2-methyl-1-(2-pyridylmethyl)benzimidazole (0.532 g) is obtained from 6-ethoxycarbonyl-2-methyl-1-(2-pyridylmethyl)benzimidazole (0.656 g). $^1$H-NMR (DMSO-d6, δ): 2.56 (3H, s), 5.56 (2H, s), 7.22 (1H, d, J=7.9 Hz), 7.28 (1H, dd, J=5.0 and 7.1 Hz), 7.45 (1H, d, J=8.3 Hz), 7.74–7.79 (2H, m), 7.95 (1H, s), 8.48 (1H, d, J=8.5 Hz).
($R_1$=2-pyridylmethyl, $R_2$=methyl, $R_3$=-carboxyl, n=1, y=0)

Example 289

1-(Butanesulfonylcarbamoyl)-2-Methyl-1-(2-Pyridylmethyl)Benzimidazole

By using the method of example 111, 1-(butanesulfonylcarbamoyl)-2-methyl-1-(2-pyridylmethyl)benzimidazole (0.142 g) is obtained from 6-carboxy-2-methyl-1-(2-pyridylmethyl)benzimidazole (0.500 g), N,N'-carbonyldiimidazole (0.394 g), 1-butanesulfonamide (0.334 g) and diazabicycloundecene (0.370 g). $^1$H-NMR (DMSO-d6, δ): 0.83 (3H, t, J=7.3 Hz), 1.28–1.36 (2H, m), 1.52–1.58 (2H, m), 2.55 (3H, s), 3.06 (2H, t, J=7.9 Hz), 5.56 (2H, s), 7.17 (1H, t, J=7.8 Hz), 7.29 (1H, dd, J=4.2 and 7.3 Hz), 7.43 (1H, d, J=8.4 Hz), 7.77 (1H, dt, J=1.8 and 7.7 Hz), 7.81 (1H, dd, J=1.4 and 8.4 Hz), 7.96 (1H, s), 8.50 (1H, d, J=4.7 Hz).
IR(Nujol): 1674 cm$^{-1}$.
mp: 139° C. (decomposition).
($R_1$=2-pyridylmethyl, $R_2$=methyl, $R_3$=—C(O)NR$_4$R$_5$, $R_4$=SO$_2$R$_6$, $R_5$=H, $R_6$=butyl, n=1, y=0)

Example 289

6-Ethoxycarbonyl-2-Methyl-1-(4-Nitrobenzyl)Benzimidazole

By using the method of example 255, 6-ethoxycarbonyl-2-methyl-1-(4-nitrobenzyl)benzimidazole (0.51 g) is obtained from 4-acetylamino-3-amino-ethylbenzoate (0.67 g), sodium carbonate (0.39 g), sodium iodide (0.14 g) and 4-nitrobenzyl bromide (0.78 g). $^1$H-NMR (CDCl$_3$, δ): 1.39 (3H, t, J=7.1 Hz), 2.59 (3H, s), 4.38 (2H, q, J=7.1 Hz), 5.49 (2H, s), 7.20 (2H, d, J=8.6 Hz), 7.76 (1H, d, J=8.5 Hz), 7.94 (1H, d, J=1.1 Hz), 8.01 (1H, dd, J=1.4 and 8.5 Hz), 8.20 (2H, d, J=8.6 Hz).
($R_1$=4-nitrobenzyl, $R_2$=methyl, $R_3$=ethoxycarbonyl, n=1, y=0)

Example 290

1-(4-Aminobenzyl)-6-Ethoxycarbonyl-2-Methylbenzimidazole

Ethanol (6 ml) and acetic acid (0.8 ml) are added to 1-(4-nitorbenzyl)-6-ethoxycarbonyl-2-methylbenzimidazole (0.50 g) and reduced iron (0.47 g), and the solution is refluxed for 4.5 hours. Water and ethyl acetate are added and extraction is performed. After the organic layer is washed with water and dried, it is concentrated under reduced pressure, and 1-(4-aminobenzyl)-6-ethoxycarbonyl-2-methylbenzimidazole (0.46 g) is obtained. $^1$H-NMR (CDCl$_3$, δ): 1.40 (3H, t, J=7.2 Hz), 2.59 (3H, s), 4.38 (2H, q, J=7.2 Hz), 5.25 (2H, s), 6.61 (2H, d, J=8.6 Hz), 6.87 (2H, d, J=8.6 Hz), 7.71 (1H, d, J=8.3 Hz), 7.96 (1H, dd, J=1.5 and 8.4 Hz), 8.05 (1H, d, J=1.3 Hz).
($R_1$=4-aminobenzyl, $R_2$=methyl, $R_3$=ethoxycarbonyl, n=1, y=0)

Example 291

1-[(4-Benzoylamino)Benzyl]-6-Ethoxycarbonyl-2-Methylbenzimidazole

A chloroform (4 ml) solution of benzoyl chloride (0.25 g) is added to a chloroform (8 ml) solution of 1-(4-aminobenzyl)-6-ethoxycarbonyl-2-methylbenzimidazole (0.45 g) and pyridine (0.15 g), and the solution is stirred for 16 hours at room temperature. After water is added, chloroform extraction is performed. The organic layer is concentrated under reduced pressure, and 1-[(4-benzoylamino)benzyl]-6-ethoxycarbonyl-2-methylbenzimidazole (0.33 g) is obtained. $^1$H-NMR (CDCl$_3$, δ): 1.40 (3H, t, J=7.1 Hz), 2.59 (3H, s), 4.38 (2H, q, J=7.1 Hz), 5.37 (2H, s), 7.06 (2H, d, J=8.5 Hz), 7.46–7.50 (2H, m), 7.53–7.57 (1H, m), 7.61 (2H, d, J=8.5 Hz), 7.72 (1H, d, J=8.4 Hz), 7.84–7.86 (2H, m), 7.89 (1H, br s), 7.98 (1H, dd, J=1.5 and 8.5 Hz), 8.03 (1H, s).
($R_1$=4-benzoylaminobenzyl, $R_2$=methyl, $R_3$=ethoxycarbonyl, n=1, y=0)

Example 292

1-[(4-Benzoylamino)Benzyl]-6-Carboxy-2-Methylbenzimidazole

By using the method of example 75, 1-[(4-benzoylamino)benzyl]-6-carboxy-2-methylbenzimidazole (365) (0.28 g) is obtained from 1-[(4-benzoylamino)benzyl]-6-ethoxycarbonyl-2-methylbenzimidazole (0.31 g). $^1$H-NMR (DMSO-d6, δ): 2.58 (3H, s), 5.52 (2H, s), 7.12 (2H, d, J=8.5 Hz), 7.48–7.52 (2H, m), 7.54–7.58 (1H, m), 7.61 (1H, d, J=8.4 Hz), 7.73 (2H, d, J=8.6 Hz), 7.79 (1H, dd, 1.5 and 8.4 Hz), 7.90–7.92 (2H, m), 8.07 (1H, d, J=1.2 Hz), 10.26 (2H, s), 12.73 (1H, br s).
($R_1$=4-benzoylaminobenzyl, $R_2$=methyl, $R_3$=carboxyl, n=1, y=0)

Example 293

1-[(4-Benzoylamino)Benzyl]-6-(1-Butanesulfonyl)carbamoyl-2-Methylbenzimidazol

By using the method of example 111, 1-[(4-benzoylamino)benzyl]-6-(1-butanesulfonylcarbamoyl-2-methylbenzimidazole (366) (0.14 g) is obtained from 1-[(4-benzoylamino)benzyl]-6-carboxy-2-methylbenzimidazole (0.26 g), N,N'-carbonyldiimidazole (0.17 g), 1-butanesulfonamide (0.14 g) and diazabicycloundecene (0.16 g). $^1$H-NMR (DMSO-d6, δ): 0.85 (3H, t, J=7.4 Hz), 1.40 (2H, m), 1.68 (2H, m), 2.56 (3H, s), 3.52 (2H, t, J=7.8 Hz), 5.50 (2H, s), 7.15 (2H, d, J=8.6 Hz), 7.50 (2H, t, J=7.5 Hz), 7.55–7.59 (1H, m), 7.64 (1H, d, J=8.5 Hz), 7.74 (2H, d, J=8.6 Hz), 7.79 (1H, dd, J=1.6 and 8.5 Hz), 7.90–7.92 (2H, m), 8.24 (1H, d, J=1.3 Hz), 10.27 (1H, s), 11.92 (1H, br s).
IR(Nujol): 1693 cm$^{-1}$.
mp: 267.5–268.1° C.
($R_1$=4-benzoylaminobenzyl, $R_2$=methyl, $R_3$=—C(O)NR$_4$R$_5$, $R_4$=SO$_2$R$_6$, $R_5$=H, $R_6$=butyl, n=1, y=0)

Example 294

6-Ethoxycarbonyl-2-Methyl-1-[4-(2-Phenylethenyl)benzyl]Benzimidazole

By using the method of example 255, 6-ethoxycarbonyl-2-methyl-1-[4-(2-phenylethenyl)benzyl]benzimidazole (0.320 g) is obtained from 4-acetylamino-3-aminoethylbenzoate (0.405 g), potassium carbonate (0.253 g), sodium iodide (0.082 g) and 4chloromethylstilbene (0.500 g). $^1$H-NMR (CDCl$_3$, δ): 1.40 (3H, t, J=7.2 Hz), 2.6 (3H, s), 4.38 (2H, q, J=7.1 Hz), 5.38 (2H, s), 7.01–7.09 (4H, m), 7.26 (1H, t, J=7.4 Hz), 7.35 (2H, t, J=7.5 Hz), 7.45 (2H, d, J=8.2 Hz), 7.49 (2H, d, J=7.5 Hz), 7.73 (1H, d, J=8.5 Hz), 7.99 (1H, dd, J=1.5 and 8.4 Hz), 8.30 (1H, d, J=1.2 Hz).
($R_1$=4-(2-phenylethenyl)benzyl, $R_2$=methyl, $R_3$=ethoxycarbonyl, n=1, y=0)

Example 295

6-Ethoxycarbonyl-2-Methyl-1-[4-(2-Phenylethyl)benzyl]-Benzimidazole

In a nitrogen environment, 5% palladium-carbon is added to an ethanol (910 ml) solution of 6-ethoxycarbonyl-2-methyl-1-[4-(2-phenylethenyl)benzyl]benzimidazole (0.320 g). The solution is stirred for 23 hours under a nitrogen environment. Solids are separated through filtration, the filtrate is concentrated, and thus, 6-ethoxycarbonyl-2-methyl-1-[4-(2-phenylethyl)benzyl]-benzimidazole is obtained. This material is immediately used for the following reaction.
($R_1$=4-(2-phenylethyl)benzyl, $R_2$=methyl, $R_3$=ethoxycarbonyl, n=1, y=0)

Example 296

6-Carboxy-2-methyl-1-[4-(2-phenylethyl)benzyl]-benzimidazole

By using the method of example 75, 6-carboxy-2-methyl-1-[4-(2-phenylethyl)benzyl]-benzimidazole (0.242 g) is obtained from 6-ethoxycarbonyl-2-methyl-1-[4-(2-phenylethyl)benzyl]-benzimidazole (0.283 g). $^1$H-NMR (DMSO-d6, δ): 2.56 (3H, s), 2.82 (4H, s), 5.51 (2H, s), 7.02 (2H, d, J=8.1 Hz), 7.11–7.27 (7H, m), 7.61 (1H, d, J=8.4 Hz), 7.78 (1H, dd, 1.5 and 8.04(1H, s), 12.72 (1H, s).
($R_1$=4-(2-phenylethyl)benzyl, $R_2$=methyl, $R_3$=carboxyl, n=1, y=0)

Example 297

6-(1-Butanesulfonylcarbamoyl)-2-Methyl-[4-(2-Phenylethyl)benzyl]Benzimidazole

By using the method of Example 111, 6-(1-butanesulfonylcarbamoyl)-2-methyl-[4-(2-phenylethyl)benzyl]benzimidazole (370) (0.249 g) is obtained from 6-carboxy-2-methyl-1-[4-(2-phenylethyl)benzyl]-benzimidazole (0.225 g), N,N'-carbonyldiimidazole (1.214 g), 1-butanesulfonamide (0.167 g) and diazabicycloundecene (0.185 g). $^1$H-NMR (DMSO-d6, δ): 0.86 (3H, t, J=7.4 Hz), 1.35–1.42 (2H, m), 1.63–1.71 (2H, m), 2.53 (3H, s), 2.83 (4H, s), 3.52 (2H, t, J=7.7 Hz), 5.49 (2H, s), 7.04 (2H, d, J=8.0 Hz), 7.12–7.25 (7H, m), 7.64 (1H, d, J=8.4 Hz), 7.79 (1H, dd, 1.7 and 8.5 Hz), 8.22 (1H, d, J=1.3 Hz), 11.92 (1H, s).

IR(Nujol): 1682 cm$^{-1}$.
mp: 95.4–99.0° C.
($R_1$=2 4-(2-phenylethyl)benzyl, $R_2$=methyl, $R_3$=—C(O)NR$_4$R$_5$, $R_4$=SO$_2$R$_6$, $R_5$=butyl, n=1, y=0)

Example 298

1-[(4-Benzoyl)benzyl]-6-ethoxycarbonyl-2-methylbenzimidazole

By using the method of example 255, 1-[(4-benzoyl)benzyl]-6-ethoxycarbonyl-2-methylbenzimidazole (371) (0.70 g) is obtained from 4-acetylamino-3-amino-ethylbenzoate (0.56 g), sodium carbonate (0.33 g), sodium iodide (0.11 g) and 4-benzoylbenzyl bromide (0.83 g). $^1$H-NMR (CDCl$_3$, δ): 1.40 (3H, t, J=7.2 Hz), 2.61 (3H, s), 4.39 (2H, q, J=7.2 Hz), 5.47 (2H, s), 7.14 (2H, d, J=8.2 Hz), &.45–7.48 (2H, m), 7.56–7.60 (1H, m), 7.74–7.77 (5H, m), 7.99–8.02 (2H, m).
($R_1$=4-benzoylbenzyl, $R_2$=methyl, $R_3$=ethoxycarbonyl, n=1, y=0)

Example 299

1-[(4-Benzoyl)benzyl]-6-Carboxy-2-Methylbenzimidazole

By using the method of example 75, 1-[(4-benzoyl)benzyl]-6-carboxy-2-methylbenzimidazole (372) (0.55 g) is obtained from 1-[(4-benzoyl)benzyl]-6-ethoxycarbonyl]-2-methylbenzimidazole (0.68 g). $^1$H-NMR (DMSO-d6, δ): 2.57 (3H, s), 5.71 (2H, s), 7.25 (2H, d, J=8.2 Hz), 7.52 (2H, t, J=7.7 Hz), 7.62–7.66 (2H, m), 7.68–7.72 (4H, m), 7.80 (1H, dd, J=1.3 and 8.4 Hz), 8.08 (1H, d, J=1.1 Hz), 12.72 (1H, br s).
($R_1$=4-benzoylbenzyl, $R_2$=methyl, $R_3$=carboxyl, n=1, y=0)

Example 300

1-[(4-Benzoyl)benzyl]-6-(1-Butanesulfonylcarbamoyl)-2-Methylbenzimidazole

By using the method of example 111, 1-[(4-benzoyl)benzyl]-6-(1-butanesulfonylcarbamoyl)-2-methylbenzimidazole (0.133 g) is obtained from 1-[(4-benzoyl)benzyl]-6-carboxy-2-methylbenzimidazole (0.52 g), N,N'-carbonyldiimidazole (0.34 g), 1-butanesulfonamide (0.29 g) and diazabicycloundecene (0.32 g). $^1$H-NMR (DMSO-d6, δ): 0.84 (3H, t, J=7.4 Hz), 1.38 (2H, m), 1.66 (2H, m), 2.54 (3H, s), 3.48 (2H, t, J=7.7 Hz), 5.67 (2H, s), 7.27 (2H, d, J=8.2 Hz), 7.51–7.55 (2H, m), 7.63–7.73 (6H, m), 7.81 (1H, dd, J=1.6 and 8.5 Hz), 8.21 (1H, d, J=1.4 Hz).
IR(Nujol): 1660 cm$^{-1}$.
mp: 111.0–112.4° C.
Mass(FAB): m/e 490(M+1).
($R_1$=4-benzoylbenzyl, $R_2$=methyl, $R_3$=—C(O)NR$_4$R$_5$, $R_4$=SO$_2$R$_6$, $R_5$=H, $R_6$=butyl, n=1, y=0)

Example 301

6-Carboxy-2-Methyl-[4-(2-Phenylethenyl)Benzyl]Benzimidazole

By using the method of example 75, 6-carboxy-2-methyl-[4-(2-phenylethenyl)benzyl]benzimidazole (0.237 g) is obtained from 6-ethoxycarbonyl-2-methyl-1-[4-(2-phenylethenyl)benzyl]benzimidazole (0.500 g). $^1$H-NMR (DMSO-d6, δ): 2.59 (3H, s), 5.58 (2H, s), 7.12 (2H, d, J=8.2 Hz), 7.21 (2H, s), 7.26 (1H, t, J=7.4 Hz), 7.36 (2H, t, J=7.6 Hz), 7.57 (4H, d, J=8.0 Hz), 7.62 (1H, d, J=8.4 Hz), 7.79 (1H, dd, J=1.5 and 8.4 Hz), 8.07 (1H, d, J=1.2 Hz), 12.73 (1H, s).
($R_1$=4-benzoylbenzyl, $R_2$=methyl, $R_3$=—C(O)NR$_4$R$_5$, $R_4$=SO$_2$R$_6$, $R_5$=H, $R_6$=butyl,1 n=1, y=0)

Example 302

6-(1-Butanesulfonylcarbamoyl)-2-Methyl-[4-(2-Phenylethenyl)Benzyl]Benzimidazole

By using the method of example 111, 6-(1-butanesulfonylcarbamoyl)-2-methyl-[4-(2-phenylethenyl)benzyl]benzimidazole (0.239 g) is obtained from 6-carboxy-2-methyl-[4-(2-phenylethenyl)benzyl]benzimidazole (0.237 g), N,N'-carbonyldiimidazole (0.209 g), 1-butanesulfonamide (0.176 g) and diazabicycloundecene (0.195 g). $^1$H-NMR (DMSO-d6, δ): 0.86 (3H, t, J=7.4 Hz), 1.35–1.43 (2H, m), 1.63–1.70 (2H, m), 2.56 (3H, s), 3.52 (2H, t, J=7.6 Hz), 5.55 (2H, s), 7.15 (2H, d, J=8.2 Hz), 7.22 (2H, s), 7.26 (1H, t, J=7.4 Hz), 7.36 (2H, t, J=7.6 Hz), 7.57 (1H, d, J=7.3 Hz), 7.58 (1H, d, J=8.2 Hz), 7.66 (1H, d, J=8.5 Hz), 7.80 (1H, d, J=8.4 Hz), 8.24 (1H, s), 11.93 (1H, brs).
IR(Nujol): 1680 cm$^{-1}$.
mp: 140.3–143.4° C.
($R_1$=2-phenylethenylbenzyl, $R_2$=methyl, $R_3$=—C(O)NR$_4$R$_5$, $R_4$=SO$_2$R$_6$, $R_5$=H, $R_6$=butyl, n=1, y=0)

Example 303

1-(Dibenzofuran-2-ylmethyl)-6-Ethoxycarbonyl-2-Methylbenzimidazole

By using the method of example 255, 1-(dibenzofuran-2-ylmethyl)-6-ethoxycarbonyl-2-methylbenzimidazole (0.47 g) is obtained from 4-acetylamino-3-amino-ethylbenzoate (0.480 g), sodium carbonate (0.274 g), sodium iodide (0.097 g) and 2-bromomethyldibenzofuran (0.56 g). $^1$H-NMR (CDCl$_3$, δ): 1.38 (3H, t, J=7.1 Hz), 2.62 (3H, s), 4.36 (2H, q, J=7.1 Hz), 5.54 (2H, s), 7.19 (2H, dd, J=1.6 and 8.5 Hz), 7.32 (1H, t, J=7.6 Hz), 7.43–7.59 (4H, m), 7.76 (1H, d, J=8.4 Hz), 7.85 (1H, d, J=7.1 Hz), 8.00 (1H, dd, J=1.3 and 8.4 Hz), 8.07 (1H, d, J=1.2 Hz).
($R_1$=2-dibenzofuranyl, $R_2$=methyl, $R_3$=ethoxycarbonyl, n=1, y=1)

Example 304

6-Carboxy-1-(Dibenzofuran-2-ylmethyl)-2-Methylbenzimidazole

By using the method of example 75, 6-carboxy-1-(dibenzofuran-2-ylmethyl)-2-methylbenzimidazole (0.336 g) is obtained from 6-ethoxycarbonyl-2-methylbenzimidazole (0.46 g). $^1$H-NMR (DMSO-d6, δ): 2.63 (3H, s), 5.71 (2H, s), 7.27 (1H, d, J=8.5 Hz), 7.36 (1H, t, J=7.5 Hz), 7.50 (1H, t), 7.61–7.68 (3H, m), 7.78 (1H, d, J=8.3 Hz), 7.97 (1H, s), 7.07–8.11 (2H, m).
($R_1$=2-dibenzofuranyl, $R_2$=methyl, $R_3$=-carboxyl, n=1, y=1)

Example 305

1-(Dibenzofuran-2-ylmethyl)-6-(1-Butanesulfonylcarbamoyl)-2-Methylbenzimidazole

By using the method of example 111, 1-(dibenzofuran-2-ylmethyl)-6-(1-butanesulfonylcarbamoyl)-2-methylbenzimidazole (0.249 g) is obtained from 6-carboxy-1-(dibenzofuran-2-ylmethyl)-2-methylbenzimidazole (0.255 g), N,N'-carbonyldiimidazole (0.197 g), 1-butanesulfonamide (0.167 g) and diazabicycloundecene (0.185 g). $^1$H-NMR (DMSO-d6, δ): 0.81 (3H, t, J=7.4 Hz), 1.36 (2H, m), 1.65 (2H, m), 2.60 (3H, s), 3.50 (2H, t, J=7.7 Hz), 5.69 (2H, s), 7.29 (1H, dd, J=1.96 and 8.7 Hz), 7.34–7.38 (1H, m), 7.48–7.52 (1H, m), 7.63–7.68 (3H, m), 7.81 (1H, dd, J=1.7 and 8.5 Hz), 8.00 (1H, d, J=1.4 Hz), 8.94 (1H, d, J=7.1 Hz), 8.28 (1H, d, J=1.4 Hz), 12.70 (1H, br s).

IR(Nujol): 1682 cm$^{-1}$.

mp: 224.1–229.8° C.

($R_1$=2-dibenzofuranyl, $R_2$=methyl, $R_3$=—C(O)NR$_4$R$_5$, $R_4$=SO$_2$R$_6$, $R_5$=H, $R_6$=butyl, n=1, y=1)

Example 306

6-Ethoxycarbonyl-2-Methyl-1-(2-Quinolylmethyl) Benzimidazole

By using the method of example 255, 6-ethoxycarbonyl-2-methyl-1-(2-quinolylmethyl)benzimidazole (0.87 g) is obtained from 4-acetylamino-3-amino-ethylbenzoate (2.22 g), sodium carbonate (1.27 g), sodium iodide (0.45 g) and 2-bromomethylquinoline (0.56 g). $^1$H-NMR (DMSO-d6, δ): 1.27 (3H, t, J=7.1 Hz), 2.62 (3H, s), 4.26 (2H, q, J=7.1 Hz), 5.85 (2H, s), 7.35 (1H, d, J=8.5 Hz), 7.58 (1H, m), 7.63 (1H, d, J=8.4 Hz), 7.73 (1H, m), 7.78 (1H, dd, J=1.3 and 8.4 Hz), 7.86 (1H, d, J=8.4 Hz), 7.95 (1H, d, J=8.0 Hz), 8.14 (1H, s), 8.36 (1H, d, J=8.5 Hz).

($R_1$=4-quinolyl, $R_2$=methyl, $R_3$=ethoxycarbonyl, n=1, y=1)

Example 307

6-Carboxy-2-Methyl-(2-Quinolylmethyl) Benzimidazole

By using the method of example 75, 6-carboxy-2-methyl-(2-quinolylmethyl)benzimidazole (381) (0.46 g) is obtained from 6-ethoxycarbonyl-2-methyl-1-(2-quinolylmethyl) benzimidazole (0.85 g) $^1$H-NMR (DMSO-d6, δ): 2.62 (3H, s), 5.83 (2H, s), 7.35 (1H, d, J=8.5 Hz), 7.57 (1H, m), 7.60 (1H, d, J=8.5 Hz), 7.72 (1H, t, J=7.6 Hz), 7.77 (1H, d, J=8.4 Hz), 7.86 (1H, d, J=8.4 Hz), 7.94 (1H, d, J=8.1 Hz), 8.11 (1H, s), 8.35 (1H, d, J=8.5 Hz).

($R_1$=4-quinolyl, $R_2$=methyl, $R_3$=carboxyl, n=1, y=1)

Example 308

6-(1-Butanesulfonylcarbamoyl)-2-methyl-1-(2-quinolylmethyl)benzimidazole

By using the method of example 111, 6-(1-butanesulfonylcarbamoyl)-2-methyl-1-(2-quinolylmethyl) benzimidazole (0.088 g) is obtained from 6-carboxy-2-methyl-1-(2-quinolylmethyl)benzimidazole (0.222 g), N,N'-carbonyldiimidazole (0.195 g), 1-butanesulfonamide (0.165 g) and diazabicycloundecene (0.183 g). $^1$H-NMR (DMSO-d6, δ): 0.82 (3H, t, J=7.3 Hz), 1.36 (2H, m), 1.64 (2H, m), 2.61 (3H, s), 3.48 (2H, t, J=7.4 Hz), 5.82 (2H, s), 7.32 (1H, d, J=8.5 Hz), 7.58 (1H, m), 7.65 (1H, d, J=8.5 Hz), 7.73 (1H, t, J=7.6 Hz), 7.78 (1H, m), 7.87 (1H, d, J=8.5 Hz), 7.95 (1H, d, J=8.1 Hz), 8.23 (1H, s), 8.37 (1H, d, J=8.5 Hz), 11.86 (1H, brs).

IR(Nujol): 1684 cm$^{-1}$.

mp: 185.5–187.5° C.

($R_1$=quinolyl, $R_2$=methyl, $R_3$=—C(O)NR$_4$R$_5$, $R_4$=SO$_2$R$_6$, $R_5$=H, $R_6$=butyl, n=1, y=1)

Example 309

6-Ethoxycarbonyl-2-Methyl-1-[3-(4-Bromoisoquinolyl)Methyl]Benzimidazole

By using the method of example 255, 6-ethoxycarbonyl-2-methyl-1-[3-(4-bromoisoquinolyl)methyl]benzimidazole (0.30 g) is obtained from 4-acetylamino-3-amino-ethylbenzoate (0.87 g), sodium carbonate (0.53 g), sodium iodide (0.18 g) and 4-bromo-3-bromomethylisoquinoline (0.87 g). $^1$H-NMR (DMSO-d6, δ): 1.26 (3H, t, J=7.0 Hz), 2.59 (3H, s), 4.24 (2H, q, J=7.0 Hz), 5.93 (2H, s), 7.61 (1H, d, J=8.4 Hz), 7.75–7.80 (2H, m), 7.99 (1H, m), 8.03 (1H, s), 8.13 (1H, d, J=8.1 Hz), 8.23 (1H, d, J=8.5 Hz), 9.12 (1H, s).

($R_1$=3-(4-bromoisoquinolyl), $R_2$=methyl, $R_3$=ethoxycarbonyl, n=1, y=1)

Example 310

6-Carboxy-2-Methyl-[3-(4-Bromoisoquinolyl) Methyl]Benzimidazole

By using the method of example 75, 6-carboxy-2-methyl-[3-(4-bromoisoquinolyl)methyl]benzimidazole (0.118 g) is obtained from 6-ethoxycarbonyl-2-methyl-1-[3-(4-bromoisoquinolyl)methyl]benzimidazole (0.290 g). This material is immediately used for the following reaction.

($R_1$=3-(4-bromoisoquinolyl), $R_2$=methyl, $R_3$=carboxyl, n=1, y=1)

Example 311

6-(1-Butanesulfonylcarbamoyl)-2-Methyl-1-[3-(4-Bromoisoquinolyl)Methyl]Benzimidazole By using the method of example 111, 6-(1-butanesulfonyl carbamoyl)-2-methyl-1-[3-(4-bromoisoquinolyl)methyl] benzimidazole (0.075 g) is obtained from 6-carboxy-2-methyl-1-[3-(4-bromoisoquinolyl)methyl]benzimidazole (0.111 g), N,N'-carbonyldiimidazole (0.097 g), 1-butanesulfonamide (0.082 g) and diazabicycloundecene (0.091 g). $^1$H-NMR (DMSO-d6, δ): 0.81 (3H, t, J=7.4 Hz), 1.35 (2H, m), 1.62 (2H, m), 2.54 (3H, s), 3.46 (2H, t, J=7.5 Hz), 5.91 (2H, s), 7.63 (1H, d, J=8.5 Hz), 7.76 (1H, dd, J=8.5 and 1.4 Hz), 7.79 (1H, t, J=7.6 Hz), 8.00 (1H, t, J=7.9 Hz), 8.08 (1H, t, J=1.1 Hz), 8.13 (1H, d, J=8.2 Hz), 8.24 (1H, d, J=8.5 Hz), 9.11 (1H, s), 11.81 (1H, brs).

IR(Nujol): 1678 cm$^{-1}$.

mp: 258–259° C.

Mass(FAB): m/e 515, 517(M+1).

($R_1$32 3-(4-bromoisoquinolyl), $R_2$=methyl, $R_3$=—C(O)NR$_4$R$_5$, $R_4$=SO$_2$R$_6$, $R_5$=H, $R_6$=butyl, n=1, y=1)

The compounds of this invention can be formulated with pharmaceutically acceptable carriers into unit dosage forms in a conventional manner so that the patient in need of therapy for precancerous lesions can periodically (e.g., once or more per day) take a compound according to the methods of this invention. The exact initial dose of the compounds of this invention can be determined with reasonable experimentation. For compounds of this invention, a dosage of from about 0.12 to about 400 mg/day of such compounds for intravenous administration to achieve a systemic circulatory therapeutic concentration.

It will be understood that various changes and modifications can be made in the details of procedure, formulation and use without departing from the spirit of the invention, especially as defined in the following claims.

What is claimed is:

1. A method of treating a mammal having precancerous lesions sensitive to the compounds of formula I comprising administering to said mammal a pharmacologically effective amount of a compound of formula I

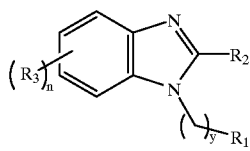

Formula I wherein

R₁ is selected from a group consisting of substituted or unsubstituted phenyl and benzyl wherein said substituents are one to three independently selected from the group consisting of halogen, lower alkyl, lower alkoxy, halo- or cyano-substituted or unsubstituted phenyloxy or benzyloxy, lower haloalkyl, CN, amino, nitro, phenyl, thiadiazole, aryloxy, arylsulfonyl methyl, arylsulfonyl amino, benzoyl, benzylamidyl, benzenesulfonyl methyl, phenylethyl, and phenylethenyl, wherein said aryl group is selected from the group consisting of phenyl, benzyl and pyridyl;

R₂ is selected from a group consisting of lower alkyl, haloalkyl and lower alkoxy;

R₃ is selected from a group consisting of halo.

2. A method for inhibiting the growth of neoplastic cells sensitive to the compounds of formula I comprising exposing the cells to a growth inhibiting effective amount of a compound of formula I

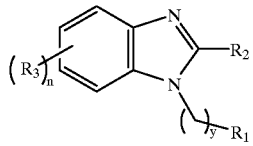

Formula I wherein

R₁ is selected from a group consisting of substituted or unsubstituted phenyl and benzyl wherein said substituents are one to three independently selected from the group consisting of halogen, lower alkyl, lower alkoxy, halo- or cyano-substituted or unsubstituted phenyloxy or benzyloxy, lower haloalkyl, CN, amino, nitro, phenyl, thiadiazole, aryloxy, arylsulfonyl methyl, arylsulfonyl amino, benzoyl, benzylamidyl, benzenesulfonyl methyl, phenylethyl, and phenylethenyl, wherein said aryl group is selected from the group consisting of phenyl, benzyl and pyridyl;

R₂ is selected from a group consisting of lower alkyl, haloalkyl and lower alkoxy;

R₃ is selected from a group consisting of halo.

\* \* \* \* \*